United States Patent
Shioda

(10) Patent No.: US 9,573,904 B2
(45) Date of Patent: Feb. 21, 2017

(54) AROMATIC COMPOUND AND USE THEREOF

(71) Applicant: Sumitomo Chemical Company, Limited, Tokyo (JP)

(72) Inventor: Takayuki Shioda, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 15/102,576

(22) PCT Filed: Dec. 10, 2014

(86) PCT No.: PCT/JP2014/083319
§ 371 (c)(1),
(2) Date: Jun. 8, 2016

(87) PCT Pub. No.: WO2015/088038
PCT Pub. Date: Jun. 18, 2015

(65) Prior Publication Data
US 2016/0311775 A1    Oct. 27, 2016

(30) Foreign Application Priority Data

Dec. 12, 2013 (JP) ................................. 2013-256703

(51) Int. Cl.
*C07D 231/12* (2006.01)
*A01N 47/06* (2006.01)
*A01N 47/10* (2006.01)

(52) U.S. Cl.
CPC ............. *C07D 231/12* (2013.01); *A01N 47/06* (2013.01); *A01N 47/10* (2013.01)

(58) Field of Classification Search
CPC .................................................... C07D 231/12
USPC .......................................... 514/406; 548/251
See application file for complete search history.

(56) References Cited

U.S. PATENT DOCUMENTS

| | | | | |
|---|---|---|---|---|
| 5,605,920 A | * | 2/1997 | Goto | A01N 47/38 514/381 |
| 6,583,090 B1 | * | 6/2003 | Gewehr | C07D 231/12 504/280 |
| 6,790,810 B2 | * | 9/2004 | Yanagi | A01N 43/713 504/261 |
| 2012/0015980 A1 | * | 1/2012 | Fischer | A01N 43/56 514/333 |
| 2015/0051171 A1 | * | 2/2015 | Yoshimoto | C07D 403/12 514/63 |
| 2015/0203511 A1 | * | 7/2015 | Arimori | C07D 403/12 514/230.5 |

* cited by examiner

*Primary Examiner* — Sabiha N Qazi
(74) *Attorney, Agent, or Firm* — Panitch Schwarze Belisario & Nadel LLP

(57) ABSTRACT

An aromatic compound represented by formula (1):

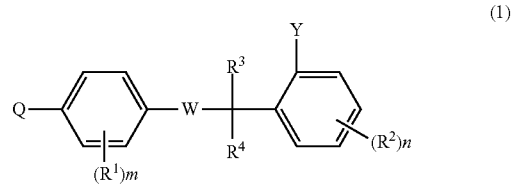

wherein $R^1$ and $R^2$ each independently represents a halogen atom, a C1-C4 alkyl group, or a C1-C4 haloalkyl group; m and n each independently represents an integer of 0 to 4; $R^3$ and $R^4$ each represents a hydrogen atom; Y represents formula: —OC(=X)$ZR^5$ or —SC(=X)$ZR^5$; $R^5$ represents a C1-C3 alkyl group optionally having one or more halogen atoms; Z represents a sulfur atom, $NR^8$, or a direct bond; $R^8$ represents a C1-C3 alkyl group or a hydrogen atom; Q represents a pyrazolyl group optionally having a substituent; and W and X each independently represents an oxygen atom or a sulfur atom, has excellent control activity against pests.

6 Claims, No Drawings

AROMATIC COMPOUND AND USE THEREOF

CROSS-REFERENCE TO RELATED APPLICATION

This application is a Section 371 of International Application No. PCT/JP2014/083319, filed Dec. 10, 2014, which was published in the Japanese language on Jun. 18, 2015, under International Publication No. WO 2015/088038 A1, and the disclosure of which is incorporated herein by reference.

TECHNICAL FIELD

The present invention relates to an aromatic compound, and application for the same.

BACKGROUND ART

Heretofore, various chemicals have been developed so as to control pests and provided in practice use, but in some cases, these chemicals may not exert enough activity.

Meanwhile, there have been known, as compounds having an aromatic group, compounds represented by the following formula (X):

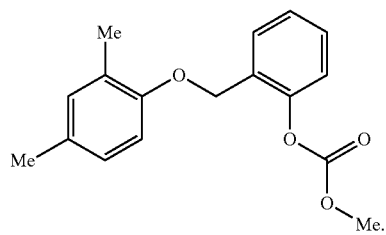

(see JP H07-179402 A)

DISCLOSURE OF THE INVENTION

The present invention provides compounds having excellent control activity against pests.

The present inventors have intensively studied so as to find compounds having excellent control activity against pests, and found that compound represented by formula (1) shown below has excellent control activity against pests, thus completing the present invention.

The present invention includes the followings [1] to [7].
[1] An aromatic compound represented by formula (1):

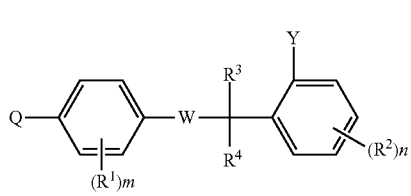

wherein $R^1$ and $R^2$ each independently represents a halogen atom, a C1-C4 alkyl group optionally having one or more halogen atoms, a C3-C4 cycloalkyl group optionally having one or more halogen atoms, a C2-C4 alkenyl group optionally having one or more halogen atoms, a C2-C4 alkynyl group optionally having one or more halogen atoms, a C1-C4 alkoxy group optionally having one or more halogen atoms, a C1-C4 alkylthio group optionally having one or more halogen atoms, a cyano group, or a nitro group (in which when m is an integer of 2 or more, two or more $R^1$(s) may be the same or different to each other and, when n is an integer of 2 or more, two or more $R^2$(s) may be the same or different to each other);
m and n each independently represents an integer of 0 to 4;
$R^3$ and $R^4$ each independently represents a hydrogen atom or a C1-C3 alkyl group optionally having one or more halogen atoms;
Y represents formula: —OC(=X)ZR$^5$ or —SC(=X)ZR$^5$;
$R^5$ represents a C1-C3 alkyl group optionally having one or more halogen atoms;
Z represents an oxygen atom, a sulfur atom, NR$^8$, or a direct bond;
$R^8$ represents a C1-C3 alkyl group optionally having one or more halogen atoms, or a hydrogen atom;
Q represents a pyrazolyl group optionally having one or more atoms or groups selected from Group P$^1$; and
W and X each independently represents an oxygen atom or a sulfur atom:
Group P$^1$: Group consisting of a halogen atom, a C1-C6 alkyl group optionally having one or more halogen atoms, a C2-C6 alkenyl group optionally having one or more halogen atoms, a C2-C6 alkynyl group optionally having one or more halogen atoms, a C3-C6 cycloalkyl group optionally having one or more halogen atoms, a C1-C6 alkoxy group optionally having one or more halogen atoms, a C1-C6 alkylthio group optionally having one or more halogen atoms, a C3-C6 cycloalkyloxy group optionally having one or more halogen atoms, a C3-C6 cycloalkylthio group optionally having one or more halogen atoms, a C3-C6 alkenyloxy group optionally having one or more halogen atoms, a C3-C6 alkynyloxy group optionally having one or more halogen atoms, a C3-C6 alkenylthio group optionally having one or more halogen atoms, a C3-C6 alkynylthio group optionally having one or more halogen atoms, a C2-C6 alkylcarbonyl group optionally having one or more halogen atoms, a C2-C6 alkylcarbonyloxy group optionally having one or more halogen atoms, a C2-C6 alkylcarbonylthio group optionally having one or more halogen atoms, a carboxy group, a formyl group, a C2-C6 alkoxycarbonyl group optionally having one or more halogen atoms, a nitro group, a cyano group, and an amino group optionally having a C1-C6 alkyl group (in which the alkyl group optionally has one or more halogen atoms).

[2] The aromatic compound according to [1], wherein the aromatic compound is a compound represented by formula (2):

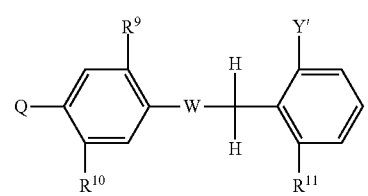

wherein $R^9$ and $R^{10}$ each independently represents a hydrogen atom, a C1-C3 alkyl group optionally having one or more halogen atoms, a halogen atom, a C3-C5 cycloalkyl group optionally having one or more halogen atoms, or a C1-C3 alkoxy group optionally having one or more halogen atoms;

$R^{11}$ represents a hydrogen atom, a C1-C3 alkyl group optionally having one or more halogen atoms, a halogen atom, a C1-C3 alkoxy group optionally having one or more halogen atoms, a C2-C3 alkenyl group optionally having one or more halogen atoms, a C3-C4 cycloalkyl group optionally having one or more halogen atoms, a C2-C3 alkynyl group optionally having one or more halogen atoms, or a C1-C3 alkylthio group optionally having one or more halogen atoms;

Y' represents formula: —OC(=X)Z'R' or —SC(=X)Z'R$^5$;
Z' represents a sulfur atom, NR$^8$, or a direct bond;
$R^5$, $R^8$, W, and X are the same as defined above; and
$Q^2$ represents a pyrazol-1-yl group optionally having one or more halogen atoms or groups selected from Group $P^2$:

Group $P^2$: Group consisting of a halogen atom, a C1-C6 alkyl group optionally having one or more halogen atoms, a C2-C6 alkenyl group optionally having one or more halogen atoms, a C2-C6 alkynyl group optionally having one or more halogen atoms, a C3-C6 cycloalkyl group optionally having one or more halogen atoms, a C1-C6 alkoxy group optionally having one or more halogen atoms, a C1-C6 alkylthio group optionally having one or more halogen atoms, a C3-C6 alkenyloxy group optionally having one or more halogen atoms, a C3-C6 alkynyloxy group optionally having one or more halogen atoms, and a cyano group.

[3] The aromatic compound according to [1], wherein the aromatic compound is a compound represented by formula (3):

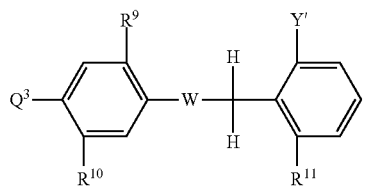

wherein $R^9$, $R^{10}$, $R^{11}$, Y', and W are the same as defined above; and
$Q^3$ represents a pyrazol-3-yl group optionally having one or more atoms or groups selected from Group $P^2$.

[4] The aromatic compound according to [1], wherein the aromatic compound is a compound represented by formula (4):

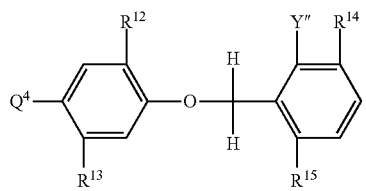

wherein $R^{12}$ represents a C1-C3 alkyl group optionally having one or more halogen atoms, or a halogen atom;
$R^{13}$ and $R^{14}$ each independently represents a hydrogen atom or a C1-C3 alkyl group optionally having one or more halogen atoms;

$R^{15}$ represents a hydrogen atom, a C1-C3 alkyl group optionally having one or more halogen atoms, a halogen atom, a C1-C3 alkoxy group optionally having one or more halogen atoms, or a C3-C4 cycloalkyl group optionally having one or more halogen atoms;
Y" represents formula: —OC(=X)Z"R';
Z" represents NR$^8$ or a direct bond;
$R^5$ and $R^8$ are the same as defined above; and
$Q^4$ represents a pyrazol-3-yl group optionally having one or more atoms or groups selected from Group $P^3$, or a pyrazol-1-yl group optionally having one or more atoms or groups selected from Group $P^3$:

Group $P^3$: Group consisting of a hydrogen atom, a halogen atom, a C1-C6 alkyl group optionally having one or more halogen atoms, and a C1-C6 alkoxy group optionally having one or more halogen atoms.

[5] A pest control agent comprising the aromatic compound according to any one of [1] to [4] (hereinafter referred to as the present control agent).

[6] A method for controlling pests, which comprises applying an effective amount of the aromatic compound according to any one of [1] to [4] to plants or soil.

[7] Use of the aromatic compound according to any one of [1] to [4] for controlling pests.

According to the present invention, pests can be controlled.

MODE FOR CARRYING OUT THE INVENTION

A compound of the present invention (hereinafter referred to as the present compound) is a compound represented by formula (1):

Formula (1)

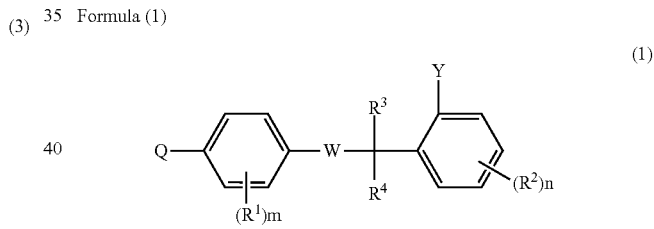

wherein symbols are the same as defined above.

Substituents as used herein will be mentioned below.

Examples of the halogen atom include a fluorine atom, a chlorine atom, a bromine atom, and an iodine atom.

Examples of the C1-C4 alkyl group optionally having one or more halogen atoms include a methyl group, an ethyl group, a propyl group, an isopropyl group, a butyl group, an isobutyl group, a sec-butyl group, a tert-butyl group, a fluoromethyl group, a chloromethyl group, a dichloromethyl group, a difluoromethyl group, a trifluoromethyl group, a trichloromethyl group, a 2-fluoroethyl group, a 2,2,2-trifluoroethyl group, and a 2,2,2-trifluoro-1-(trifluoromethyl)ethyl group.

Examples of the C3-C4 cycloalkyl group optionally having one or more halogen atoms include a cyclopropyl group, a cyclobutyl group, a 2,2-dichlorocyclopropyl group, and a 2,2-difluorocyclopropyl group.

Examples of the C2-C4 alkenyl group optionally having one or more halogen atoms include a vinyl group, a 1-propenyl group, an isopropenyl group, a 3-butenyl group, a 2-fluorovinyl group, a 2-chlorovinyl group, a 2-bromovinyl group, a 2-iodovinyl group, a 2,2-difluorovinyl group, a 2,2-dichlorovinyl group, a 2,2-dibromovinyl group, a 3,3- difluoro-2-propenyl group, a 3,3-dichloro-2-propenyl group, a 3,3-dibromo-2-propenyl group, a 3-chloro-2-propenyl group, and a 4-fluoro-3-butenyl group.

Examples of the C2-C4 alkynyl group optionally having one or more halogen atoms include an ethynyl group, a propargyl group, a 3-butyn-2-yl group, a 3-butynyl group, a fluoroethynyl group, a 3-chloro-2-propynyl group, a 3-bromo-2-propynyl group, and a 4-chloro-1-butynyl group.

Examples of the C1-C4 alkoxy group optionally having one or more halogen atoms include a methoxy group, an ethoxy group, a propoxy group, an isopropoxy group, a butoxy group, an isobutoxy group, a sec-butoxy group, a tert-butoxy group, a trifluoromethoxy group, a difluoromethoxy group, a 2-fluoroethoxy group, a 2,2,2-trifluoroethoxy group, a 3-chloropropoxy group, and a perfluorobutoxy group.

Examples of the C1-C4 alkylthio group optionally having one or more halogen atoms include a methylthio group, an ethylthio group, a propylthio group, an isopropylthio group, a butylthio group, a sec-butylthio group, a tert-butylthio group, a fluoromethylthio group, a difluoromethylthio group, a trifluoromethylthio group, a trichloromethylthio group, and a 4,4,4-trifluorobutylthio group.

Examples of the C1-C3 alkyl group optionally having one or more halogen atoms include a methyl group, an ethyl group, a propyl group, an isopropyl group, a fluoromethyl group, a chloromethyl group, a bromomethyl group, a difluoromethyl group, a trifluoromethyl group, a trichloromethyl group, a 2,2,2-trifluoroethyl group, a 2,2,2-trifluoro-1-(trifluoromethyl)ethyl group, a 1,2,2,2-tetrafluoro-1-(trifluoromethyl)ethyl group, and a 3-fluorobutyl group.

Examples of the C1-C3 alkoxy group optionally having one or more halogen atoms include a methoxy group, an ethoxy group, a propoxy group, an isopropoxy group, a trifluoromethoxy group, a difluoromethoxy group, a 2-fluoroethoxy group, a 2,2,2-trifluoroethoxy group, and a 3-chloropropoxy group.

Examples of the C2-C3 alkenyl group optionally having one or more halogen atoms include a vinyl group, a 1-propenyl group, an isopropenyl group, a 2-fluorovinyl group, a 2-chlorovinyl group, a 2-bromovinyl group, a 2-iodovinyl group, a 2,2-difluorovinyl group, a 2,2-dichlorovinyl group, a 2,2-dibromovinyl group, a 3,3-difluoro-2-propenyl group, a 3,3-dichloro-2-propenyl group, a 3,3-dibromo-2-propenyl group, and a 3-chloro-2-propenyl group.

Examples of the C2-C3 alkynyl group optionally having one or more halogen atoms include an ethynyl group, a propargyl group, a fluoroethynyl group, a 3-chloro-2-propynyl group, and a 3-bromo-2-propynyl group.

Examples of the C1-C3 alkylthio group optionally having one or more halogen atoms include a methylthio group, an ethylthio group, a propylthio group, an isopropylthio group, a difluoromethylthio group, a trifluoromethylthio group, and a 1,1,2,2,2-pentafluoroethylthio group.

Examples of the C1-C6 alkyl group optionally having one or more halogen atoms include a methyl group, an ethyl group, a propyl group, an isopropyl group, a butyl group, an isobutyl group, a sec-butyl group, a tert-butyl group, a pentyl group, a hexyl group, a fluoromethyl group, a chloromethyl group, a bromomethyl group, a difluoromethyl group, a trifluoromethyl group, a trichloromethyl group, a 2,2,2-trifluoroethyl group, a 2,2,2-trifluoro-1-(trifluoromethyl)ethyl group, a 1,2,2,2-tetrafluoro-1-trifluoromethylethyl group, and a 6-fluorohexyl group.

Examples of the C2-C6 alkenyl group optionally having one or more halogen atoms include a vinyl group, a 1-propenyl group, an isopropenyl group, a 5-hexenyl group, a 2-fluorovinyl group, a 2-chlorovinyl group, a 2-bromovinyl group, a 2-iodovinyl group, a 2,2-difluorovinyl group, a 2,2-dichlorovinyl group, a 2,2-dibromovinyl group, a 3,3-difluoro-2-propenyl group, a 3,3-dichloro-2-propenyl group, a 3,3-dibromo-2-propenyl group, a 3-chloro-2-propenyl group, and a 6,6-difluoro-5-hexenyl group.

Examples of the C2-C6 alkynyl group optionally having one or more halogen atoms include an ethynyl group, a propargyl group, a 3-butyn-2-yl group, a 5-hexynyl group, a fluoroethynyl group, a 3-chloro-2-propynyl group, a 3-bromo-2-propynyl group, and a 6-fluoro-1-hexynyl group.

Examples of the C3-C6 cycloalkyl group optionally having one or more halogen atoms include a cyclopropyl group, a cyclobutyl group, a cyclopentyl group, a cyclohexyl group, a 2-fluorocyclopropyl group, a 2,2-difluorocyclopropyl group, a 2,2-dichlorocyclopropyl group, a 2,2-dibromocyclopropyl group, and a 4-chlorocyclohexyl group.

Examples of the C1-C6 alkoxy group optionally having one or more halogen atoms include a methoxy group, an ethoxy group, a propoxy group, an isopropoxy group, a butoxy group, an isobutoxy group, a sec-butoxy group, a tert-butoxy group, a hexyloxy group, a trifluoromethoxy group, a difluoromethoxy group, a 2-fluoroethoxy group, a 2,2,2-trifluoroethoxy group, a 3-chloropropoxy group, and a perfluorohexyloxy group.

Examples of the C1-C6 alkylthio group optionally having one or more halogen atoms include a methylthio group, an ethylthio group, a propylthio group, an isopropylthio group, a butylthio group, a sec-butylthio group, a tert-butylthio group, a hexylthio group, a fluoromethylthio group, a difluoromethylthio group, a trifluoromethylthio group, a trichloromethylthio group, and a 6,6,6-trifluorohexylthio group.

Examples of the C3-C6 cycloalkyloxy group optionally having one or more halogen atoms include a cyclopropyloxy group, a cyclobutyloxy group, a cyclopentyloxy group, a cyclohexyloxy group, a 2-fluorocyclopropyloxy group, a 2,2-difluorocyclopropyloxy group, a 2,2-dichlorocyclopropyloxy group, a 2,2-dibromocyclopropyloxy group, and a 2-chlorocyclohexyloxy group.

Examples of the C3-C6 cycloalkylthio group optionally having one or more halogen atoms include a cyclopropylthio group, a cyclobutylthio group, a cyclopentylthio group, a cyclohexylthio group, a 2,2-dichlorocyclopropylthio group, and a 2,2-difluorocyclopropylthio group.

Examples of the C3-C6 alkenyloxy group optionally having one or more halogen atoms include a 2-propenyloxy group, a 2-butenyloxy group, a 1-methyl-2-propenyloxy group, a 5-hexenyloxy group, a 3-fluoro-2-propenyloxy group, a 3-chloro-2-propenyloxy group, a 3-bromo-2-propenyloxy group, a 3,3-difluoro-2-propenyloxy group, a 3,3-dichloro-2-propenyloxy group, a 3,3-dibromo-2-propenyloxy group, and a 5,5,5-trifluoro-2-pentenyloxy group.

Examples of the C3-C6 alkynyloxy group optionally having one or more halogen atoms include a propargyloxy group, a 3-butyn-2-yloxy group, a 2-butynyloxy group, a 5-hexynyloxy group, a 3-chloro-2-propynyloxy group, a 3-bromo-2-propynyloxy group, a 3-iodo-2-propynyloxy group, and a 6,6-difluoro-3-hexynyloxy group.

Examples of the C3-C6 alkenylthio group optionally having one or more halogen atoms include a 2-propenylthio group, a 2-butenylthio group, a 1-methyl-2-propenylthio group, a 5-hexenylthio group, a 3-chloro-2-propenylthio group, a 3,3-difluoro-2-propenylthio group, a 3,3-dichloro-2-propenylthio group, a 3,3-dibromo-2-propenylthio group, and a 6-fluoro-2-hexenylthio group.

Examples of the C3-C6 alkynylthio group optionally having one or more halogen atoms or groups include a propargylthio group, a 3-butyn-2-ylthio group, a 2-methyl-3-butyn-2-ylthio group, a 5-hexynylthio group, a 3-chloro-2-propynylthio group, a 3-bromo-2-propynylthio group, a 3-iodo-2-propynylthio group, and a 6-fluoro-2-hexynylthio group.

The C2-C6 alkylcarbonyl group optionally having one or more halogen atoms represents a group having the alkyl moiety and the carbonyl moiety, in which the total number of carbon atoms is within a range of 2 to 6, and examples thereof include an acetyl group, a propionyl group, a butanoyl group, a pentanoyl group, a hexanoyl group, a trichloroacetyl group, a fluoroacetyl group, a difluoroacetyl group, a trifluoroacetyl group, and a perfluorohexanoyl group.

The C2-C6 alkylcarbonyloxy group optionally having one or more halogen atoms represents a group having the alkyl moiety and the carbonyloxy moiety, in which the total number of carbon atoms is within a range of 2 to 6, and examples thereof include an acetoxy group, a propionyloxy group, a butanoyloxy group, a pentanoyloxy group, a hexanoyloxy group, a difluoroacetoxy group, and a trifluoroacetoxy group.

The C2-C6 alkylcarbonylthio group optionally having one or more halogen atoms represents a group having the alkyl moiety and the carbonylthio moiety, in which the total number of carbon atoms is within a range of 2 to 6, and examples thereof include an acetylthio group, a propionylthio group, a butanoylthio group, a pentanoylthio group, a hexanoylthio group, a difluoroacetylthio group, and a trifluoroacetylthio group.

The C2-C6 alkoxycarbonyl group optionally having one or more halogen atoms represents a group having the alkoxy moiety and the carbonyl moiety, in which the total number of carbon atoms is within a range of 2 to 6, and examples thereof include a methoxycarbonyl group, an ethoxycarbonyl group, a propyloxycarbonyl group, a 2-methylbutyloxycarbonyl group, a difluoromethoxycarbonyl group, and a trifluoromethoxycarbonyl group.

The amino group optionally having a C1-C6 alkyl group (in which the alkyl group optionally has one or more halogen atoms) represents an amino group in which one or two hydrogen atoms on nitrogen are optionally substituted with the same or different C1-C6 alkyl group(s) (in which the C1-C6 alkyl group optionally has one or more halogen atoms), and examples thereof include an amino group, a methylamino group, an ethylamino group, a propylamino group, an isopropylamino group, a butylamino group, a dimethylamino group, a diethylamino group, a propyl(methyl)amino group, and a 2,2,2-trifluoroethylamino group.

Examples of the pyrazolyl group include a pyrazol-1-yl group, a pyrazol-3-yl group, and a pyrazol-4-yl group, and "pyrazolyl group optionally having one or more atoms or groups selected from Group P¹" is preferably the following groups A1 to A4:

A:

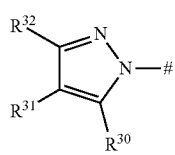

A1

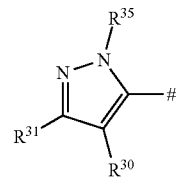

A2

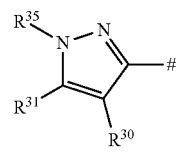

A3

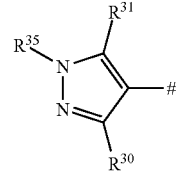

A4 wherein # represents a binding site for Q, $R^{30}$, $R^{31}$, and $R^{32}$ each independently represents a hydrogen atom, a halogen atom, a C1-C6 alkyl group optionally having one or more halogen atoms, a C2-C6 alkenyl group optionally having one or more halogen atoms, a C2-C6 alkynyl group optionally having one or more halogen atoms, a C3-C6 cycloalkyl group optionally having one or more halogen atoms, a C1-C6 alkoxy group optionally having one or more halogen atoms, a C1-C6 alkylthio group optionally having one or more halogen atoms, a C3-C6 cycloalkyloxy group optionally having one or more halogen atoms, a C3-C6 cycloalkylthio group optionally having one or more halogen atoms, a C3-C6 alkenyloxy group optionally having one or more halogen atoms, a C3-C6 alkynyloxy group optionally having one or more halogen atoms, a C3-C6 alkenylthio group optionally having one or more halogen atoms or groups, a C3-C6 alkynylthio group optionally having one or more halogen atoms, a C2-C6 alkylcarbonyl group optionally having one or more halogen atoms, a C2-C6 alkylcarbonyloxy group optionally having one or more halogen atoms, a C2-C6 alkylcarbonylthio group optionally having one or more halogen atoms, a carboxy group, a formyl group, a C2-C6 alkoxycarbonyl group optionally having one or more halogen atoms, a nitro group, a cyano group, or an amino group optionally having a C1-C6 alkyl group (in which the alkyl group optionally has one or more halogen atoms), and $R^{35}$ represents a hydrogen atom, a C1-C6 alkyl group optionally having one or more halogen atoms, a C2-C6 alkenyl group optionally having one or more halogen atoms, a C2-C6 alkynyl group optionally having one or more halogen atoms, a C3-C6 cycloalkyl group optionally having one or more halogen atoms, or a C2-C6 alkylcarbonyl group optionally having one or more halogen atoms.

Examples of Aspect of the present compound include the following compounds.

An aromatic compound in which Q is a group A1 in formula (1).

An aromatic compound in which Q is a group A2 in formula (1).

An aromatic compound in which Q is a group A3 in formula (1).

An aromatic compound in which Q is a group A4 in formula (1).
An aromatic compound in which X is an oxygen atom in formula (1).
An aromatic compound in which X is a sulfur atom in formula (1).
An aromatic compound in which Y is formula: —OC(=X)ZR$^5$ in formula (1).
An aromatic compound in which Y is formula: —SC(=O)ZR$^5$ in formula (1).
An aromatic compound in which Y is formula: —OC(=X)OR$^5$ in formula (1).
An aromatic compound in which Y is formula: —OC(=O)OR$^5$ in formula (1).
An aromatic compound in which Y is formula: —OC(=X)OCH$_3$ in formula (1).
An aromatic compound in which Y is formula: —OC(=O)OCH$_3$ in formula (1).
An aromatic compound in which Y is formula: —OC(=X)NHR$^5$ in formula (1).
An aromatic compound in which Y is formula: —OC(=O)NHR$^3$ in formula (1).
An aromatic compound in which Y is formula: —OC(=X)NHCH$_3$ in formula (1).
An aromatic compound in which Y is formula: —OC(=O)NHCH$_3$ in formula (1).
An aromatic compound in which Y is formula: —OC(=X)SR$^5$ in formula (1).
An aromatic compound in which Y is formula: —OC(=O)SR$^5$ in formula (1).
An aromatic compound in which Y is formula: —OC(=X)SCH$_3$ in formula (1).
An aromatic compound in which Y is formula: —OC(=O)SCH$_3$ in formula (1).
An aromatic compound in which Y is formula: —OC(=X)R$^5$ in formula (1).
An aromatic compound in which Y is formula: —OC(=O)R$^5$ in formula (1).

[Aspect 1]
An aromatic compound represented by formula (2):

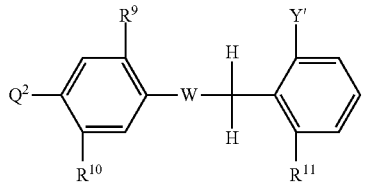

(2)

wherein R$^9$, R$^{10}$, R$^{11}$, Y', W, and Q$^2$ are the same as defined above.
An aromatic compound in which X is an oxygen atom in [Aspect 1].
An aromatic compound in which X is a sulfur atom in [Aspect 1].
An aromatic compound in which Y' is formula: —OC(=X)Z'R$^5$ in [Aspect 1].
An aromatic compound in which Y' is formula: —SC(=O)Z'R$^5$ in [Aspect 1].
An aromatic compound in which Y' is formula: —OC(=X)OR$^5$ in [Aspect 1].
An aromatic compound in which Y' is formula: —OC(=O)OR$^5$ in [Aspect 1].
An aromatic compound in which Y' is formula: —OC(=X)OCH$_3$ in [Aspect 1].
An aromatic compound in which Y' is formula: —OC(=O)OCH$_3$ in [Aspect 1].
An aromatic compound in which Y' is formula: —OC(=X)NHR$^5$ in [Aspect 1].
An aromatic compound in which Y' is formula: —OC(=O)NHR$^5$ in [Aspect 1].
An aromatic compound in which Y' is formula: —OC(=X)NHCH$_3$ in [Aspect 1].
An aromatic compound in which Y' is formula: —OC(=O)NHCH$_3$ in [Aspect 1].
An aromatic compound in which Y' is formula: —OC(=X)SR$^5$ in [Aspect 1].
An aromatic compound in which Y' is formula: —OC(=O)SR$^5$ in [Aspect 1].
An aromatic compound in which Y' is formula: —OC(=X)SCH$_3$ in [Aspect 1].
An aromatic compound in which Y' is formula: —OC(=O)SCH$_3$ in [Aspect 1].
An aromatic compound in which Y' is formula: —OC(=X)R$^5$ in [Aspect 1].
An aromatic compound in which Y' is formula: —OC(=O)R$^5$ in [Aspect 1].

[Aspect 2]
An aromatic compound represented by formula (3):

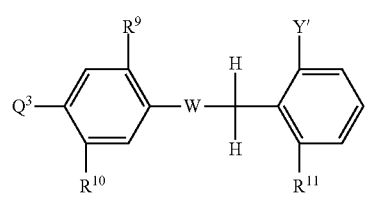

(3)

wherein R$^9$, R$^{10}$, R$^{11}$, Y', W, and Q$^3$ are the same as defined above.
An aromatic compound in which X is an oxygen atom in [Aspect 2].
An aromatic compound in which X is a sulfur atom in [Aspect 2].
An aromatic compound in which Y' is formula: —OC(=X)Z'R$^5$ in [Aspect 2].
An aromatic compound in which Y' is formula: —SC(=O)Z'R$^5$ in [Aspect 2].
An aromatic compound in which Y' is formula: —OC(=X)OR$^5$ in [Aspect 2].
An aromatic compound in which Y' is formula: —OC(=O)OR$^5$ in [Aspect 2].
An aromatic compound in which Y' is formula: —OC(=X)OCH$_3$ in [Aspect 2].
An aromatic compound in which Y' is formula: —OC(=O)OCH$_3$ in [Aspect 2].
An aromatic compound in which Y' is formula: —OC(=X)NHR$^5$ in [Aspect 2].
An aromatic compound in which Y' is formula: —OC(=O)NHR$^5$ in [Aspect 2].
An aromatic compound in which Y' is formula: —OC(=X)NHCH$_3$ in [Aspect 2].
An aromatic compound in which Y' is formula: —OC(=O)NHCH$_3$ in [Aspect 2].
An aromatic compound in which Y' is formula: —OC(=X)SR$^5$ in [Aspect 2].

An aromatic compound in which Y' is formula: —OC(=O)SR$^5$ in [Aspect 2].
An aromatic compound in which Y' is formula: —OC(=X)SCH$_3$ in [Aspect 2].
An aromatic compound in which Y' is formula: —OC(=O)SCH$_3$ in [Aspect 2].
An aromatic compound in which Y' is formula: —OC(=X)R$^5$ in [Aspect 2].
An aromatic compound in which Y' is formula: —OC(=O)R$^5$ in [Aspect 2].
An aromatic compound in which Q$^3$ is a pyrazol-3-yl group optionally having one or more atoms or groups selected from the group consisting of a C1-C6 alkyl group optionally having one or more halogen atoms and a halogen atom; R$^9$ and R$^{10}$ each independently represents a hydrogen atom or a C1-C3 alkyl group optionally having one or more halogen atoms; R$^{11}$ is a hydrogen atom or a C1-C3 alkyl group optionally having one or more halogen atoms; R$^5$ is a C1-C3 alkyl group optionally having one or more halogen atoms; W and X are oxygen atoms; and Z' is an oxygen atom in [Aspect 2].
An aromatic compound in which Q$^3$ is a pyrazol-3-yl group optionally having one or more atoms or groups selected from the group consisting of a C1-C6 alkyl group optionally having one or more halogen atoms and a halogen atom; R$^9$ and R$^{10}$ each independently represents a hydrogen atom or a C1-C3 alkyl group optionally having one or more halogen atoms; R$^{11}$ is a hydrogen atom; R$^5$ is a C1-C3 alkyl group optionally having one or more halogen atoms; W and X are oxygen atoms, and Z' is an oxygen atom in [Aspect 2].
An aromatic compound in which Q$^3$ is a pyrazol-3-yl group optionally having one or more atoms or groups selected from the group consisting of a C1-C6 alkyl group optionally having one or more halogen atoms and a halogen atom; R$^9$ and R$^{10}$ each independently represents a hydrogen atom or a C1-C3 alkyl group optionally having one or more halogen atoms; R$^{11}$ is a C1-C3 alkyl group optionally having one or more halogen atoms; R$^5$ is a C1-C3 alkyl group optionally having one or more halogen atoms; W and X are oxygen atoms; and Z' is a direct bond in [Aspect 2].

[Aspect 3]
An aromatic compound represented by formula (4):

wherein R$^{12}$, R$^3$, R$^{14}$, R$^{15}$, Y" and Q$^4$ are the same as defined above.
An aromatic compound in which X is an oxygen atom in [Aspect 3].
An aromatic compound in which X is a sulfur atom in [Aspect 3].
An aromatic compound in which Y" is formula: —OC(=X)Z"R$^5$ in [Aspect 3].
An aromatic compound in which Y" is formula: —SC(=O)Z"R$^5$ in [Aspect 3].
An aromatic compound in which Y" is formula: —OC(=X)OR$^5$ in [Aspect 3].
An aromatic compound in which Y" is formula: —OC(=O)OR$^5$ in [Aspect 3].
An aromatic compound in which Y" is formula: —OC(=X)OCH$_3$ in [Aspect 3].
An aromatic compound in which Y" is formula: —OC(=O)OCH$_3$ in [Aspect 3].
An aromatic compound in which Y" is formula: —OC(=X)NHR$^5$ in [Aspect 3].
An aromatic compound in which Y" is formula: —OC(=O)NHR in [Aspect 3].
An aromatic compound in which Y" is formula: —OC(=X)NHCH$_3$ in [Aspect 3].
An aromatic compound in which Y" is formula: —OC(=O)NHCH$_3$ in [Aspect 3].
An aromatic compound in which Y" is formula: —OC(=X)SR$^5$ in [Aspect 3].
An aromatic compound in which Y" is formula: —OC(=O)SR$^5$ in [Aspect 3].
An aromatic compound in which Y" is formula: —OC(=X)SCH$_3$ in [Aspect 3].
An aromatic compound in which Y" is formula: —OC(=O)SCH$_3$ in [Aspect 3].
An aromatic compound in which Y" is formula: —OC(=X)R$^5$ in [Aspect 3].
An aromatic compound in which Y" is formula: —OC(=O)R$^5$ in [Aspect 3].
An aromatic compound in which Q$^4$ is a pyrazol-3-yl group optionally having one or more atoms selected from the group consisting of a C1-C6 alkyl group optionally having one or more halogen atoms and a halogen atom, or a pyrazol-3-yl group optionally having a C1-C6 alkyl group which optionally has one or more halogen atoms; R$^{12}$ is a C1-C3 alkyl group optionally having one or more halogen atoms; R$^{13}$ and R$^{14}$ each independently represents a hydrogen atom or a C1-C3 alkyl group optionally having one or more halogen atoms; Y" is formula: —OC(=X)Z"R$^5$; R$^5$ is a C1-C3 alkyl group optionally having one or more halogen atoms; X is an oxygen atom; and Z" is an oxygen atom in [Aspect 3].
An aromatic compound in which Q$^4$ is a pyrazol-3-yl group optionally having one or more atoms or groups selected from the group consisting of a C1-C6 alkyl group optionally having one or more halogen atoms and a halogen atom, or a pyrazol-3-yl group optionally having a C1-C6 alkyl group which optionally has one or more halogen atoms; R$^{12}$ is a C1-C3 alkyl group optionally having one or more halogen atoms; R$^3$ and R$^4$ each independently represents a hydrogen atom or a C1-C3 alkyl group optionally having one or more halogen atoms; Y" is formula: —OC(=X)Z"R$^5$; R$^5$ is a C1-C3 alkyl group optionally having one or more halogen atoms; X is an oxygen atom; and Z" is a nitrogen atom in [Aspect 3].
An aromatic compound in which Q$^4$ is a pyrazol-3-yl group optionally having one or more atoms or groups selected from the group consisting of a C1-C6 alkyl group optionally having one or more halogen atoms and a halogen atom, or a pyrazol-3-yl group optionally having a C1-C6 alkyl group pyrazol-3-yl group which optionally has one or more halogen atoms; R$^{12}$ is a C1-C3 alkyl group optionally having one or more halogen atoms; R$^{13}$ and R$^{14}$ each independently represents a hydrogen atom or a C1-C3 alkyl group optionally having one or more halogen atoms; Y" is formula: —OC(=X)Z"R$^5$; R$^5$ is a C1-C3 alkyl group optionally having one or more halogen atoms; X is an oxygen atom; and Z" is a direct bond in [Aspect 3].

Next, a process for producing the present compound will be described.

The present compound can be produced, for example, by the following Production Processes.

(Production Process A)

The present compound represented by formula (1) (hereinafter referred to as the compound (1)) can be produced by reacting a compound represented by formula (A) (hereinafter referred to as the compound (A)) with a compound represented by formula (B) (hereinafter referred to as the compound (B)) in the presence of a base:

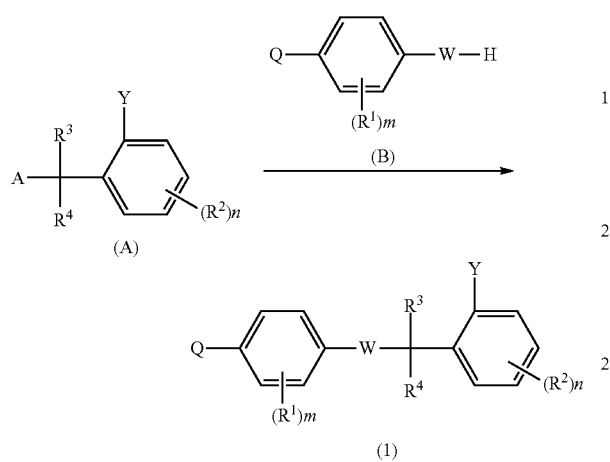

wherein $R^1$, $R^2$, $R^3$, $R^4$, Y, Q, W, m, and n are the same as defined above, and A represents a leaving group such as a chlorine atom or a bromine atom.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water and mixtures thereof.

It is possible to add, as the base to be used in the reaction, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate and potassium hydrogen carbonate. These compounds are usually used in the proportion within a range of 0.05 to 5 mols based on 1 mol of the compound (A).

In the reaction, the compound (B) is usually used in the proportion within a range of 1 to 10 mols based on 1 mol of the compound (A).

The reaction temperature of the reaction is usually within a range of −20 to 150° C. The reaction time of the reaction is usually within a range of 0.1 to 24 hours.

After completion of the reaction, the compound (1) can be isolated by performing post-treatment operations such as extraction of the reaction mixture with an organic solvent, and drying and concentration of the organic layer. The isolated compound may be further purified by operations such as distillation, chromatography, and recrystallization.

(Production Process B)

The compound (1) can be produced by reacting a compound represented by formula (C) (hereinafter referred to as the compound (C)) with a compound represented by formula (D) (hereinafter referred to as the compound (D)):

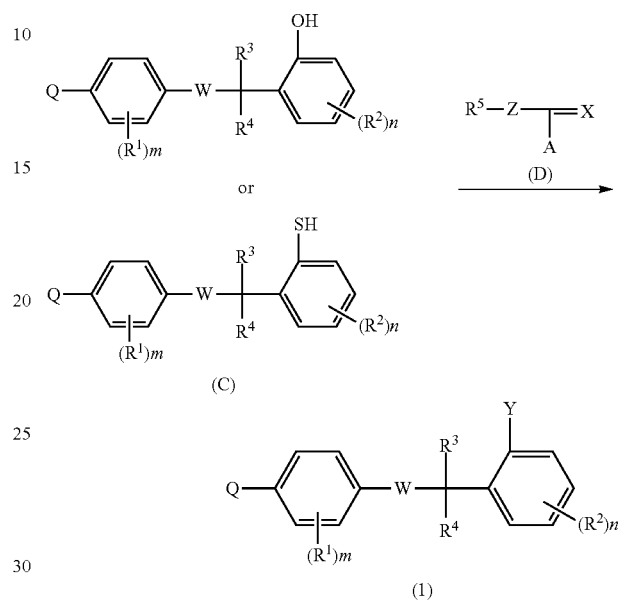

wherein symbols are the same as defined above.

The compound (D) to be used in the reaction can be synthesized before use, and it is also possible to use commercially available products such as methyl chlorocarbonate, ethyl chlorocarbonate, acetyl chloride, and propionyl chloride.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water and mixtures thereof.

In the reaction, the compound (D) is usually used in the proportion within a range of 1 to 10 mols based on 1 mol of the compound (C).

The reaction temperature of the reaction is usually within a range of −20 to 150° C. The reaction time of the reaction is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate and potassium hydrogen carbonate may be added, and these compounds are usually used in the proportion within a range of 0.05 to 5 mols based on 1 mol of the compound (C).

After completion of the reaction, the compound (1) can be isolated by performing post-treatment operations such as extraction of the reaction mixture with an organic solvent, and drying and concentration of the organic layer. The isolated compound may be further purified by operations such as distillation, chromatography, and recrystallization.

(Production Process C)

Among compounds (1), a compound represented by formula (1-S) in which X is a sulfur atom (hereinafter referred to as the compound (1-S)) can be produced by reacting a compound in which X is an oxygen atom (hereinafter referred to as the compound (1-O)) among compounds (1) with a sulfurizing agent:

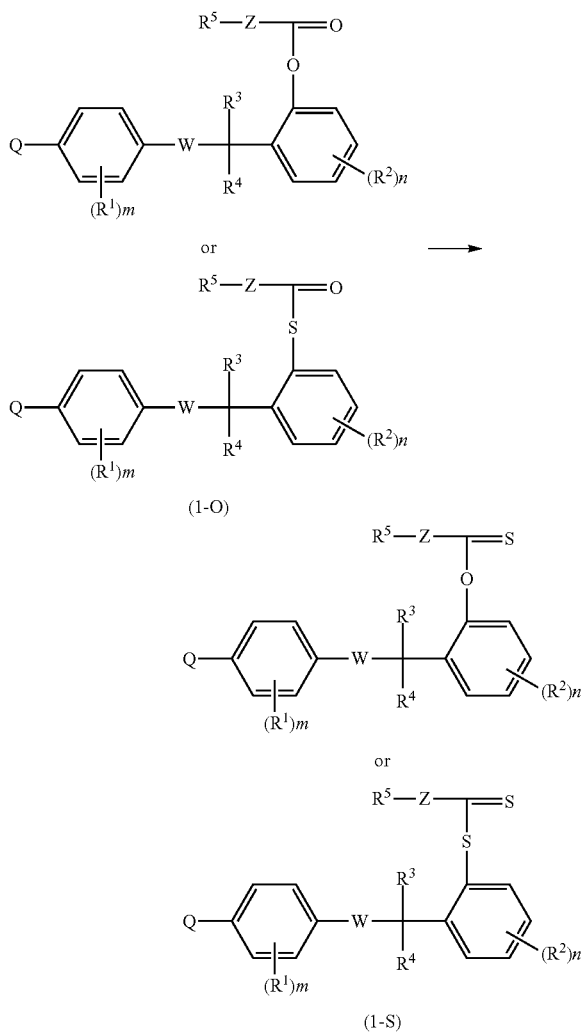

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; nitriles such as acetonitrile; and mixtures thereof.

Examples of the sulfurizing agent to be used in the reaction include phosphorous pentasulfide and Lawesson's reagent (2,4-Bis(4-methoxyphenyl)-1,3,2,4-dithiadiphosphetane 2,4-disulfide).

In the reaction, the sulfurizing agent is usually used in the proportion within a range of 0.5 to 1.5 mols based on 1 mol of the compound (1-O).

The reaction temperature of the reaction is usually within a range of −20 to 150° C. The reaction time of the reaction is usually within a range of 0.1 to 24 hours.

In the reaction, if necessary, organic bases such as pyridine and triethylamine; and inorganic bases such as alkali metal hydroxide and alkali metal carbonates may be added, and the amount of the base to be added is within a range of 0.5 to 1.5 mols based on the compound (1-O).

After completion of the reaction, the compound (1-S) can be isolated by performing post-treatment operations such as extraction of the reaction mixture with an organic solvent, and drying and concentration of the organic layer. The isolated present compound can be further purified by chromatography, recrystallization, and the like.

The process for synthesizing an intermediate compound for production will be mentioned in detail below.

(Reference Production Process A)

The compound (A) can be produced by reacting a compound represented by formula (A1) (hereinafter referred to as the compound (A1)) with a halogenating agent:

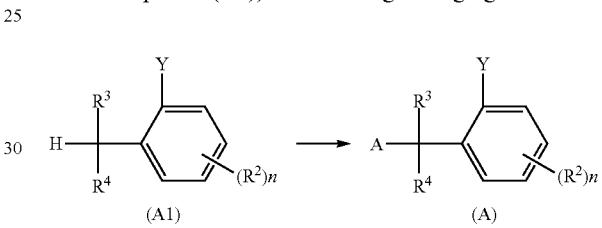

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent to be used in the reaction include a chlorinating agent, a brominating agent, and an iodinating agent, for example, chlorine, bromine, iodine, sulfuryl chloride, N-chlorosuccinimide, and N-bromosuccinimide.

In the reaction, a radical initiator can also be used.

Examples of the radical initiator to be used in the reaction include benzoyl peroxide and azobisisobutyronitrile (AIBN).

In the reaction, the halogenating agent is usually used in the proportion within a range of 1 to 10 mols, and the radical initiator is usually used in the proportion within a range of 0.01 to 5 mols, based on 1 mol of the compound (A1).

The reaction temperature of the reaction is usually within a range of −20 to 150° C. The reaction time of the reaction is usually within a range of 0.1 to 24 hours.

After completion of the reaction, the compound (A) can be isolated by performing post-treatment operations such as extraction of the reaction mixture with an organic solvent, and drying and concentration of the organic layer. The isolated compound may be further purified by operations such as distillation, chromatography, and recrystallization.

A pest control agent of the present invention includes the present compound and an inert carrier. The pest control agent of the present invention is obtained by mixing the present compound with inert carriers such as solid carriers, liquid carriers, and gaseous carriers, and optionally adding auxiliary agents for formulation, such as surfactants to thereby formulate into emulsifiable concentrates, oil solutions, dusts, granules, wettable powders, flowables, microcapsules, and the like. The present compound is usually contained within a range of 0.01 to 95% by weight.

Examples of the solid carriers used in the formulation include clays (kaolin clay, diatomaceous earth, bentonite, Fubasami clay, and acid clay), synthetic hydrated silicon dioxide, talc, ceramic, other inorganic minerals (sericite, quartz powder, sulfur powder, activated charcoal, calcium carbonate, and hydrated silica), chemical fertilizers (ammonium sulfate, ammonium phosphate, ammonium nitrate, urea, and ammonium chloride) in the form of fine powders or particulates, and synthetic resins (polyester resins such as polypropylene, polyacrylonitrile, methyl polymethacrylate, and polyethylene terephthalate, nylon resins such as nylon-6, nylon-11, and nylon-66, polyamide resin, polyvinyl chloride, polyvinylidene chloride, vinyl chloride-propylene copolymer).

Examples of the liquid carriers include water, alcohols (methanol, ethanol, isopropyl alcohol, butanol, hexanol, benzyl alcohol, ethylene glycol, propylene glycol, and phenoxyethanol), ketones (acetone, methyl ethyl ketone, and cyclohexanone), aromatic hydrocarbons (toluene, xylene, ethylbenzene, dodecylbenzene, phenylxylylethane, methylnaphthalene), aliphatic hydrocarbons (hexane, cyclohexane, kerosene, and light oil), esters (ethyl acetate, butyl acetate, isopropyl myristate, ethyl oleate, diisopropyl adipate, diisobutyl adipate, and propylene glycol monomethyl ether acetate), nitriles (acetonitrile and isobutyronitrile), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, and 3-methoxy-3-methyl-1-butanol), acid amides (N,N-dimethylformamide and N,N-dimethylacetamide), halogenated hydrocarbons (dichloromethane, trichloroethane, and carbon tetrachloride), sulfoxides (dimethyl sulfoxide), propylene carbonate, and vegetable oil (soybean oil and cottonseed oil).

Examples of the gaseous carriers include fluorocarbon, butane gas, liquefied petroleum gas (LPG), dimethyl ether, and carbonic acid gas.

Examples of the surfactants include nonionic surfactants such as polyoxyethylene alkyl ether, polyoxyethylene alkyl aryl ether, and polyethylene glycol fatty acid ester; and anionic surfactants such as alkyl sulfonate, alkylbenzene sulfonate, and alkyl sulfate.

Examples of other auxiliary agents for formulation include stickers, dispersers, colorants and stabilizers, specifically casein, gelatin, saccharides (starch, gum arabic, cellulose derivatives, and alginic acid), lignin derivatives, bentonite, water-soluble synthetic polymers (polyvinyl alcohol, polyvinylpyrrolidone, and polyacrylic acids), PAP (acidic isopropyl phosphate), BHT (2,6-di-tert-butyl-4-methylphenol), and BHA (a mixture of 2-tert-butyl-4-methoxyphenol and 3-tert-butyl-4-methoxyphenol).

The present compound may be used as a mixture with various oils or surfactants such as mineral oils or vegetable oils. Specific examples of oils or surfactants, which can be used as a mixture with various oils or surfactants, include Nimbus (registered trademark), Assist (registered trademark), Aureo (registered trademark), Iharol (registered trademark), Silwet L-77 (registered trademark), BreakThru (registered trademark), SundanceII (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITONX 45 (registered trademark), AGRAL 90 (registered trademark), AGROTIN (registered trademark), ARPON (registered trademark), EnSpray N (registered trademark), BANOLE (registered trademark), and the like.

Examples of plants, for which the present compound can be used, include the followings.

Crops: corn, rice, wheat, barley, rye, triticale, oat, sorghum, cotton, soybean, peanut, kidney bean, lime bean, adzuki bean, cowpea, mung bean, urd bean, scarlet runner bean, ricebean, moth bean, teparybean, broad bean, garden pea, chickpea, lentil, lupine, pigeon pea, alfalfa, buckwheat, sugar beet, rapeseed, sunflower, sugar cane, tobacco, and the like;

Vegetables: solanaceous vegetables (for example, eggplant, tomato, pimento, pepper, bell pepper, and potato), cucurbitaceous vegetables (for example, cucumber, pumpkin, zucchini, watermelon, melon, and squash), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), umbelliferous vegetables (for example, carrot, parsley, celery, and parsnip), chenopodiaceous vegetables (for example, spinach and Swiss chard), lamiaceous vegetables (for example, *Perilla frutescens*, mint, basil, and lavender), strawberry, sweet potato, *Dioscorea japonica, colocasia*, and the like;

Fruits: pomaceous fruits (for example, apple, pear, Japanese pear, Chinese quince, and quince), stone fruits (for example, peach, plum, nectarine, *Prunus mume*, cherry fruit, apricot, and prune), citrus fruits (for example, *Citrus unshiu*, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, persimmon, olive, loquat, banana, coffee, date palm, coconuts, and the like;

tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus*, spruce, and yew); flowering plants, foliage plants, *zoysia*, grasses, and the like.

The above-mentioned plants are not limited as long as cultivars thereof are generally cultivated.

The above-mentioned plants may also be plants bled by hybrid technology.

Namely, plants bled by hybrid technology mean an F1 hybrid obtained by crossbleeding of cultivars of two different lines, and are generally plants having properties of a hybrid vigor (which generally brings an increase in yield potential, improvement in resistance to biotic and abiotic stress factors, and the like) with nature better than those of parents.

Examples of pests, which can be controlled by the present compound, include plant pathogenic bacteria such as filamentous fungi and bacteria, and specific examples include, but are not limited, to the followings.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), pink snow mould (*Micronectriella nivale, M. majus*), typhula snow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), damping-off by Rhizoctonia (*Rhizoctonia solani*), and take-all disease (*Gaeumannomyces graminis*); Barley diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia leaf spot (*Ramularia collo-cygni*), and damping-off by Rhizoctonia (*Rhizoctonia solani*); Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-maydis*), eyespot (*Kabatiella zeae*), and phaeosphaeria leaf spot (*Phaeosphaeria maydis*); Cotton diseases: anthracnose (*Colletotrichum gossypii*), grey mildew (*Ramularia areola*), and alternaria leaf spot (*Alternaria macrospora, A. gossypii*); Coffee diseases: rust (*Hemileia vastatrix*); Rapeseed diseases: sclerotinia rot (*Sclerotinia sclerotiorum*), black spot (*Alternaria brassicae*), and black leg (*Phoma lingam*); Citrus diseases: melanose (*Diaporthe citri*), scab (*Elsinoe fawcetti*), and fruit rot (*Penicillium digitatum, P. italicum*); Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), bitter rot (*Glomerella cingulata*), brown spot (*Diplocarpon mali*), and ring spot (*Botryosphaeria berengeriana*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and Phomopsis rot (*Phomopsis* sp.); Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), fusarium wilt (*Fusarium oxysporum*), downy mildew (*Pseudoperonospora cubensis*), phytophthora rot (*Phytophthora* sp.), and damping-off (*Pythium* sp.); Tomato diseases: early blight (*Alternaria solani*), leaf mold (*Cladosporium fulvum*), leaf mold (*Pseudocercospora fuligena*), and late blight (*Phytophthora infestans*), powdery mildew (*Leveillula taurica*); Eggplant diseases: brown spot (*Phomopsis vexans*) and powdery mildew (*Erysiphe cichoracearum*); Cruciferous vegetables diseases: alternaria leaf spot (*Alternaria japonica*), white spot (*Cercosporella brassicae*), clubroot (*Plasmodiophora brassicae*), and downy mildew (*Peronospora parasitica*); Welsh onion diseases: rust (*Puccinia allii*); Soybean diseases: purple stain (*Cercospora kikuchii*), sphaceloma scad (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum glycines, C. truncatum*), Rhizoctonia aerial blight (*Rhizoctonia solani*), septoria brown spot (*Septoria glycines*), and frog eye leaf spot (*Cercospora sojina*); Kidney bean diseases: anthracnose (*Colletotrichum lindemuthianum*); Peanut diseases: early leaf spot (*Cercospora personata*), late leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), and verticillium wilt (*Verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tobacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*); Sugar beet diseases: cercospora leaf spot (*Cercospora beticola*), leaf blight (*Thanatephorus cucumeris*), root rot (*Thanatephorus cucumeris*), and aphanomyces root rot (*Aphanomyces cochlioides*); Rose diseases: black spot (*Diplocarpon rosae*) and powdery mildew (*Sphaerotheca pannosa*); Chrysanthemum diseases: leaf blight (*Septoria chrysanthemi-indici*) and white rust (*Puccinia horiana*); Onion diseases: botrytis leaf blight (*Botrytis cinerea, B. byssoidea, B. squamosa*), gray-mold neck rot (*Botrytis alli*), and small sclerotial rot (*Botrytis squamosa*); various crops diseases: gray mold (*Botrytis cinerea*) and sclerotinia rot (*Sclerotinia sclerotiorum*); Japanese radish diseases: alternaria leaf spot (*Alternaria brassicicola*); Turfgrass diseases: dollar spot (*Sclerotinia homoeocarpa*) and brown patch and large patch (*Rhizoctonia solani*); and Banana diseases: Sigatoka disease (*Mycosphaerella fijiensis, Mycosphaerella musicola*).

Seed diseases or diseases in the early growth phase in various crops caused by bacteria from genera of *Aspergillus, Penicillium, Fusarium, Gibberella, Tricoderma, Thielaviopsis, Rhizopus, Mucor, Corticium, Phoma, Rhizoctonia, Diplodia*, and the like. Viral diseases intermediated by genera of *Polymyxa, Olpidium*, or the like in various crops.

Rice damping-off (*Burkholderia plantarii*); cucumber bacterial blight (*Pseudomonas syringae* pv. *Lachrymans*); eggplant bacterial wilt disease (*Ralstonia solanacearum*), citrus canker (*Xanthomonas citri*); Chinese cabbage soft rod (*Erwinia carotovora*) and the like.

Examples of pests, against which the present compound has control activity, include pests such as pest insects and pest mites. Specific examples of these pests include, but are not limited, to the followings.

Hemiptera: planthoppers such as small brown planthopper (*Laodelphax striatellus*), brown rice planthopper (*Nilaparvata lugens*), white-backed rice planthopper (*Sogatella furcifera*), and corn planthopper (*Peregrinus maidis*); leafhoppers such as green rice leafhopper (*Nephotettix cincticeps*), Taiwan green rice leafhopper (*Nephotettix virescens*), rice green leafhopper (*Nephotettix nigropictus*), zigzag rice leafhopper (*Recilia dorsalis*), tea green leafhopper (*Empoasca onukii*), potato leafhopper (*Empoasca fabae*), corn leafhopper (*Dalbulus maidis*), Sugarcane froghopper (*Mahanarva posticata*), Sugarcane root spittlebug (*Mahanarva fimbriolata*), white giant leafhopper (*Cofana spec-

*tra*), cross-di-green rice leafhopper (*Nephotettix nigropictus*), and zig-zag rice leafhopper (*Recilia dorsalis*); aphids such as cotton aphid (*Aphis gossypii*), green peach aphid (*Myzus persicae*), cabbage aphid (*Brevicoryne brassicae*), spiraea aphid (*Aphis spiraecola*), tulip aphid (*Macrosiphum euphorbiae*), potato aphid (*Aulacorthum solani*), oat bird-cherry aphid (*Rhopalosiphum padi*), tropical citrus aphid (*Toxoptera citricidus*), mealy plum aphid (*Hyalopterus pruni*), soybean aphid (*Aphis glycines* Matsumura), corn aphid (*Rhopalosiphum maidis*), rice root aphid (*Tetraneura nigriabdominalis*), grape root aphid (*Viteus vitifoliae*), grape *phylloxera* (*Daktulosphaira vitifoliae*), pecan *phylloxera* (*Phylloxera devastatrix* Pergande), pecan leaf *phylloxera* (*Phylloxera notabilis* pergande), and southern pecan leaf *phylloxera* (*Phylloxera russellae* Stoetzel); stink bugs such as Japanese black rice bug (*Scotinophara lurida*), Malayan rice black bug (*Scotinophara coarctata*), green stink bug (*Nezara antennata*), white spotted spined bug (*Eysarcoris parvus*), stink bug (*Halyomorpha mista*), southern green stink bug (*Nezara viridula*), Brown stink bug (*Euschistus heros*), Southern green stink bug (*Nezara viridula*), Red banded stink bug (*Piezodorus guildinii*), Burrower brown bug (*Scaptocoris castanea*), *Oebalus pugnax*, and *Dichelops melacanthus*; broad-headed bugs such as bean bug (*Riptortus clavetus*), rice bug (*Leptocorisa chinensis*), rice seed bug (*Leptocorisa acuta*), and *Leptocorisa* genus; plant bugs such as rice leaf bug (*Trigonotylus caelestialium*), sorghum plant bug (*Stenotus rubrovittatus*), tarnished plant bug (*Lygus lineolaris*), and chinchi bug (*Blissus leucopterus leucopterus*); whiteflies such as greenhouse whitefly (*Trialeurodes vaporariorum*), tobacco whitefly (*Bemisia tabaci*), citrus whitefly (*Dialeurodes citri*), and orange spiny whitefly (*Aleurocanthus spiniferus*); scales such as California red scale (*Aonidiella aurantii*), san jose scale (*Comstockaspis perniciosa*), citrus north scale (*Unaspis citri*), red wax scale (*Ceroplastes rubens*), cottony cushion scale (*Icerya purchasi*), Japanese mealybug (*Planococcus kraunhiae*), comstock mealybug (*Pseudococcus longispinus*), white peach scale (*Pseudaulacaspis pentagona*), and tuttle mealybug (*Brevennia rehi*); psylla such as Asian citrus psyllid (*Diaphorina citri*), pear sucker (*Psylla* pyrisuga), and potato psyllid (*Bactericerca cockerelli*); lace bugs such as pear lace bug (*Stephanitis nashi*); bed bugs such as bed bug (*Cimex lectularius*); and Giant Cicada (*Quesada gigas*).

Lepidoptera: pyralid moths such as rice stem borer (*Chilo suppressalis*), Darkheaded stm borer (*Chilo polychrysus*), yellow rice borer (*Tryporyza incertulas*), tropical borer (*Chilo suppressalis*), white rice borer (*Scirpophaga innotata*), Yellow stem borer (*Scirpophaga incertulas*), Pink borer (*Sesamia inferens*), *Rupela albinellam*, rice leafroller (*Cnaphalocrocis medinalis*), *Marasmia patnalis, Marasmia exigna*, cotton leafroller (*Notarcha derogata*), Indian meal moth (*Plodia interpunctella*), oriental corn borer (*Ostrinia furnacalis*), cabbage webworm (*Hellula undalis*), bluegrass webworm (*Pediasia teterrellus*), Rice Caseworm (*Nymphula depunctalis*), *Marasmia* genus, Hop vine borer (*Hydraecia immanis*), European corn borer (*Ostrinia nubilalis*), Lesser cornstalk borer (*Elasmopalpus lignosellus*), Bean Shoot Borer (*Epinotia aporema*), Sugarcane borer (*Diatraea saccharalis*), and Giant Sugarcane borer (*Telchin licus*); owlet moths such as common cutworm (*Spodoptera litura*), beet armyworm (*Spodoptera exigua*), armyworm (*Pseudaletia separata*), cabbage armyworm (*Mamestra brassicae*), pink borer (*Sesamia inferens*), lawn armyworm (*Spodoptera mauritia*), fall armyworm (*Spodoptera frugiperda*), *Spodoptera exempta*, black cutworm (*Agrotis ipsilon*), beet semilooper (*Plusia nigrisigna*), Soybean looper (*Pseudoplusia includens*), *Thoricoplusia* genus, *Heliothis* genus such as oriental tobacco budworm (*Heliothis virescens*), *Helicoverpa* genus such as corn earworm (*Helicoverpa armigera*), velvetbean caterpillar (*Anticarsia gemmatalis*), and Cotton leafworm (*Alabama argillacea*); white butterflies such as common white (*Pieris rapae*); tortricid moths such as *Adoxophyes* genus, oriental fruit moth (*Grapholita molesta*), soybean pod borer (*Leguminivora glycinivorella*), azuki bean podworm (*Matsumuraeses azukivora*), summer fruit *tortrix* (*Adoxophyes orana fasciata*), smaller tea *tortrix* (*Adoxophyes honmai.*), oriental tea *tortrix* (*Homona magnanima*), apple *tortrix* (*Archips fuscocupreanus*), and codling moth (*Cydia pomonella*); leafblotch miners such as tea leafroller (*Caloptilia theivora*) and apple leaf miner (*Phyllonorycter ringoneella*); fruitwormmoths such as peach fruit moth (*Carposina niponensis*) and Citrus fruit borer (*Ecdytolopha aurantiana*); lyonetiid moths such as coffee Leaf miner (*Leucoptera coffeela*) and *Lyonetia* genus; tussock moths such as *Lymantria* genus and *Euproctis* genus; yponomeutid moths such as diamondback (*Plutella xylostella*); gelechiid moths such as pink bollworm (*Pectinophora gossypiella*) and potato tubeworm (*Phthorimaea operculella*); tiger moths such as fall webworm (*Hyphantria cunea*).

Thysanoptera: *thrips* such as yellow citrus *thrips* (*Frankliniella occidentalis*), melon *thrips* (*Thrips palmi*), yellow tea *thrips* (*Scirtothrips dorsalis*), onion *thrips* (*Thrips tabaci*), flower *thrips* (*Frankliniella intonsa*), western flower *thrips* (*Frankliniella occidentalis*), rice aculeated *thrips* (*Haplothrips aculeatus*), and rice *thrips* (*Stenchaetothrips biformis*).

Diptera: anthomyiid flies such as seedcorn maggot (*Delia platura*), onion maggot (*Delia antiqua*), and sugar beet root maggot (*Tetanops myopaeformis*); leafminers such as rice leafminer (*Agromyza oryzae*), rice leafminer (*Hydrellia griseola*), tomato leafminer (*Liriomyza sativae*), bean leafminer (*Liriomyza trifolii*), and garden pea leafminer (*Chromatomyia horticola*); grass flies such as rice stem maggot (*Chlorops oryzae*); fruit flies such as melon fly (*Dacus cucurbitae*) and Mediterranean fruit fly (*Ceratitis capitata*); shore flies such as oriental rice whorl maggot (*Hydrellia philippina*), and rice whorl maggot (*Hydrellia sasakii*); *drosophila*; phorid flies such as humpbacked fly (*Megaselia spiracularis*); moth flies such as bath room fly (*Clogmia albipunctata*); Sciarid flies. Gall midges such as Hessian fly (*Mayetiola destructor*) and rice gall midge (*Orseolia oryzae*); Stalk-eyed flies such as Diopsis macrophthalma; craneflies such as Common cranefly (*Tipula oleracea*) and European cranefly (*Tipula paludosa*).

Coleoptera: leaf beetles such as western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata* LeConte), San Antonio beetle (*Diabrotica speciosa*), Cucurbit Beetle (*Diabrotica speciosa*), bean leaf beetle (*Cerotoma trifurcata*), cereal leaf beetle (*Oulema melanopus*), cucurbit leaf beetle (*Aulacophora femoralis*), yellow striped flea beetle (*Phyllotreta striolata*), colorado potato beetle (*Leptinotarsa decemlineata*), rice leaf beetle (*Oulema oryzae*), grape *colaspis* (*Colaspis brunnea*), corn flea beetle (*Chaetocnema pulicaria*), potato flea beetle (*Epitrix cucumeris*), rice hispa (*Dicladispa armigera*), Seedcorn beetle (*Stenolophus lecontei*), and Slender seedcorn beetle (*Clivinia impressifrons*); chafers such as cupreous chafer (*Anomala cuprea*), soybean beetle (*Anomala* rufocuprea), Japanese beetle (*Popillia japonica*), European chafer (*Rhizotrogus majalis*), carrot beetle (*Bothynus gibbosus*), Grape *Colaspis* (*Colaspis brunnea*), southern corn leaf beetle (*Myochrous denticollis*), *Holotrichia* genus, *Phyllophaga* genus, for example June beetle (*Phyllophaga crinita*); rice plant weevils such as maize weevil (*Sitophilus zeamais*), rice plant weevil (*Echinocnemus squameus*), rice water weevil (*Lissorhoptrus oryzophilus*), and hunting billbug (*Sphenophorus venatus*); weevils such as boll weevil (*Anthonomus grandis*), southern corn billbug (*Sphenophorus callosus*), Soybean stalk weevil (*Sternechus subsignatus*) and *Sphenophorus* genus, for example *Sphenophorus levis; Epilachna* such as twenty-eight-spotted ladybirds (*Epilachna vigintioctopunctata*); bark beetles such as powder post beetle (*Lyctus brunneus*) and pine shoot beetle (*Tomicus piniperda*); larger grain borers; museum beetles; longicorn beetles such as white-spotted longicorn beetle (*Anoplophora malasiaca*) and *Migdolus fryanus*; click beetles (*Agriotes* sp., *Aelous* sp., *Anchastus* sp., *Melanotus* sp., *Limonius* sp., *Conoderus* sp., *Ctenicera* sp.) such as sugarcane wireworm (*Melanotus okinawensis*), barley wireworm (*Agriotes ogurae fuscicollis*), and click beetle (*Melanotus legatus*); staphylinids such as rove beetles (*Paederus fuscipes*); and Coffee Barry Borer (*Hypothenemus hampei*).

Orthoptera: crickets such as asiatic locusts (*Locusta migratoria*), African mole cricket (*Gryllotalpa africana*), Moroccan locust (*Dociostaurus maroccanus*), Australian plague locust (*Chortoicetes terminifera*), red locust (*Nomadacris septemfasciata*), brown locust (*Locustana pardalina*), tree locust (*Anacridium melanorhodon*), Italian locust (*Calliptamus italicus*), differential grasshopper (*Melanoplus differentialis*), twostriped grasshopper (*Melanoplus bivittatus*), migratory grasshopper (*Melanoplus sanguinipes*), redlegged grasshopper (*Melanoplus femurrubrum*), clear-winged grasshopper (*Camnula pellucida*), desert locust (*Schistocerca gregaria*), yellow-winged locust (*Gastrimargus musicus*), spur-throated locust (*Austracris Guttulosa*), rice grasshopper (*Oxya yezoensis*), Japanese grasshopper (*Oxya japonica*), Bombay locust (*Patanga succincta*), house cricket (*Acheta domesticus*), emma field cricket (*Teleogryllus emma*), and Mormon cricket (*Anabrus simplex*).

Hymenoptera: sawflies such as cabbage sawflies (*Athalia rosae*) and Japanese cabbage sawfly (*Athalia japonica*). Fire ants. Leaf cutting ants such as Brown leaf-cutting ant (*Atta capiguara*).

Nematodes: white-tip nematode (*Aphelenchoides besseyi*), strawberry bud nematode (*Nothotylenchus acris*), southern root-knot nematode (*Meloidogyne incognita*), northern root-knot nematode (*Meloidogyne hapla*), javanese root-knot nematode (*Meloidogyne javanica*), soybean cyst nematode (*Heterodera glycines*), golden nematode (*Globodera rostochiensis*), coffee root-lesion nematode (*Pratylenchus coffeae*), california root-lesion nematode (*Pratylenchus neglectus*), *Meloidogyne javanica*, *Meloidogyne incognita*, *Rotylenchulus reniformis*, and *Pratylenchus brachyurus*.

Blattariae: German cockroach (*Blattella germanica*), smoky-brown cockroach (*Periplaneta fuliginosa*), American cockroach (*Periplaneta americana*), brown cockroach (*Periplaneta brunnea*), and oriental cockroach (*Blatta orientalis*).

Isoptera: Japanese subterranean termite (*Reticulitermes speratus*), formosan subterranean termite (*Coptotermes formosanus*), western drywood termite (*Incisitermes minor*), drywood termite (*Cryptotermes domesticus*), Taiwan termite (*Odontotermes formosanus*), Kosyun termite (*Neotermes koshunensis*), Satsuma termite (*Glyptotermes satsumensis*), Nakajima termite (*Glyptotermes nakajimai*), Katan termite (*Glyptotermes fuscus*), Kodama termite (*Glyptotermes kodamai*), Kushimoto termite (*Glyptotermes kushimensis*), Japanese damp-wood termite (*Hodotermopsis japonica*), Koshu formosan termite (*Coptotermes guangzhoensis*), Amami termite (*Reticulitermes miyatakei*), Kiashi termite (*Reticulitermes flaviceps amamianus*), Kanmon termite (*Reticulitermes* sp.), Takasago termite (*Nasutitermes takasagoensis*), Nitobe termite (*Pericapritermes nitobei*), Musya termite (*Sinocapritermes mushae*), Cornitermes cumulans, and the like.

Acarina: Tetranychidae such as two-spotted spider mite (*Tetranychus urticae*), kanzawa spider mite (*Tetranychus kanzawai*), citrus red mite (*Panonychus citri*), European red mite (*Panonychus ulmi*), *Oligonychus* genus and southern turkey spider mites (*Brevipalpus phoenicis*); Eriophyidae such as pink citrus rust mite (*Aculops pelekassi*), Ryukyu tangerine rust mite (*Phyllocoptruta citri*), tomato russet mite (*Aculops lycopersici*), tea rust mite (*Calacarus carinatus*), tea Roh Naga rust mite (*Acaphylla theavagrans*), fake pear rust mite (*Eriophyes chibaensis*), and apple rust mite (*Aculus schlechtendali*); Tarsonemidae such as tea dust mite (*Polyphagotarsonemus latus*); Tenuipalpidae such as Southern Hime spider mite (*Brevipalpus phoenicis*); Tuckerellidae; Ixodidae such as cattle tick (*Haemaphysalis longicornis*), Yamatochi tick (*Haemaphysalis flava*), Taiwan Kaku tick (*Dermacentor taiwanicus*), American dog Kaku tick (*Dermacentor variabilis*), tick (*Ixodes ovatus*), Schultz tick (*Ixodes persulcatus*), black-legged tick (*Ixodes scapularis*), lone star tick (*Amblyomma americanum*), Oshima tick (*Boophilus microplus*), and brown dog tick (*Rhipicephalus sanguineus*); Acaridae such as common grain mite (*Tyrophagus putrescentiae*) and spinach common grain mite (*Tyrophagus similis*); Pyroglyphidae such as American house dust mite (*Dermatophagoides farinae*) and house dust mite (*Dermatophagoides pteronyssinus*).

Cheyletidae such as cheyletid mite (*Cheyletus eruditus*), Stag Tsumedani (*Cheyletus malaccensis*), Minami Tsumedani (*Cheyletus moorei*), and Inutsumedani (*Cheyletiella yasguri*); Cheyletidae such as ear mite (*Otodectes cynotis*) and itch mite (*Sarcoptes scabiei*); Demodicidae such as dog follicle mite (*Demodex canis*); Listrophoridae; Oribatulidae; Dermanyssidae such as tropical rat mite (*Ornithonyssus bacoti*), northern fowl mite (*Ornithonyssus sylvairum*), and red mite (*Dermanyssus gallinae*); Trombiculidae such as blue chigger (*Leptotrombidium akamushi*); and Araneida such as Japanese foliage spider (*Chiracanthium japonicum*) and red back spider (*Latrodectus hasseltii*).

Chilopoda: house centipede (*Thereuonema hilgendorfi*), Chinese red headed centipede (*Scolopendra subspinipes*) and the like.

Diplopoda: garden millipede (*Oxidus gracilis*), garden millipede (*Nedyopus tambanus*) and the like.

Isopoda: pill bug (*Armadillidium vulgare*) and the like.

Gastropoda: tree slug (*Limax marginatus*), yellow slug (*Limax flavus*) and the like.

Target pest insects and pest mites may also be insects and mites each having reduced chemical sensitivity or enhanced chemical resistance to insecticides and acaricides. When chemical sensitivity is significantly reduced or chemical resistance is significantly enhanced, use of the present composition containing insecticides and acaricides other than target insecticides and acaricides is desirable.

The present compound can also be used to protect plants from plant diseases due to insect-borne virus.

Examples of plant diseases caused by insect-borne viruses, against which the present compound has control activity, include the followings.

Rice waika (Rice waika virus), rice tungro (Rice tungro spherical virus, Rice tungro bacilliform virus), rice grassy stunt (Rice grassy stunt virus), rice ragged stunt (Rice ragged stunt virus), rice stripe (Rice stripe virus), rice black streaked dwarf (Rice black streaked dwarf virus), southern rice black-streaked dwarf (Southern rice black-streaked dwarf virus), rice gall dwarf (Rice gall dwarf virus), rice hoja blanca (Rice hoja blanca virus), rice white leaf (White leaf disease of rice), yellow dwarf (Yellow dwarf virus), red disease (Rice penyakit merah virus), rice yellow stunt (Rice yellow stunt virus), rice transitory yellowing (Rice transitory yellowing virus), rice yellow mottle (Rice Yellow Mottle Virus), rice necrosis mosaic (Rice necrosis mosaic virus), rice dwarf stunt (Rice dwarf stunt virus), northern cereal mosaic (Northern Cereal Mosaic Virus), barley yellow dwarf (Barley Yellow Dwarf Virus), wheat yellow dwarf (Wheat yellow dwarf virus), Oat sterile dwarf (Oat sterile dwarf virus), wheat streak mosaic (Wheat streak mosaic virus), maize dwarf mosaic (Maize dwarf mosaic virus), maize stripe disease (maize stripe tenuivirus), maize chlorotic dwarf (Maize chlorotic dwarf virus), maize chlorotic mottle (maize chlorotic mottle virus), maize rayado fino (maize rayado finomarafivirus), corn stunt (Corn stunt spiroplasma), maize bushy stunt (Maize bushy stunt phytoplasma), sugarcane mosaic (Sugarcane mosaic virus), soybean mild mosaic (Soybean mild mosaic virus), alfalfa mosaic (Alfalfa Mosaic Virus, Bean yellow-spot mosaic virus, Soybean mosaic virus, Bean yellow mosaic virus, Cowpea severe mosaic virus), broad bean wilt (Broad bean wilt virus, Bean common mosaic virus, Peanut stunt virus, Southern bean mosaic virus), soybean dwarf (Soybean dwarf luteovirus, Milk-vetch dwarf luteovirus), bean-pod mottle (Bean-pod mottle virus), brazilian bud blight (Tobacco streak virus), cowpea chlorotic mottle (Cowpea chlorotic mottle), mung bean yellow mosaic (Mung bean yellow mosaic virus), peanut stripe (Peanut stripe mottle), soybean crinkle leaf (Soybean crinkle leaf virus), soybean severe stunt (Soybean severe stunt virus), tomato chlorosis (Tomato chlorosis virus), tomato spotted wilt (Tomato spotted wilt virus), tomato yellow leaf curl (Tomato yellow leaf curl virus), melon yellow spot (Melon yellow spot virus), watermelon mosaic (Watermelon mosaic virus), cucumber mosaic (Cucumber mosaic virus), zucchini yellow mosaic (Zucchini yellow mosaic virus), turnip mosaic (Turnip mosaic virus), cucurbit chlorotic yellows (Cucurbit chlorotic yellows virus), *capsicum* chlorosis (*Capsicum* chlorosis virus), beet pseudo yellows (Beet pseudo yellows virus), *chrysanthemum* stem necrosis (*chrysanthemum* stem necrosis virus), *impatiens* necrotic spot (*Impatiens* necrotic spot virus), *iris* yellow spot (*Iris* yellow spot virus), sweet potato internal cork (Sweet potato internal cork virus), sweet potato shukuyo mosaic (Sweet potato shukuyo mosaic virus), and mosaic virus diseases of various plants transmitted by the genus *Polymyxa* or *Olpidium*.

The formulation comprising the present compound or salts thereof can be used in the field relating to a treatment of livestock diseases or livestock industry, and can exterminate the living things or parasites which are parasitic on the inside and/or the outside of vertebrates such as human being, cow, sheep, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *Dermacentor* spp., *Ornithodoros* spp. (for example, *Ornithodoros moubata*), red mite (*Dermanyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Aedes* spp. (for example, Asian tiger mosquito (*Aedes albopictus*)), *Anopheles* spp., *Culex* spp., *Culicoides* spp., *Musca* spp., *Hypoderma* spp., *Gasterophilus* spp., *Haematobia* spp., *Tabanus* spp., *Simulium* spp., *Triatoma* spp., lice (*Phthiraptera*) (for example, *Damalinia* spp., *Linognathus* spp., *Haematopinus* spp.), *Ctenocephalides* spp. (for example, cat flea (*Ctenocephalides felis*)) *Xenopsylla* spp., Pharaoh's ant (*Monomorium pharaonis*) and nematodes [for example, hairworm (for example, *Nippostrongylus brasiliensis, Trichostrongylus axei, Trichostrongylus colubriformis*), *Trichinella* spp. (for example, *Trichinella spiralis*), barber pole worm (*Haemonchus contortus*), *Nematodirus* spp. (for example, *Nematodirus battus*), *Ostertagia circumcincta, Cooperia* spp., *Hymenolepis nana*, and the like.

EXAMPLES

The present invention will be described in more detail below by way of Production Examples, Formulation Examples, and Test Examples, but the present invention is not limited to these Examples.

First, Production Examples will be described.

Production Example 1

A mixture of 0.23 g of 2-(bromomethyl)phenyl=acetate, 0.24 g of 4A mentioned in Reference Production Example 4, 0.28 g of potassium carbonate, and 4 mL of acetonitrile was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.15 g of the present compound 1.

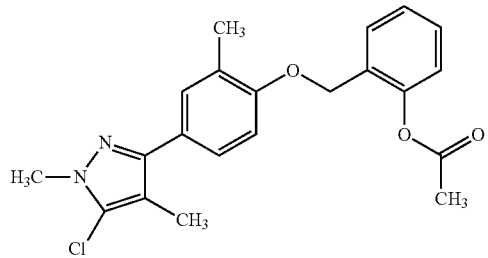 [SMILES: CC(=O)Oc1ccccc1COc1ccc(-c2nn(C)c(Cl)c2C)cc1C]

$^1$H-NMR (CDCl$_3$) δ: 7.57-7.53 (1H, m), 7.47-7.45 (1H, m), 7.40-7.35 (2H, m), 7.30-7.27 (1H, m), 7.15-7.11 (1H, m), 6.90 (1H, d, J=8.5 Hz), 5.06 (2H, s), 3.86 (3H, s), 2.34 (3H, s), 2.28 (3H, s), 2.15 (3H, s).

In accordance with the method mentioned in Production Example 1, the present compound 2 was synthesized.

The structural formulas and $^1$H-NMR data thereof are shown below.

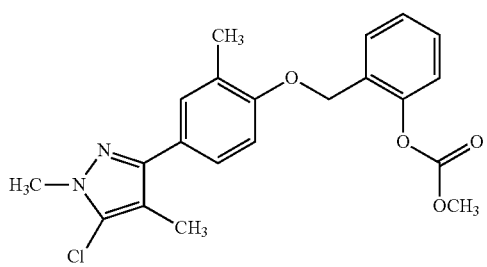 [SMILES: COC(=O)Oc1ccccc1COc1ccc(-c2nn(C)c(Cl)c2C)cc1C]

¹H-NMR (CDCl₃) δ: 7.61-7.56 (1H, m), 7.41-7.34 (2H, m), 7.32-7.27 (1H, m), 7.23 (1H, d, J=8.0 Hz), 6.99-6.94 (1H, m), 6.91 (1H, d, J=8.5 Hz), 5.12 (2H, s), 3.90 (3H, s), 3.86 (3H, s), 2.31 (3H, s), 2.15 (3H, s).

Production Example 2

To a mixture of 0.36 g of 7A mentioned in Reference Production Example 7, 0.095 g of methyl chlorocarbonate and 4 mL of chloroform, 0.42 ml of triethylamine was added, followed by stirring at room temperature for 4 hours. After the reaction solution was concentrated under reduced pressure, the residue thus obtained was subjected to silica gel column chromatography to obtain 0.30 g of the present compound 3.

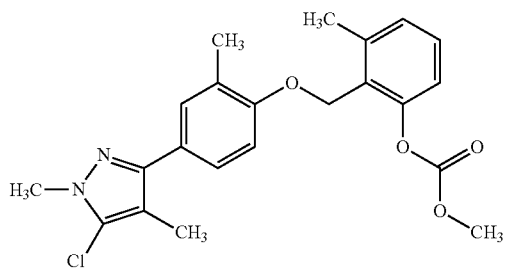

¹H-NMR (CDCl₃) δ: 7.44-7.41 (2H, m), 7.34-7.28 (1H, m), 7.16 (1H, d, J=7.6 Hz), 7.07 (1H, d, J=8.2 Hz), 7.03 (1H, d, J=8.2 Hz), 5.06 (2H, s), 3.86 (3H, s), 3.84 (3H, s), 2.46 (3H, s), 2.20 (3H, s), 2.17 (3H, s).

In accordance with the method mentioned in Production Example 2, the present compounds 4 to 5 and 8 to 10 were synthesized.

The structural formulas and ¹H-NMR data thereof are shown below.

Present Compound 4

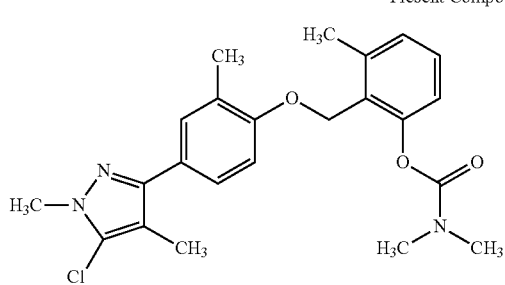

Present Compound 5

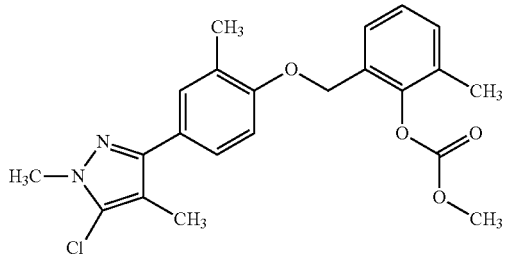

Present Compound 8

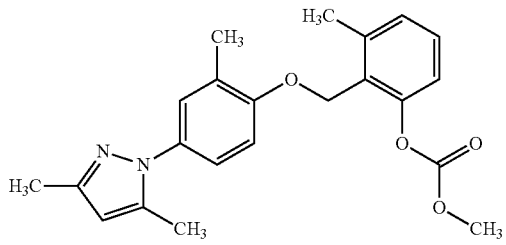

Present Compound 9

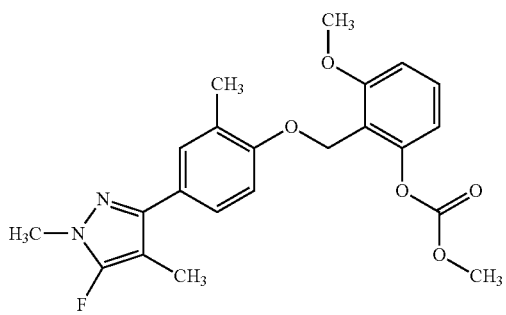

Present Compound 10

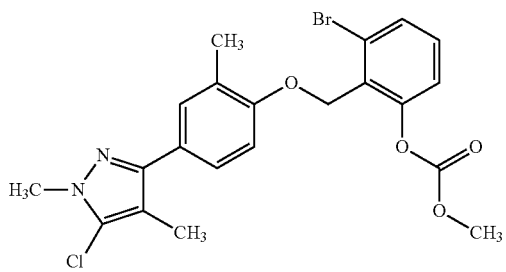

Present Compound 4

¹H-NMR (CDCl₃) δ: 7.45-7.41 (2H, m), 7.29-7.25 (1H, m), 7.11-7.09 (1H, m), 7.05-7.01 (2H, m), 5.04 (2H, s), 3.87 (3H, s), 3.15 (3H, s), 3.04 (3H, s), 2.45 (3H, s), 2.21 (3H, s), 2.17 (3H, s)

Present Compound 5

¹H-NMR (CDCl₃) δ: 7.47-7.45 (1H, m), 7.39-7.35 (2H, m), 7.23-7.19 (2H, m), 6.90 (1H, d, J=8.5 Hz), 5.08 (2H, s), 3.88 (3H, s), 3.86 (3H, s), 2.30 (3H, s), 2.26 (3H, s), 2.15 (3H, s)

Present Compound 8

$^1$H-NMR (CDCl$_3$) δ: 7.34-7.28 (1H, m), 7.22-7.14 (3H, m), 7.07 (1H, d, J=8.0 Hz), 7.01 (1H, d, J=8.5 Hz), 5.96 (1H, s), 5.06 (2H, s), 3.84 (3H, s), 2.45 (3H, s), 2.29 (3H, s), 2.26 (3H, s), 2.18 (3H, s).

Present Compound 9

$^1$H-NMR (CDCl$_3$) δ: 7.42-7.33 (3H, m), 7.04 (1H, d, J=8.5 Hz), 6.85 (2H, d, J=8.5 Hz), 5.12 (2H, s), 3.87 (3H, s), 3.80 (3H, s), 3.74 (3H, s), 2.18 (3H, s), 2.09 (3H, s)

Present Compound 10

$^1$H-NMR (CDCl$_3$) δ: 7.56 (1H, d, J=7.8 Hz), 7.43-7.40 (2H, m), 7.31-7.26 (1H, m), 7.21 (1H, d, J=8.0 Hz), 7.02 (1H, d, J=8.2 Hz), 5.19 (2H, s), 3.86 (3H, s), 3.82 (3H, s), 2.21 (3H, s), 2.16 (3H, s).

Production Example 3

To a mixture of 0.36 g of 10A mentioned in Reference Production Example 10, 0.14 ml of triethylamine, and 2 ml of tetrahydrofuran under ice cooling, 0.30 g of triphosgene was added at room temperature, followed by stirring for 2 hours. To the reaction solution, methylamine (7% tetrahydrofuran solution) was added, followed by stirring at room temperature for 2 hours. The reaction solution was concentrated under reduced pressure and the residue thus obtained was subjected to silica gel column chromatography to obtain 0.20 g of the present compound 6.

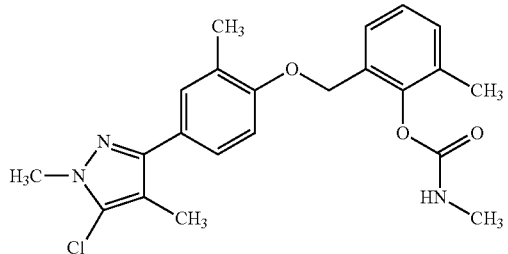

$^1$H-NMR (CDCl$_3$) δ: 7.47-7.45 (1H, m), 7.38-7.35 (2H, m), 7.22-7.13 (2H, m), 6.91 (1H, d, J=8.5 Hz), 5.07 (2H, s), 5.02-4.97 (1H, m), 3.86 (3H, s), 2.89 (3H, d, J=5.0 Hz), 2.31 (3H, s), 2.24 (3H, s), 2.15 (3H, s).

In accordance with the method mentioned in Production Example 3, the present compounds 11 to 14 were synthesized.

The structural formulas and $^1$H-NMR data thereof are shown below.

Present Compound 11

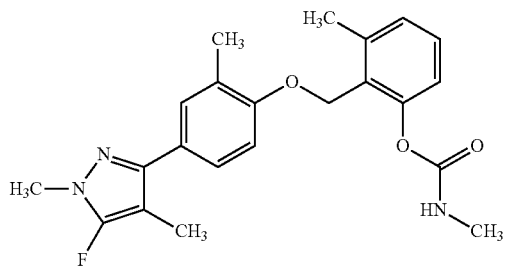

Present Compound 12

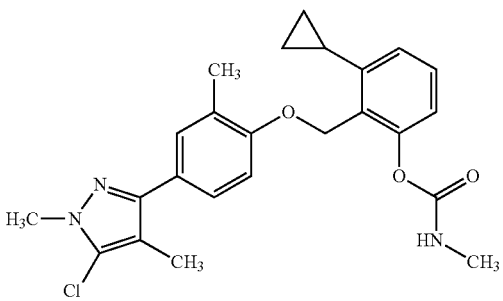

Present Compound 13

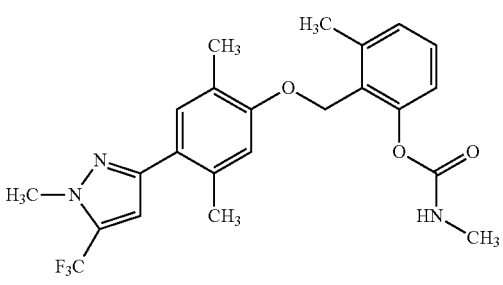

Present Compound 14

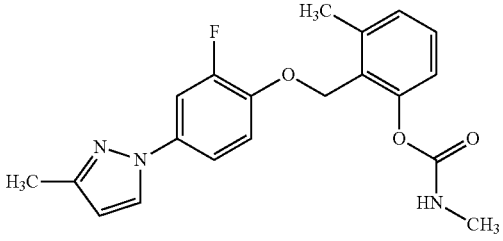

Present Compound 11

$^1$H-NMR (CDCl$_3$) δ: 7.45-7.41 (2H, m), 7.30-7.24 (1H, m), 7.10 (1H, d, J=7.6 Hz), 7.05-7.00 (2H, m), 5.03 (2H, s), 4.98-4.95 (1H, m), 3.75 (3H, s), 2.85 (3H, d, J=4.8 Hz), 2.43 (3H, s), 2.19 (3H, s), 2.10 (3H, s).

Present Compound 12

$^1$H-NMR (CDCl$_3$) δ: 7.45-7.41 (2H, m), 7.31-7.28 (1H, m), 7.08-7.01 (2H, m), 6.94 (1H, d, J=7.8 Hz), 5.21 (2H, s), 4.95-4.89 (1H, m), 3.86 (3H, s), 2.84 (3H, d, J=5.0 Hz), 2.19 (3H, s), 2.17 (3H, s), 2.13-2.06 (1H, m), 0.95-0.88 (2H, m), 0.74-0.69 (2H, m).

Present Compound 13

$^1$H-NMR (CDCl$_3$) δ: 7.31-7.26 (2H, m), 7.11 (1H, d, J=7.6 Hz), 7.03 (1H, d, J=8.2 Hz), 6.86 (1H, s), 6.69 (1H, s), 5.02 (2H, s), 5.00-4.94 (1H, m), 4.03 (3H, s), 2.85 (3H, d, J=5.0 Hz), 2.45 (3H, s), 2.42 (3H, s), 2.14 (3H, s)

Present Compound 14

$^1$H-NMR (CDCl$_3$) δ: 7.69 (1H, d, J=2.3 Hz), 7.46-7.40 (1H, m), 7.31-7.23 (2H, m), 7.13-7.05 (2H, m), 7.00 (1H, d, J=8.2 Hz), 6.22 (1H, d, J=2.3 Hz), 5.10 (2H, s), 5.08-5.02 (1H, m), 2.86 (3H, d, J=4.8 Hz), 2.44 (3H, s), 2.35 (3H, s).

In accordance with the method mentioned in Production Example 3, the present compound 7 was synthesized.

The structural formulas and ¹H-NMR data thereof are shown

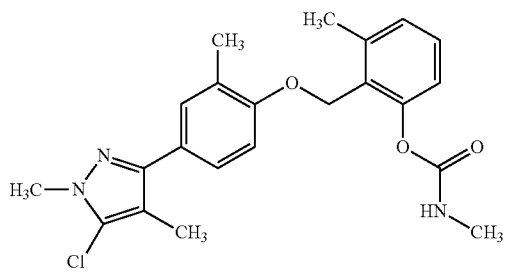

¹H-NMR (CDCl₃) δ: 7.46-7.40 (2H, m), 7.31-7.25 (1H, m), 7.11 (1H, d, J=7.6 Hz), 7.06-7.01 (2H, m), 5.03 (2H, s), 4.98-4.90 (1H, m), 3.86 (3H, s), 2.86 (3H, d, J=5.0 Hz), 2.44 (3H, s), 2.20 (3H, s), 2.17 (3H, s).

With respect to the production of intermediates for the production of the above-mentioned present compounds, Reference Production Examples are shown below.

Reference Production Example 1

A mixture of 9.24 g of 2-methylphenyl=methyl=carbonate, 5.42 g of 1,1'-azobis(cyclohexane-1-carbonitrile), 11.4 g of N-bromosuccinimide, and 170 mL of chlorobenzene was stirred with heating under reflux for 5 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 10.2 g of 1A.

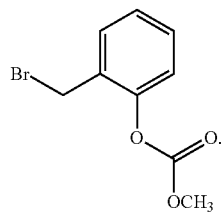

¹H-NMR (CDCl₃) δ: 7.43 (1H, dd, J=7.8, 1.6 Hz), 7.36 (1H, td, J=7.8, 1.6 Hz), 7.25-7.20 (2H, m), 4.48 (2H, s), 3.94 (3H, s).

Reference Production Example 2

A mixture of 3.5 g of ethyl 3-(4-methoxy-3-methylphenyl)-2-methyl-3-oxopropionate, 100 ml of toluene, and 7.4 g of methylhydrazine was stirred with heating under reflux for 18 hours. Toluene was distilled off and 3N hydrochloric acid was added, and then the precipitate was filtered and washed with hexane to obtain 1.4 g of 2A.

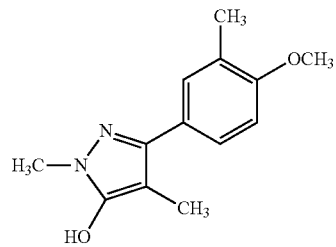 [SMILES: COc1ccc(-c2nn(C)c(O)c2C)cc1C]

¹H-NMR (DMSO-D₆) δ: 7.47-7.44 (2H, m), 7.07 (1H, d, J=8.2 Hz), 3.84 (3H, s), 3.66 (3H, s), 2.20 (3H, s), 2.05 (3H, s).

Reference Production Example 3

A mixture of 1.4 g of 2A mentioned in Reference Production Example 2 and 31.8 g of phosphorus oxychloride was stirred at 100° C. for 11 hours. After concentration under reduced pressure and extraction with ethyl acetate, the organic layer was washed with water, dried over anhydrous magnesium sulfate, and then concentrated under reduced pressure. The residue was subjected to column chromatography to obtain 0.4 g of 3A.

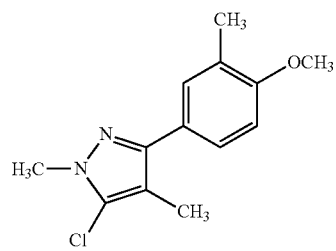 [SMILES: COc1ccc(-c2nn(C)c(Cl)c2C)cc1C]

¹H-NMR (DMSO-D₆) δ: 7.42-7.40 (2H, m), 6.98 (1H, d, J=9.2 Hz), 3.81 (3H, s), 3.80 (3H, s), 2.19 (3H, s), 2.11 (3H, s).

Reference Production Example 4

A mixture of 0.4 g of 3A mentioned in Reference Production Example 3, 3 ml of 47% hydrobromic acid, and 3 ml of acetic acid was stirred with heating under reflux for 15 hours. The solvent was distilled off and 20 ml of ethyl acetate was added to the residue, followed by stirring at room temperature for 1 hour. The precipitate was filtered, washed with hexane, and then dried under reduced pressure to obtain 0.3 g of 4A.

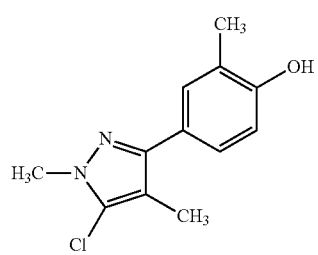 [SMILES: Cc1cc(-c2nn(C)c(Cl)c2C)ccc1O]

$^1$H-NMR (DMSO-D$_6$) δ: 7.33 (1H, s), 7.24 (1H, d, J=8.2 Hz), 6.83 (1H, d, J=8.2 Hz), 3.78 (3H, s), 2.15 (3H, s), 2.09 (3H, s).

Reference Production Example 5

Using 2-(bromomethyl)-3-methyl-nitrobenzene in place of 2-(bromomethyl)phenyl=acetate, 5A was obtained in accordance with the method mentioned in Production Example 1.

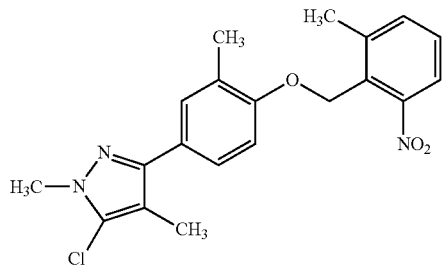 [SMILES: Cc1cc(-c2nn(C)c(Cl)c2C)ccc1OCc1c(C)cccc1[N+](=O)[O-]]

$^1$H-NMR (CDCl$_3$) δ: 7.69-7.64 (1H, m), 7.48 (1H, d, J=7.1 Hz), 7.45-7.38 (3H, m), 6.96 (1H, d, J=8.2 Hz), 5.26 (2H, s), 3.86 (3H, s), 2.53 (3H, s), 2.19 (3H, s), 2.16 (3H, s).

Reference Production Example 6

To a mixture of 41.2 g of 5A mentioned in Reference Production Example 5, 31.8 g of copper(I) chloride, and 1,100 ml of methanol, 38.7 g of potassium borohydride was added under ice cooling, followed by stirring at 0° C. for 1 hour. After stirring at room temperature for 2 hours, the reaction solution was filtered with Celite (registered trademark) and the filtrate was concentrated under reduced pressure. Water was added to the residue thus obtained and the mixture was extracted with chloroform. The organic layer was washed with water and a saturated saline solution, dried over anhydrous magnesium sulfate, and then concentrated under reduced pressure to obtain 30.8 g of 6A.

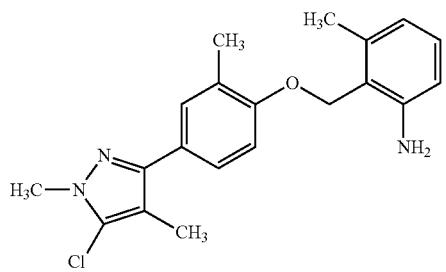 [SMILES: Cc1cc(-c2nn(C)c(Cl)c2C)ccc1OCc1c(C)cccc1N]

$^1$H-NMR (CDCl$_3$) δ: 7.47-7.42 (2H, m), 7.10-7.05 (2H, m), 6.66 (1H, d, J=7.3 Hz), 6.63 (1H, d, J=8.0 Hz), 5.10 (2H, s), 4.03 (2H, brs), 3.87 (3H, s), 2.37 (3H, s), 2.24 (3H, s), 2.17 (3H, s).

Reference Production Example 7

To a mixture of 2.85 g of 6A mentioned in Reference Production Example 6 and 8 ml of dimethyl sulfoxide, 8 ml of 35% hydrochloric acid was added under ice cooling, and then a mixture of 0.66 g of sodium nitrite and 4 ml of water was added dropwise, followed by stirring at 0° C. for 2 hours. To the reaction solution, 80 ml of water and 80 ml of methyl tert-butyl ether were added, followed by stirring at 60° C. for 2 hours. The reaction solution was extracted with chloroform. The organic layer was washed with water and a saturated saline solution, dried over anhydrous magnesium sulfate, and then concentrated under reduced pressure. The residue thus obtained was subjected to silica gel column chromatography to obtain 1.73 g of 7A.

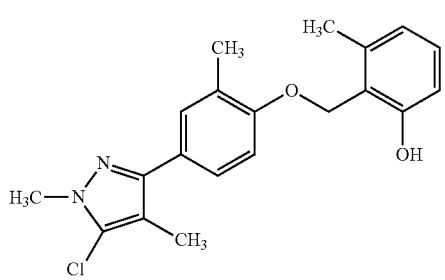 [SMILES: Cc1cc(-c2nn(C)c(Cl)c2C)ccc1OCc1c(C)cccc1O]

$^1$H-NMR (CDCl$_3$) δ: 7.49-7.47 (1H, m), 7.44 (1H, dd, J=8.4, 2.2 Hz), 7.17-7.12 (1H, m), 7.06 (1H, d, J=8.2 Hz), 6.88 (1H, s), 6.79 (2H, d, J=7.8 Hz), 5.29 (2H, s), 3.87 (3H, s), 2.38 (3H, s), 2.30 (3H, s), 2.16 (3H, s).

Reference Production Example 8

Using 2-(bromomethyl)-6-methyl-nitrobenzene in place of 2-(bromomethyl)phenyl=acetate, 8A was obtained in accordance with the method mentioned in Production Example 1.

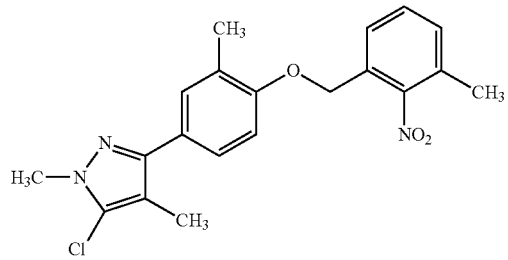

$^1$H-NMR (CDCl$_3$) δ: 7.52 (1H, d, J=7.6 Hz), 7.48-7.41 (2H, m), 7.40-7.36 (1H, m), 7.31 (1H, d, J=7.1 Hz), 6.86 (1H, d, J=8.5 Hz), 5.17 (2H, s), 3.87 (3H, s), 2.42 (3H, s), 2.31 (3H, s), 2.16 (3H, s).

Reference Production Example 9

Using 8A mentioned in Production Example 8 in place of 5A mentioned in Reference Production Example 5, 9A was obtained in accordance with the method mentioned in Reference Production Example 6.

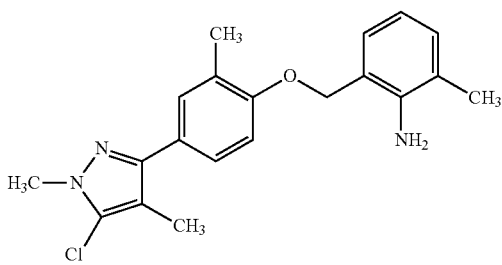

¹H-NMR (CDCl₃) δ: 7.47 (1H, s), 7.42 (1H, d, J=8.5 Hz), 7.15-7.08 (2H, m), 7.05 (1H, d, J=8.5 Hz), 6.75-6.70 (1H, m), 5.10 (2H, s), 4.13 (2H, brs), 3.87 (3H, s), 2.28 (3H, s), 2.23 (3H, s), 2.17 (3H, s).

Reference Production Example 10

Using 9A mentioned in Production Example 9 in place of 6A mentioned in Reference Production Example 6, 10A was obtained in accordance with the method mentioned in Reference Production Example 7.

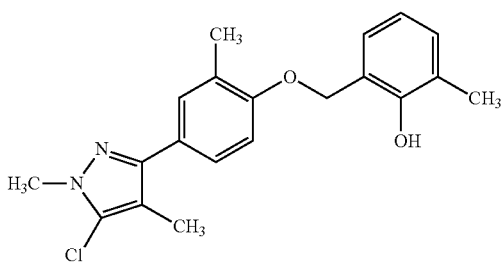

¹H-NMR (CDCl₃) δ: 7.50-7.48 (1H, m), 7.45-7.41 (1H, m), 7.15 (1H, d, J=7.6 Hz), 7.08 (1H, d, J=7.3 Hz), 7.03 (1H, d, J=8.2 Hz), 6.88-6.83 (1H, m), 6.78 (1H, s), 5.25 (2H, s), 3.87 (3H, s), 2.34 (3H, s), 2.30 (3H, s), 2.17 (3H, s).

Reference Production Example 11

A mixture of 10 g of 4-methoxy-3-methylphenylboronic acid, 7.3 g of 3,5-dimethyl-1H-pyrazole, 18.4 g of copper(II) acetate, 10.0 g of pyridine, 20.0 g of Molecular Sieves 4A, and 300 ml of acetonitrile was stirred with heating under reflux for 30 hours. The reaction mixture was filtered with Celite, concentrated under reduced pressure, and then subjected to column chromatography to obtain 7.3 g of 11A.

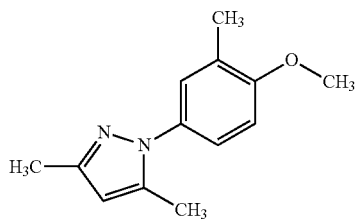

¹H-NMR (CDCl₃) δ: 7.20 (1H, d, J=2.0 Hz), 7.16 (1H, dd, J=8.5, 2.7 Hz), 6.84 (1H, d, J=8.5 Hz), 5.95 (1H, s), 3.86 (3H, s), 2.29 (3H, s), 2.24 (3H, s), 2.24 (3H, s).

Reference Production Example 12

Using 11A mentioned in Production Example 11 in place of 3A mentioned in Reference Production Example 3, 12A was obtained in accordance with the method mentioned in Reference Production Example 4.

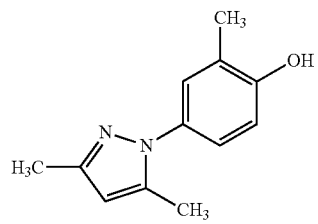

¹H-NMR (DMSO-D₆) δ: 9.68 (1H, brs), 7.19 (1H, s), 7.10 (1H, dd, J=8.8, 2.3 Hz), 6.87 (1H, d, J=8.8 Hz), 6.13 (1H, s), 2.20 (6H, s), 2.16 (3H, s).

Reference Production Example 13

Using 2-(bromomethyl)-3-methyl-nitrobenzene in place of 2-(bromomethyl)phenyl=acetate, and using 12A mentioned in Reference Production Example 12 in place of 4A mentioned in Reference Production Example 4, 13A was obtained in accordance with the method mentioned in Production Example 1.

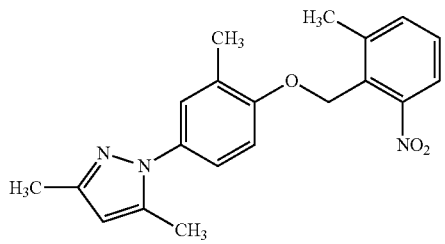

¹H-NMR (DMSO-D₆) δ: 7.68 (1H, d, J=8.0 Hz), 7.49 (1H, d, J=7.8 Hz), 7.42 (1H, t, J=7.8 Hz), 7.23-7.16 (2H, m), 6.95 (1H, d, J=8.7 Hz), 5.96 (1H, s), 5.27 (2H, s), 2.54 (3H, s), 2.29 (3H, s), 2.27 (3H, s), 2.17 (3H, s).

Reference Production Example 14

Using 13A mentioned in Production Example 13 in place of 5A mentioned in Reference Production Example 5, 14A was obtained in accordance with the method mentioned in Reference Production Example 6.

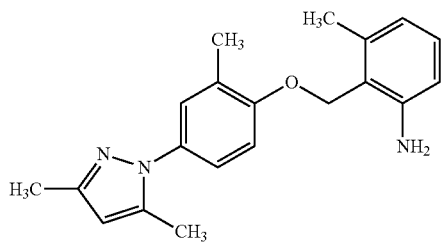 [SMILES: Cc1cc(C)n(-c2ccc(OCc3c(C)cccc3N)c(C)c2)n1]

¹H-NMR (CDCl₃) δ: 7.44 (1H, s), 7.43-7.38 (2H, m), 7.14-7.08 (2H, m), 6.39-6.37 (1H, m), 6.37-6.35 (1H, m), 5.27 (2H, s), 4.21 (2H, brs), 3.85 (3H, s), 3.75 (3H, s), 2.26 (3H, s), 2.10 (3H, s).

Reference Production Example 15

Using 14A mentioned in Production Example 14 in place of 6A mentioned in Reference Production Example 6, 15A was obtained in accordance with the method mentioned in Reference Production Example 7.

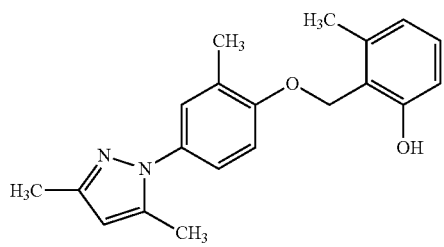 [SMILES: Cc1cc(C)n(-c2ccc(OCc3c(C)cccc3O)c(C)c2)n1]

¹H-NMR (CDCl₃) δ: 7.70 (1H, s), 7.24-7.03 (2H, m), 6.81-6.75 (1H, m), 6.75-6.72 (1H, m), 6.70 (1H, d, J=7.6 Hz), 6.63 (1H, s), 5.96 (1H, s), 5.27 (2H, s), 2.38 (3H, s), 2.29 (3H, s), 2.26 (3H, s), 2.26 (3H, s).

Reference Production Example 16

To a mixture of 9.4 g of 1-(4-isopropoxy-3-methylphenyl) ethanone and 150 ml of tetrahydrofuran, 11.6 g of diethyl carbonate, 4.5 g of 55% sodium hydride, 0.04 g of dibenzo-18-crown-6, and 3 ml of ethanol were added at room temperature, followed by stirring with heating under reflux for 9 hours. Water was added the reaction mixture, which was acidified by adding 10% hydrochloric acid and then extracted with ethyl acetate. The organic layer was washed with water, dried over anhydrous magnesium sulfate, and then concentrated under reduced pressure. The residue thus obtained was subjected to silica gel column chromatography to obtain 12.1 g of 16A.

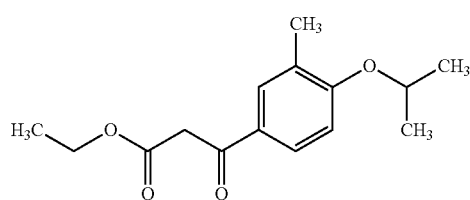 [SMILES: CCOC(=O)CC(=O)c1ccc(OC(C)C)c(C)c1]

¹H-NMR (CDCl₃) δ: 7.79-7.76 (2H, m), 6.85-6.83 (1H, m), 4.68-4.62 (1H, m), 4.21 (2H, q, J=7.2 Hz), 3.93 (2H, s), 2.22 (3H, s), 1.37 (6H, d, J=6.0 Hz), 1.26 (3H, t, J=7.1 Hz).

Reference Production Example 17

Using 16A mentioned in Reference Production Example 16 in place of ethyl 3-(4-methoxy-3-methylphenyl)-2-methyl-3-oxopropionate, 17A was obtained in accordance with the method mentioned in Reference Production Example 2.

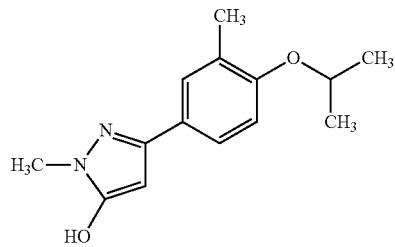 [SMILES: Cc1cc(-c2cc(O)n(C)n2)ccc1OC(C)C]

¹H-NMR (DMSO-D₆) δ: 7.58-7.54 (2H, m), 7.01-6.98 (1H, m), 5.95 (1H, s), 4.66-4.60 (1H, m), 3.62 (3H, s), 2.16 (3H, s), 1.28 (6H, d, J=5.1 Hz).

Reference Production Example 18

To 150 g of phosphorus oxychloride, 10.9 g of N,N-dimethylformamide was added at 0° C. and, after stirring for 0.5 hour, 28 g of 17A mentioned in Reference Production Example 17 was added. The mixture was stirred at 100° C. for 10 hours and then concentrated under reduced pressure. To the reaction mixture, 100 ml of ice water was added, and then the mixture was extracted with ethyl acetate. The organic layer was washed with water, dried over anhydrous magnesium sulfate, and then concentrated under reduced pressure. The residue thus obtained was subjected to silica gel column chromatography to obtain 21.0 g of 18A.

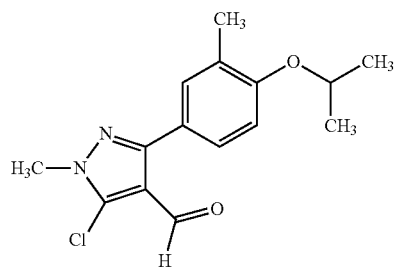 [SMILES: Cc1cc(-c2nn(C)c(Cl)c2C=O)ccc1OC(C)C]

¹H-NMR (CDCl₃) δ: 9.93 (1H, s), 7.52-7.50 (2H, m), 6.91-6.89 (1H, m), 4.63-4.54 (1H, m), 3.92 (3H, s), 2.25 (3H, s), 1.36 (6H, d, J=6.0 Hz).

Reference Production Example 19

A mixture of 28.5 g of 18A mentioned in Reference Production Example 18, 28.0 g of potassium fluoride, 125 ml of sulfolane, and 120 ml of toluene was heated with stirring at 120° C. to thereby distill off toluene, followed by stirring at 220° C. for 2 hours. To the reaction mixture, 200 ml of water was added, and then the mixture was extracted with ethyl acetate. The organic layer was washed with water, dried over anhydrous magnesium sulfate, and then concentrated under reduced pressure. The residue thus obtained was subjected to silica gel column chromatography to obtain 23.4 g of 19A.

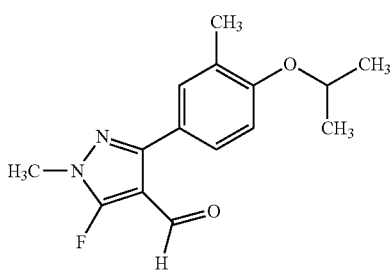 [SMILES: Cc1cc(-c2nn(C)c(F)c2C=O)ccc1OC(C)C]

¹H-NMR (CDCl₃) δ: 9.85 (1H, s), 7.53-7.50 (2H, m), 6.90 (1H, d, J=9.1 Hz), 4.67-4.50 (1H, m), 3.81 (3H, d, J=1.6 Hz), 2.25 (3H, s), 1.37 (3H, s), 1.36 (3H, s).

Reference Production Example 20

To a mixture of 23.4 g of 19A mentioned in Reference Production Example 19 and 100 ml of trifluoroacetic acid, 24.7 g of triethylsilane was added at 0° C. After stirring at room temperature for 6 hours and concentration under reduced pressure, 75 ml of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 17.8 g of 20A.

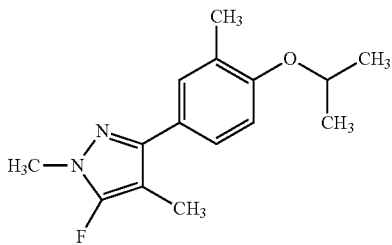 [SMILES: Cc1cc(-c2nn(C)c(F)c2C)ccc1OC(C)C]

¹H-NMR (CDCl₃) δ: 7.45-7.43 (1H, m), 7.38-7.36 (1H, m), 6.87 (1H, d, J=8.4 Hz), 4.59-4.52 (1H, m), 3.75 (3H, d, J=1.1 Hz), 2.24 (3H, s), 2.10 (3H, d, J=0.9 Hz), 1.35 (6H, d, J=6.1 Hz).

Reference Production Example 21

A mixture of 17.8 g of 20A mentioned in Reference Production Example 20 and 170 ml of 30% sulfuric acid was stirred with heating under reflux for 24 hours. The mixture was cooled to 0° C. and 100 ml of water was added, and then the mixture was neutralized with an aqueous sodium carbonate solution so as to adjust the pH to 7. After extraction with ethyl acetate, the organic layer was washed with water, dried over anhydrous magnesium sulfate, and then concentrated under reduced pressure. The residue thus obtained was subjected to silica gel column chromatography to obtain 6.78 g of 21A.

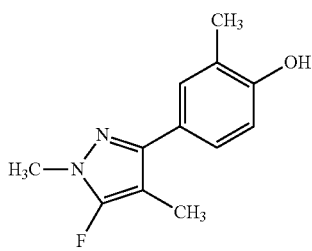 [SMILES: Cc1cc(-c2nn(C)c(F)c2C)ccc1O]

¹H-NMR (CDCl₃) δ: 7.44-7.42 (1H, m), 7.34-7.29 (1H, m), 6.79 (1H, d, J=8.2 Hz), 5.12 (1H, s), 3.75 (3H, d, J=1.1 Hz), 2.29 (3H, s), 2.10-2.08 (3H, m).

Reference Production Example 22

Using 2-(bromomethyl)-3-methyl-nitrobenzene in place of 2-(bromomethyl)phenyl=acetate, and using 21A mentioned in Reference Production Example 21 in place of 4A mentioned in Reference Production Example 4, 22A was obtained in accordance with the method mentioned in Production Example 1.

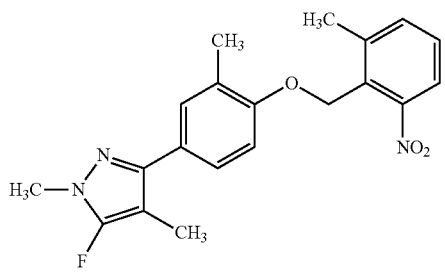

¹H-NMR (CDCl₃) δ: 7.67-7.64 (1H, m), 7.49-7.37 (4H, m), 6.95 (1H, d, J=8.4 Hz), 5.25 (2H, s), 3.74 (3H, d, J=0.9 Hz), 2.52 (3H, s), 2.17 (3H, s), 2.09 (3H, d, J=0.9 Hz).

Reference Production Example 23

Using 22A mentioned in Reference Production Example 22 in place of 5A mentioned in Reference Production Example 5, 23A was obtained in accordance with the method mentioned in Reference Production Example 6.

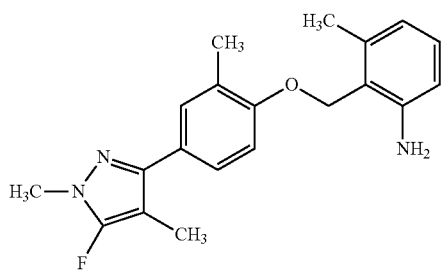 [SMILES: Cc1cc(-c2nn(C)c(F)c2C)ccc1OCc1c(C)cccc1N]

¹H-NMR (CDCl₃) δ: ¹H-NMR (CDCl₃) δ: 7.47-7.43 (2H, m), 7.10-7.05 (2H, m), 6.66 (1H, d, J=7.6 Hz), 6.62 (1H, d, J=8.0 Hz), 5.10 (2H, s), 4.03 (2H, brs), 3.76 (3H, d, J=0.9 Hz), 2.37 (3H, s), 2.23 (3H, s), 2.11 (3H, d, J=0.9 Hz).

Reference Production Example 24

Using 23A mentioned in Reference Production Example 23 in place of 6A mentioned in Reference Production Example 6, 24A was obtained in accordance with the method mentioned in Reference Production Example 7.

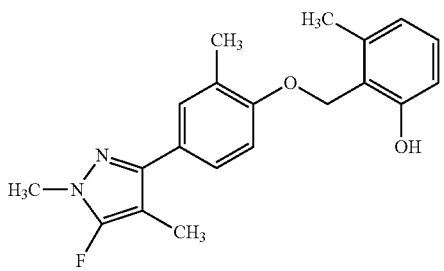 [SMILES: Cc1cc(-c2nn(C)c(F)c2C)ccc1OCc1c(C)cccc1O]

$^1$H-NMR (CDCl$_3$) δ: 7.50-7.48 (1H, m), 7.46-7.42 (1H, m), 7.17-7.12 (1H, m), 7.05 (1H, d, J=8.5 Hz), 6.82 (1H, s), 6.80-6.77 (2H, m), 5.29 (2H, s), 3.76 (3H, s), 2.37 (3H, s), 2.30 (3H, s), 2.10 (3H, s).

Reference Production Example 25

Using 2-(bromomethyl)-3-methoxy-nitrobenzene in place of 2-(bromomethyl)phenyl=acetate, and using 21A mentioned in Reference Production Example 21 in place of 4A mentioned in Reference Production Example 4, 25A was obtained in accordance with the method mentioned in Production Example 1.

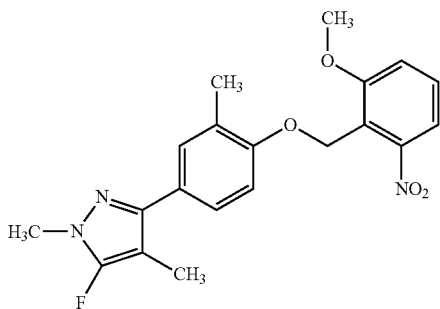 [SMILES: COc1cccc([N+](=O)[O-])c1COc1ccc(-c2nn(C)c(F)c2C)cc1C]

$^1$H-NMR (CDCl$_3$) δ: 7.47-7.36 (4H, m), 7.17-7.13 (1H, m), 6.96 (1H, d, J=8.4 Hz), 5.40 (2H, s), 3.94 (3H, s), 3.74 (3H, d, J=0.9 Hz), 2.15 (3H, s), 2.09 (3H, d, J=0.9 Hz).

Reference Production Example 26

Using 25A mentioned in Reference Production Example 25 in place of 5A mentioned in Reference Production Example 5, 26A was obtained in accordance with the method mentioned in Reference Production Example 6.

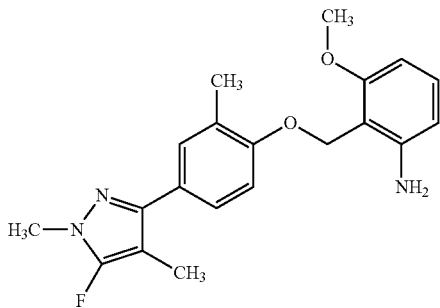

$^1$H-NMR (CDCl$_3$) δ: 7.45-7.42 (1H, m), 7.41-7.37 (1H, m), 7.13-7.07 (2H, m), 6.38-6.34 (2H, m), 5.26 (2H, s), 4.20 (2H, brs), 3.84 (3H, s), 3.74 (3H, s), 2.25 (3H, s), 2.09 (3H, s).

Reference Production Example 27

Using 26A mentioned in Reference Production Example 26 in place of 6A mentioned in Reference Production Example 6, 27A was obtained in accordance with the method mentioned in Reference Production Example 7.

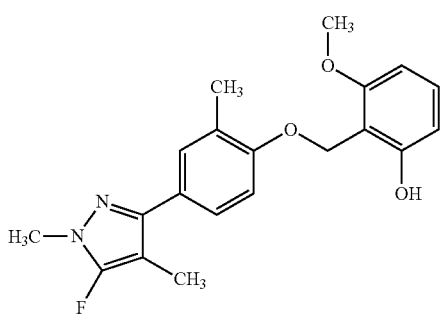

$^1$H-NMR (CDCl$_3$) δ: 7.50-7.48 (1H, m), 7.37-7.33 (1H, m), 7.13-7.05 (2H, m), 6.45-6.34 (2H, m), 5.29 (2H, s), 3.84 (3H, s), 3.76 (3H, s), 2.30 (3H, s), 2.08 (3H, s).

Reference Production Example 28

Using 2-(bromomethyl)-3-bromo-nitrobenzene in place of 2-(bromomethyl)phenyl=acetate, 25A was obtained in accordance with the method mentioned in Production Example 1.

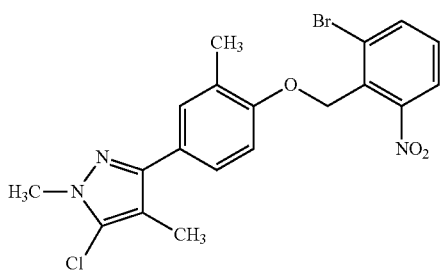

$^1$H-NMR (CDCl$_3$) δ: 7.88-7.84 (1H, m), 7.78-7.74 (1H, m), 7.44-7.35 (3H, m), 6.94 (1H, d, J=8.4 Hz), 5.46 (2H, s), 3.85 (3H, s), 2.17 (3H, s), 2.15 (3H, s).

Reference Production Example 29

Using 28A mentioned in Reference Production Example 28 in place of 5A mentioned in Reference Production Example 5, 29A was obtained in accordance with the method mentioned in Reference Production Example 6.

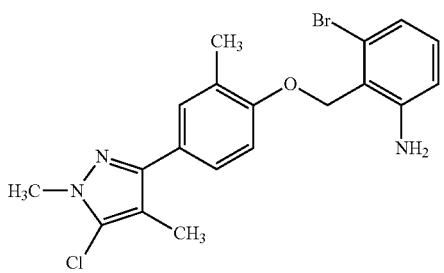 [SMILES: Cc1cc(-c2nn(C)c(Cl)c2C)ccc1OCc1c(N)cccc1Br]

<sup>1</sup>H-NMR (CDCl<sub>3</sub>) δ: 7.47-7.45 (1H, m), 7.45-7.40 (1H, m), 7.23-7.19 (1H, m), 7.10 (1H, d, J=8.2 Hz), 7.01-6.98 (1H, m), 6.67-6.64 (1H, m), 5.34 (2H, s), 4.31 (2H, s), 3.86 (3H, s), 2.27 (3H, s), 2.16 (3H, s).

Reference Production Example 30

Using 29A mentioned in Reference Production Example 29 in place of 6A mentioned in Reference Production Example 6, 30A was obtained in accordance with the method mentioned in Reference Production Example 7.

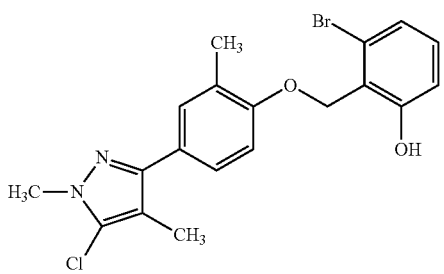

<sup>1</sup>H-NMR (CDCl<sub>3</sub>) δ: 7.61 (1H, s), 7.46-7.39 (2H, m), 7.16-7.12 (1H, m), 7.09 (1H, d, J=8.2 Hz), 7.07-7.03 (1H, m), 6.89-6.86 (1H, m), 5.47 (2H, s), 3.85 (3H, s), 2.30 (3H, s), 2.14 (3H, s).

Reference Production Example 31

A mixture of 0.87 g of 25A mentioned in Reference Production Example 25, 0.34 g of cyclopropylboronic acid, 1.95 g of cesium carbonate, 0.16 g of [1,1'-bis(diphenylphosphino)ferrocene]palladium(II) dichloride dichloromethane adduct, and 8 mL of methyl tert-butyl ether was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.74 g of 31A.

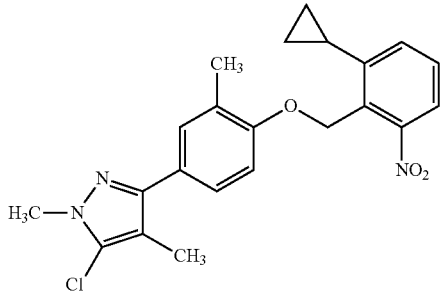 [SMILES: Cc1cc(-c2nn(C)c(Cl)c2C)ccc1OCc1c(C2CC2)cccc1[N+](=O)[O-]]

<sup>1</sup>H-NMR (CDCl<sub>3</sub>) δ: 7.65 (1H, d, J=8.0 Hz), 7.45-7.38 (3H, m), 7.35 (1H, d, J=7.6 Hz), 7.00 (1H, d, J=8.2 Hz), 5.48 (2H, s), 3.86 (3H, s), 2.18 (3H, s), 2.16 (3H, s), 2.15-2.09 (1H, m), 1.08-1.02 (2H, m), 0.79-0.74 (2H, m).

Reference Production Example 32

Using 31A mentioned in Reference Production Example 31 in place of 5A mentioned in Reference Production Example 5, 32A was obtained in accordance with the method mentioned in Reference Production Example 6.

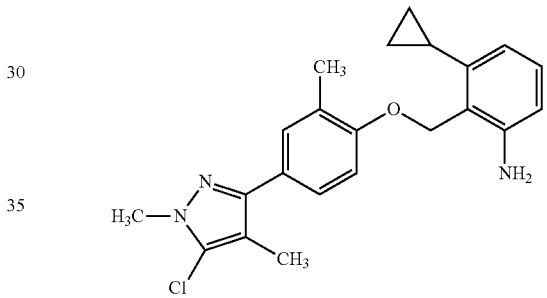

<sup>1</sup>H-NMR (CDCl<sub>3</sub>) δ: 7.48-7.43 (2H, m), 7.14-7.07 (2H, m), 6.63 (1H, d, J=7.8 Hz), 6.60 (1H, d, J=7.8 Hz), 5.35 (2H, s), 4.06 (2H, brs), 3.87 (3H, s), 2.25 (3H, s), 2.17 (3H, s), 2.02-1.95 (1H, m), 0.91-0.86 (2H, m), 0.69-0.65 (2H, m).

Reference Production Example 33

Using 32A mentioned in Reference Production Example 32 in place of 6A mentioned in Reference Production Example 6, 33A was obtained in accordance with the method mentioned in Reference Production Example 7.

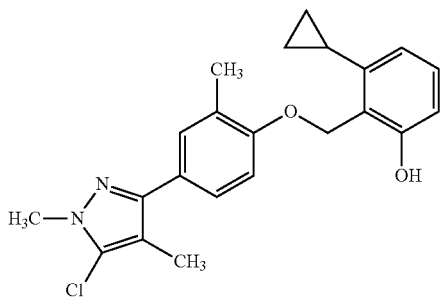 [SMILES: Cc1cc(-c2nn(C)c(Cl)c2C)ccc1OCc1c(O)cccc1C1CC1]

<sup>1</sup>H-NMR (CDCl<sub>3</sub>) δ: 7.50-7.49 (1H, m), 7.47-7.44 (1H, m), 7.19-7.14 (1H, m), 7.11 (1H, d, J=8.4 Hz), 7.02 (1H, s), 6.81 (1H, d, J=7.5 Hz), 6.72 (1H, d, J=7.7 Hz), 5.54 (2H, s), 3.87 (3H, s), 2.32 (3H, s), 2.17 (3H, s), 1.98-1.91 (1H, m), 0.97-0.92 (2H, m), 0.71-0.67 (2H, m).

Reference Production Example 34

To a mixture of 5.0 g of 1-(4-methoxy-2, 5-dimethyl) ethanone and 200 ml of tetrahydrofuran, 7.9 g of ethyl trifluoroacetate and 19 g of a 20% sodium ethoxide ethanol solution were added and, after stirring with heating under reflux for 7 hours, the reaction mixture was acidified by adding 70 ml of water and 6N hydrochloric acid. After extraction with ethyl acetate, the organic layer was washed with water, dried over anhydrous magnesium sulfate, and then concentrated under reduced pressure. The residue thus obtained was subjected to silica gel column chromatography to obtain 6.8 g of 34A.

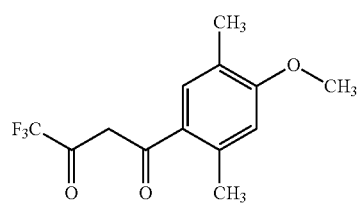

$^1$H-NMR (CDCl$_3$: 23° C.) δ: 7.44 (1H, s), 6.69 (1H, s), 6.35 (1H, s), 3.89 (3H, s), 2.57 (3H, s), 2.21 (3H, s).

Reference Production Example 35

To a mixture of 6.8 g of 34A mentioned in Reference Production Example 34 and 100 ml of ethanol, 1.7 g of methylhydrazine was added under ice cooling, followed by heating to room temperature and further stirring for 1 hour. The mixture was concentrated under reduced pressure and the residue thus obtained was subjected to silica gel column chromatography to obtain 3.0 g of 35A.

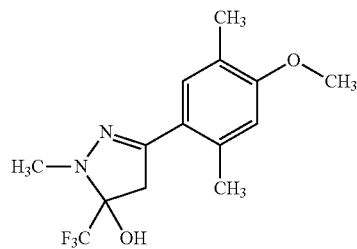

$^1$H-NMR (CDCl$_3$) δ: 7.06 (1H, s), 6.67 (1H, s), 3.84 (3H, s), 3.59 (1H, d, J=17.4 Hz), 3.27 (1H, d, J=17.4 Hz), 3.06 (3H, s), 2.78 (1H, s), 2.53 (3H, s), 2.18 (3H, s)

Reference Production Example 36

A mixture of 3.2 g of 35A mentioned in Reference Production Example 35, 5.3 ml of 6N hydrochloric acid, and 50 ml of tetrahydrofuran was stirred with heating under reflux for 1 hour. After extraction with ethyl acetate, the organic layer was washed with an aqueous saturated sodium hydrogen carbonate solution and a saturated saline solution, and then the organic layer was dried over anhydrous magnesium sulfate and concentrated under reduced pressure. The residue thus obtained was subjected to silica gel column chromatography to obtain 3.0 g of 36A.

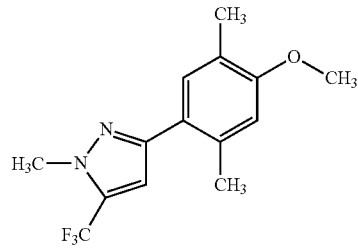

$^1$H-NMR (CDCl$_3$) δ: 7.30 (1H, s), 6.70 (1H, s), 6.69 (1H, s), 4.03 (3H, s), 3.85 (3H, s), 2.43 (3H, s), 2.21 (3H, s).

Reference Production Example 37

Using 36A mentioned in Reference Production Example 36 in place of 3A mentioned in Reference Production Example 3, 37A was obtained in accordance with the method mentioned in Reference Production Example 4.

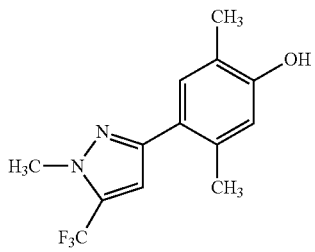

$^1$H-NMR (DMSO-D$_6$) δ: 9.37 (1H, s), 7.26 (1H, s), 7.02 (1H, s), 6.66 (1H, s), 3.98 (3H, s), 2.32 (3H, s), 2.10 (3H, s).

Reference Production Example 38

Using 2-(bromomethyl)-3-methyl-nitrobenzene in place of 2-(bromomethyl)phenyl=acetate, and using 37A mentioned in Reference Production Example 37 in place of 4A mentioned in Reference Production Example 4, 38A was obtained in accordance with the method mentioned in Production Example 1.

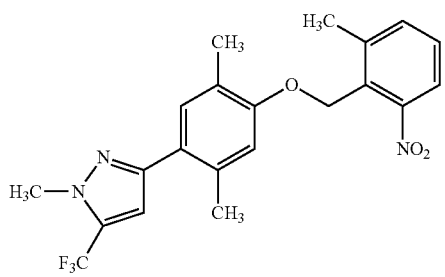

$^1$H-NMR (CDCl$_3$) δ: 7.67 (1H, d, J=7.8 Hz), 7.48 (1H, d, J=7.3 Hz), 7.43-7.37 (1H, m), 7.31 (1H, s), 6.80 (1H, s), 6.70 (1H, s), 5.25 (2H, s), 4.03 (3H, s), 2.54 (3H, s), 2.45 (3H, s), 2.13 (3H, s).

Reference Production Example 39

Using 38A mentioned in Reference Production Example 38 in place of 5A mentioned in Reference Production Example 5, 39A was obtained in accordance with the method mentioned in Reference Production Example 6.

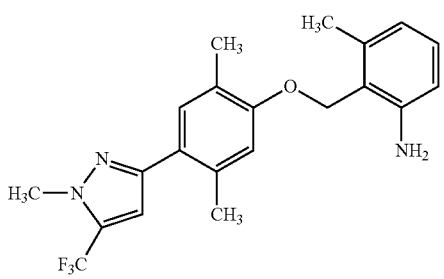 [SMILES: Cc1cc(-c2cc(C(F)(F)F)n(C)n2)c(C)cc1OCc1c(C)cccc1[N+](=O)[O-]]

$^1$H-NMR (CDCl$_3$) δ: 7.34 (1H, s), 7.32-7.30 (1H, m), 7.11-7.06 (1H, m), 6.93 (1H, s), 6.71-6.63 (2H, m), 5.10 (2H, s), 4.06-4.02 (5H, m), 2.48 (3H, s), 2.39 (3H, s), 2.19 (3H, s).

Reference Production Example 40

Using 39A mentioned in Reference Production Example 39 in place of 6A mentioned in Reference Production Example 6, 40A was obtained in accordance with Reference Production Example 7.

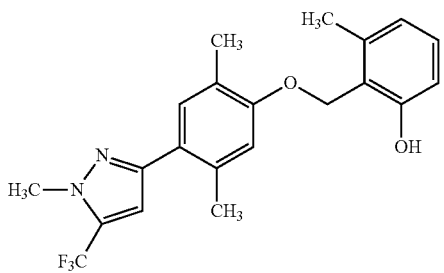 [SMILES: Cc1cc(-c2cc(C(F)(F)F)n(C)n2)c(C)cc1OCc1c(C)cccc1O]

$^1$H-NMR (CDCl$_3$) δ: 7.49 (1H, s), 7.35 (1H, s), 7.31 (1H, s), 7.18-7.12 (1H, m), 6.90 (1H, s), 6.82-6.78 (1H, m), 6.71-6.66 (1H, m), 5.27 (2H, s), 4.04 (3H, s), 2.45 (3H, s), 2.38 (3H, s), 2.13 (3H, s).

Reference Production Example 41

Using 3-fluoro-4-methoxyphenylboronic acid in place of 4-methoxy-3-methyl-phenylboronic acid, and using 3-methyl-1H-pyrazole in place of 3,5-dimethyl-1H-pyrazole, 41A was obtained in accordance with the method mentioned in Reference Production Example 11.

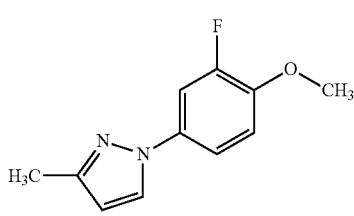

$^1$H-NMR (CDCl$_3$) δ: 7.70 (1H, d, J=2.4 Hz), 7.44 (1H, dd, J=12.2, 2.7 Hz), 7.33 (1H, dq, J=8.9, 1.4 Hz), 6.99 (1H, t, J=8.9 Hz), 6.22 (1H, d, J=2.4 Hz), 3.91 (3H, s), 2.36 (3H, s).

Reference Production Example 42

Using 41A mentioned in Reference Production Example 41 in place of 3A mentioned in Reference Production Example 3, 42A was obtained in accordance with the method mentioned in Reference Production Example 4.

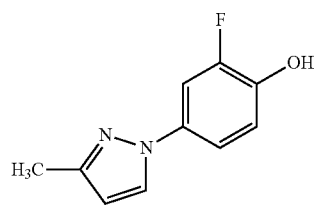

$^1$H-NMR (DMSO-D$_6$) δ: 8.24 (1H, d, J=2.4 Hz), 7.59 (1H, dd, J=12.6, 2.6 Hz), 7.41 (1H, dq, J=8.8, 1.2 Hz), 7.01 (1H, t, J=8.8 Hz), 6.28 (1H, d, J=2.4 Hz), 2.24 (3H, s).

Reference Production Example 43

Using 2-(bromomethyl)-3-methyl-nitrobenzene in place of 2-(bromomethyl)phenyl=acetate, and using 42A mentioned in Reference Production Example 42 in place of 4A mentioned in Reference Production Example 4, 43A was obtained in accordance with the method mentioned in Production Example 1.

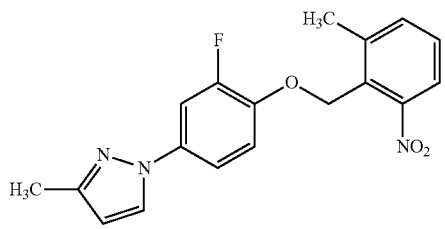

$^1$H-NMR (CDCl$_3$) δ: 7.73-7.71 (1H, m), 7.69 (1H, d, J=8.0 Hz), 7.51-7.38 (3H, m), 7.35-7.31 (1H, m), 7.14-7.09 (1H, m), 6.24 (1H, d, J=2.5 Hz), 5.32 (2H, s), 2.56 (3H, s), 2.37 (3H, s).

Reference Production Example 44

Using 43A mentioned in Reference Production Example 43 in place of 5A mentioned in Reference Production Example 5, 44A was obtained in accordance with the method mentioned in Reference Production Example 6.

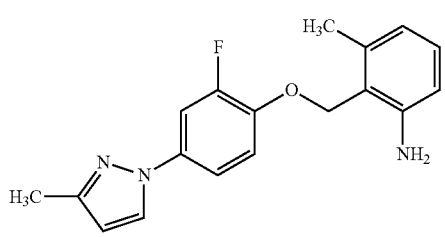 [SMILES: Cc1ccn(-c2ccc(OCc3c(C)cccc3[N+](=O)[O-])c(F)c2)n1]

$^1$H-NMR (CDCl$_3$) δ: 7.73 (1H, d, J=2.5 Hz), 7.50-7.44 (1H, m), 7.36-7.31 (1H, m), 7.19-7.13 (1H, m), 7.10-7.04 (1H, m), 6.66-6.61 (2H, m), 6.25 (1H, d, J=2.5 Hz), 5.18 (2H, s), 4.11 (2H, brs), 2.38 (3H, s), 2.36 (3H, s).

Reference Production Example 45

Using 44A mentioned in Reference Production Example 44 in place of 6A mentioned in Reference Production Example 6, 45A was obtained in accordance with the method mentioned in Reference Production Example 7.

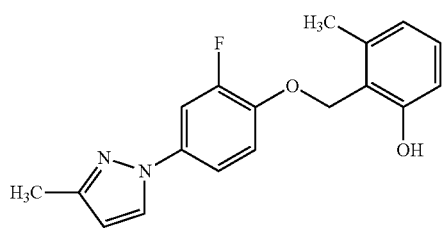 [SMILES: Cc1ccn(-c2ccc(OCc3c(C)cccc3O)c(F)c2)n1]

$^1$H-NMR (CDCl$_3$) δ: 7.72 (1H, d, J=2.5 Hz), 7.50-7.44 (1H, m), 7.36-7.33 (1H, m), 7.22-7.16 (1H, m), 7.16-7.11 (1H, m), 6.80-6.74 (2H, m), 6.33 (1H, s), 6.25 (1H, d, J=2.5 Hz), 5.33 (2H, s), 2.38 (3H, s), 2.37 (3H, s).

In accordance with the process mentioned above, it is possible to obtain compounds HA1001-0001 to HC2132-0961.

The compounds HA1001-0001 to HC2132-0961 (hereinafter referred to as the present compounds A) represent aromatic compounds shown below [wherein E represents any one of the following substituent numbers 1 to 961].

In [substituent number; E] mentioned below, F represents fluoro, Cl represents chloro, Br represents bromo, CN represents cyano, Me represents methyl, Et represents ethyl, CF3 represents trifluoromethyl, CHF2 represents difluoromethyl, OMe represents methoxy, OEt represents ethoxy, OPr represents propoxy, PYR1 represents pyrazol-1-yl group, and PYR3 represents pyrazol-3-yl group.

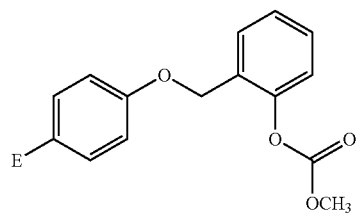
(HA1001)

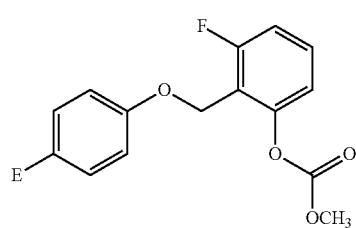
(HA1002)

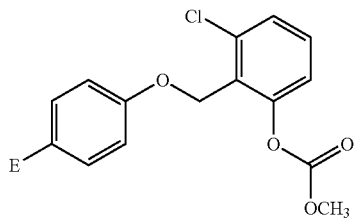
(HA1003)

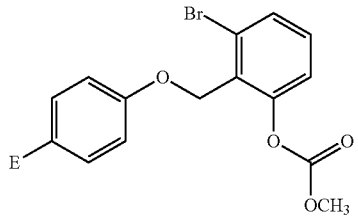
(HA1004)

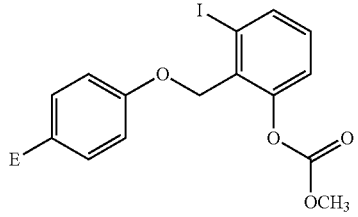
(HA1005)

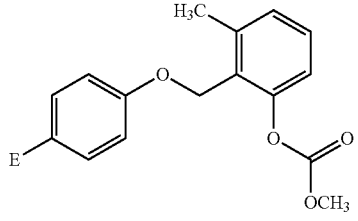
(HA1006)

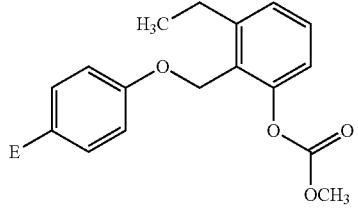
(HA1007)

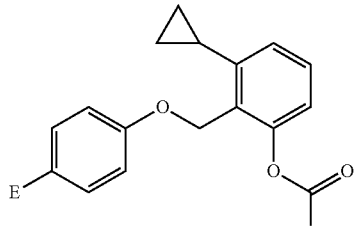
(HA1008)

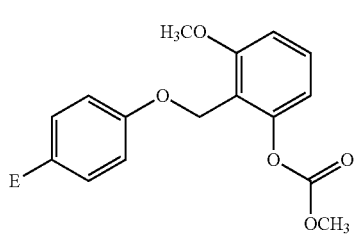
(HA1009)

-continued
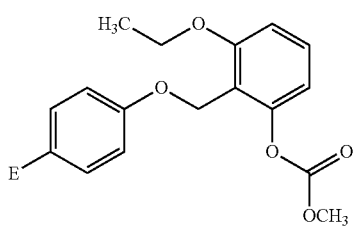
(HA1010)
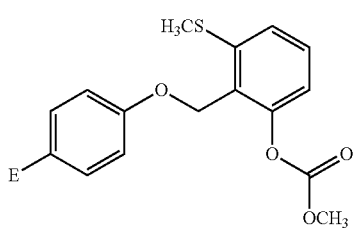
(HA1011)
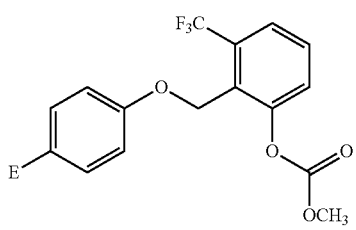
(HA1012)
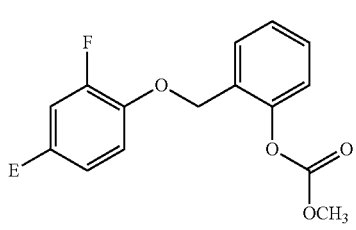
(HA1013)
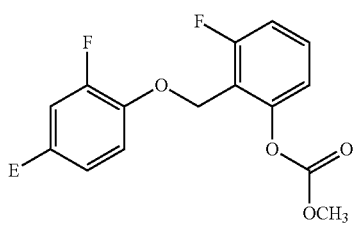
(HA1014)
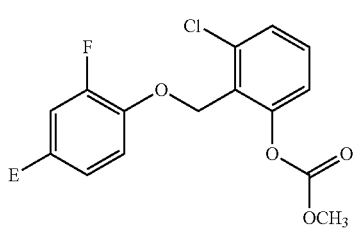
(HA1015)
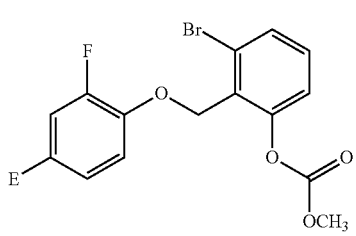
(HA1016)
-continued
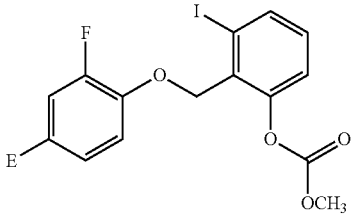
(HA1017)
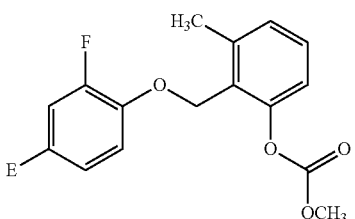
(HA1018)
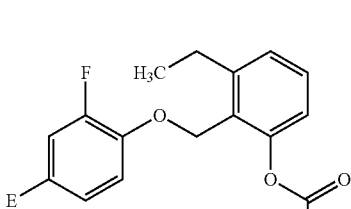
(HA1019)
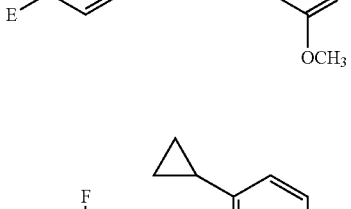
(HA1020)
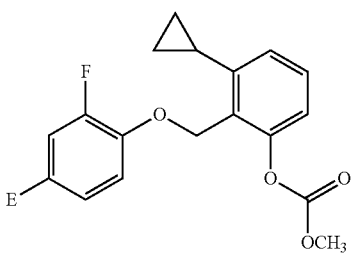
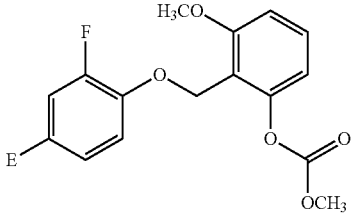
(HA1021)
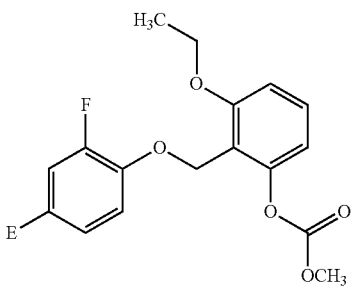
(HA1022)

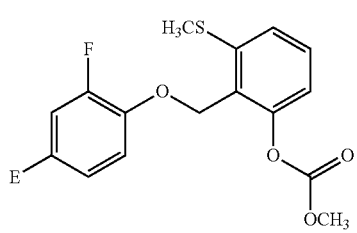 (HA1023)
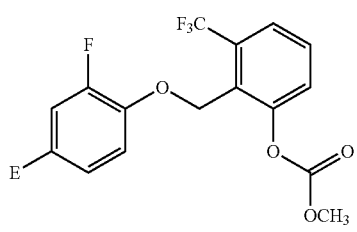 (HA1024)
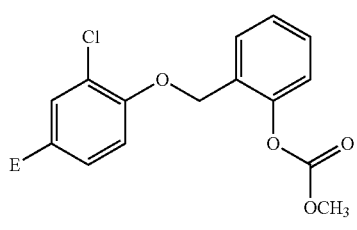 (HA1025)
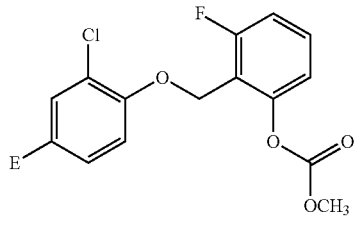 (HA1026)
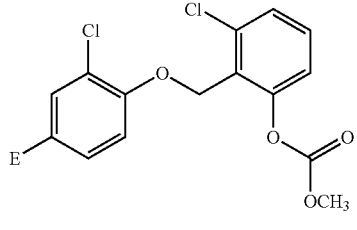 (HA1027)
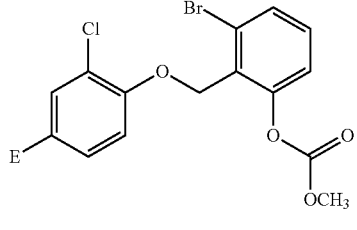 (HA1028)
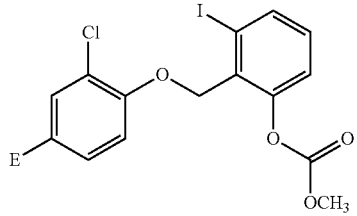 (HA1029)
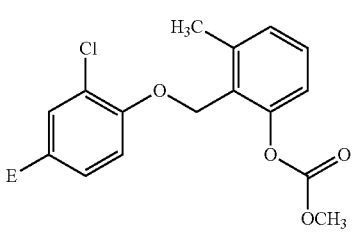 (HA1030)
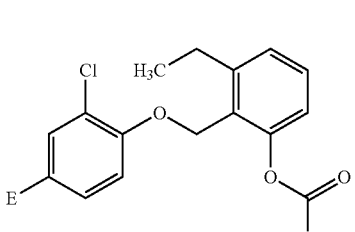 (HA1031)
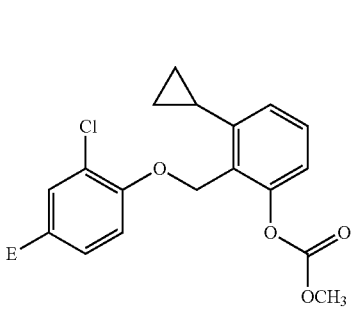 (HA1032)
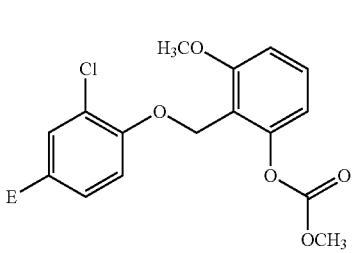 (HA1033)
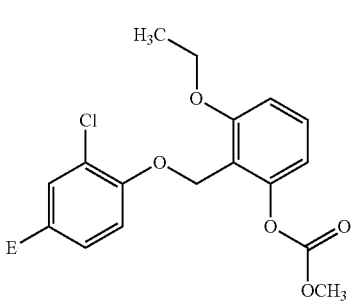 (HA1034)
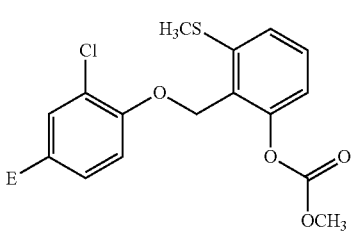 (HA1035)

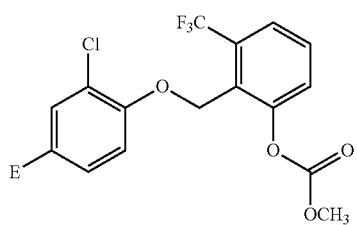
(HA1036)
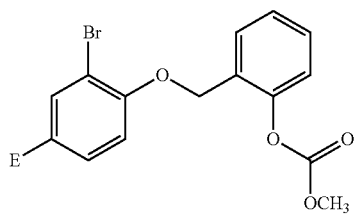
(HA1037)
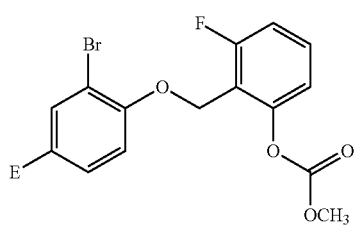
(HA1038)
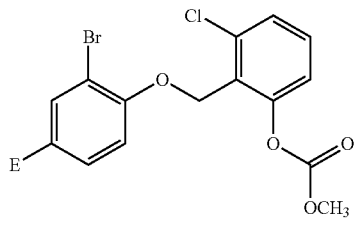
(HA1039)
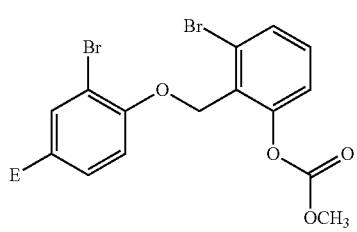
(HA1040)
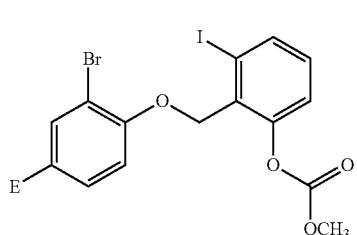
(HA1041)
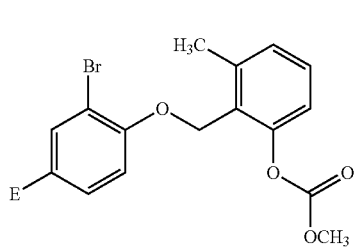
(HA1042)
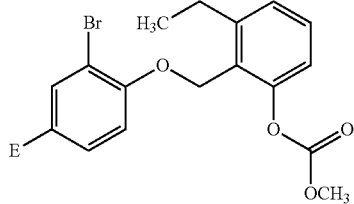
(HA1043)
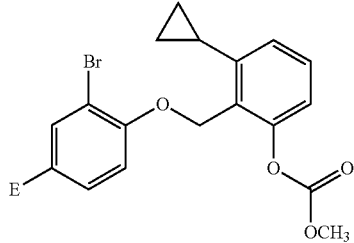
(HA1044)
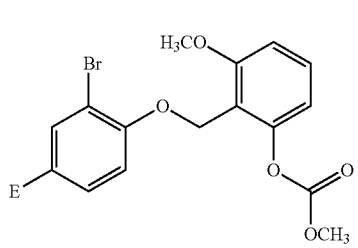
(HA1045)
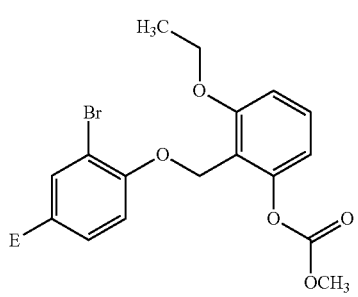
(HA1046)
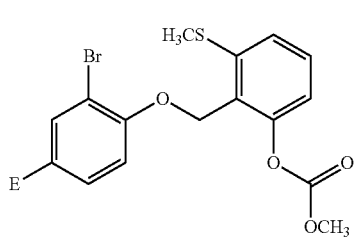
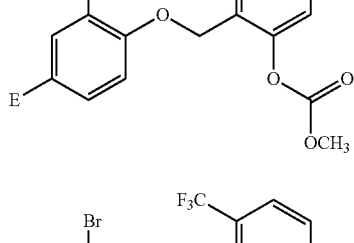
(HA1047)
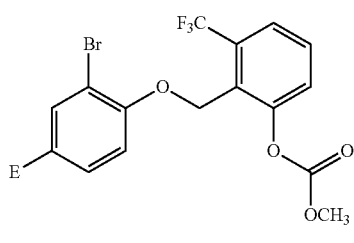
(HA1048)

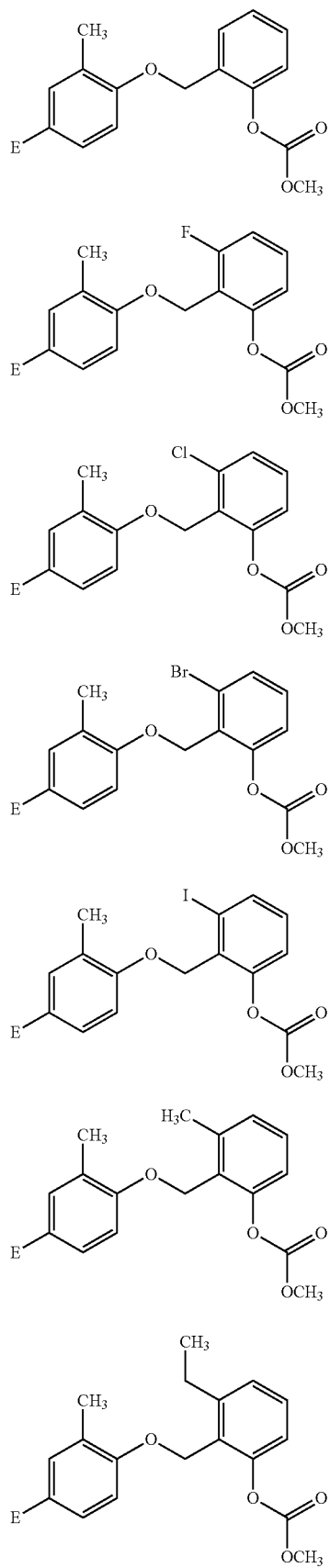
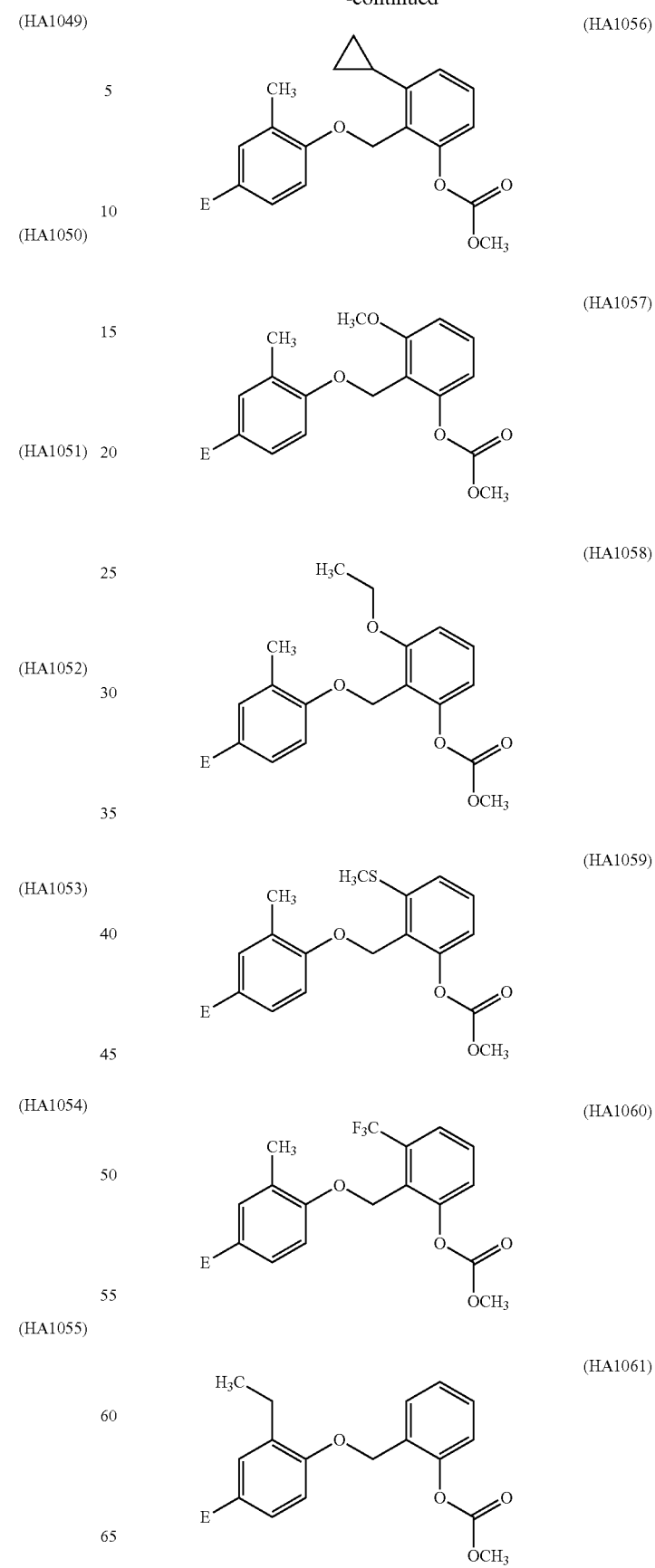

(HA1062) 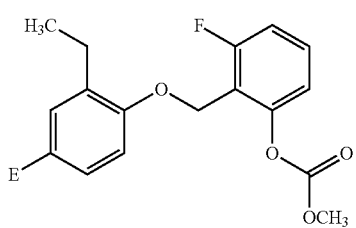
(HA1063) 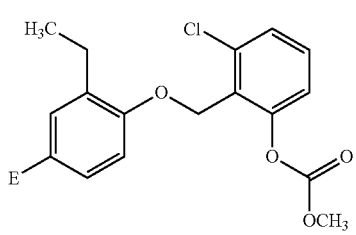
(HA1064) 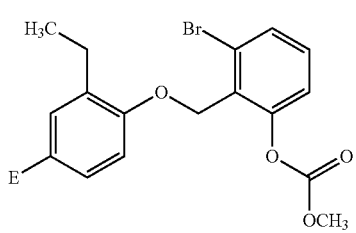
(HA1065) 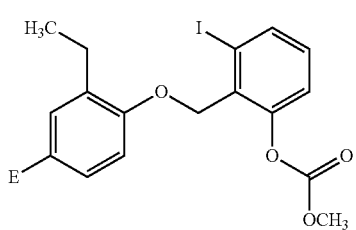
(HA1066) 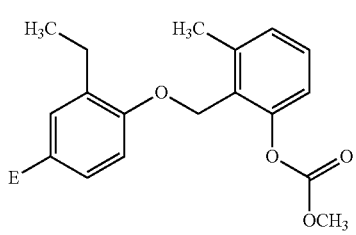
(HA1067) 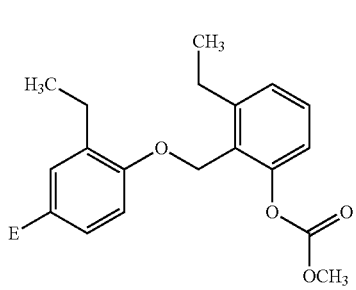
(HA1068) 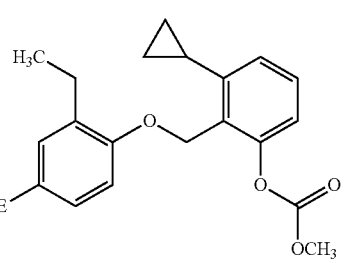
(HA1069) 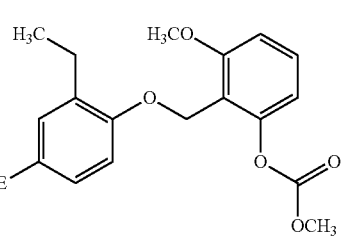
(HA1070) 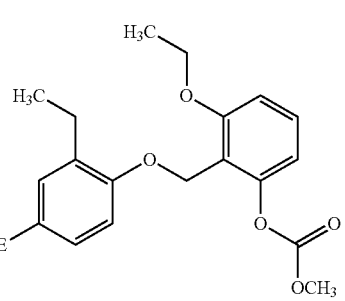
(HA1071) 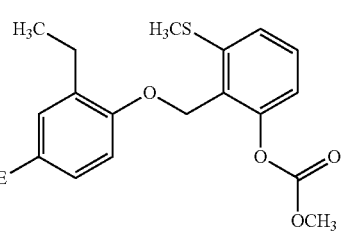
(HA1072) 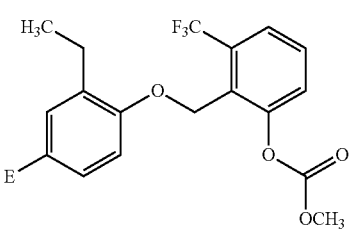
(HA1073) 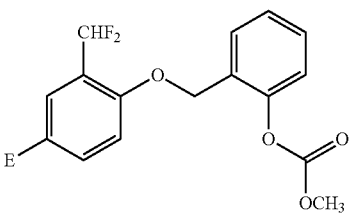

(HA1074) 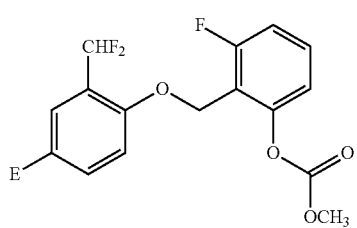
(HA1075) 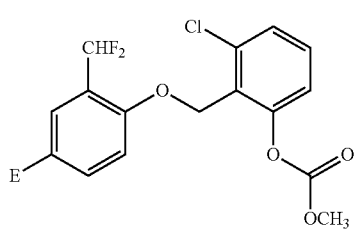
(HA1076) 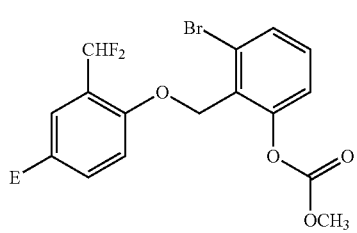
(HA1077) 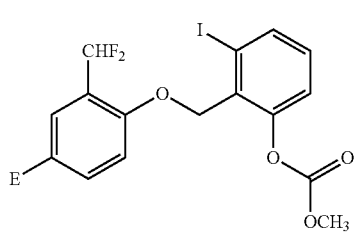
(HA1078) 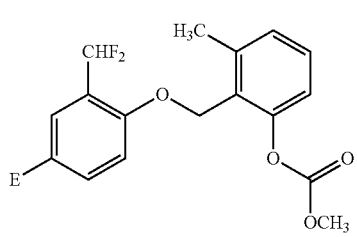
(HA1079) 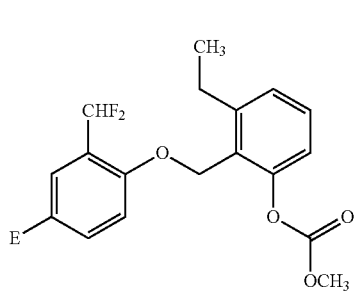
(HA1080) 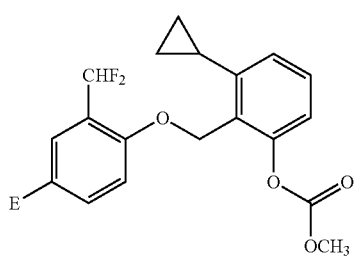
(HA1081) 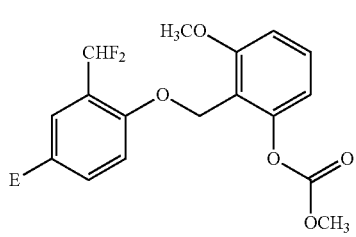
(HA1082) 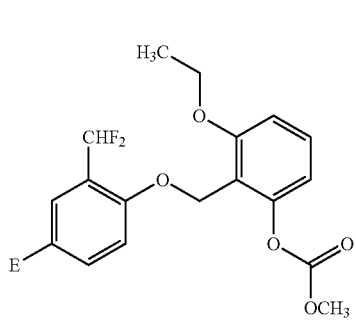
(HA1083) 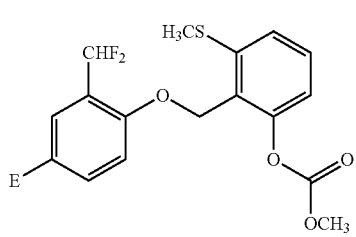
(HA1084) 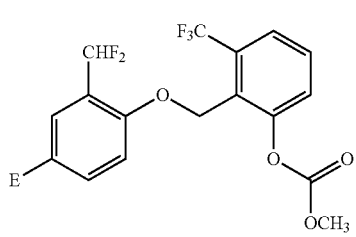
(HA1085) 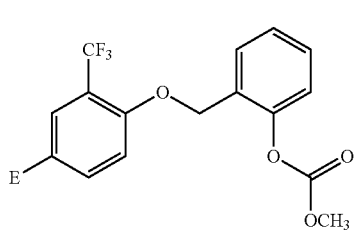

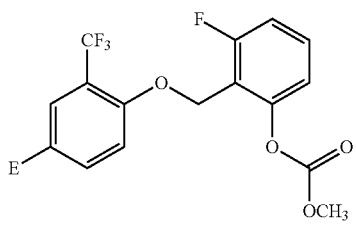
(HA1086)
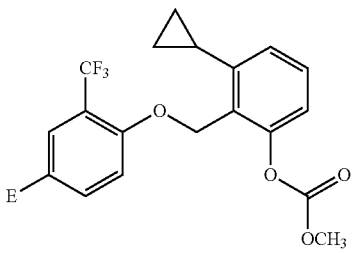
(HA1092)
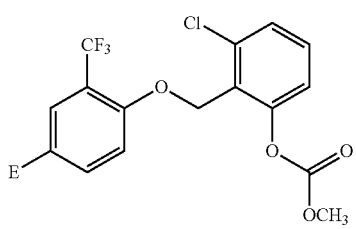
(HA1087)
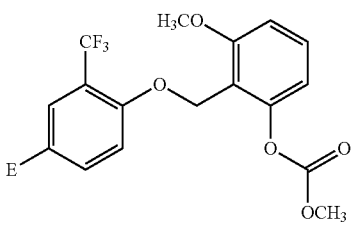
(HA1093)
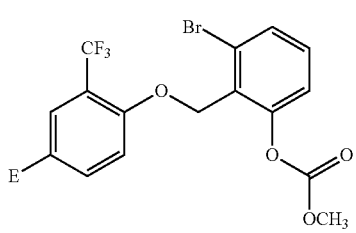
(HA1088)
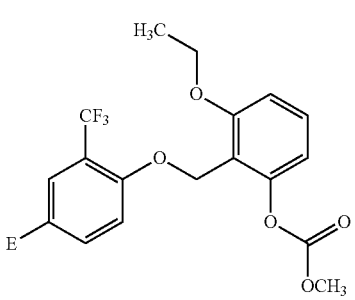
(HA1094)
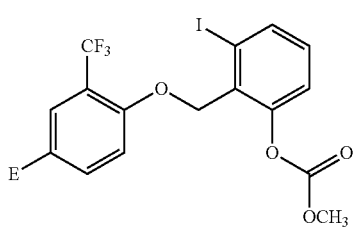
(HA1089)
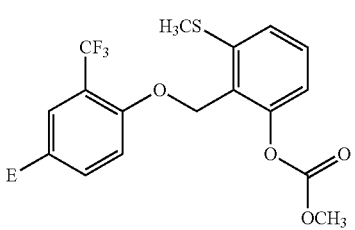
(HA1095)
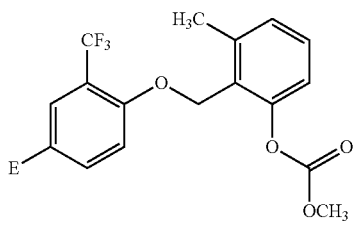
(HA1090)
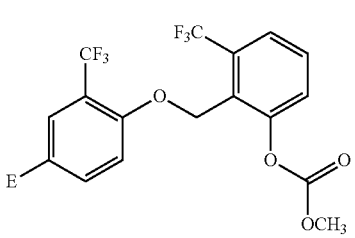
(HA1096)
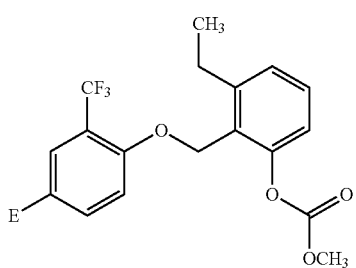
(HA1091)
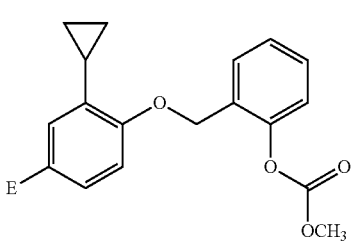
(HA1097)

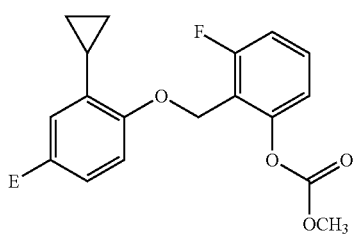 (HA1098)
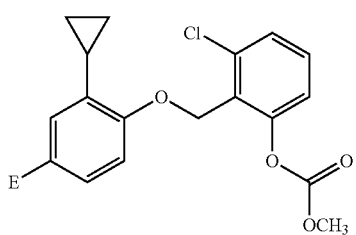 (HA1099)
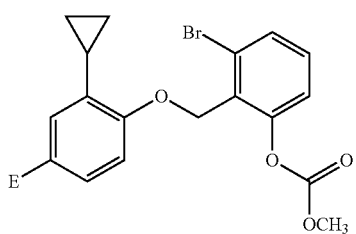 (HA1100)
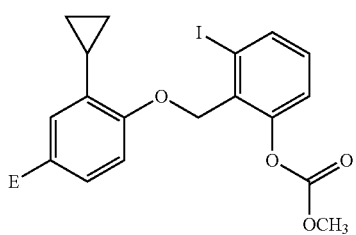 (HA1101)
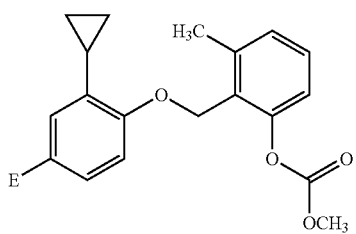 (HA1102)
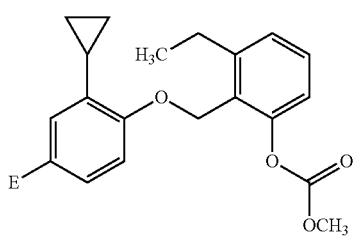 (HA1103)
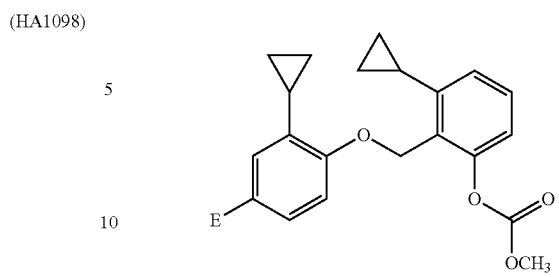 (HA1104)
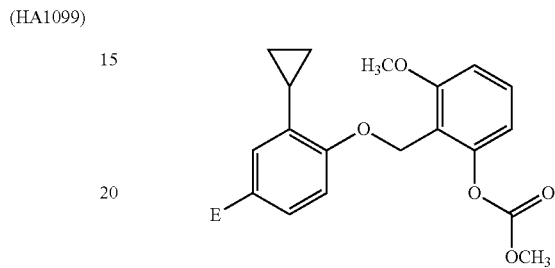 (HA1105)
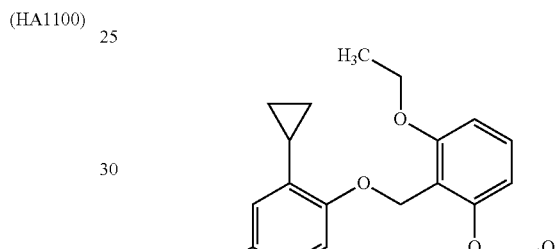 (HA1106)
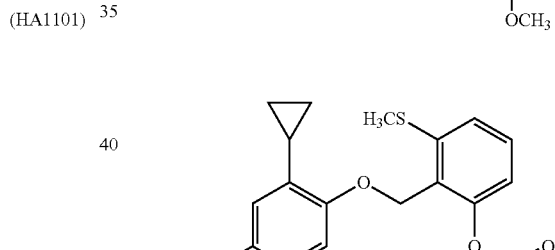 (HA1107)
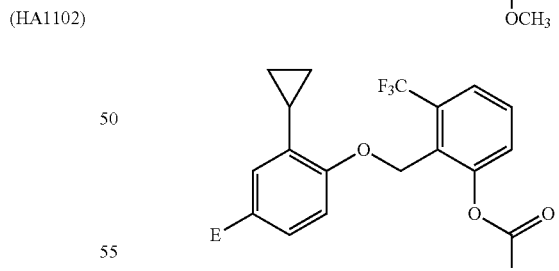 (HA1108)
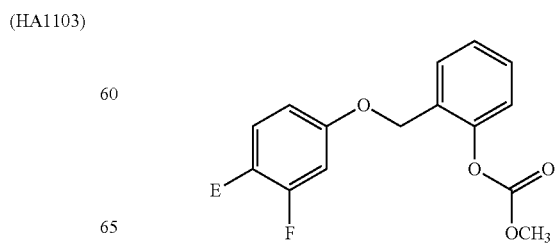 (HA2001)

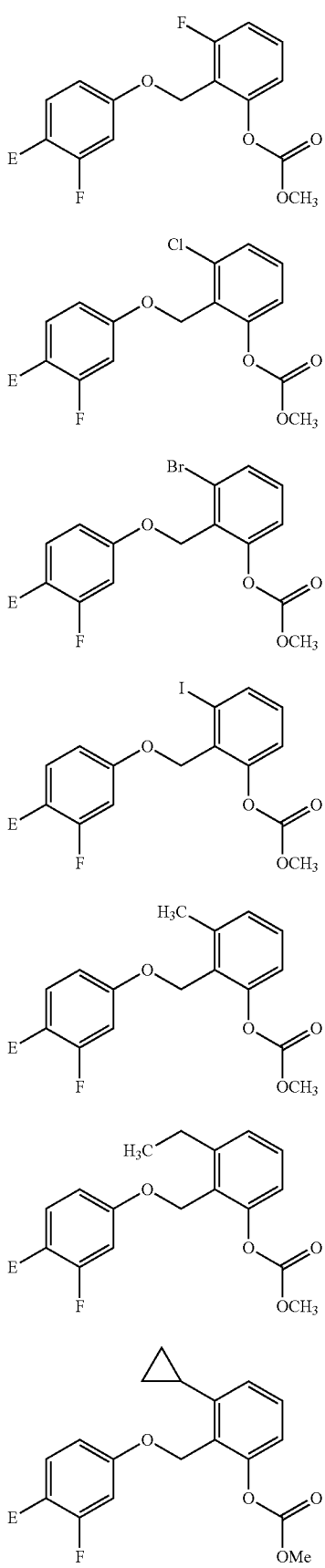
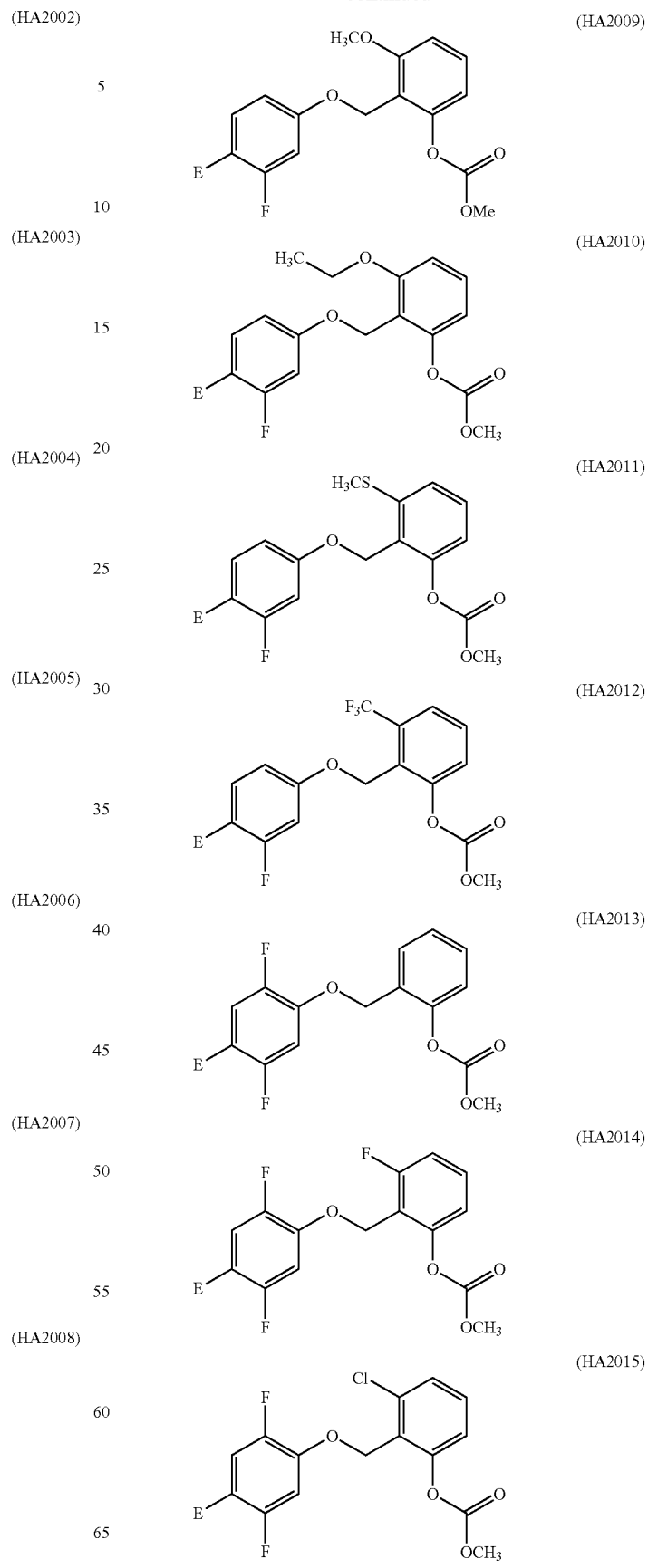

69
-continued
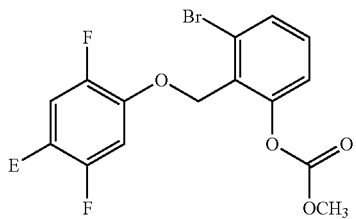
(HA2016)
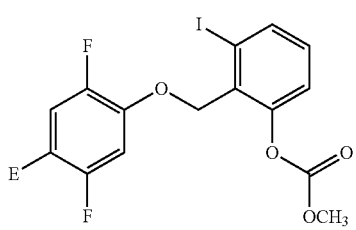
(HA2017)
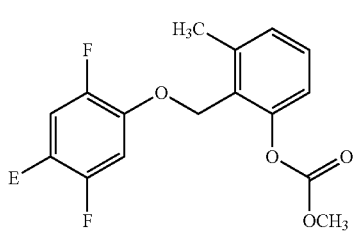
(HA2018)
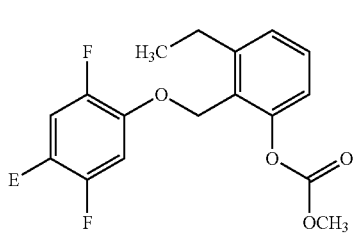
(HA2019)
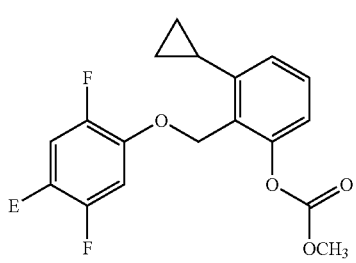
(HA2020)
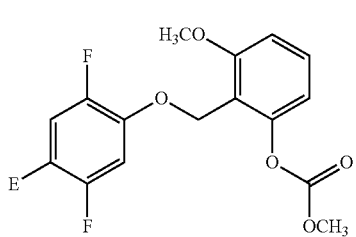
(HA2021)
70
-continued
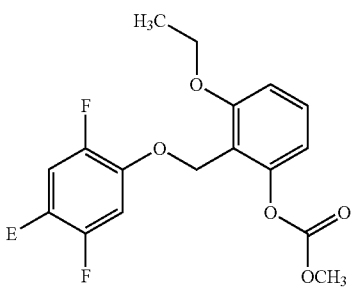
(HA2022)
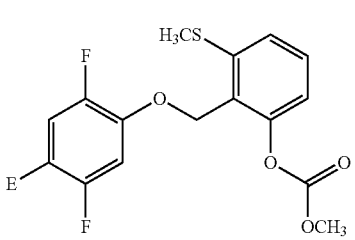
(HA2023)
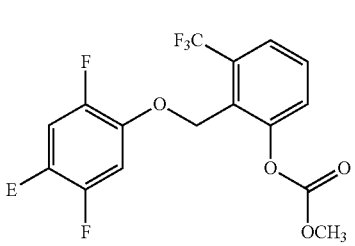
(HA2024)
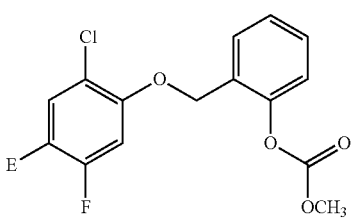
(HA2025)
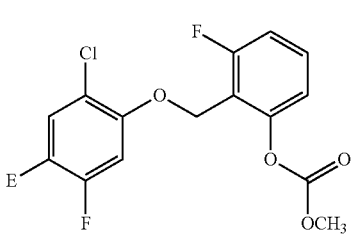
(HA2026)
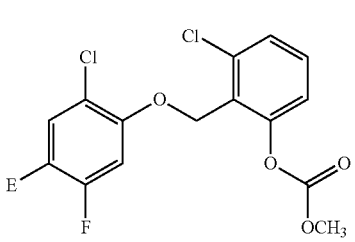
(HA2027)

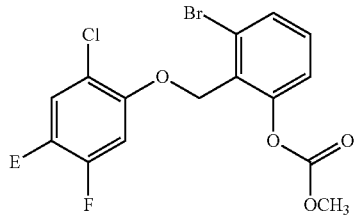
(HA2028)
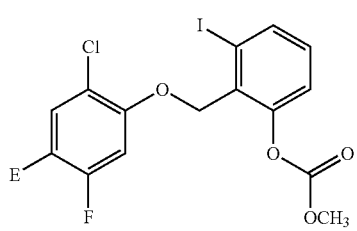
(HA2029)
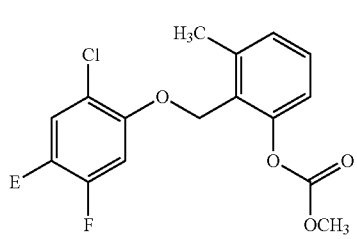
(HA2030)
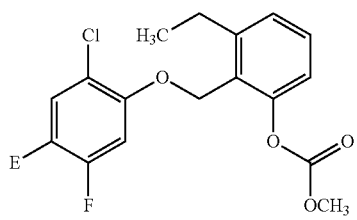
(HA2031)
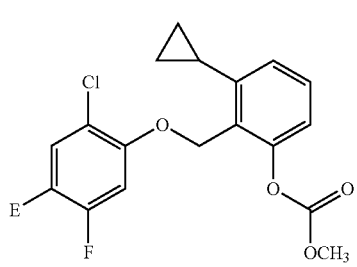
(HA2032)
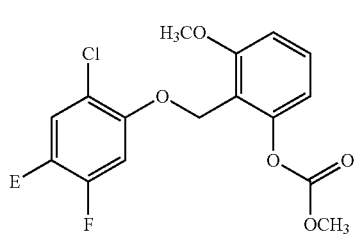
(HA2033)
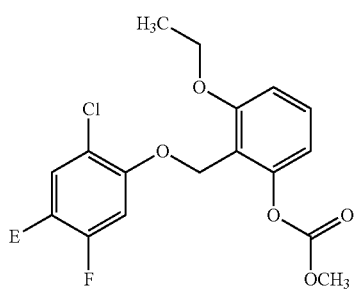
(HA2034)
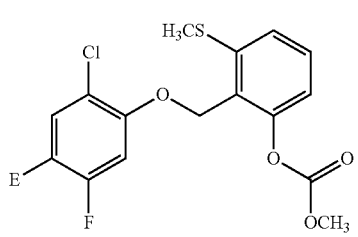
(HA2035)
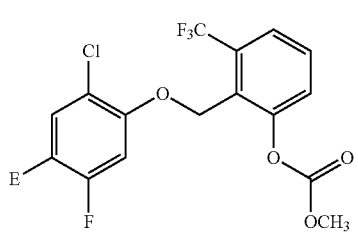
(HA2036)
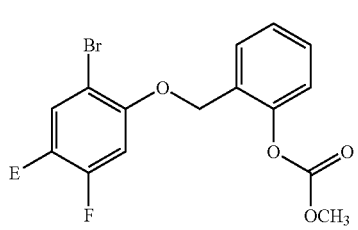
(HA2037)
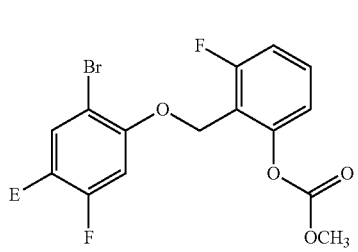
(HA2038)
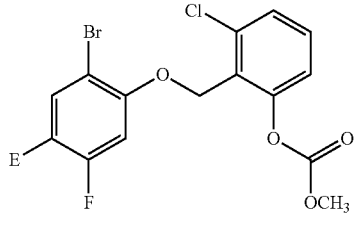
(HA2039)

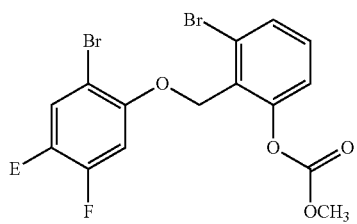
(HA2040)
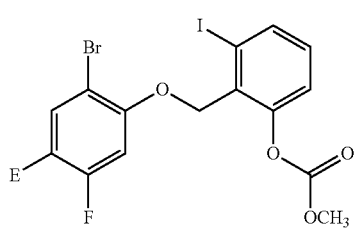
(HA2041)
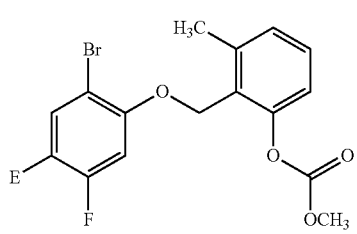
(HA2042)
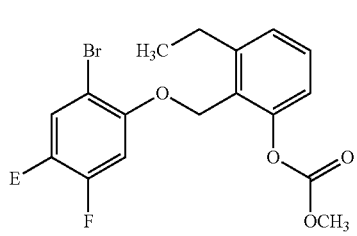
(HA2043)
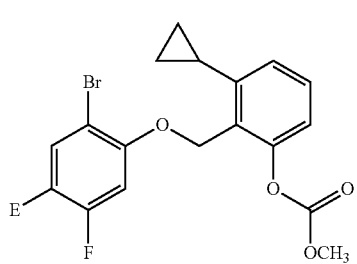
(HA2044)
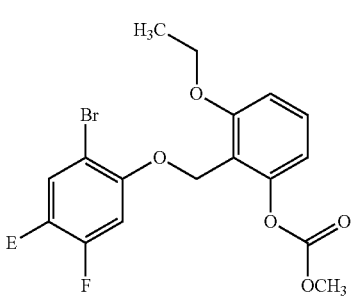
(HA2045)
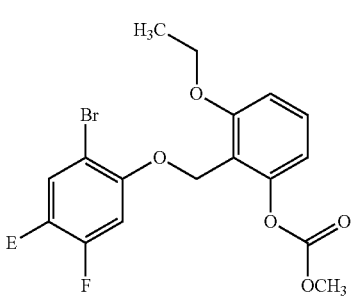
(HA2046)
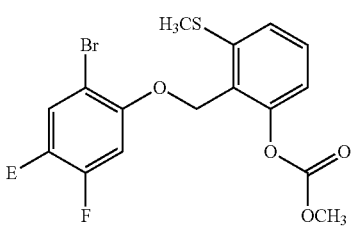
(HA2047)
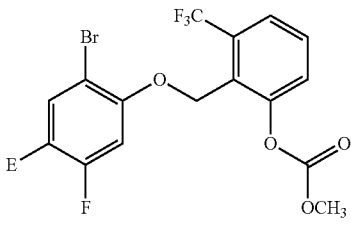
(HA2048)
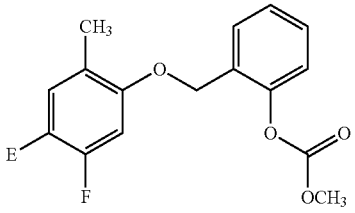
(HA2049)
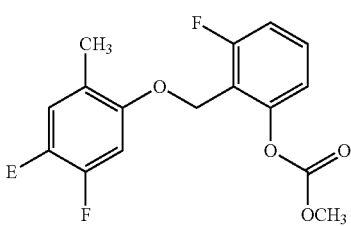
(HA2050)
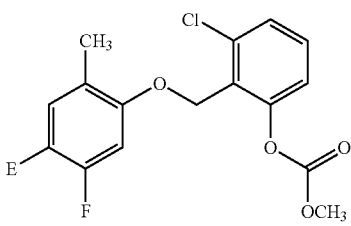
(HA2051)
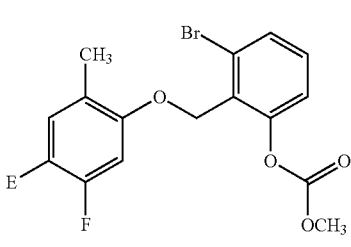
(HA2052)

-continued
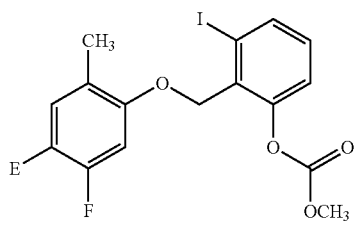
(HA2053)
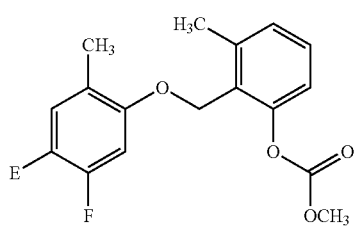
(HA2054)
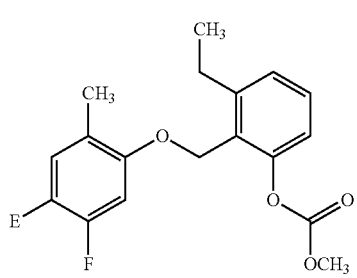
(HA2055)
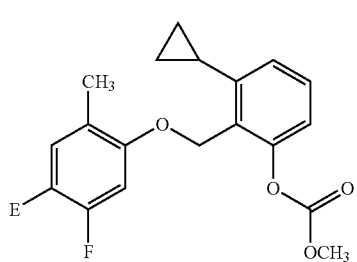
(HA2056)
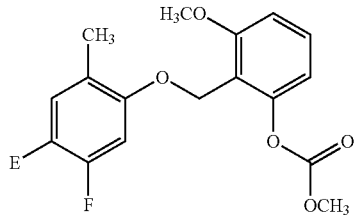
(HA2057)
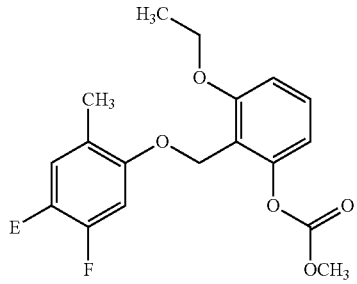
(HA2058)
-continued
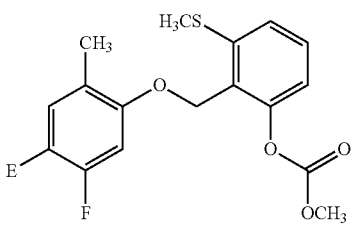
(HA2059)
(HA2060)
(HA2061)
(HA2062)
(HA2063)
(HA2064)
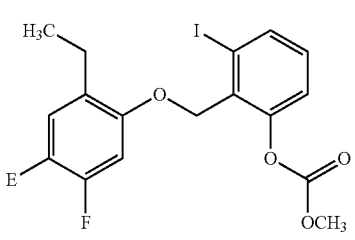
(HA2065)

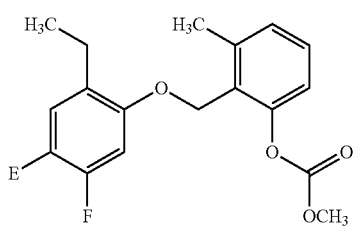
(HA2066)
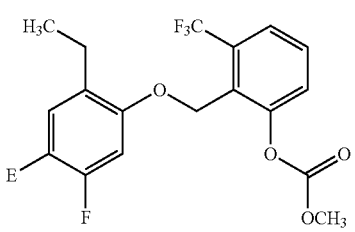
(HA2072)
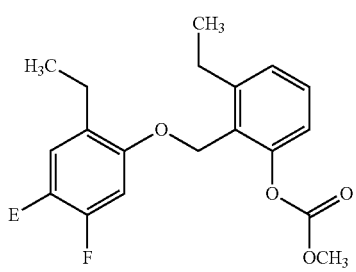
(HA2067)
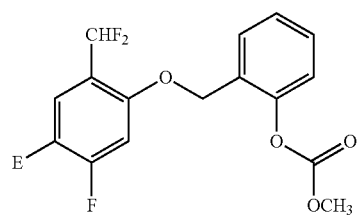
(HA2073)
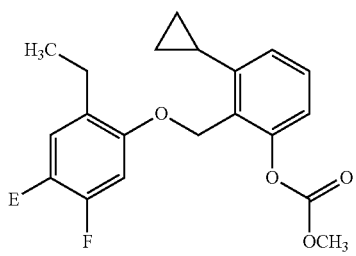
(HA2068)
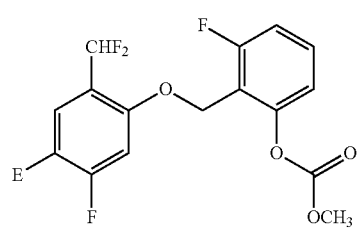
(HA2074)
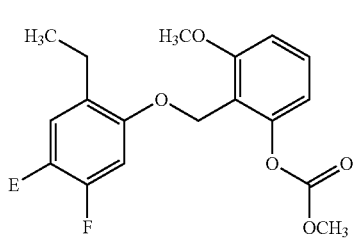
(HA2069)
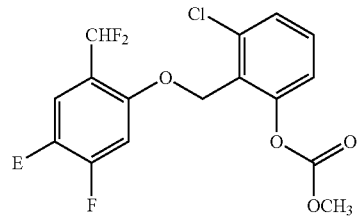
(HA2075)
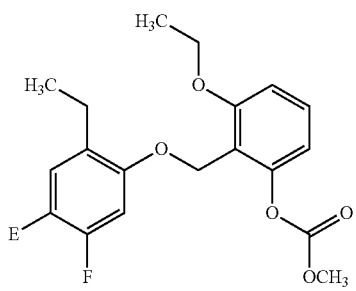
(HA2070)
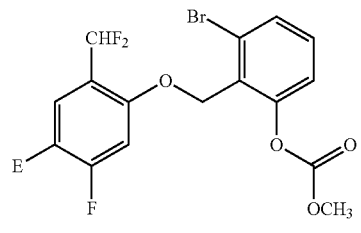
(HA2076)
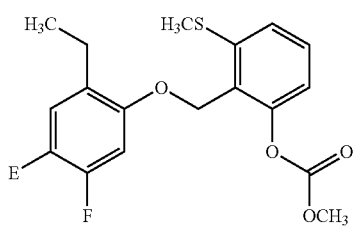
(HA2071)
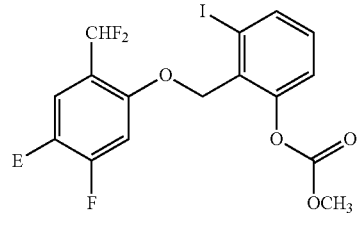
(HA2077)

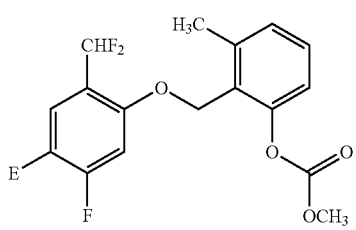
(HA2078)
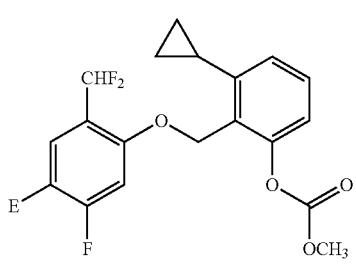
(HA2079)
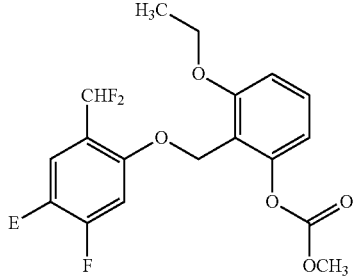
(HA2080)
(HA2081)
(HA2082)
(HA2083)
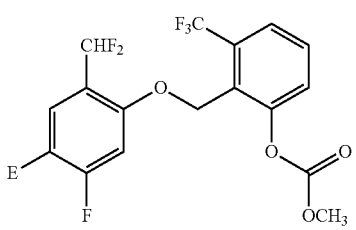
(HA2084)
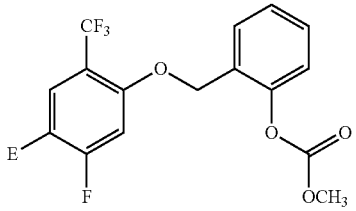
(HA2085)
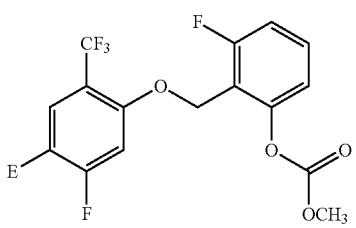
(HA2086)
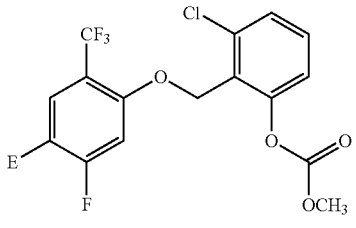
(HA2087)
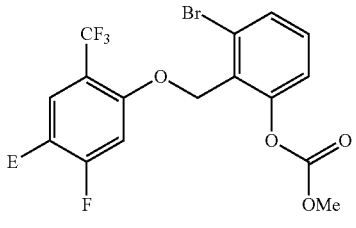
(HA2088)
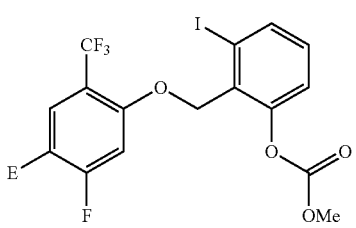
(HA2089)
(HA2090)

(HA2091) 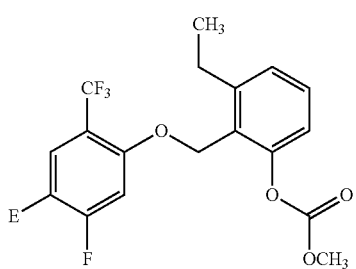
(HA2092) 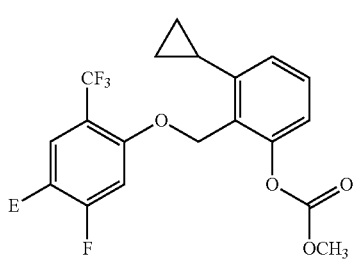
(HA2093) 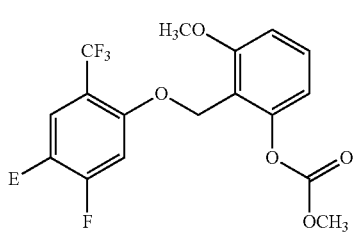
(HA2094) 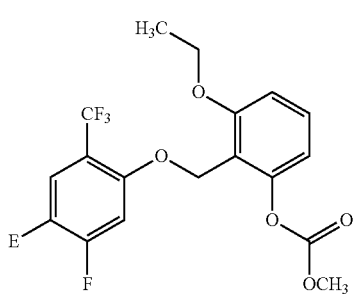
(HA2095) 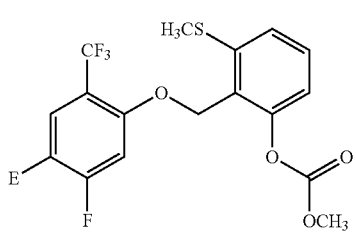
(HA2096) 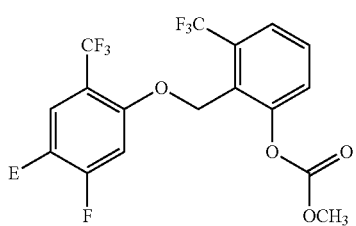
(HA2097) 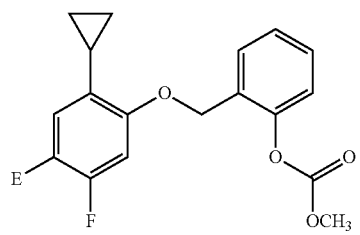
(HA2098) 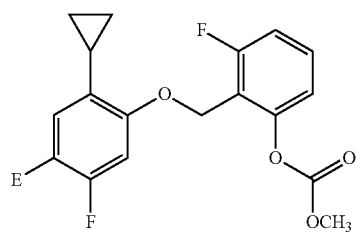
(HA2099) 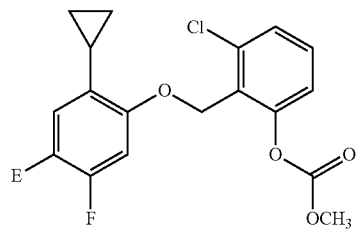
(HA2100) 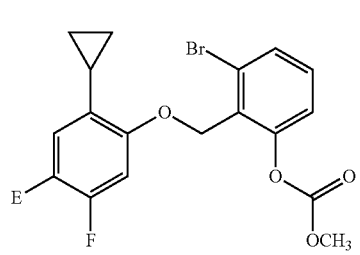
(HA2101) 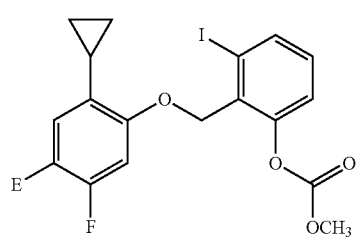
(HA2102) 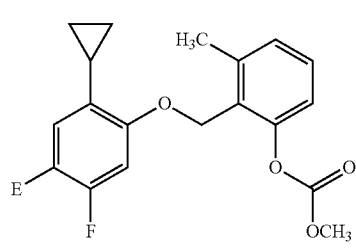

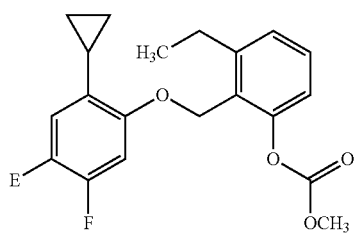 (HA2103)
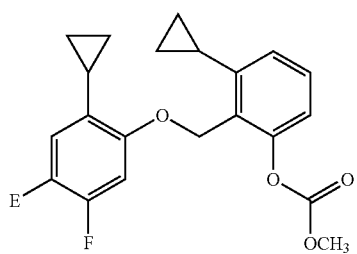 (HA2104)
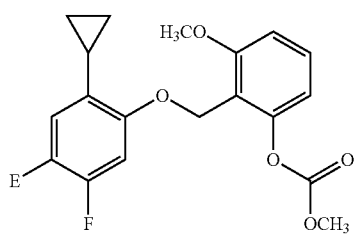 (HA2105)
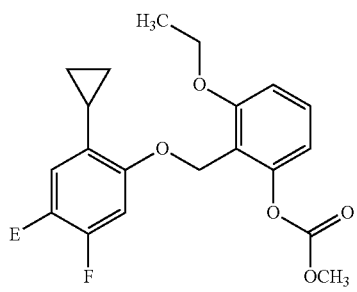 (HA2106)
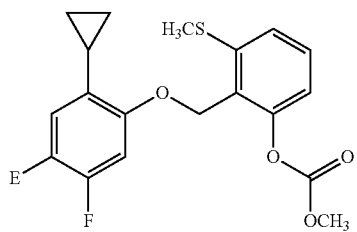 (HA2107)
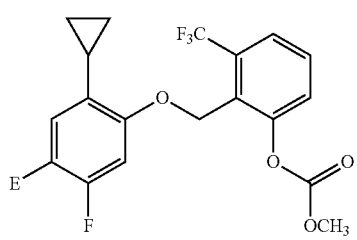 (HA2108)
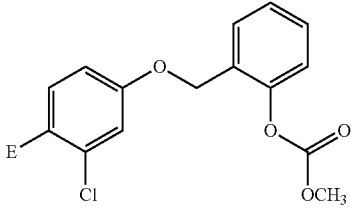 (HA3001)
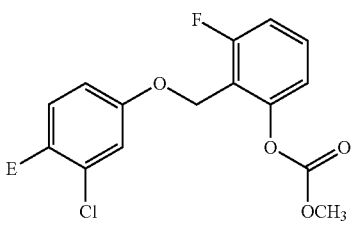 (HA3002)
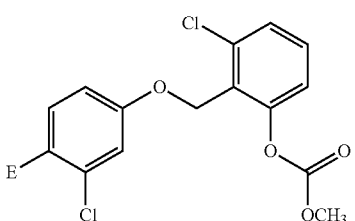 (HA3003)
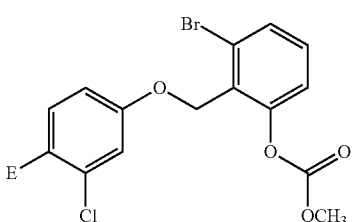 (HA3004)
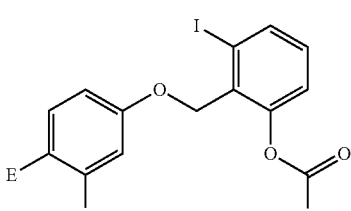 (HA3005)
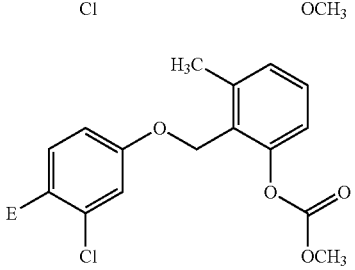 (HA3006)
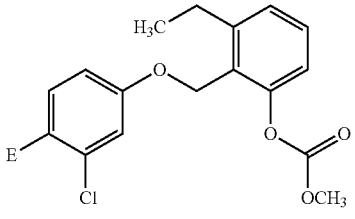 (HA3007)

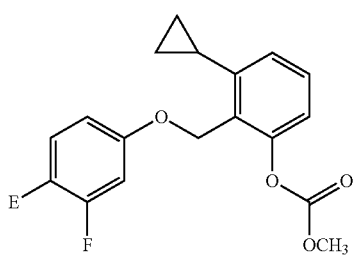
(HA3008)
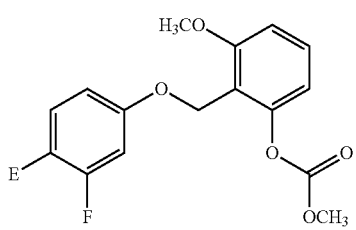
(HA3009)
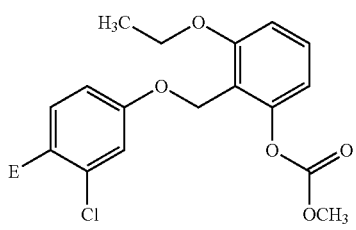
(HA3010)
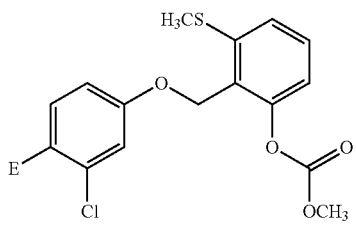
(HA3011)
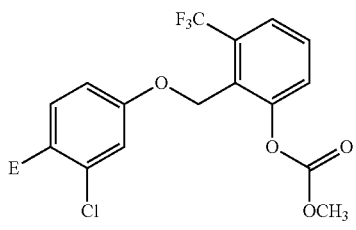
(HA3012)
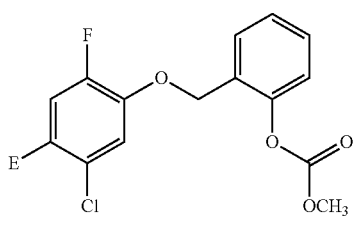
(HA3013)
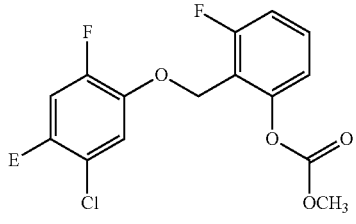
(HA3014)
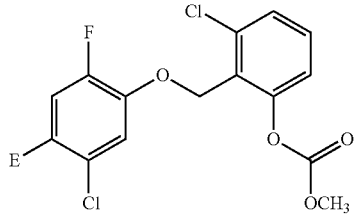
(HA3015)
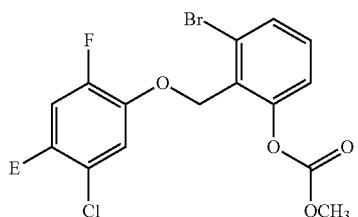
(HA3016)
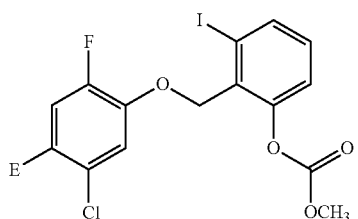
(HA3017)
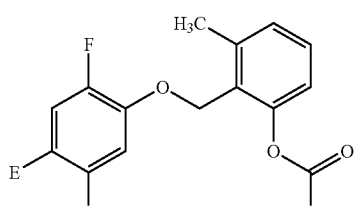
(HA3018)
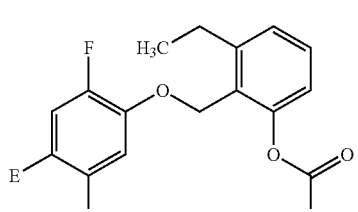
(HA3019)
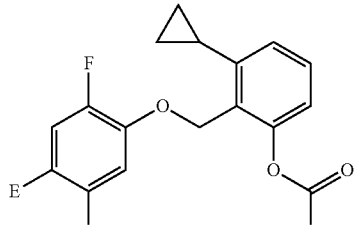
(HA3020)
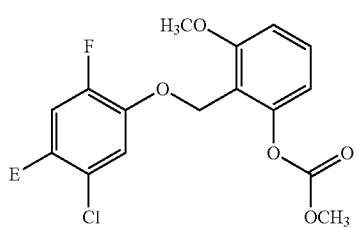
(HA3021)

(HA3022)
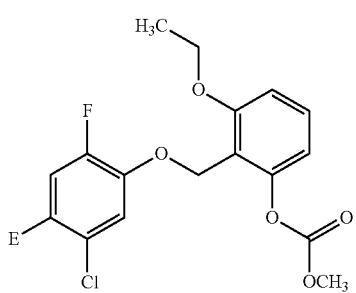
(HA3023)
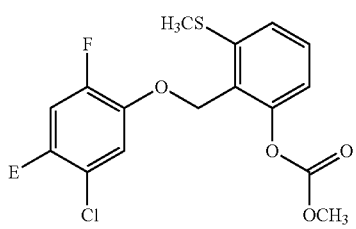
(HA3024)
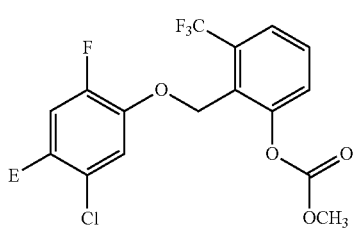
(HA3025)
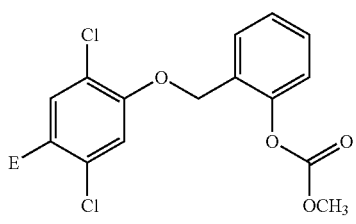
(HA3026)
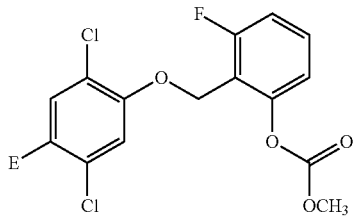
(HA3027)
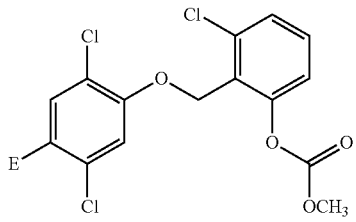
(HA3028)
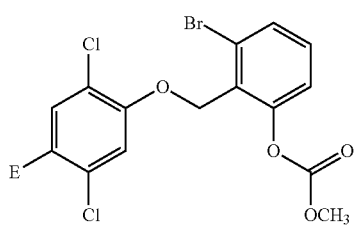
(HA3029)
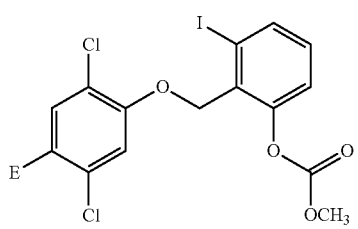
(HA3030)
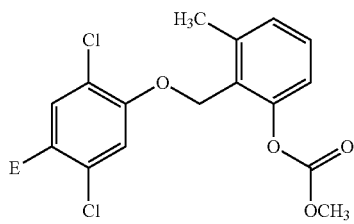
(HA3031)
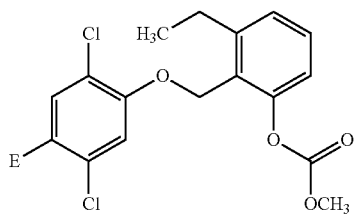
(HA3032)
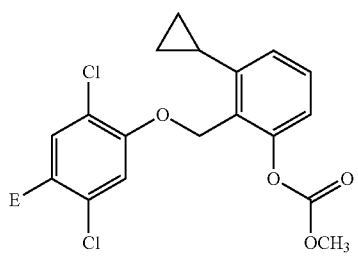
(HA3033)
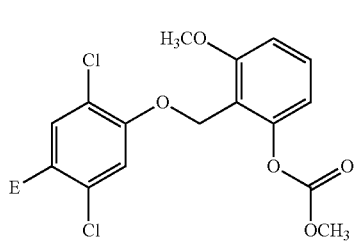

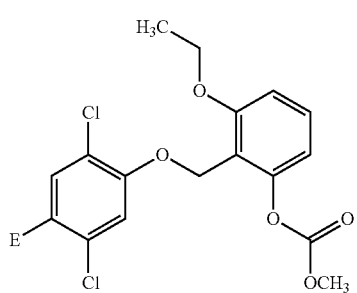
(HA3034)
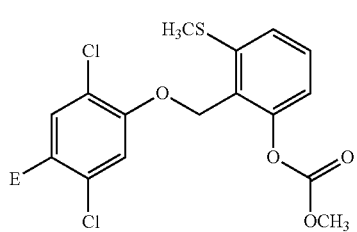
(HA3035)
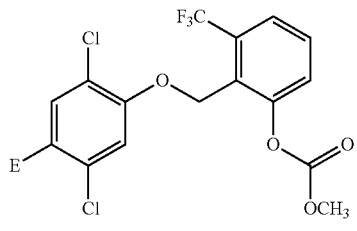
(HA3036)
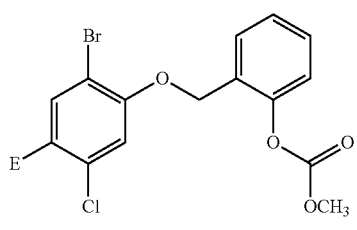
(HA3037)
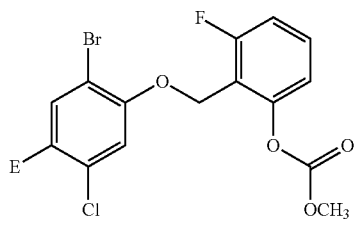
(HA3038)
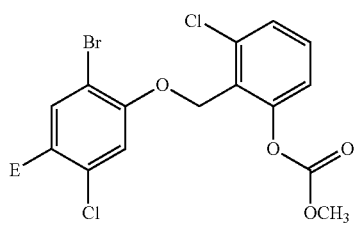
(HA3039)
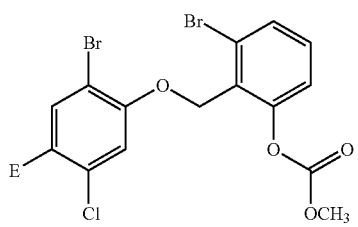
(HA3040)
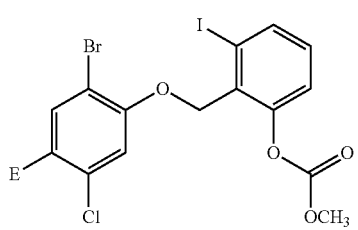
(HA3041)
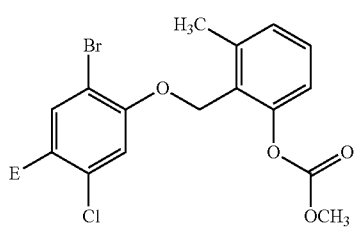
(HA3042)
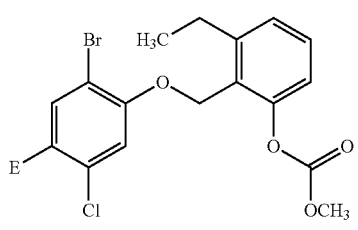
(HA3043)
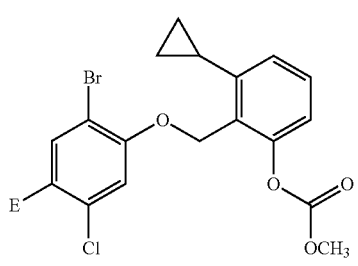
(HA3044)
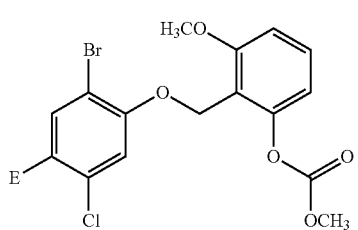
(HA3045)

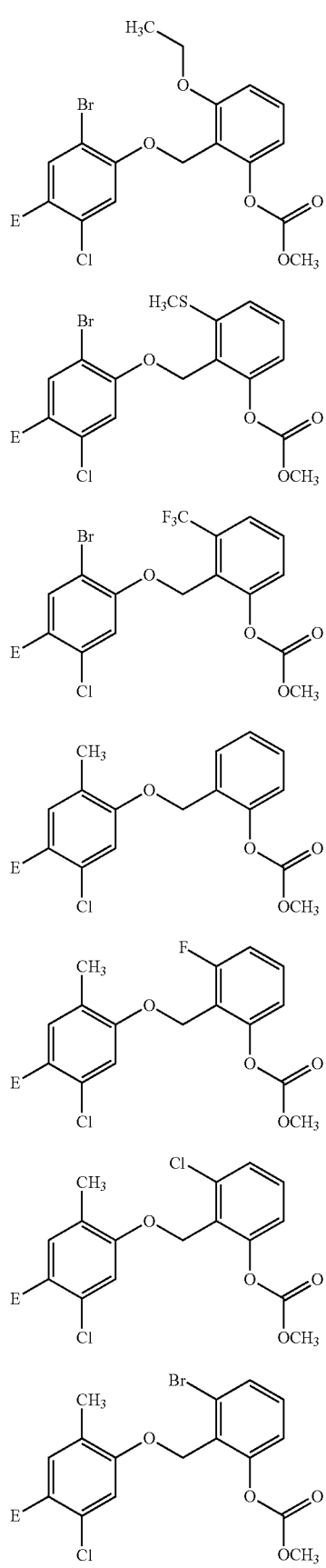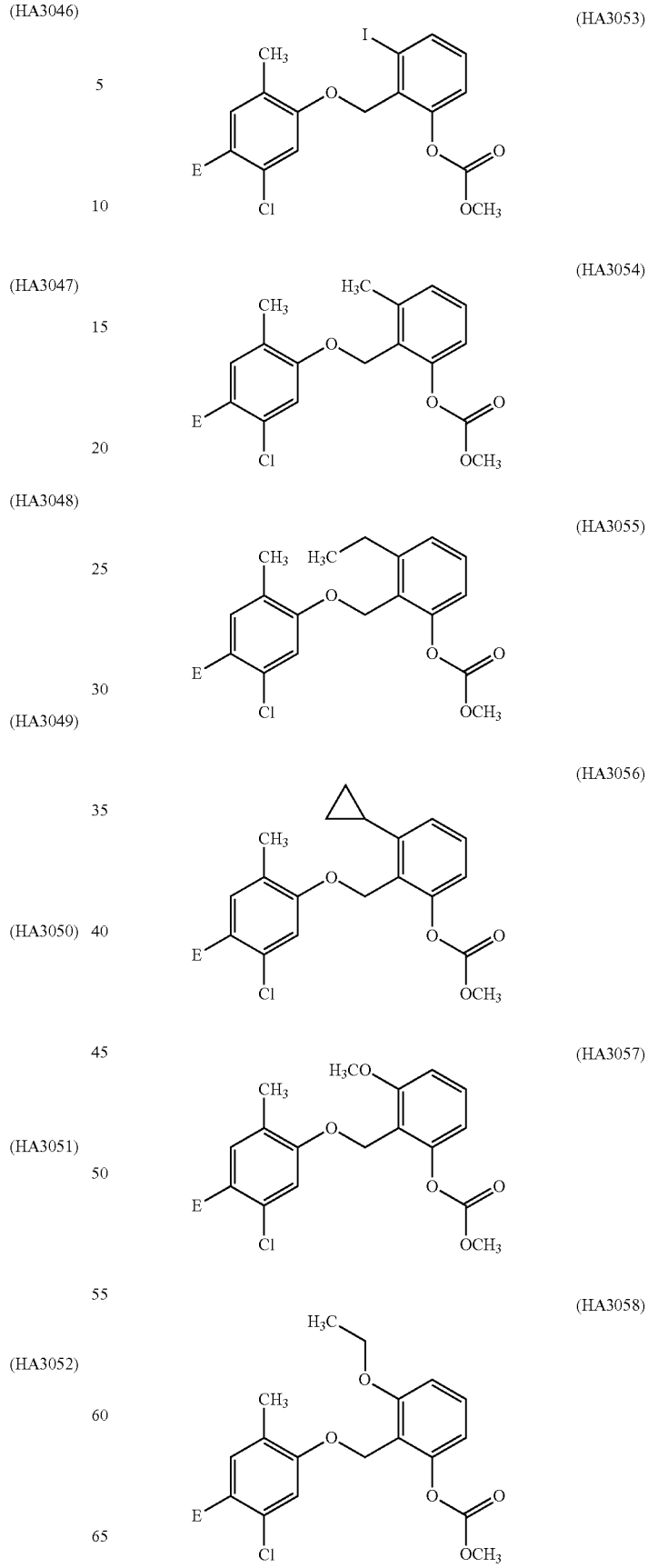

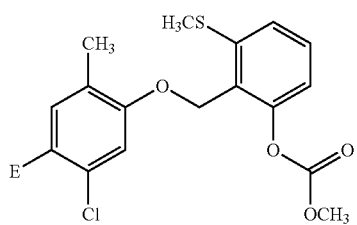
(HA3059)
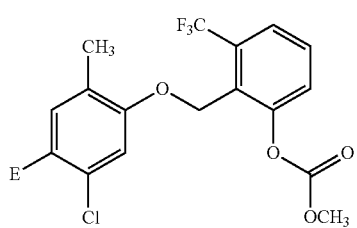
(HA3060)
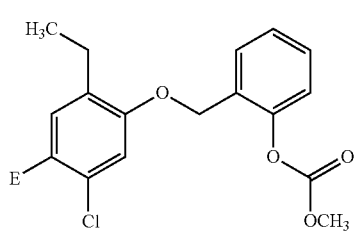
(HA3061)
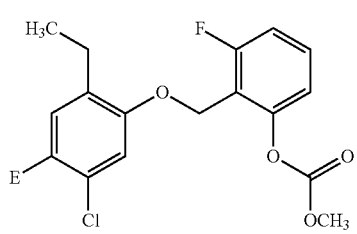
(HA3062)
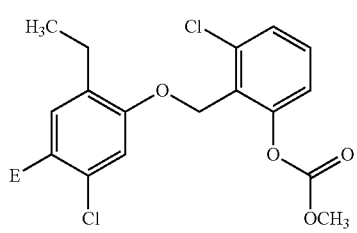
(HA3063)
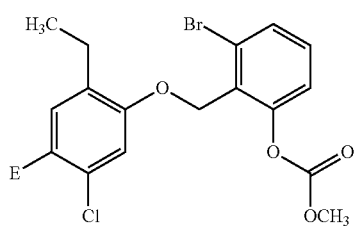
(HA3064)
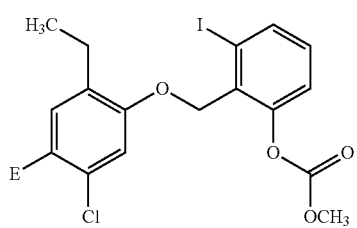
(HA3065)
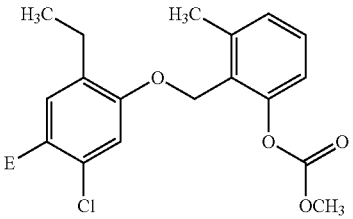
(HA3066)
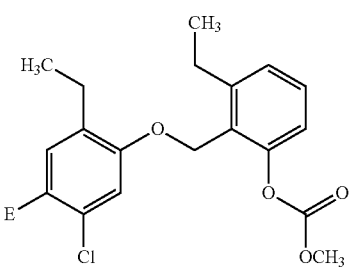
(HA3067)
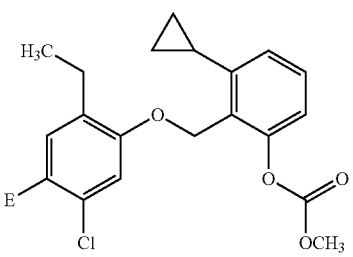
(HA3068)
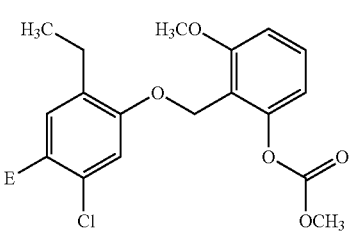
(HA3069)
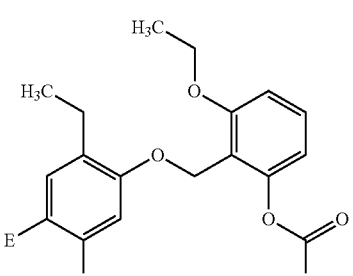
(HA3070)
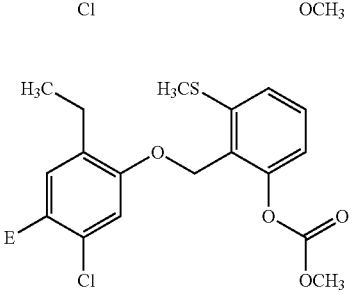
(HA3071)

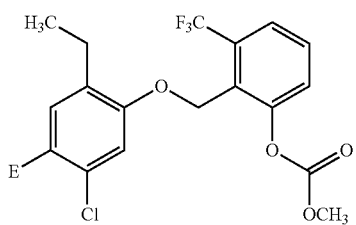
(HA3072)
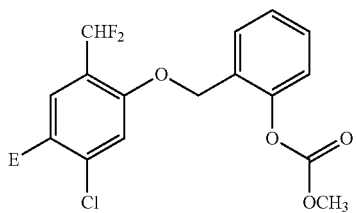
(HA3073)
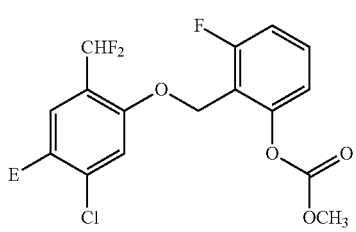
(HA3074)
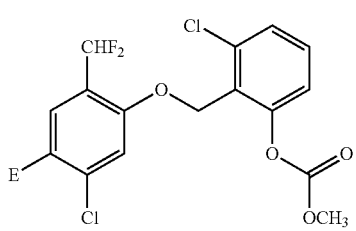
(HA3075)
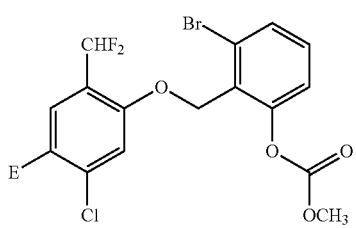
(HA3076)
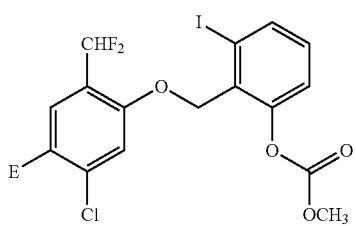
(HA3077)
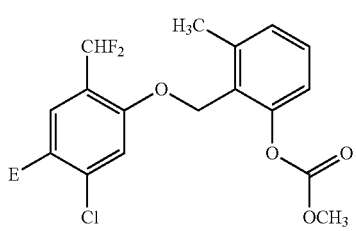
(HA3078)
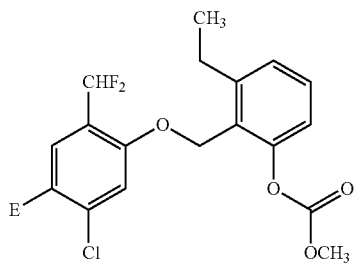
(HA3079)
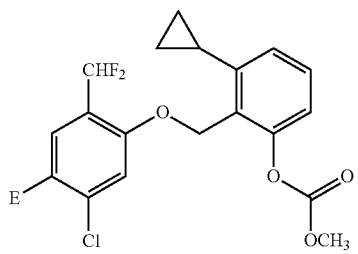
(HA3080)
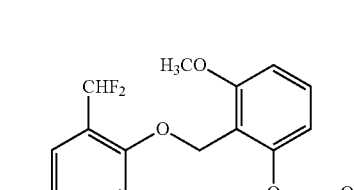
(HA3081)
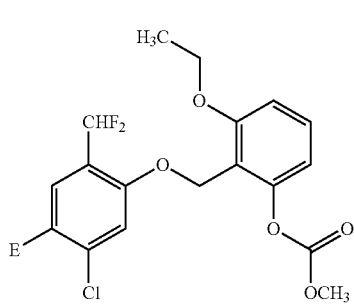
(HA3082)
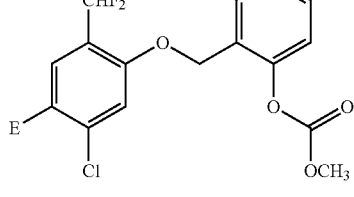
(HA3083)
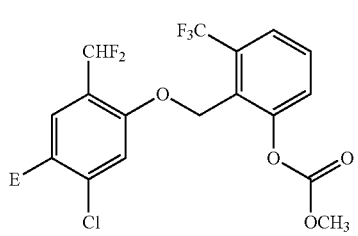
(HA3084)

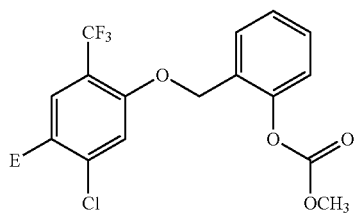
(HA3085)
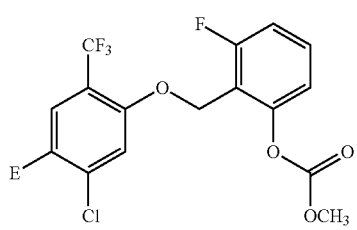
(HA3086)
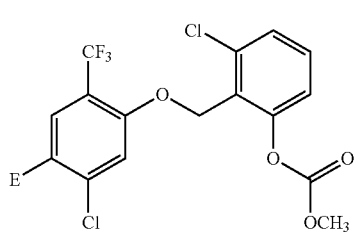
(HA3087)
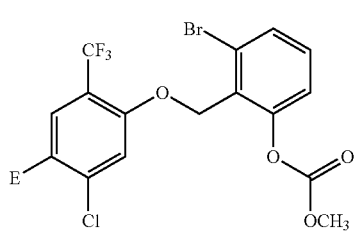
(HA3088)
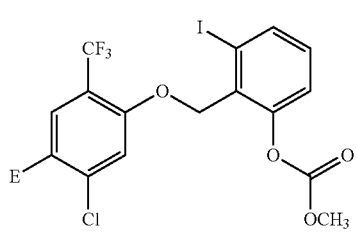
(HA3089)
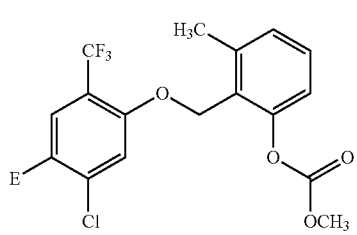
(HA3090)
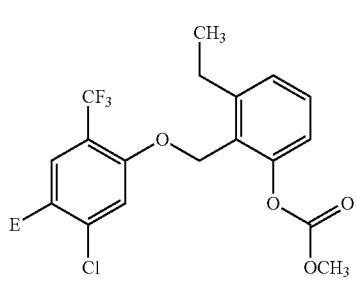
(HA3091)
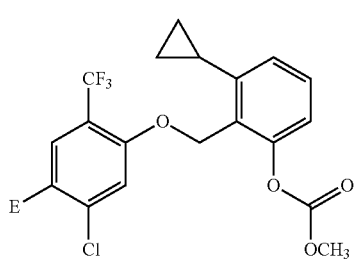
(HA3092)
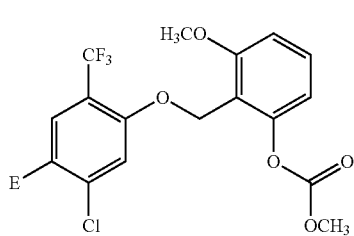
(HA3093)
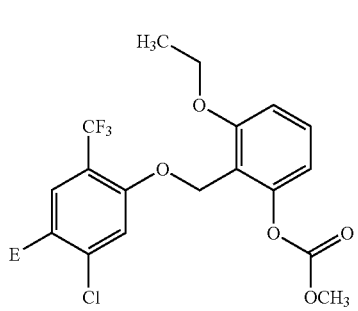
(HA3094)
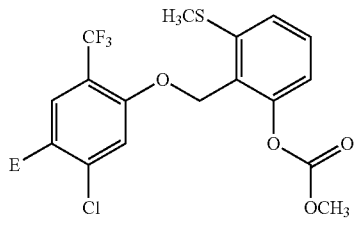
(HA3095)
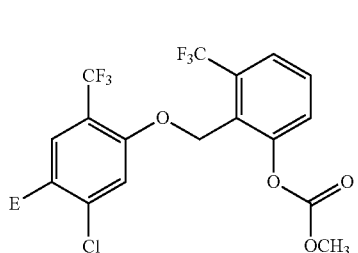
(HA3096)
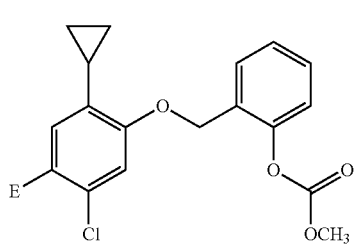
(HA3097)

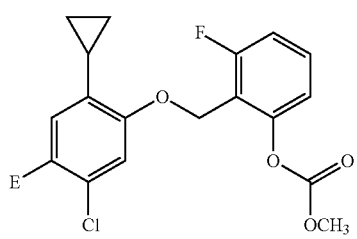
(HA3098)
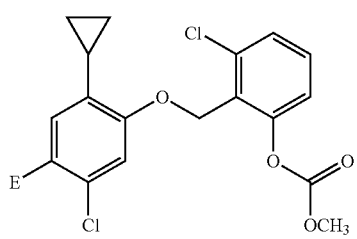
(HA3099)
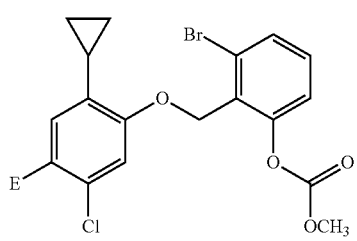
(HA3100)
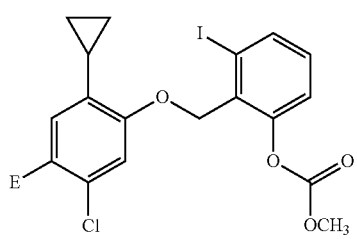
(HA3101)
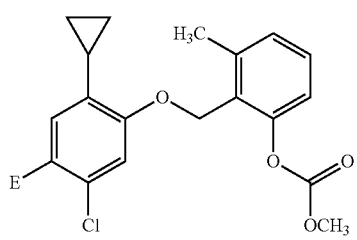
(HA3102)
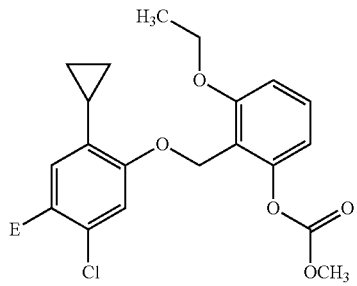
(HA3106)
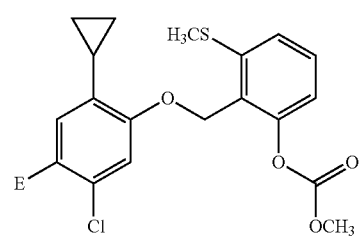
(HA3107)
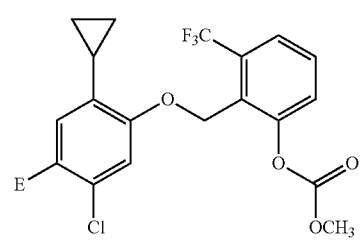
(HA3108)
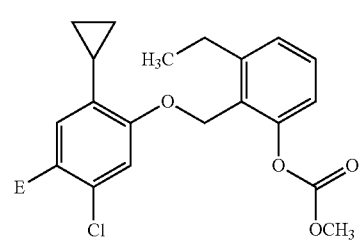
(HA3103)
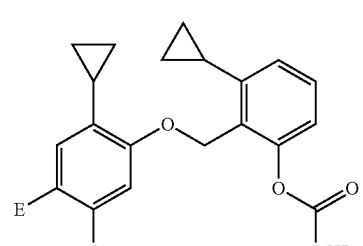
(HA3104)
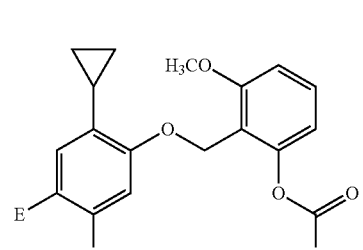
(HA3105)
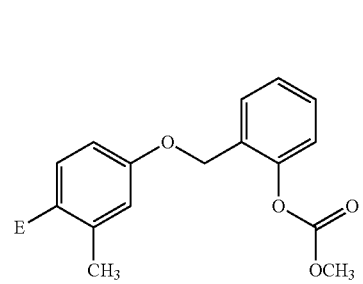
(HA4001)

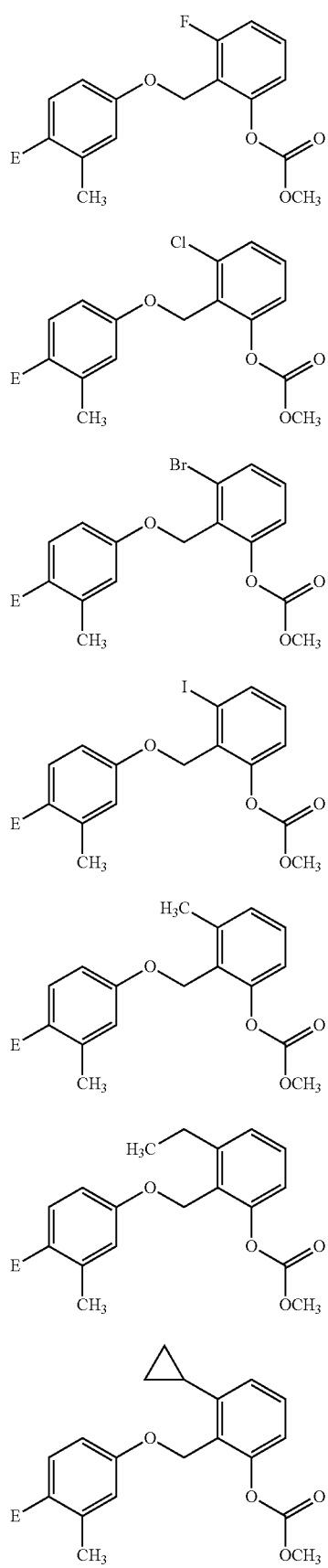
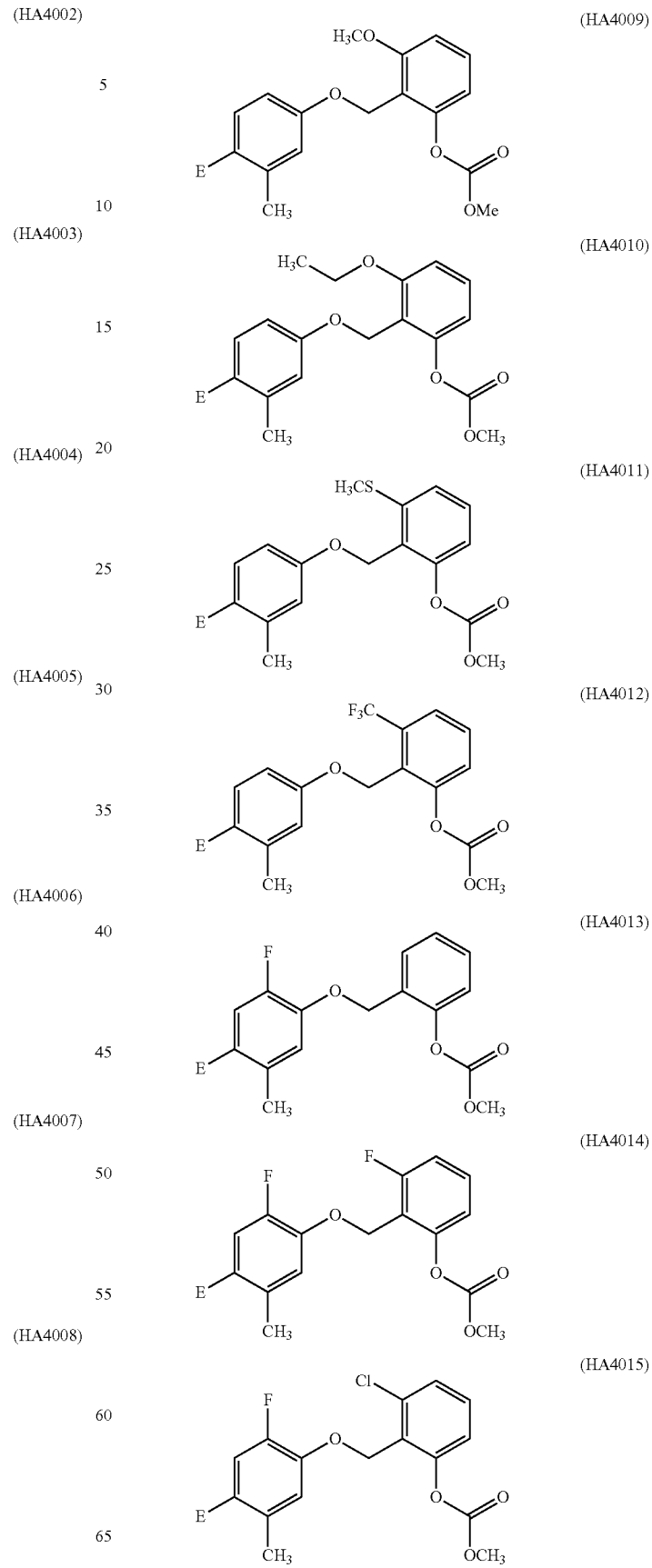

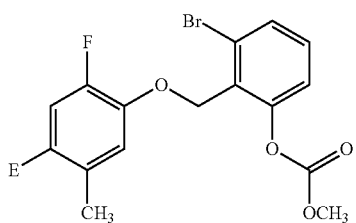
(HA4016)
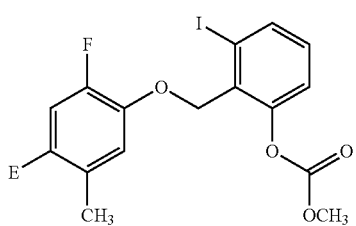
(HA4017)
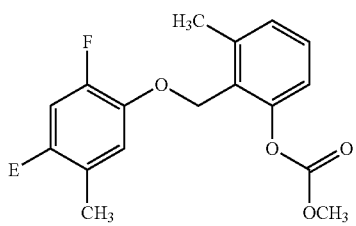
(HA4018)
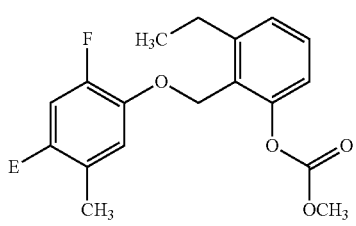
(HA4019)
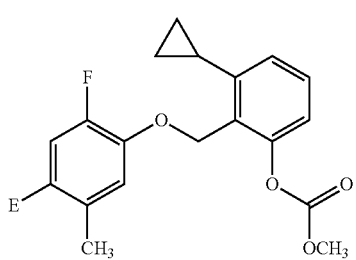
(HA4020)
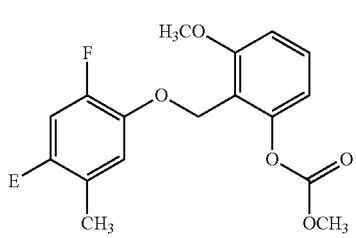
(HA4021)
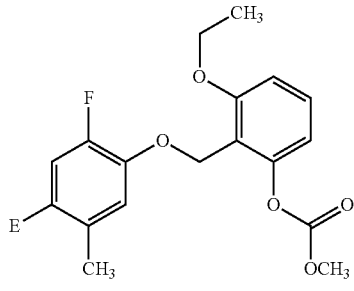
(HA4022)
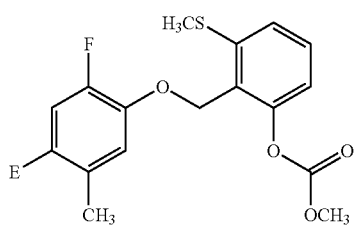
(HA4023)
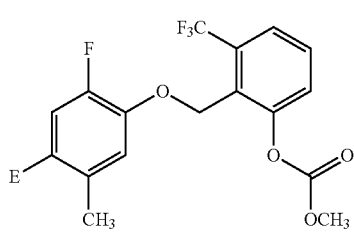
(HA4024)
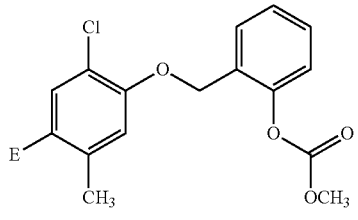
(HA4025)
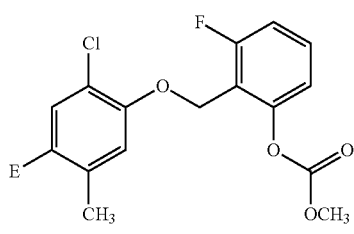
(HA4026)
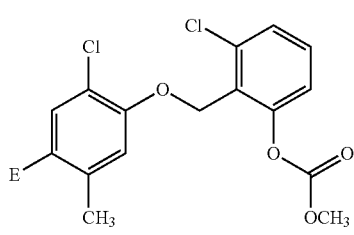
(HA4027)
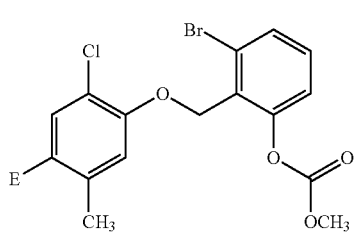
(HA4028)

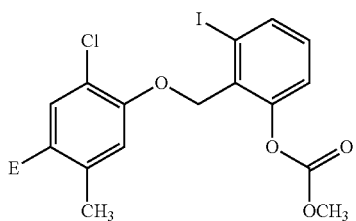
(HA4029)
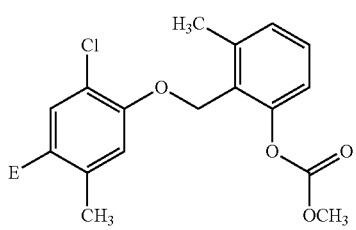
(HA4030)
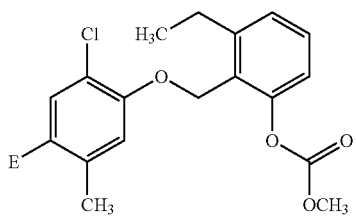
(HA4031)
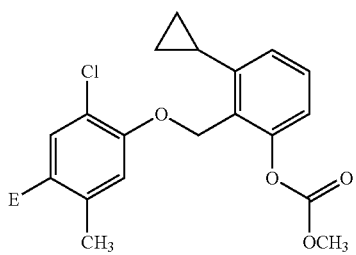
(HA4032)
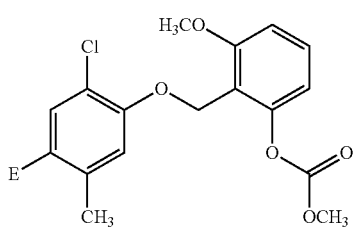
(HA4033)
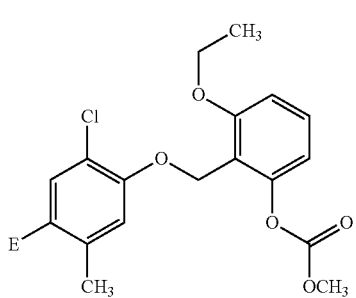
(HA4034)
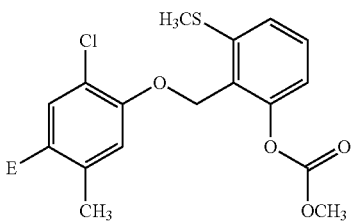
(HA4035)
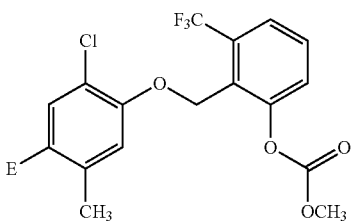
(HA4036)
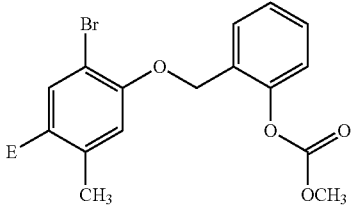
(HA4037)
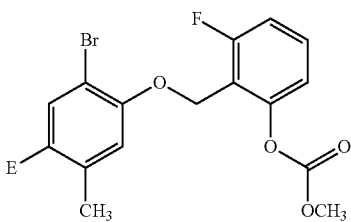
(HA4038)
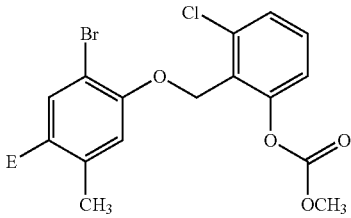
(HA4039)
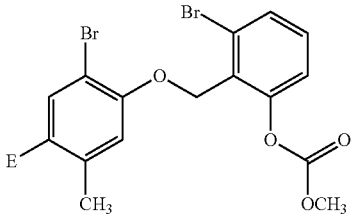
(HA4040)
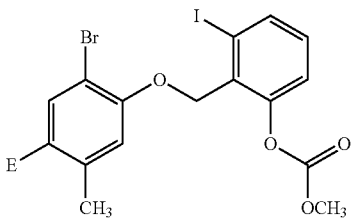
(HA4041)

(HA4042) 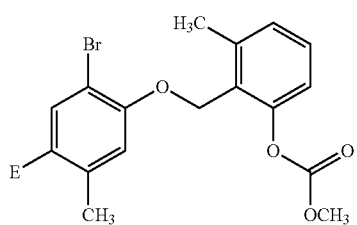
(HA4043) 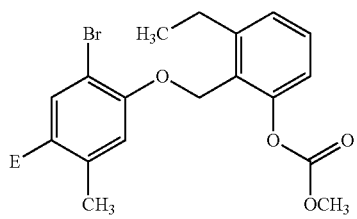
(HA4044) 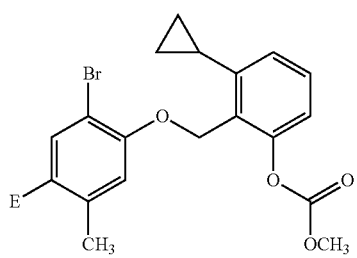
(HA4045) 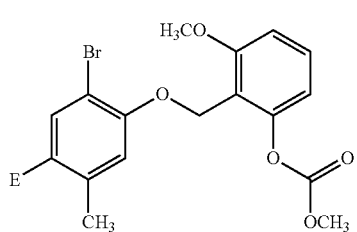
(HA4046) 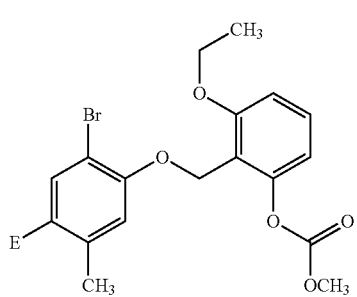
(HA4047) 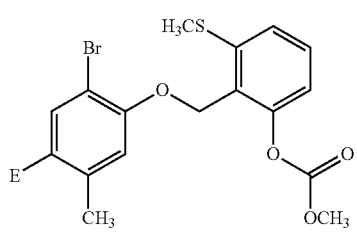
(HA4048) 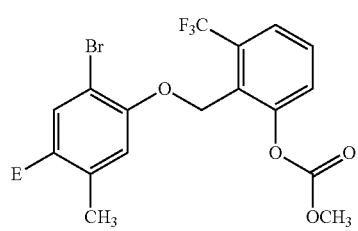
(HA4049) 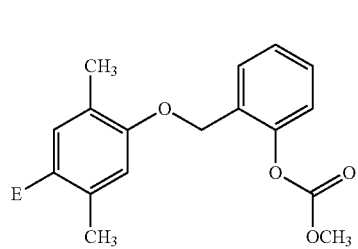
(HA4050) 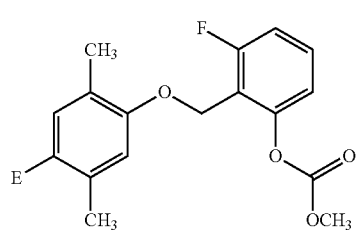
(HA4051) 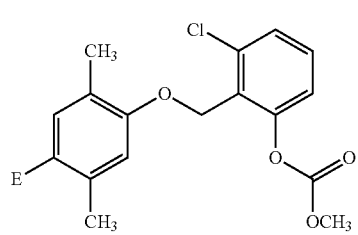
(HA4052) 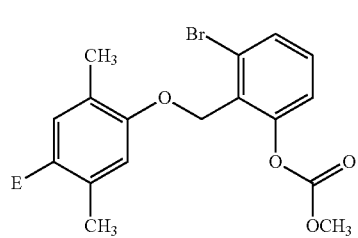
(HA4053) 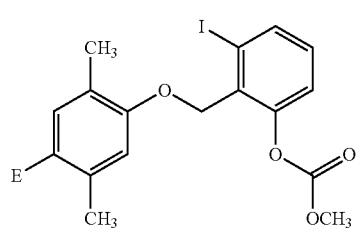

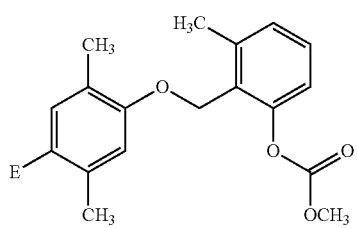
(HA4054)
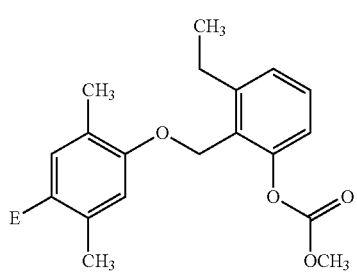
(HA4055)
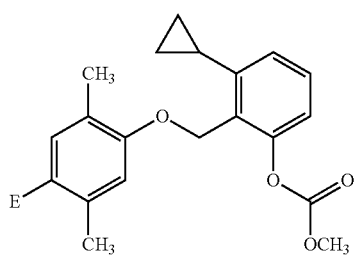
(HA4056)
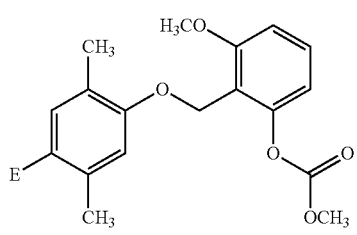
(HA4057)
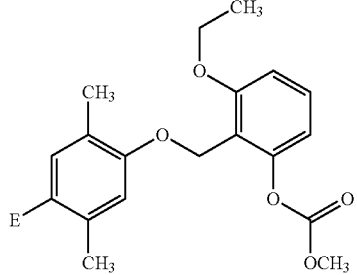
(HA4058)
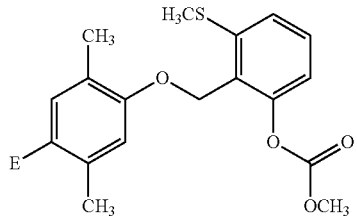
(HA4059)
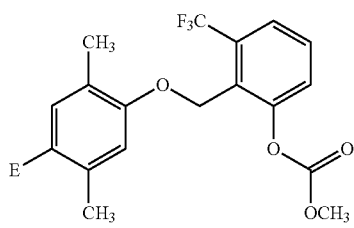
(HA4060)
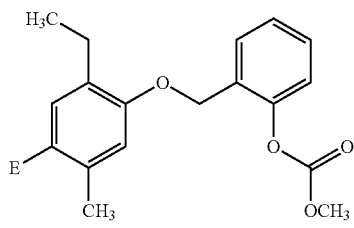
(HA4061)
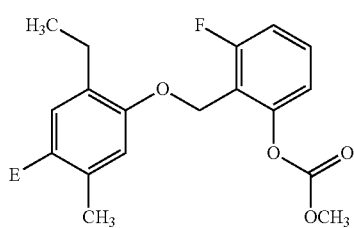
(HA4062)
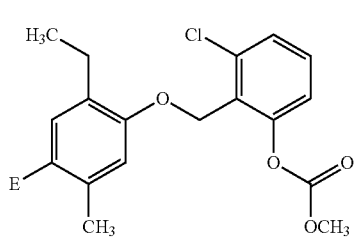
(HA4063)
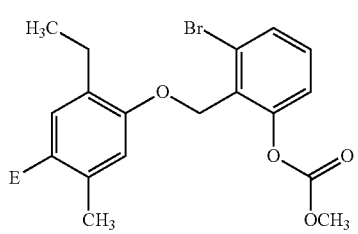
(HA4064)
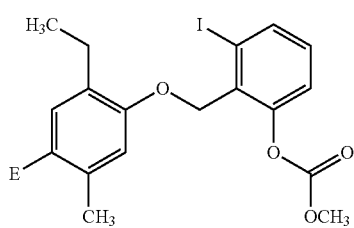
(HA4065)
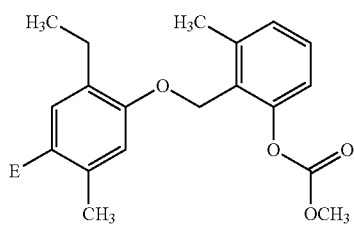
(HA4066)

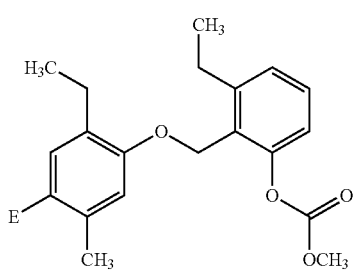
(HA4067)
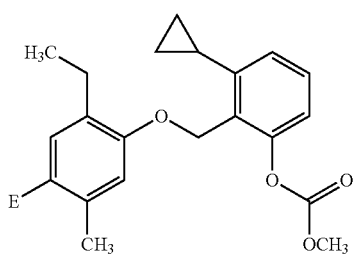
(HA4068)
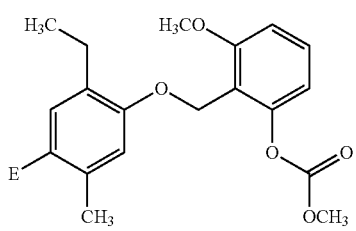
(HA4069)
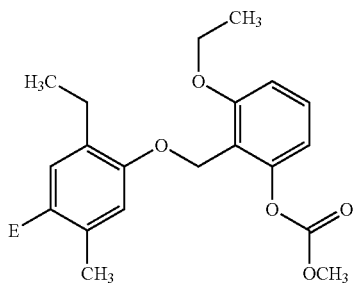
(HA4070)
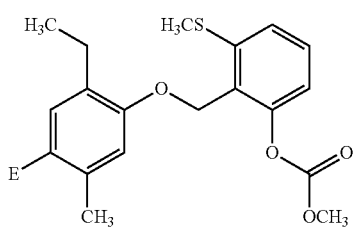
(HA4071)
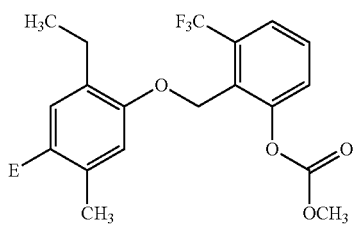
(HA4072)
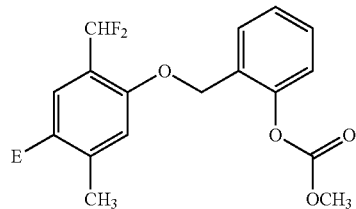
(HA4073)
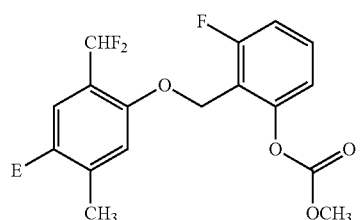
(HA4074)
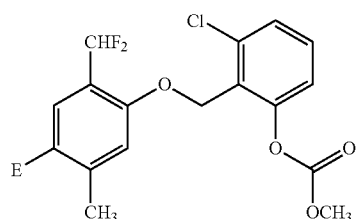
(HA4075)
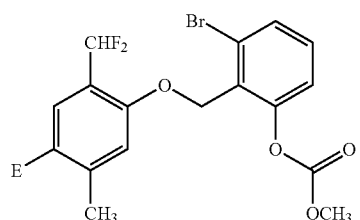
(HA4076)
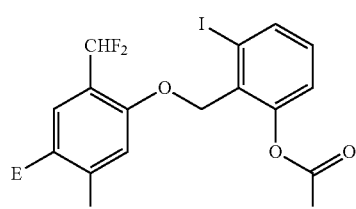
(HA4077)
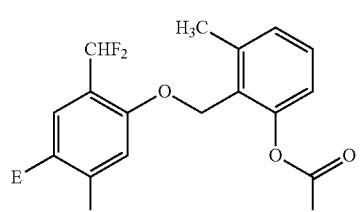
(HA4078)
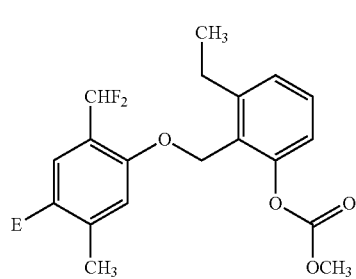
(HA4079)

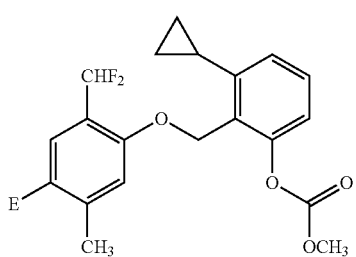 (HA4080)
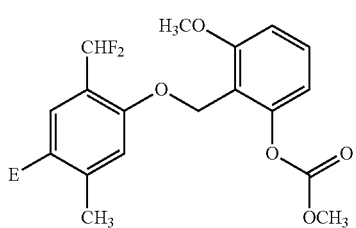 (HA4081)
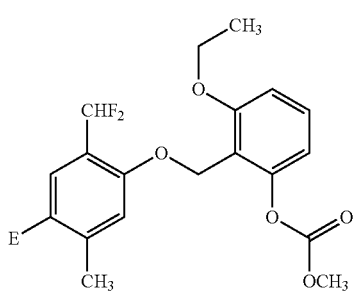 (HA4082)
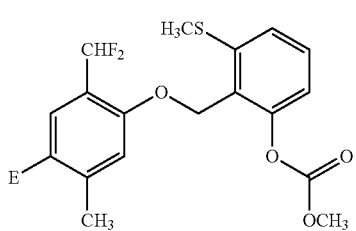 (HA4083)
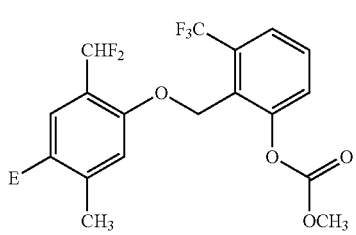 (HA4084)
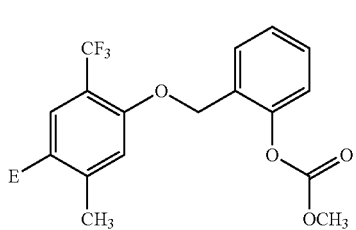 (HA4085)
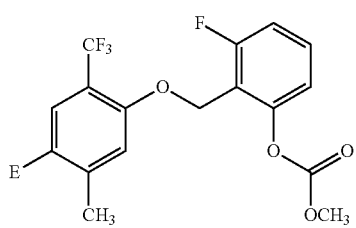 (HA4086)
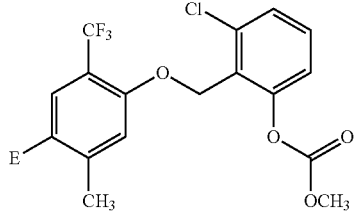 (HA4087)
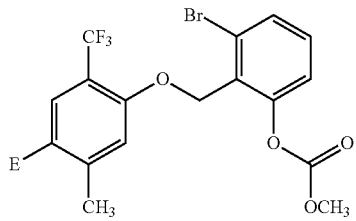 (HA4088)
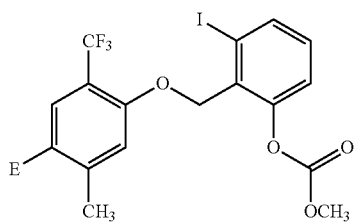 (HA4089)
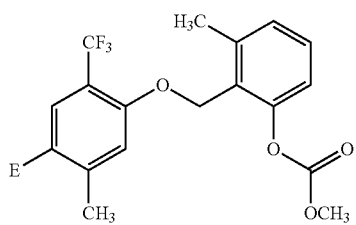 (HA4090)
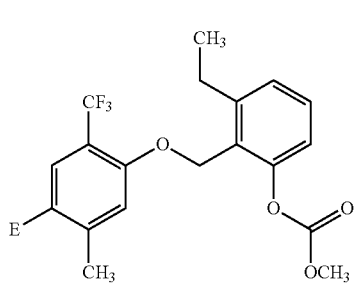 (HA4091)

| | |
|---|---|
| (HA4092) 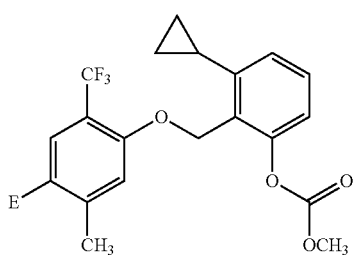 | (HA4098) 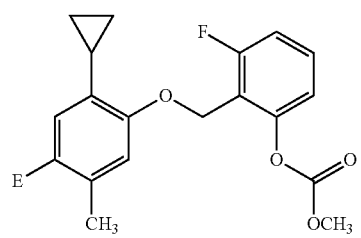 |
| (HA4093) 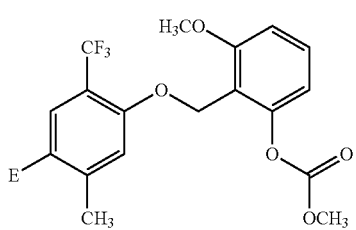 | (HA4099) 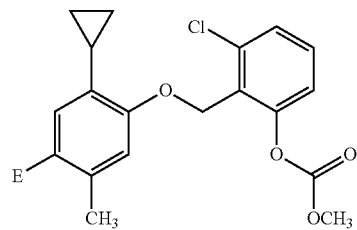 |
| (HA4094) 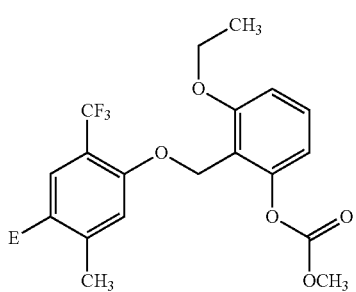 | (HA4100) 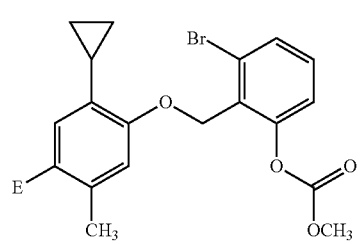 |
| (HA4095) 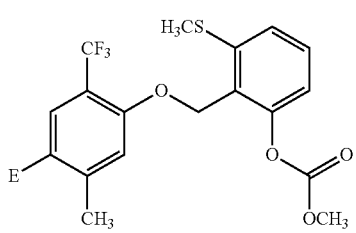 | (HA4101) 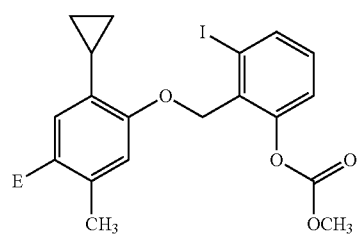 |
| (HA4096) 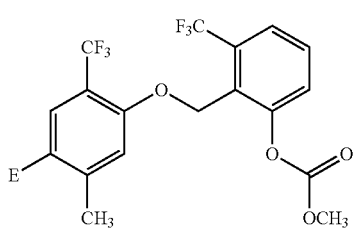 | (HA4102) 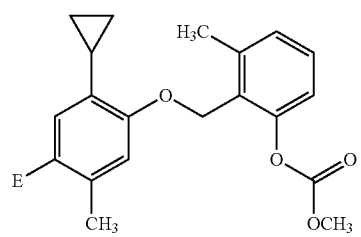 |
| (HA4097) 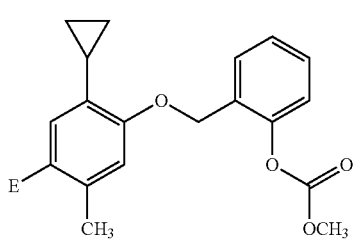 | (HA4103) 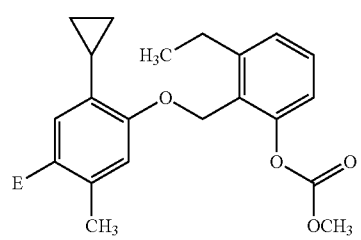 |

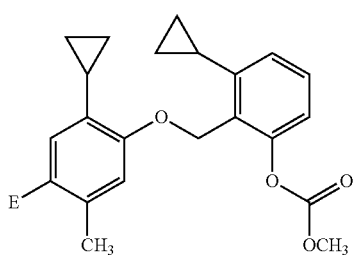
(HA4104)
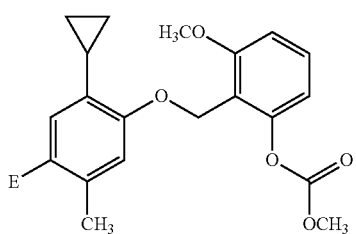
(HA4105)
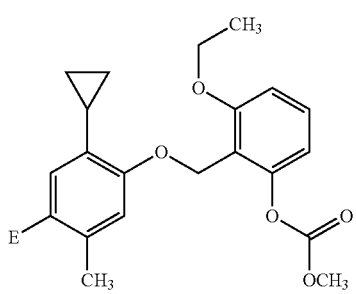
(HA4106)
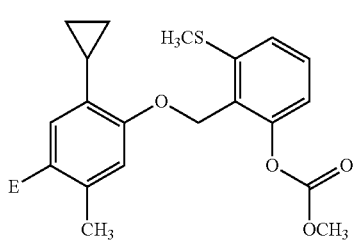
(HA4107)
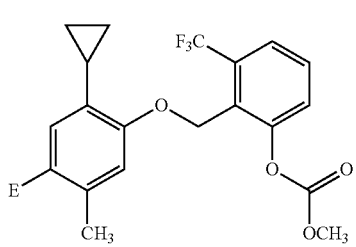
(HA4108)
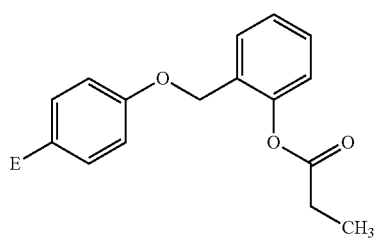
(HB1001)
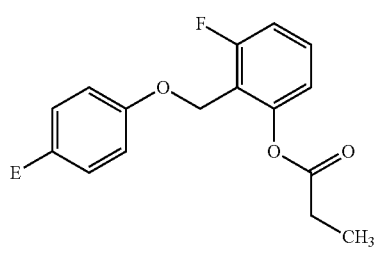
(HB1002)
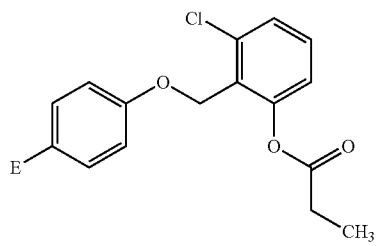
(HB1003)
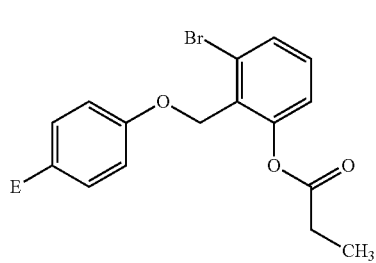
(HB1004)
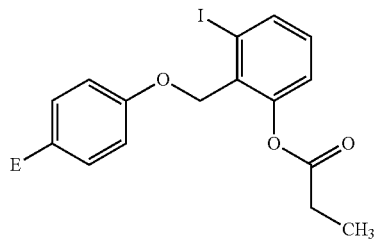
(HB1005)
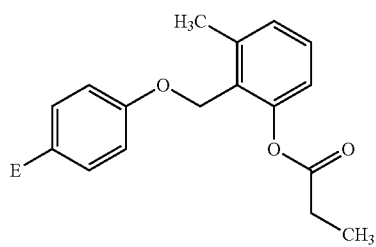
(HB1006)
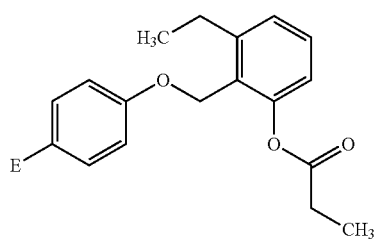
(HB1007)

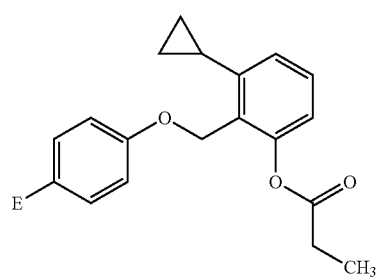
(HB1008)
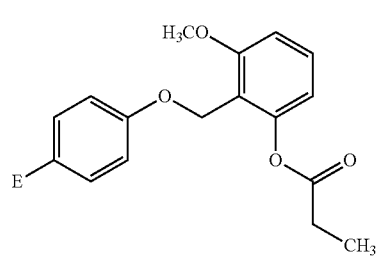
(HB1009)
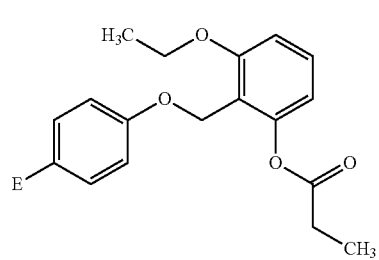
(HB1010)
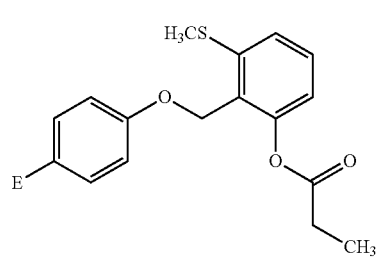
(HB1011)
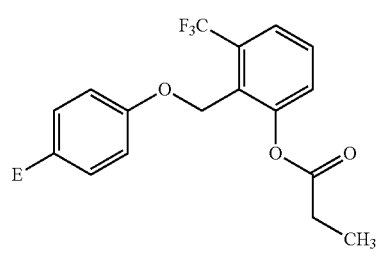
(HB1012)
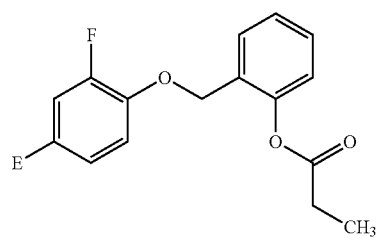
(HB1013)
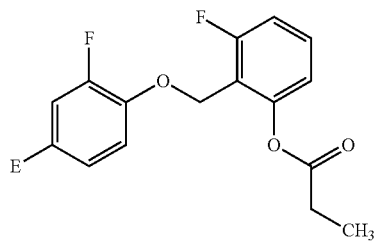
(HB1014)
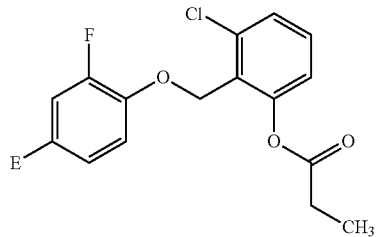
(HB1015)
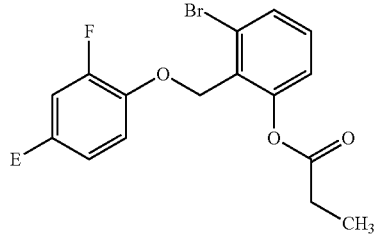
(HB1016)
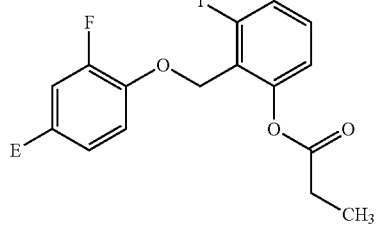
(HB1017)
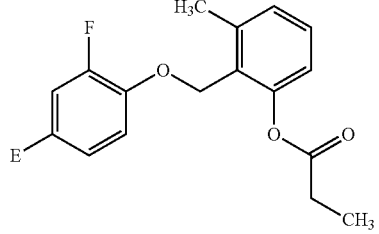
(HB1018)
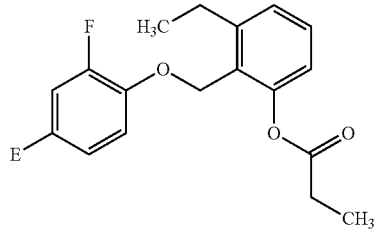
(HB1019)

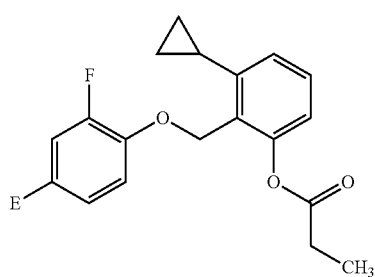
(HB1020)
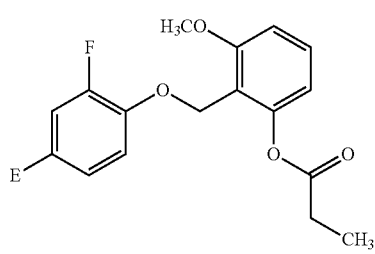
(HB1021)
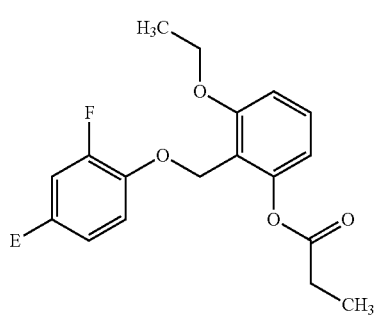
(HB1022)
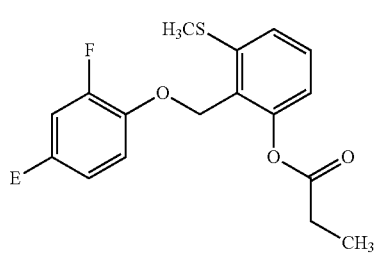
(HB1023)
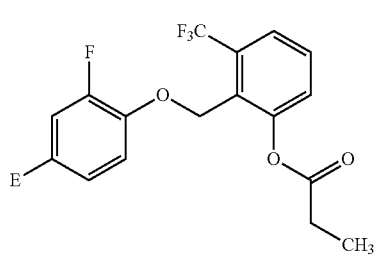
(HB1024)
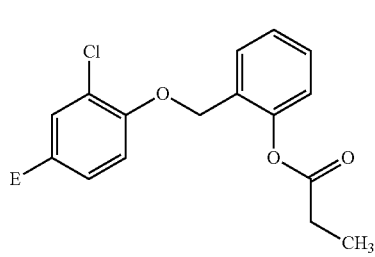
(HB1025)
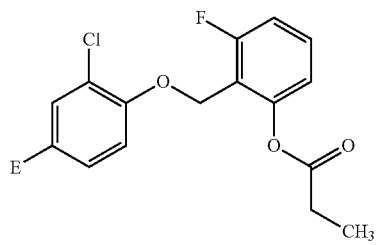
(HB1026)
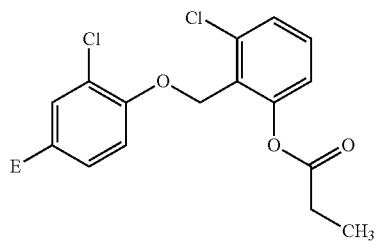
(HB1027)
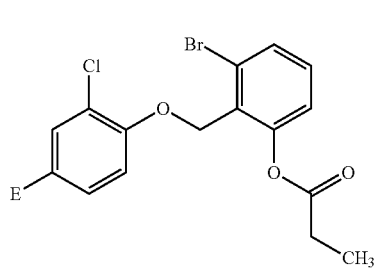
(HB1028)
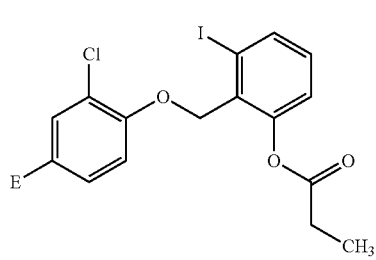
(HB1029)
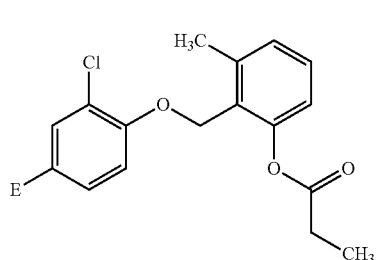
(HB1030)
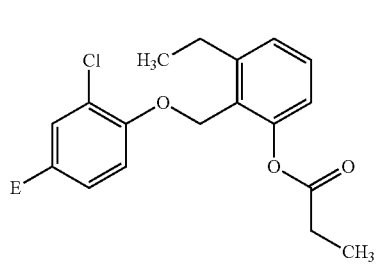
(HB1031)

-continued
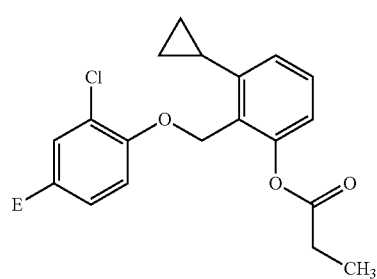 (HB1032)
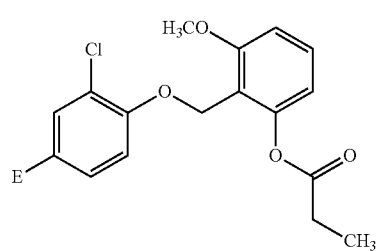 (HB1033)
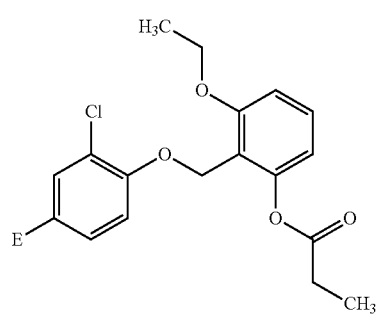 (HB1034)
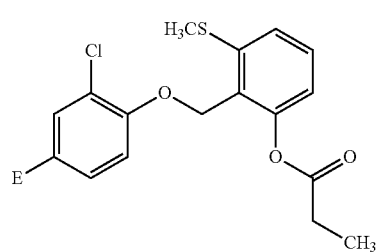 (HB1035)
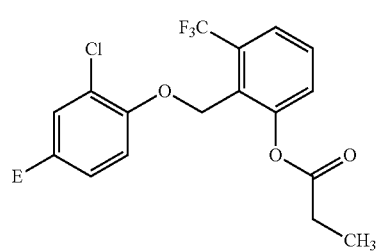 (HB1036)
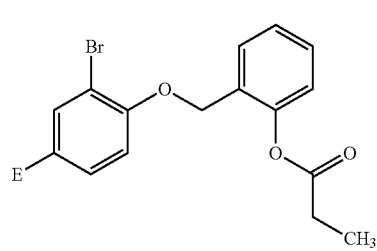 (HB1037)
-continued
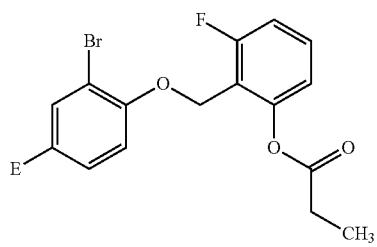 (HB1038)
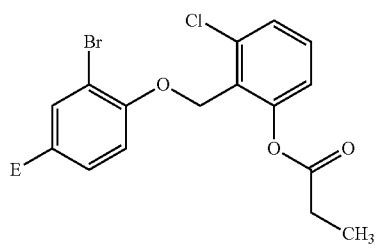 (HB1039)
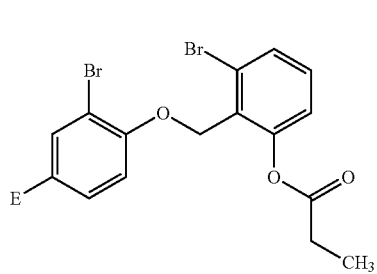 (HB1040)
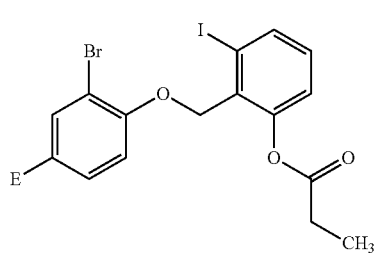 (HB1041)
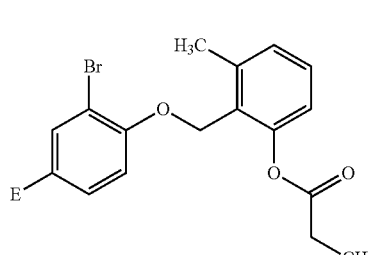 (HB1042)
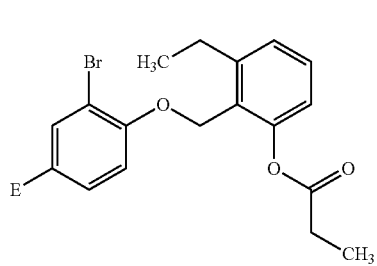 (HB1043)

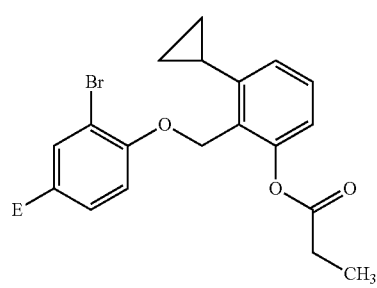
(HB1044)
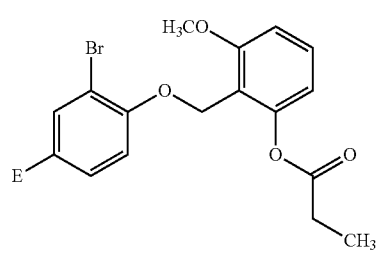
(HB1045)
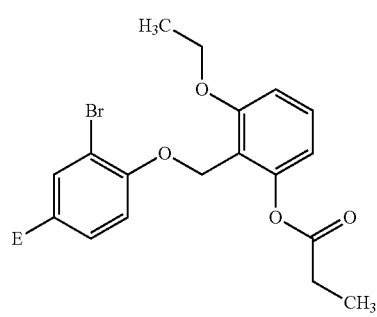
(HB1046)
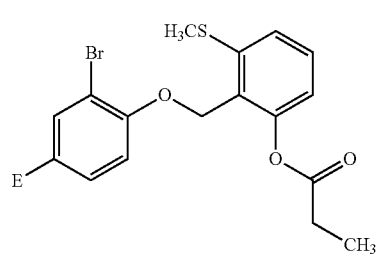
(HB1047)
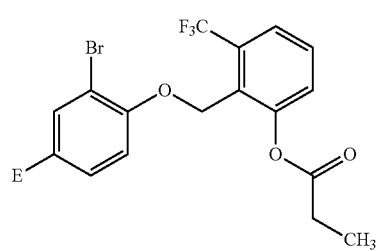
(HB1048)
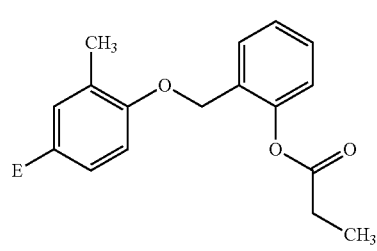
(HB1049)
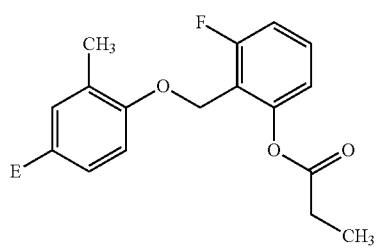
(HB1050)
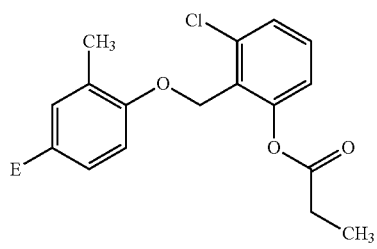
(HB1051)
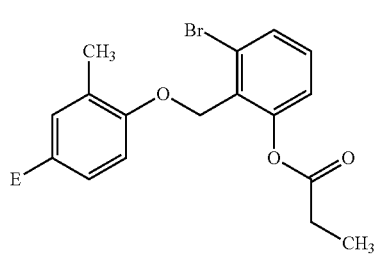
(HB1052)
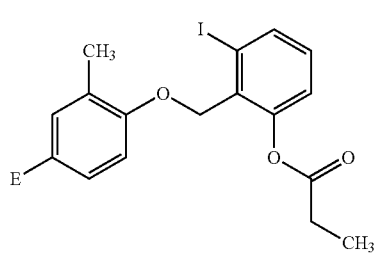
(HB1053)
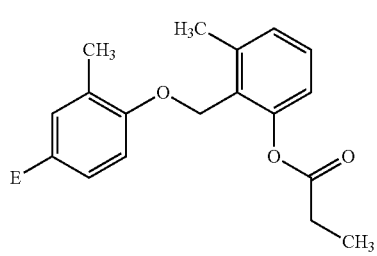
(HB1054)
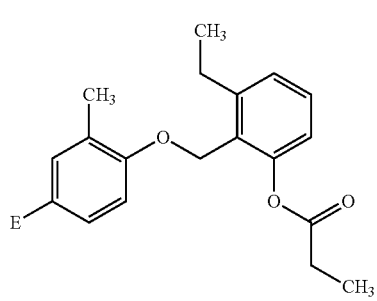
(HB1055)

(HB1056)
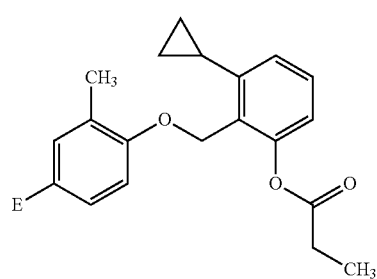
(HB1057)
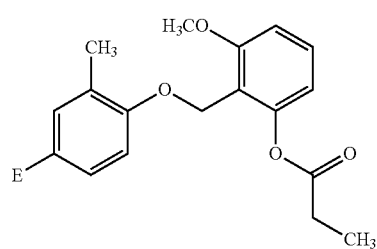
(HB1058)
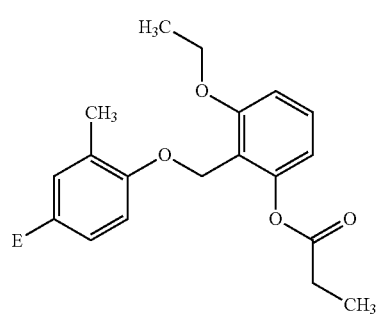
(HB1059)
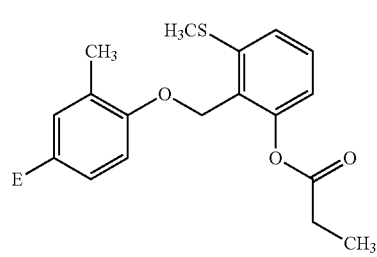
(HB1060)
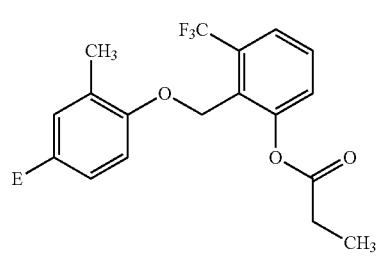
(HB1061)
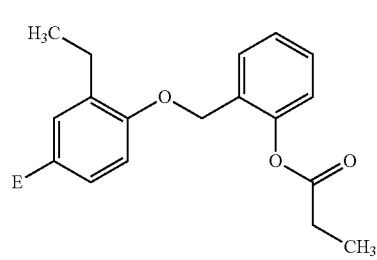
(HB1062)
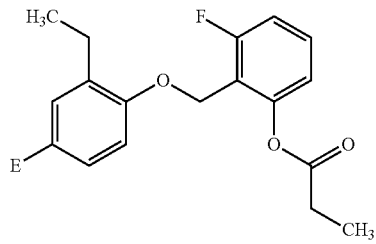
(HB1063)
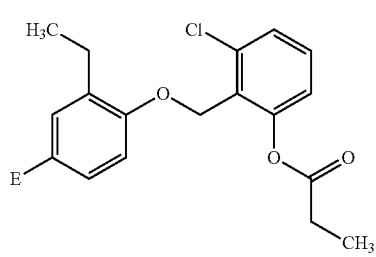
(HB1064)
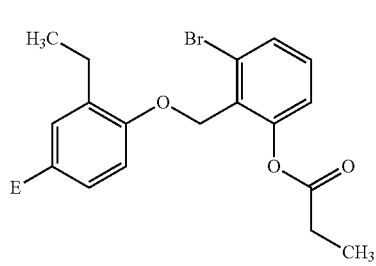
(HB1065)
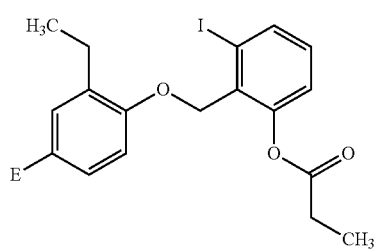
(HB1066)
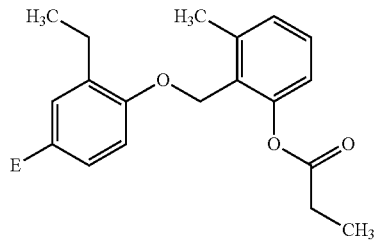
(HB1067)
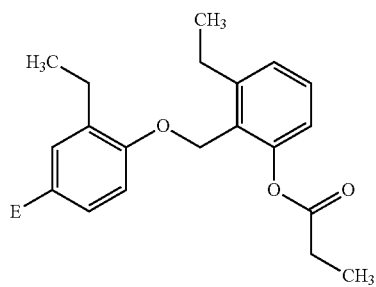

(HB1068) 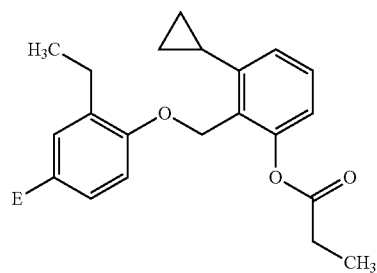
(HB1069) 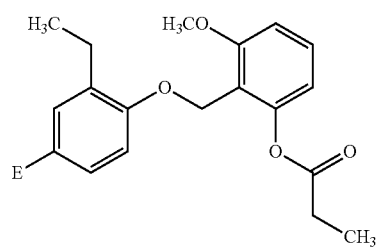
(HB1070) 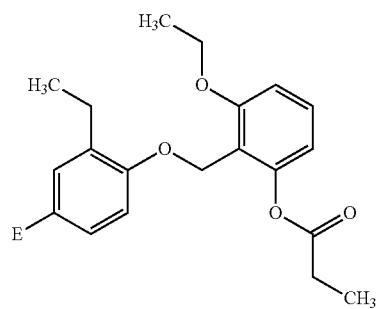
(HB1071) 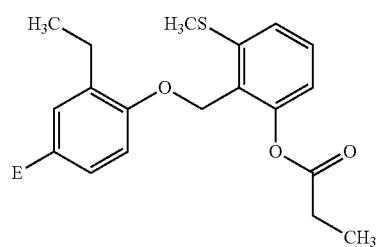
(HB1072) 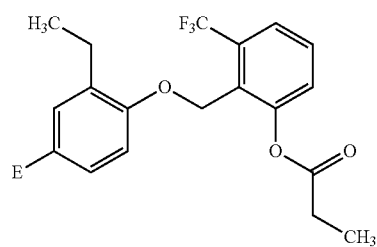
(HB1073) 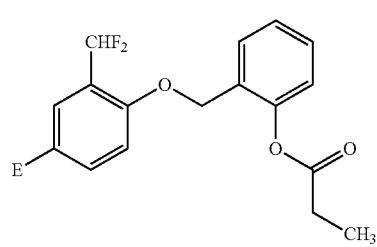
(HB1074) 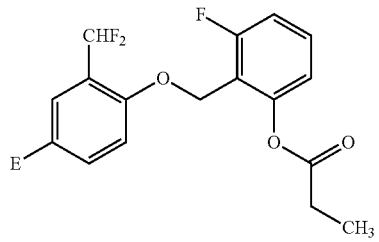
(HB1075) 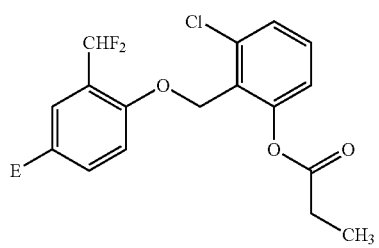
(HB1076) 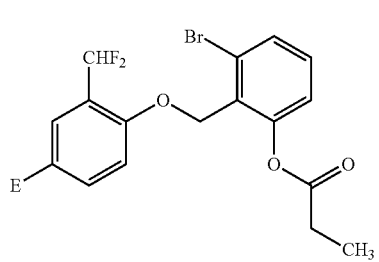
(HB1077) 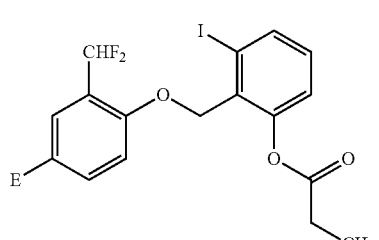
(HB1078) 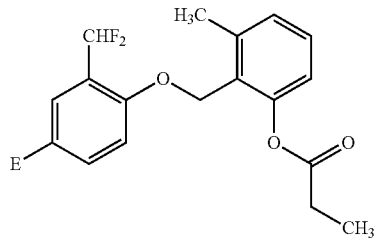
(HB1079) 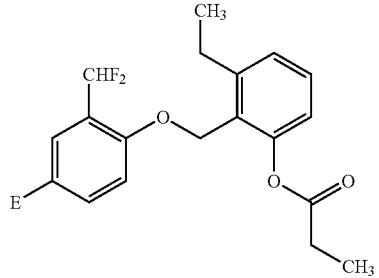

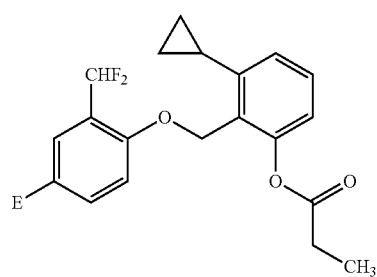
(HB1080)
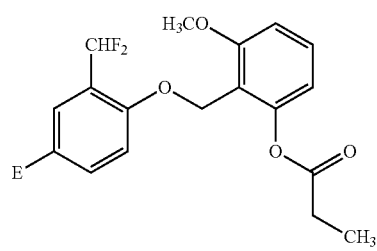
(HB1081)
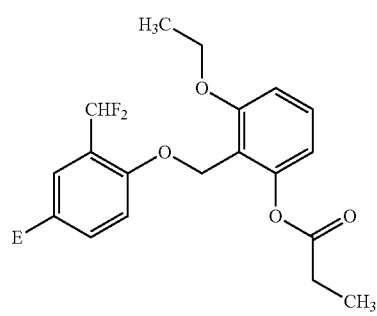
(HB1082)
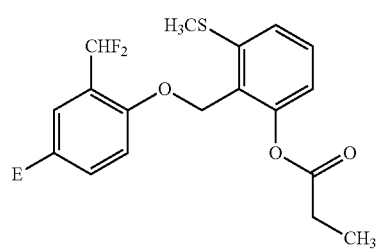
(HB1083)
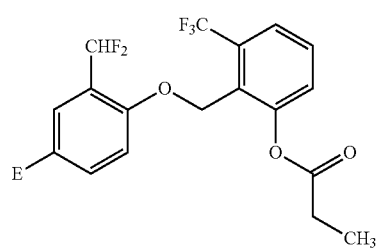
(HB1084)
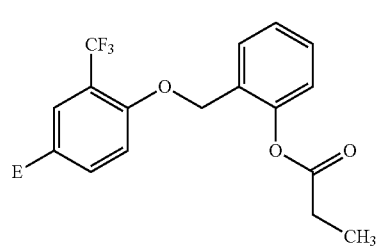
(HB1085)
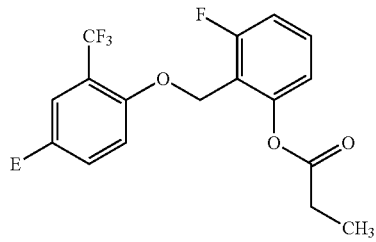
(HB1086)
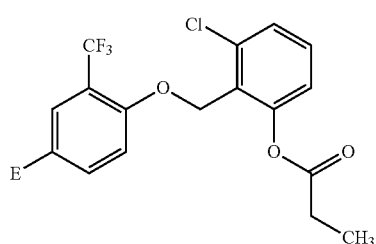
(HB1087)
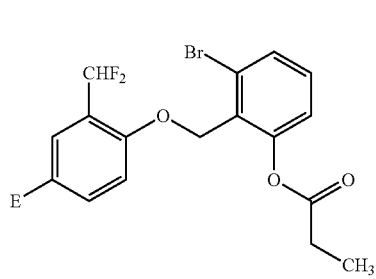
(HB1088)
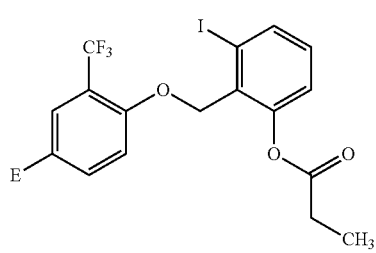
(HB1089)
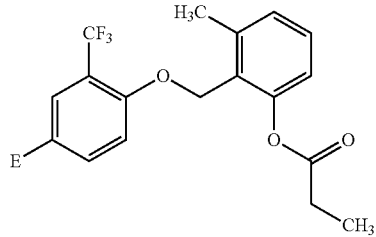
(HB1090)
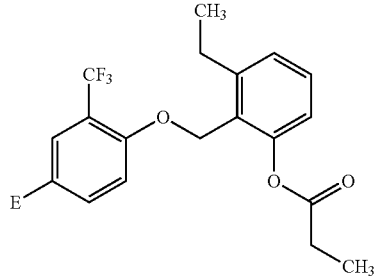
(HB1091)

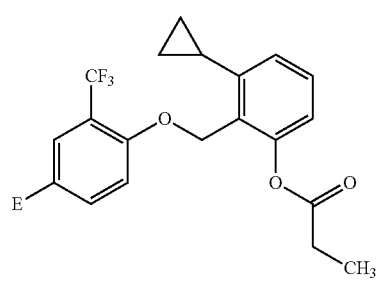 (HB1092)
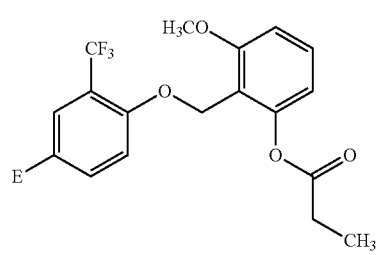 (HB1093)
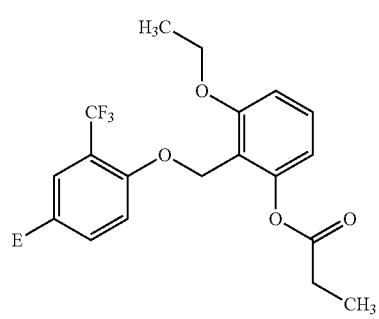 (HB1094)
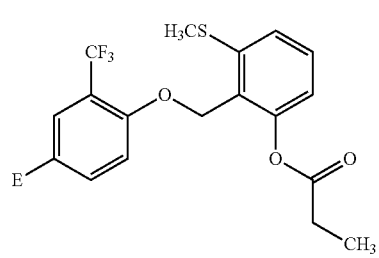 (HB1095)
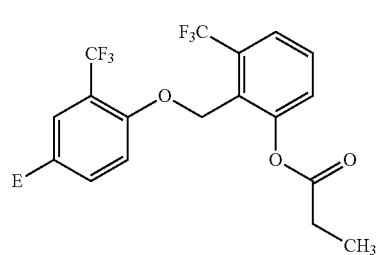 (HB1096)
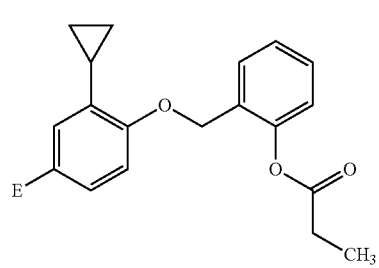 (HB1097)
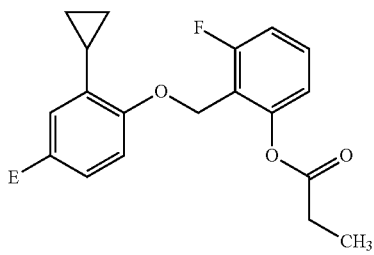 (HB1098)
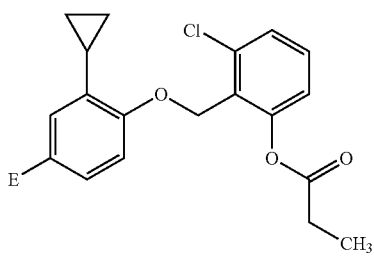 (HB1099)
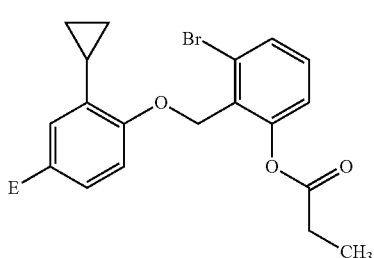 (HB1100)
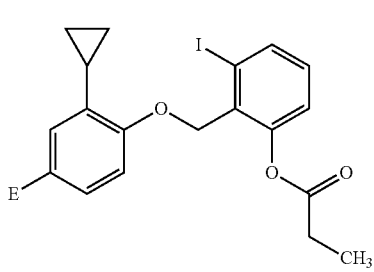 (HB1101)
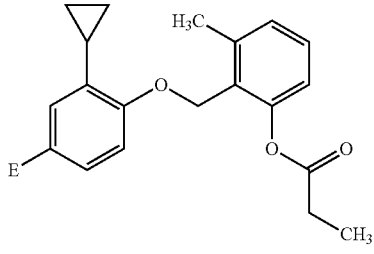 (HB1102)
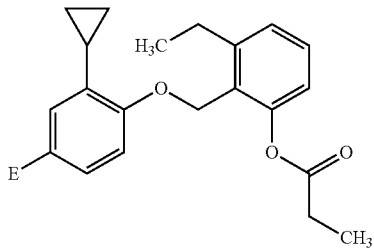 (HB1103)

(HB1104)
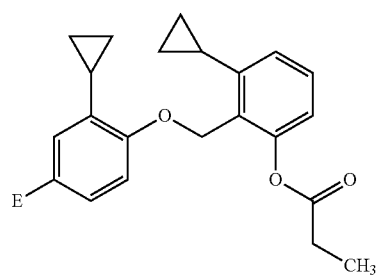
(HB1105)
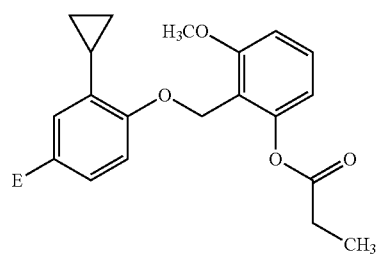
(HB1106)
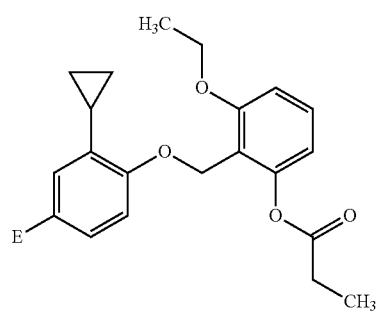
(HB1107)
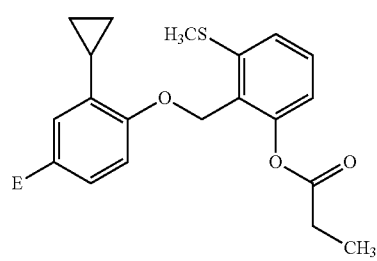
(HB1108)
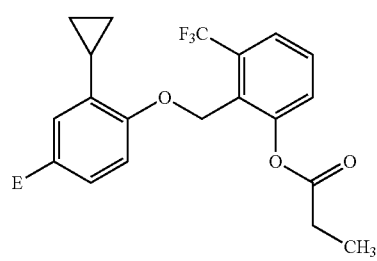
(HB2001)
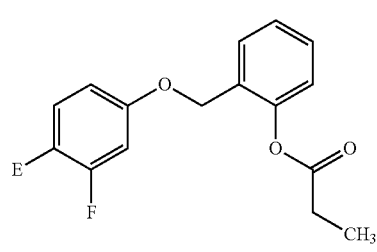
(HB2002)
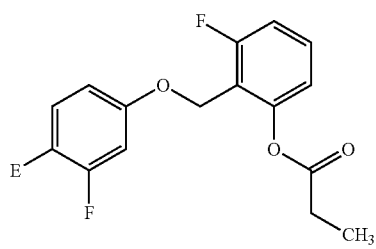
(HB2003)
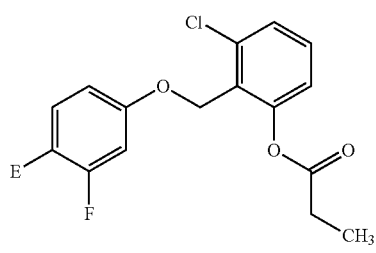
(HB2004)
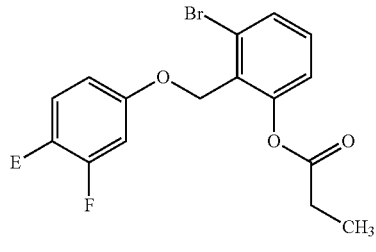
(HB2005)
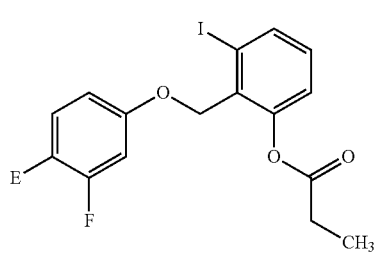
(HB2006)
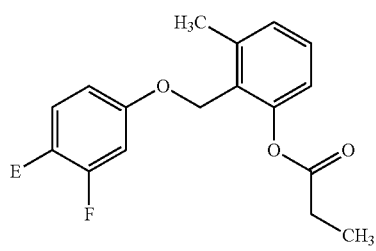
(HB2007)
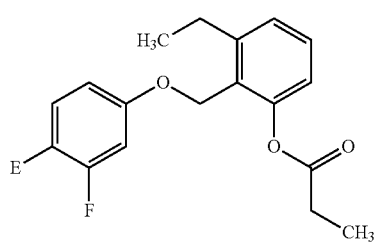

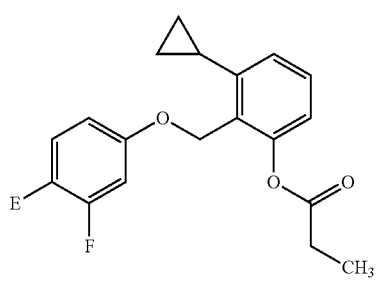
(HB2008)
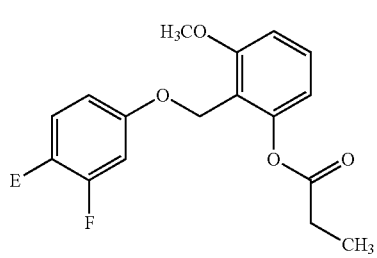
(HB2009)
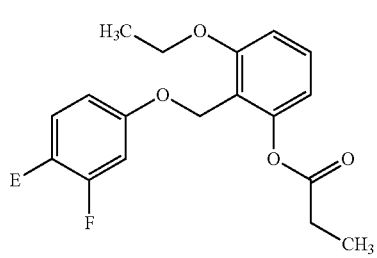
(HB2010)
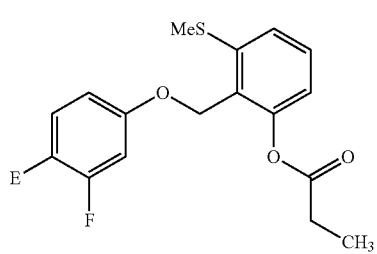
(HB2011)
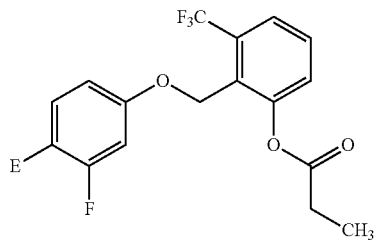
(HB2012)
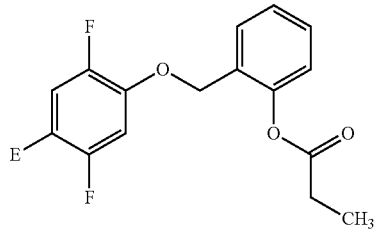
(HB2013)
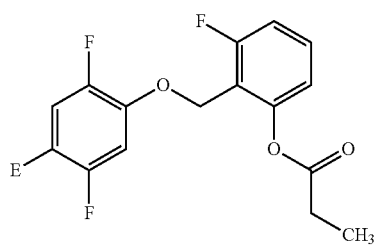
(HB2014)
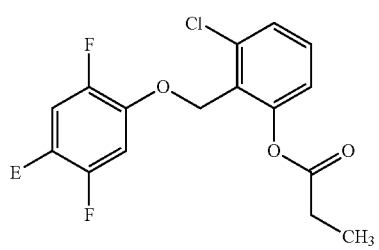
(HB2015)
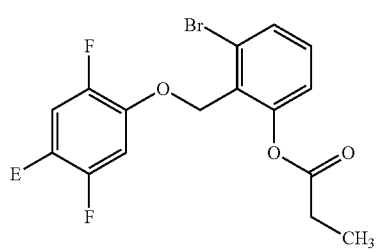
(HB2016)
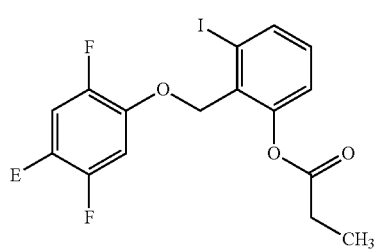
(HB2017)
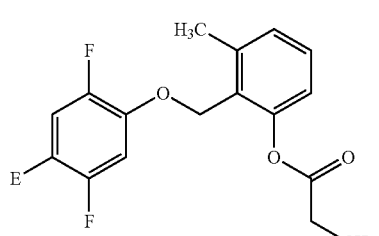
(HB2018)
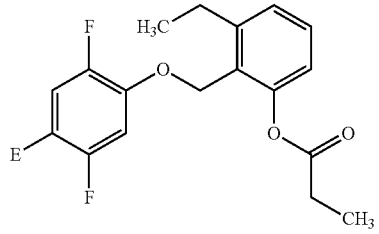
(HB2019)

-continued
(HB2020)
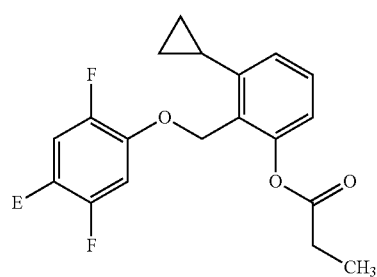
(HB2021)
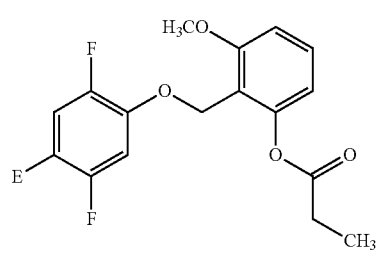
(HB2022)
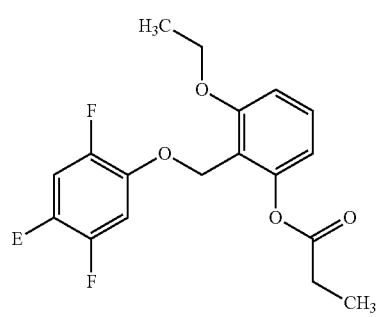
(HB2023)
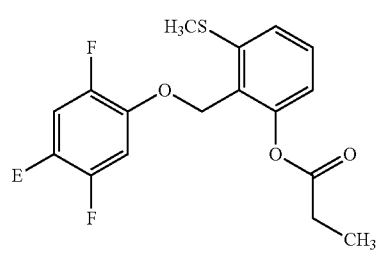
(HB2024)
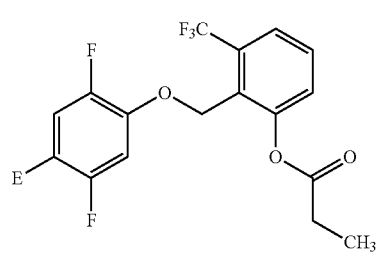
(HB2025)
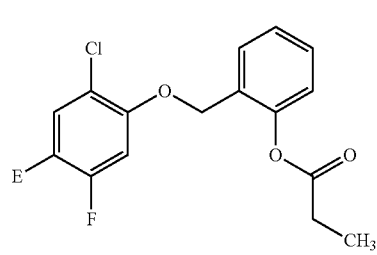
-continued
(HB2026)
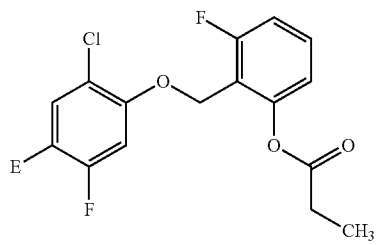
(HB2027)
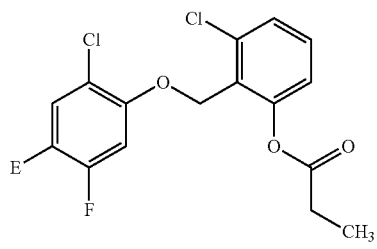
(HB2028)
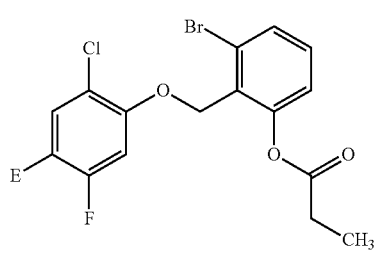
(HB2029)
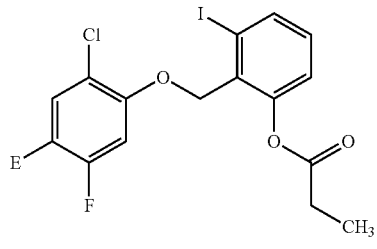
(HB2030)
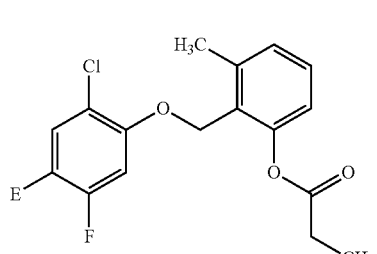
(HB2031)
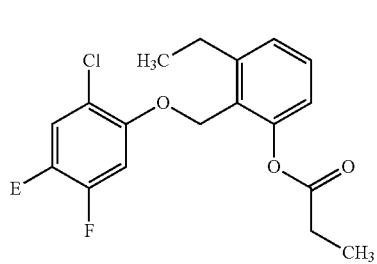

(HB2032)
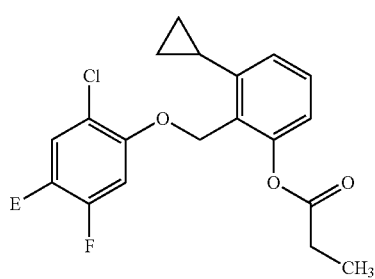
(HB2033)
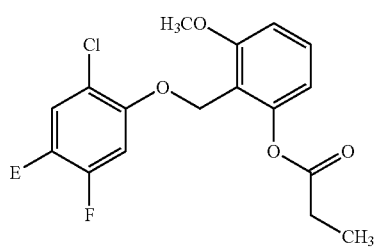
(HB2034)
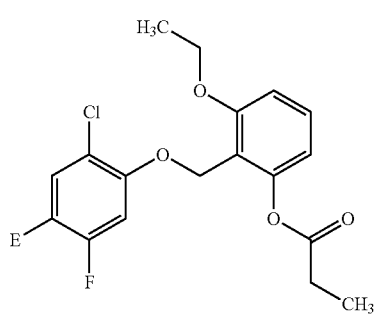
(HB2035)
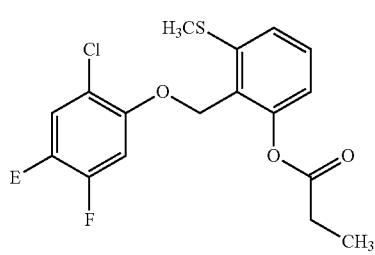
(HB2036)
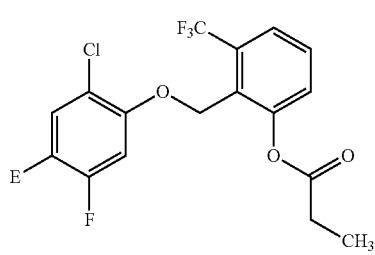
(HB2037)
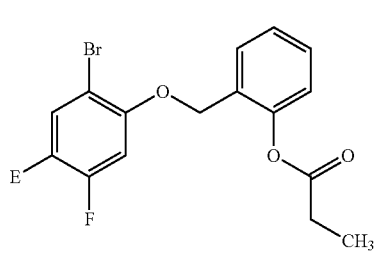
(HB2038)
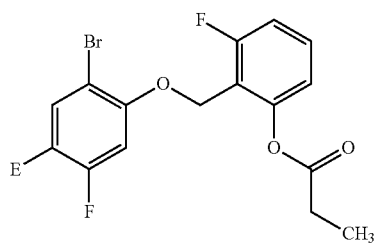
(HB2039)
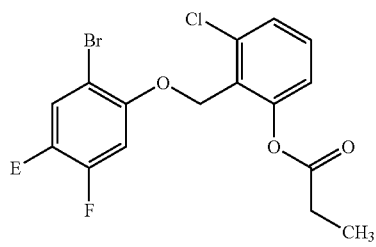
(HB2040)
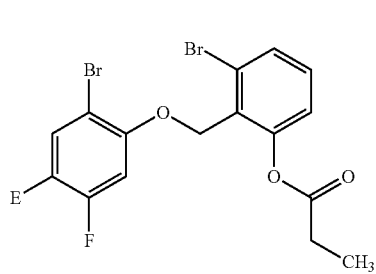
(HB2041)
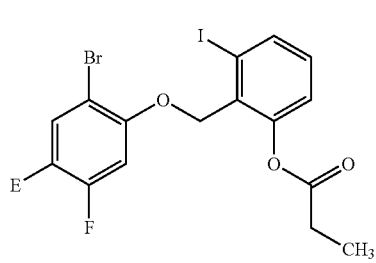
(HB2042)
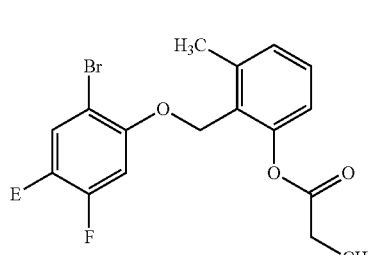
(HB2043)
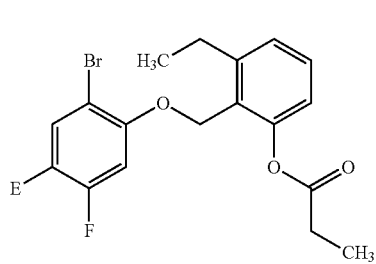

(HB2044)
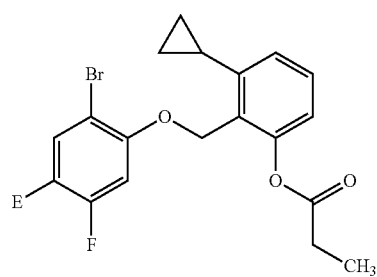
(HB2045)
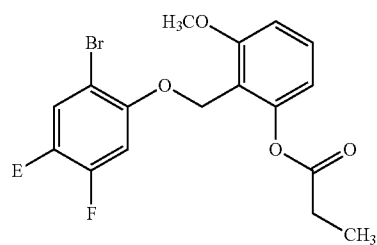
(HB2046)
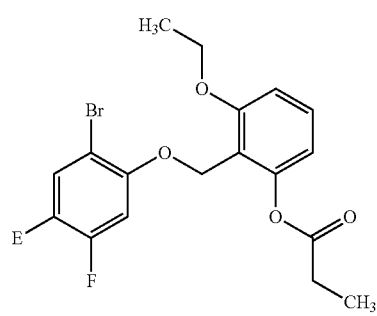
(HB2047)
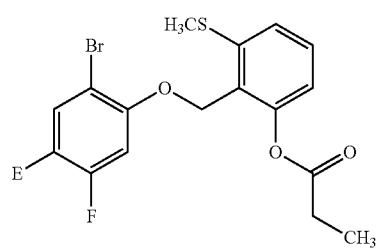
(HB2048)
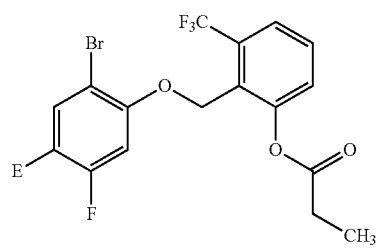
(HB2049)
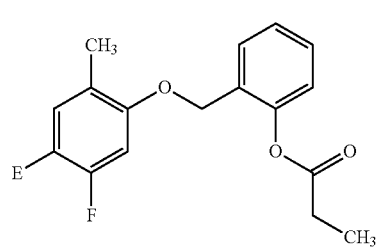
(HB2050)
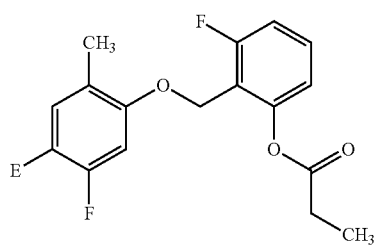
(HB2051)
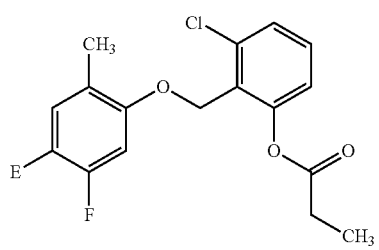
(HB2052)
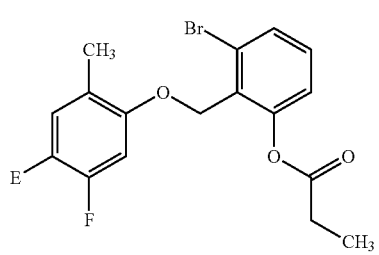
(HB2053)
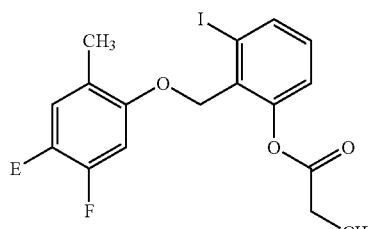
(HB2054)
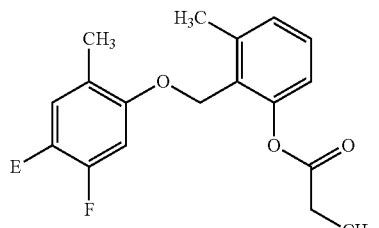
(HB2055)
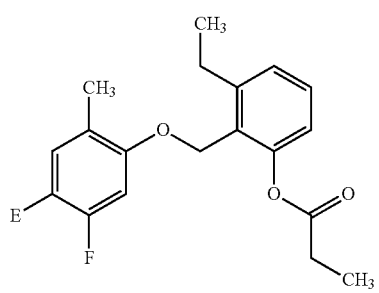

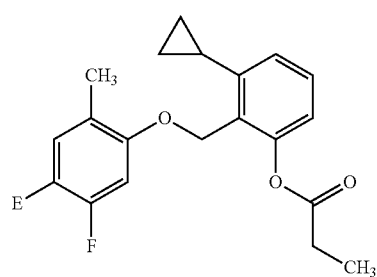
(HB2056)
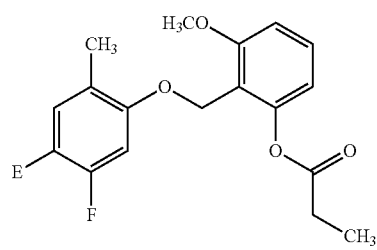
(HB2057)
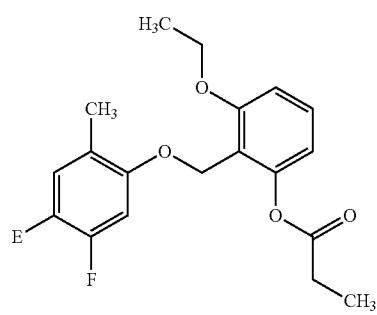
(HB2058)
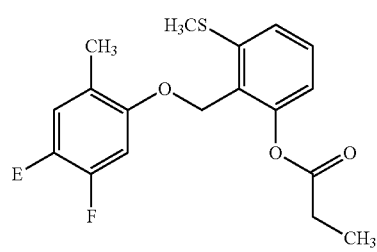
(HB2059)
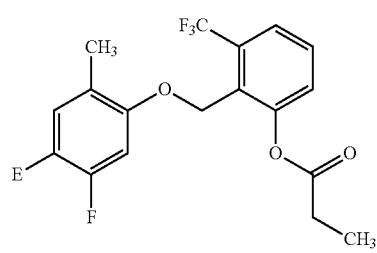
(HB2060)
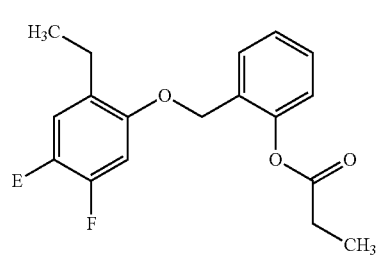
(HB2061)
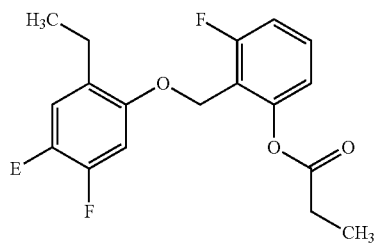
(HB2062)
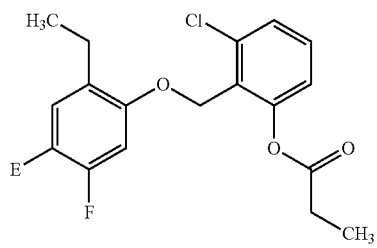
(HB2063)
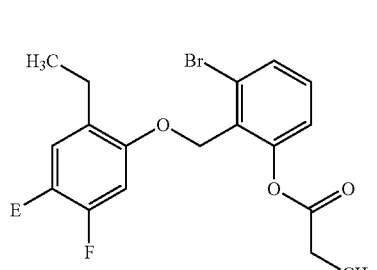
(HB2064)
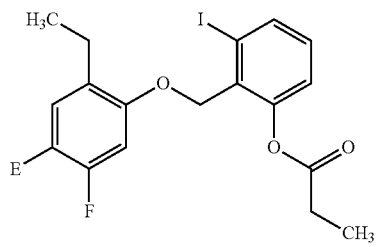
(HB2065)
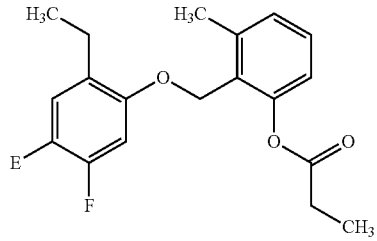
(HB2066)
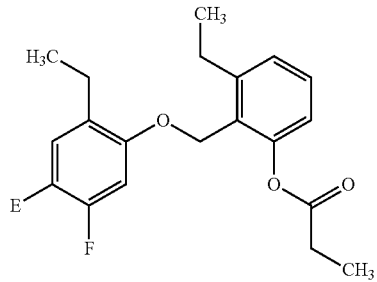
(HB2067)

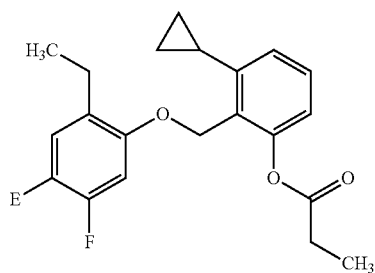
(HB2068)
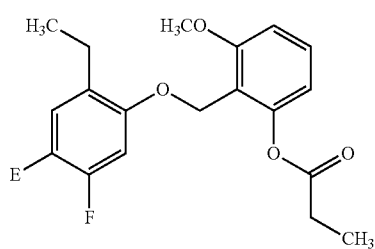
(HB2069)
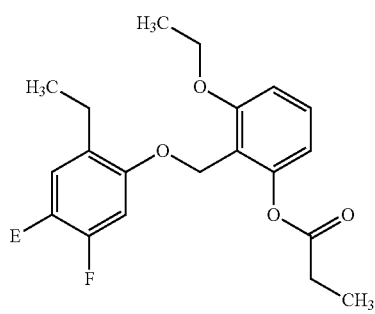
(HB2070)
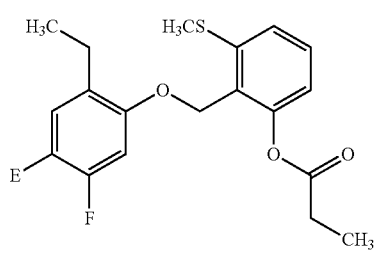
(HB2071)
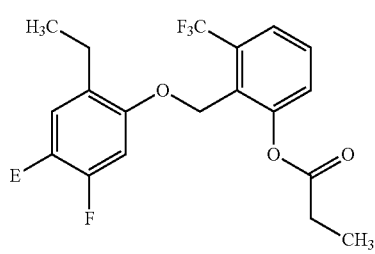
(HB2072)
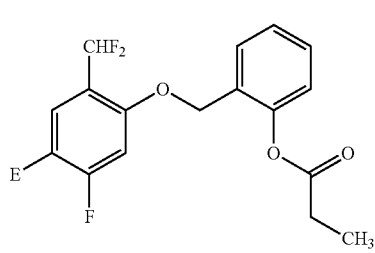
(HB2073)
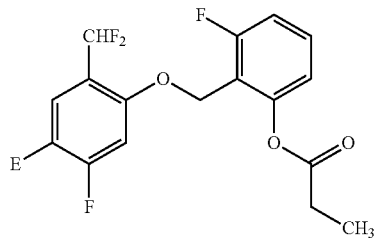
(HB2074)
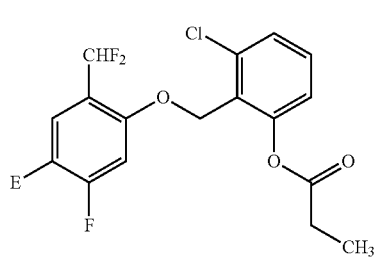
(HB2075)
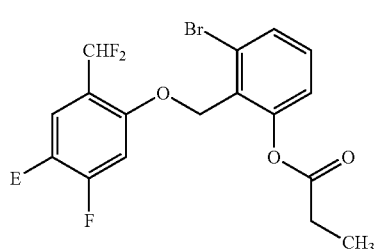
(HB2076)
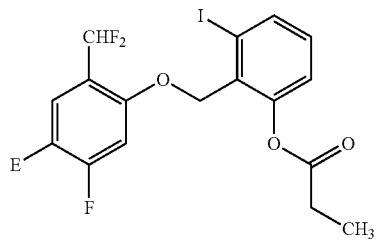
(HB2077)
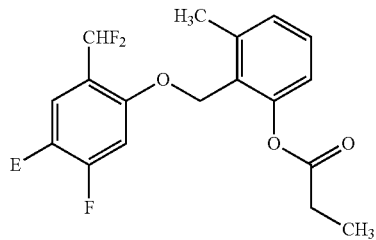
(HB2078)
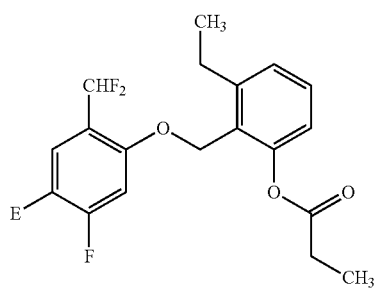
(HB2079)

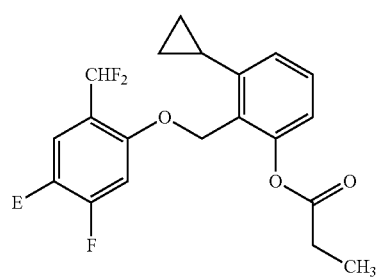
(HB2080)
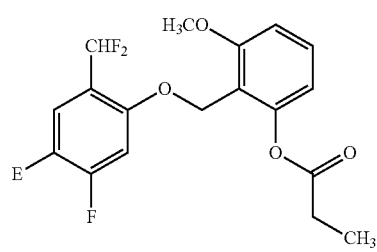
(HB2081)
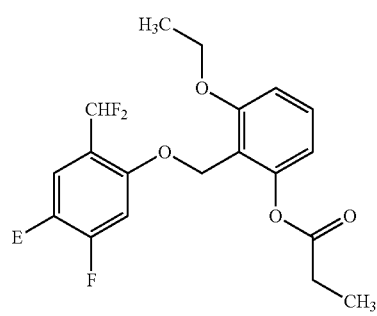
(HB2082)
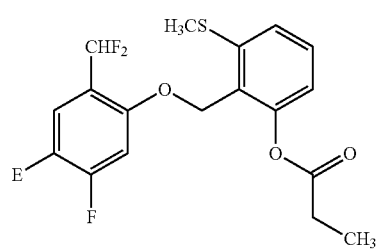
(HB2083)
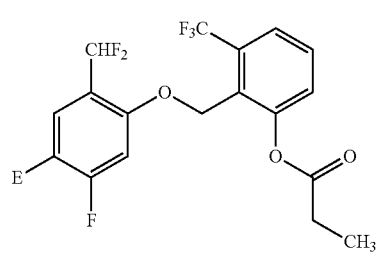
(HB2084)
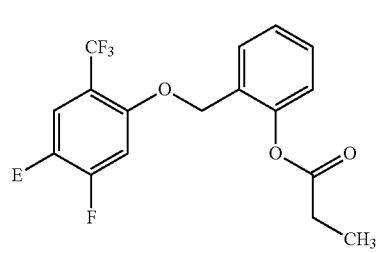
(HB2085)
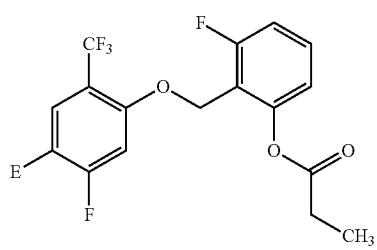
(HB2086)
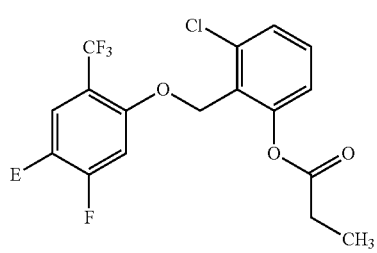
(HB2087)
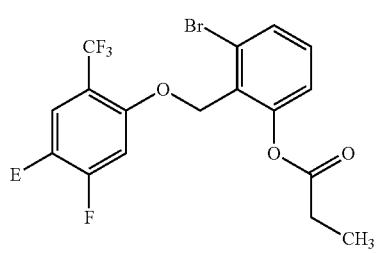
(HB2088)
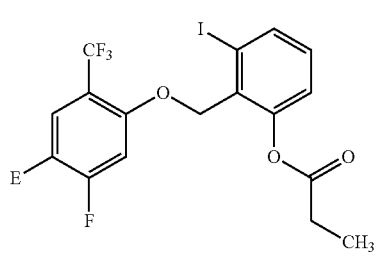
(HB2089)
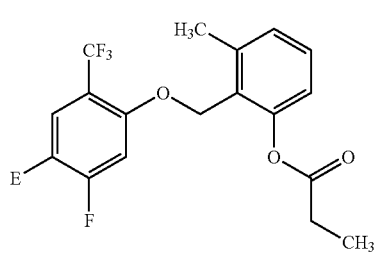
(HB2090)
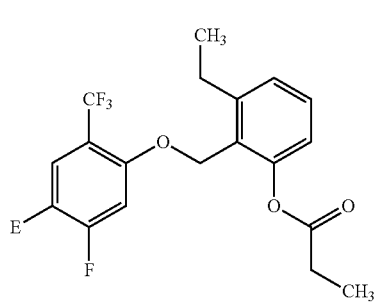
(HB2091)

151
-continued
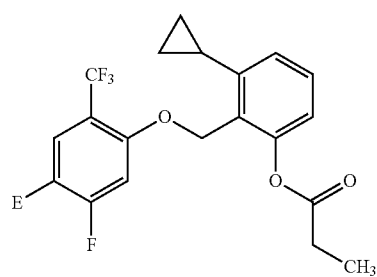
(HB2092)
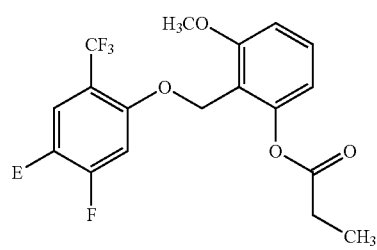
(HB2093)
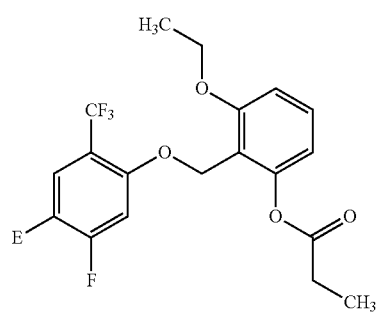
(HB2094)
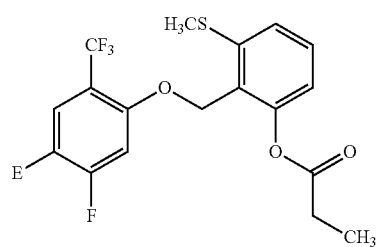
(HB2095)
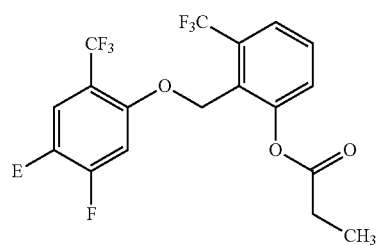
(HB2096)
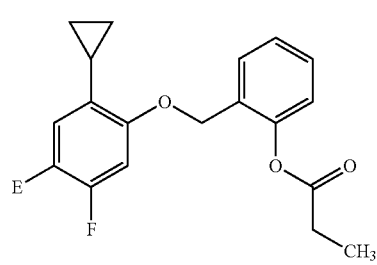
(HB2097)
152
-continued
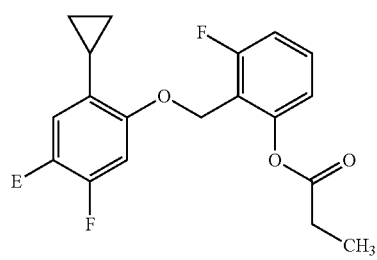
(HB2098)
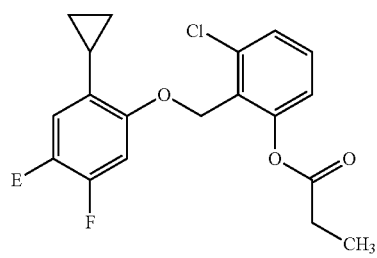
(HB2099)
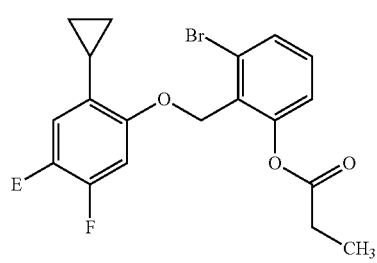
(HB2100)
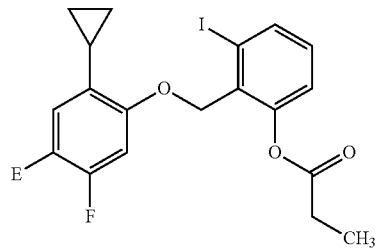
(HB2101)
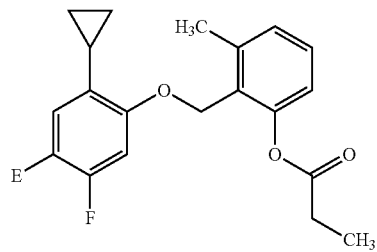
(HB2102)
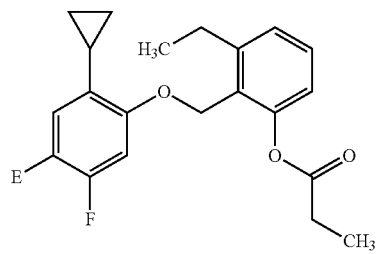
(HB2103)

| | |
|---|---|
| (HB2104) 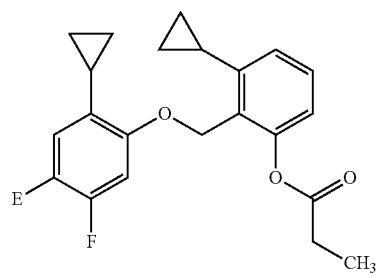 | (HB3002) 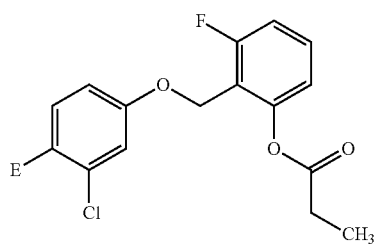 |
| (HB2105) 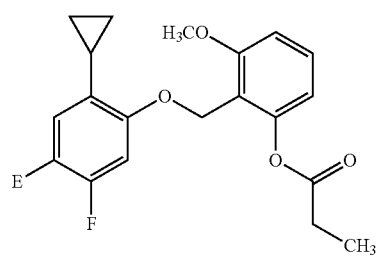 | (HB3003) 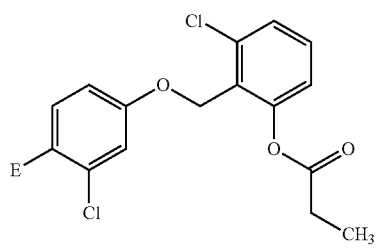 |
| (HB2106) 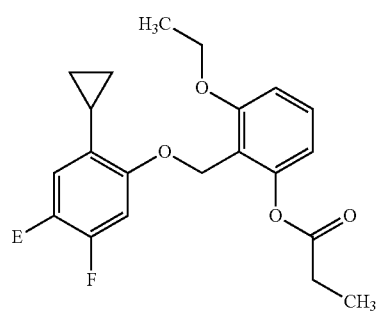 | (HB3004) 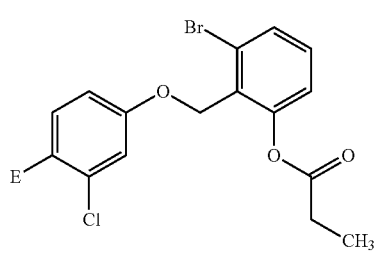 |
| (HB2107) 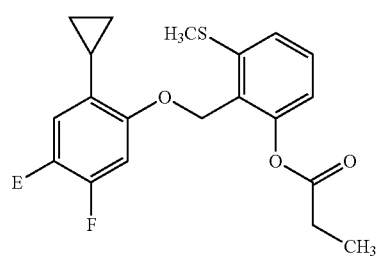 | (HB3005) 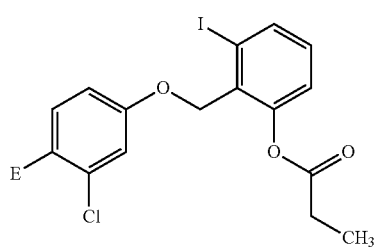 |
| (HB2108) 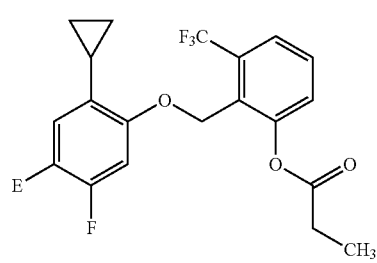 | (HB3006) 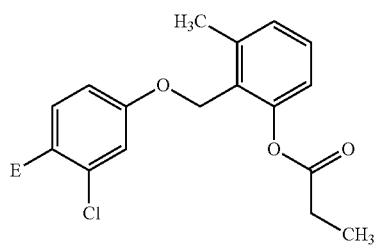 |
| (HB3001) 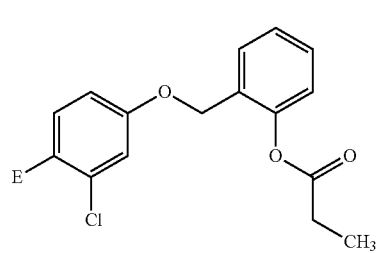 | (HB3007) 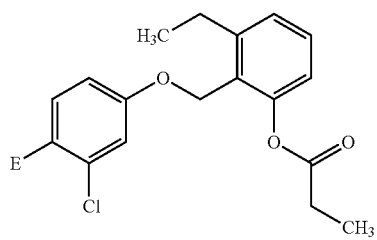 |

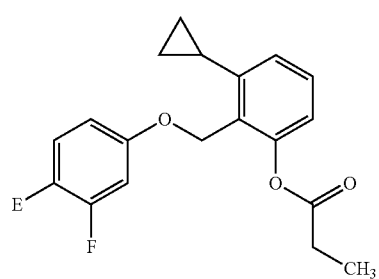
(HB3008)
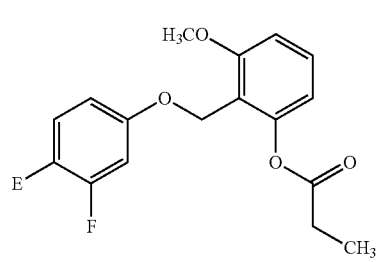
(HB3009)
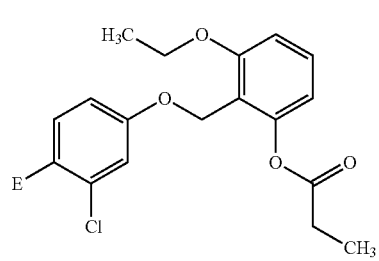
(HB3010)
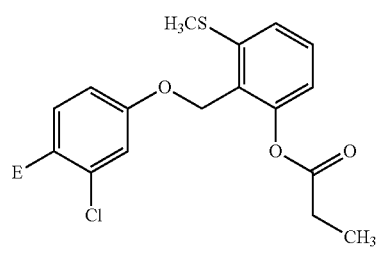
(HB3011)
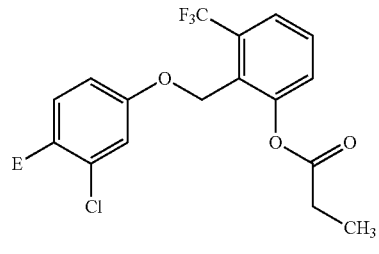
(HB3012)
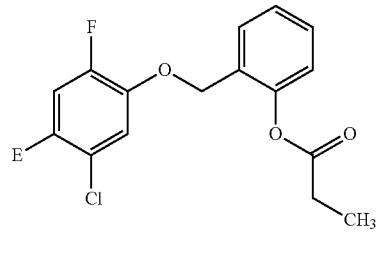
(HB3013)
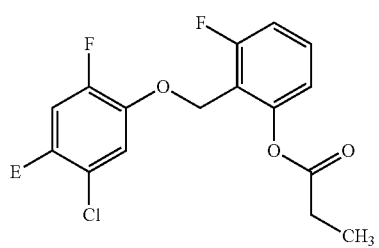
(HB3014)
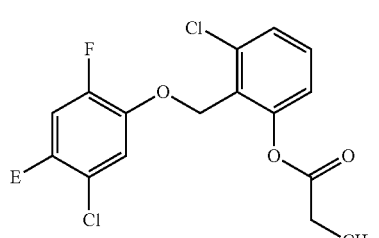
(HB3015)
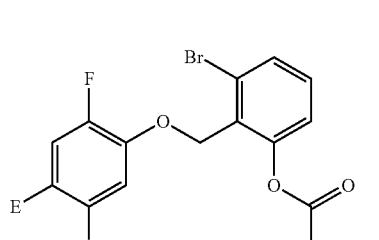
(HB3016)
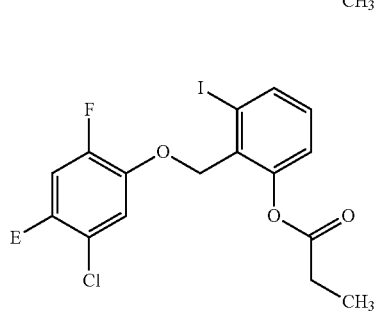
(HB3017)
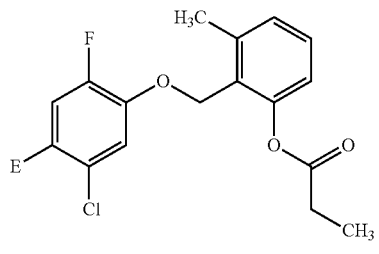
(HB3018)
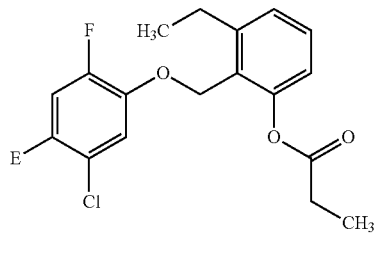
(HB3019)

(HB3020) 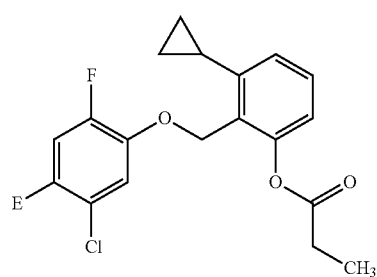
(HB3021) 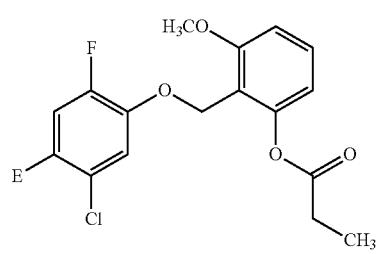
(HB3022) 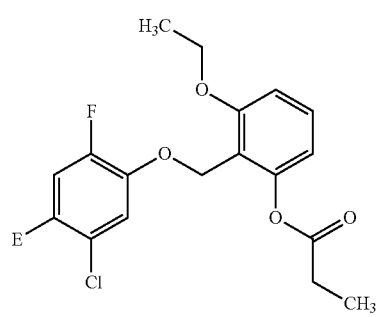
(HB3023) 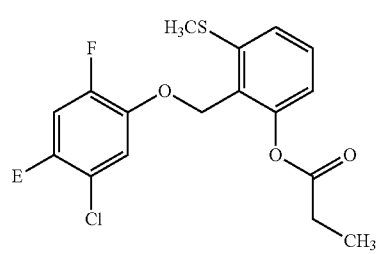
(HB3024) 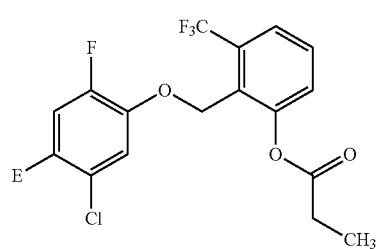
(HB3025) 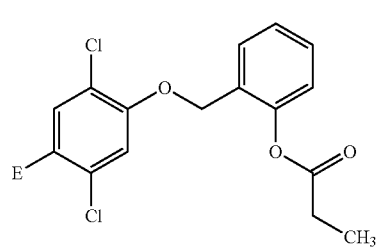
(HB3026) 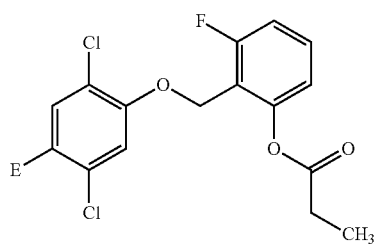
(HB3027) 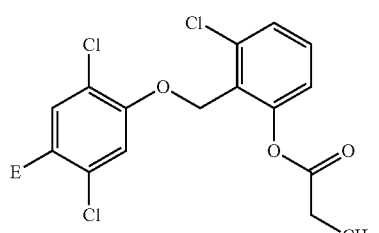
(HB3028) 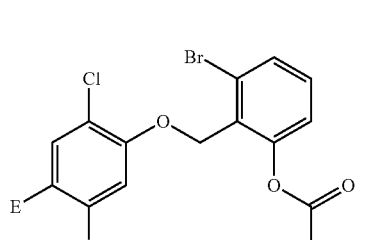
(HB3029) 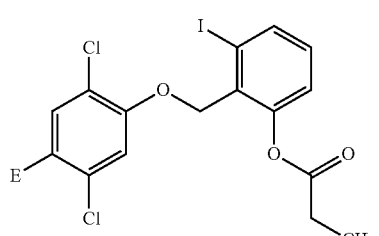
(HB3030) 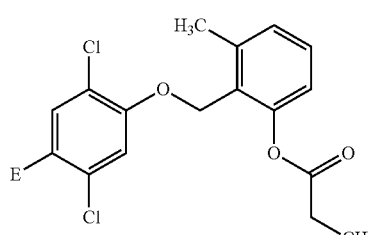
(HB3031) 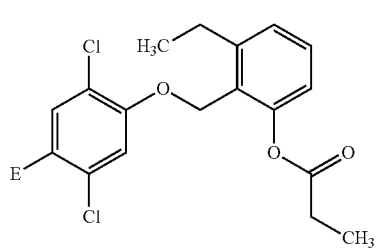

-continued
(HB3032)
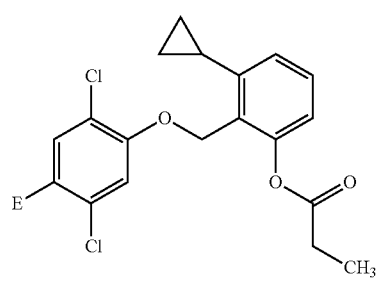
(HB3033)
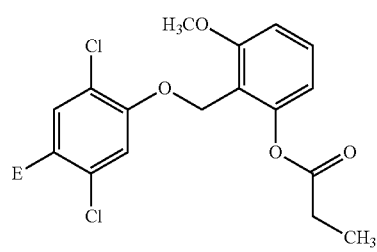
(HB3034)
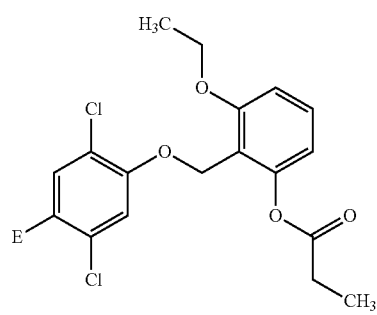
(HB3035)
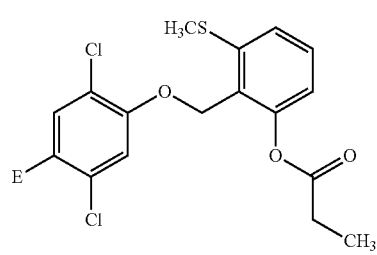
(HB3036)
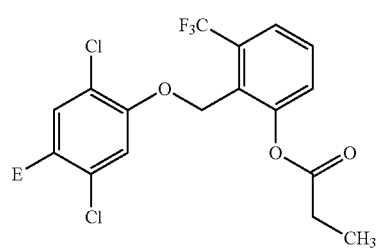
(HB3037)
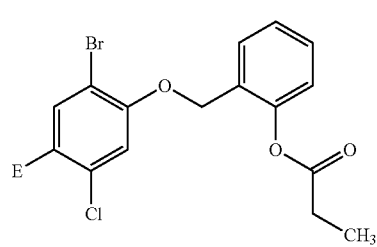
-continued
(HB3038)
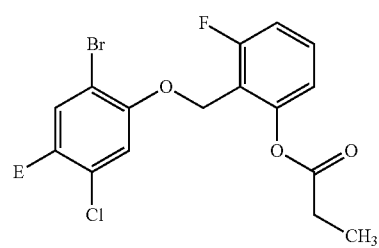
(HB3039)
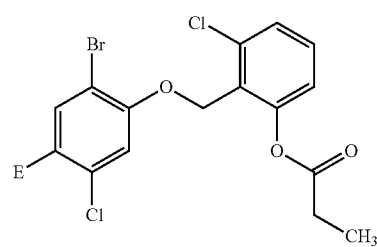
(HB3040)
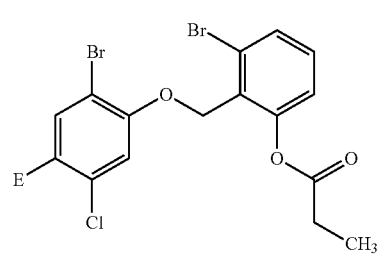
(HB3041)
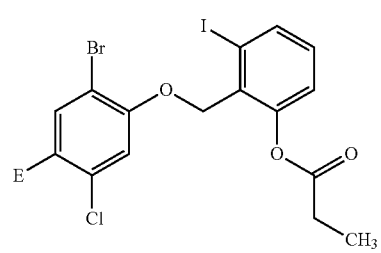
(HB3042)
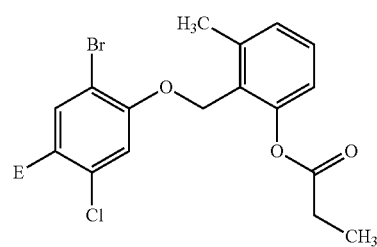
(HB3043)
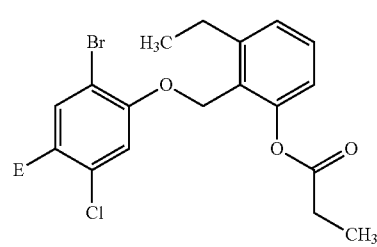

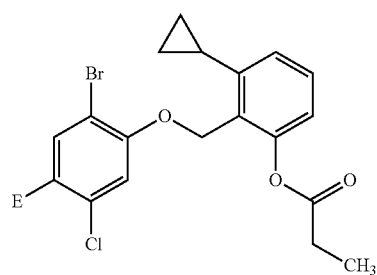
(HB3044)
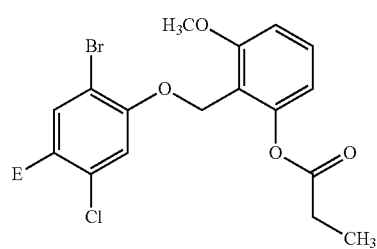
(HB3045)
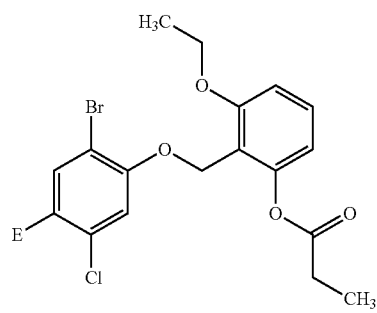
(HB3046)
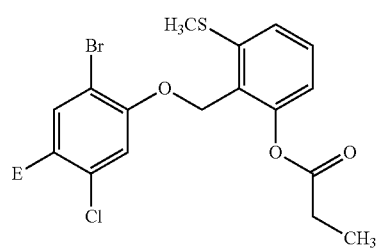
(HB3047)
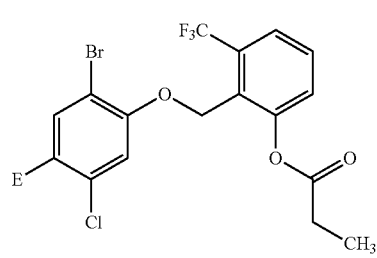
(HB3048)
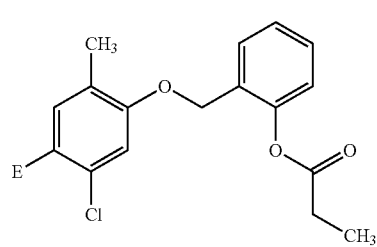
(HB3049)
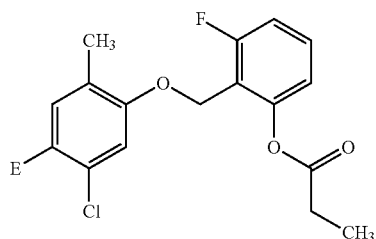
(HB3050)
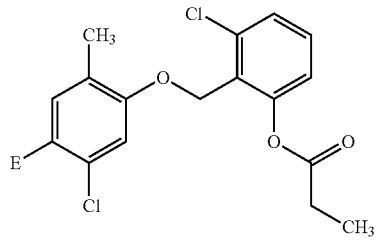
(HB3051)
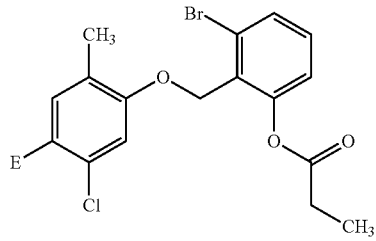
(HB3052)
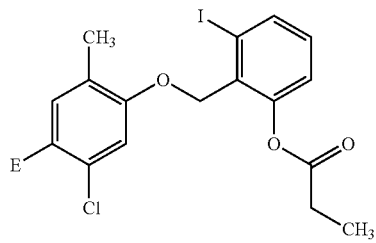
(HB3053)
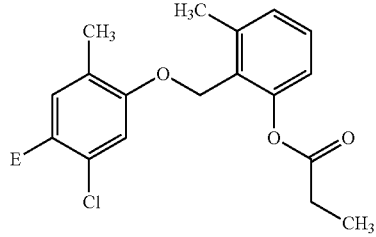
(HB3054)
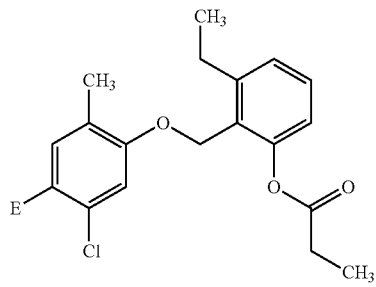
(HB3055)

(HB3056) 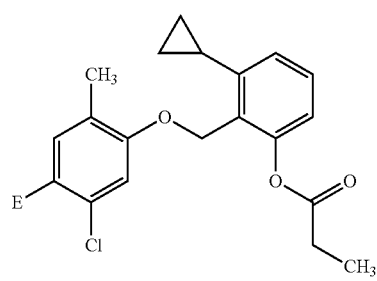
(HB3057) 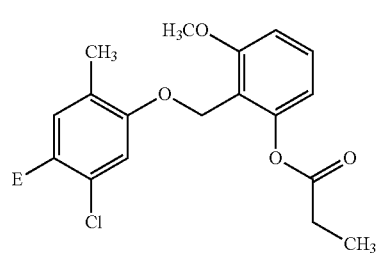
(HB3058) 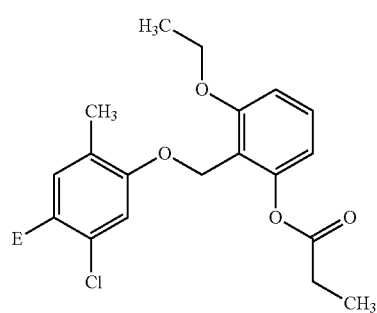
(HB3059) 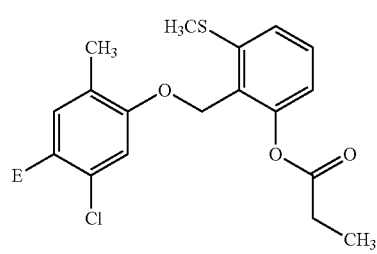
(HB3060) 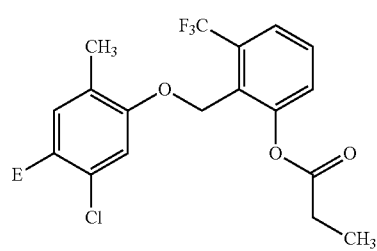
(HB3061) 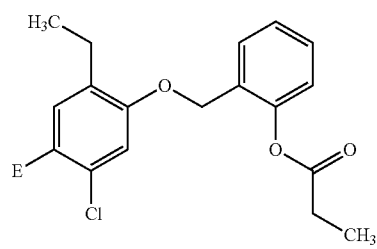
(HB3062) 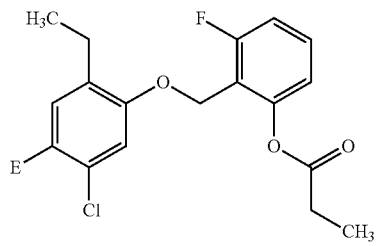
(HB3063) 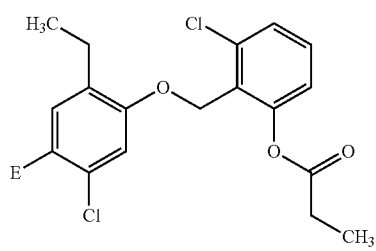
(HB3064) 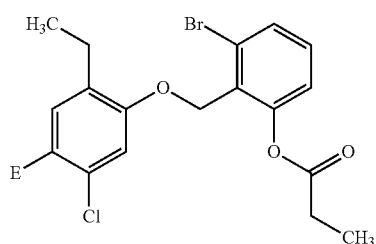
(HB3065) 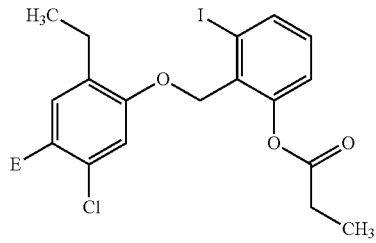
(HB3066) 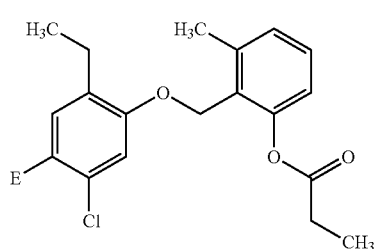
(HB3067) 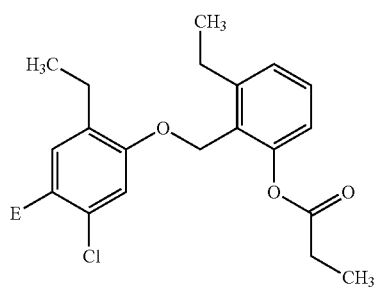

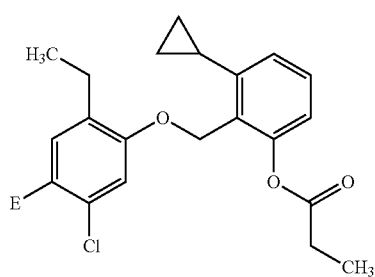
(HB3068)
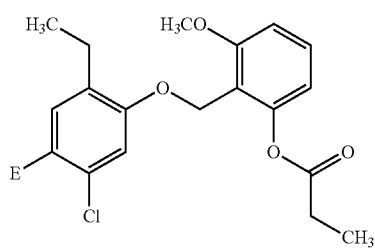
(HB3069)
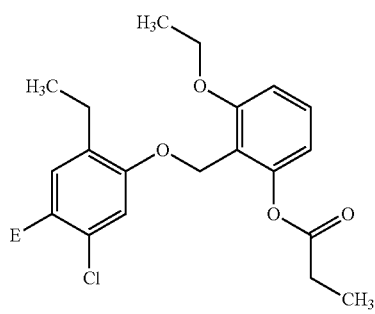
(HB3070)
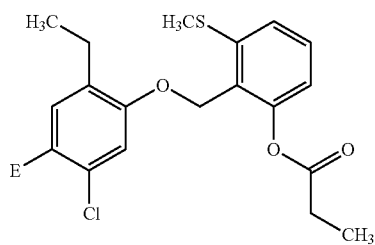
(HB3071)
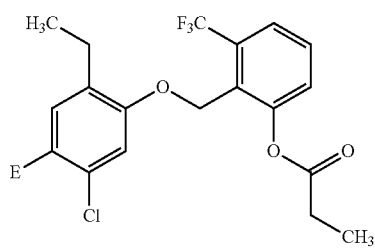
(HB3072)
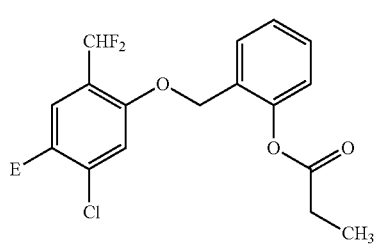
(HB3073)
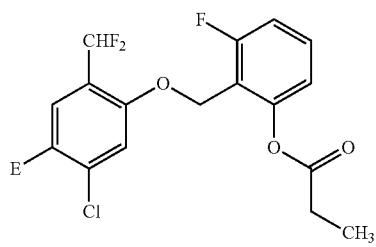
(HB3074)
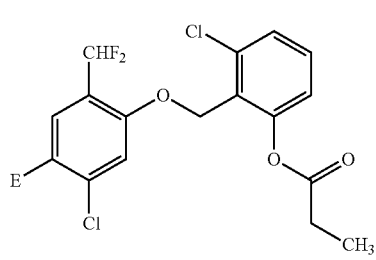
(HB3075)
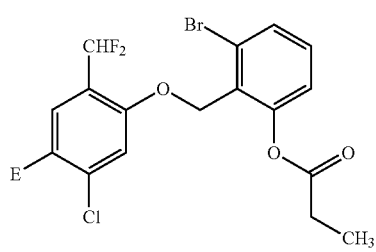
(HB3076)
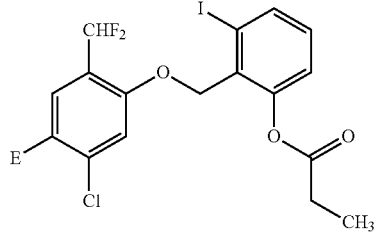
(HB3077)
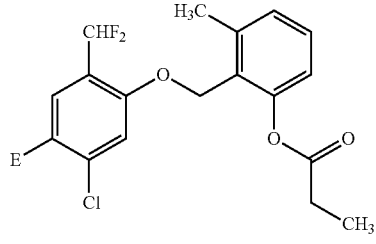
(HB3078)
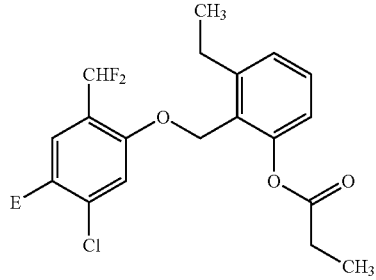
(HB3079)

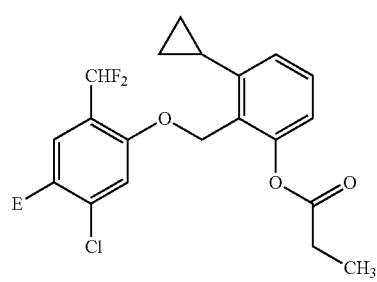
(HB3080)
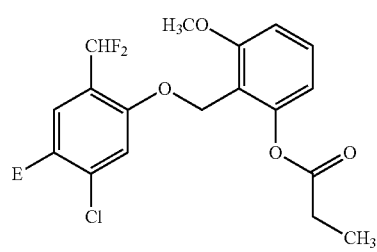
(HB3081)
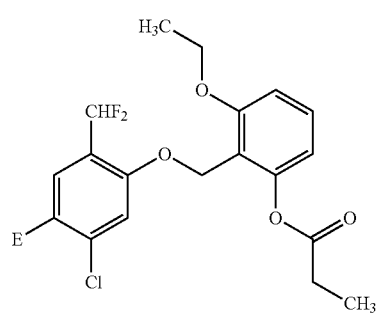
(HB3082)
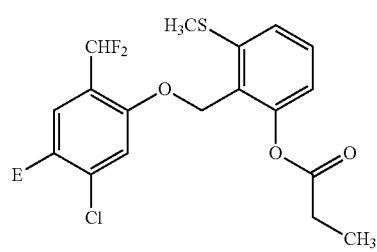
(HB3083)
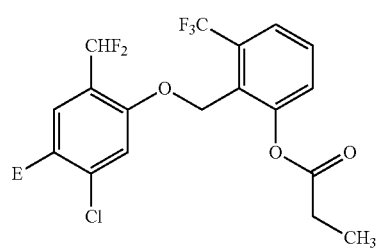
(HB3084)
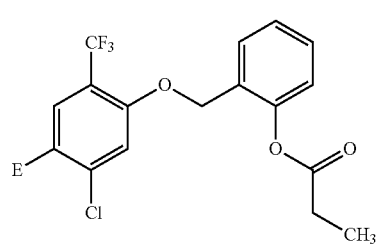
(HB3085)
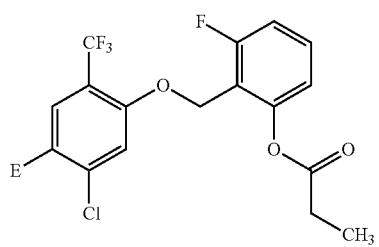
(HB3086)
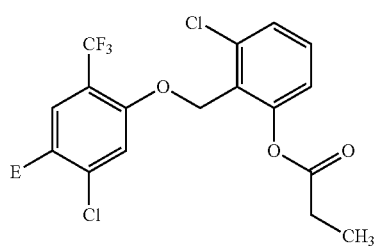
(HB3087)
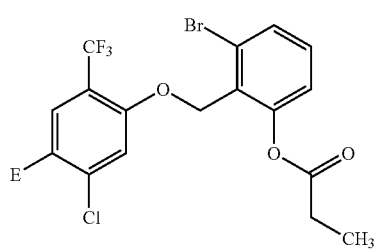
(HB3088)
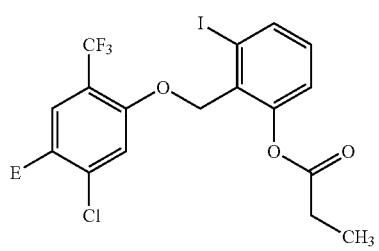
(HB3089)
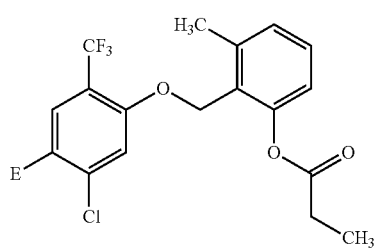
(HB3090)
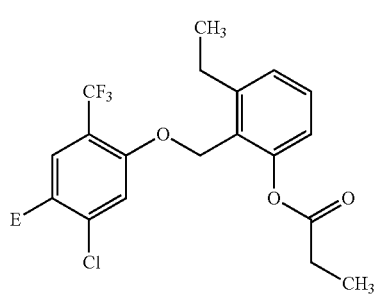
(HB3091)

-continued
(HB3092)
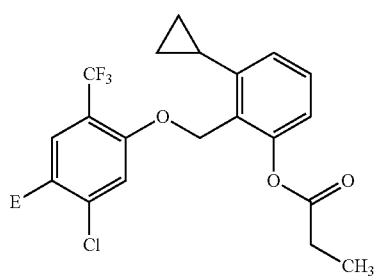
(HB3093)
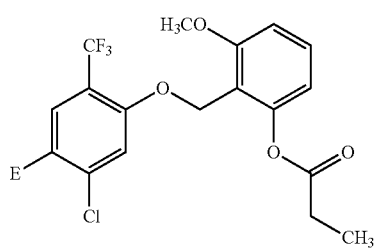
(HB3094)
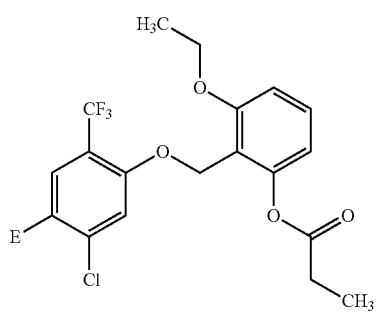
(HB3095)
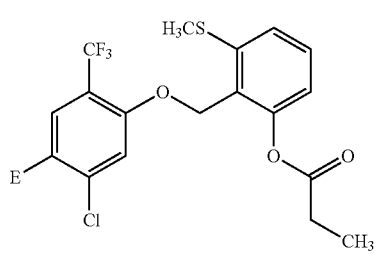
(HB3096)
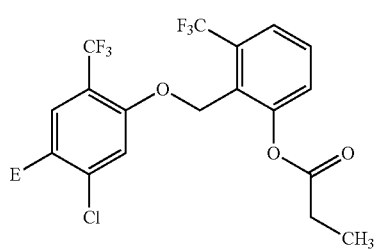
(HB3097)
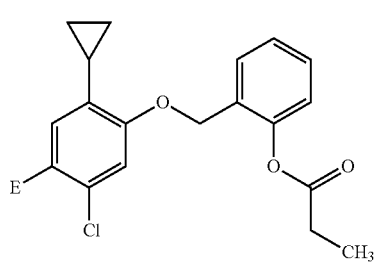
-continued
(HB3098)
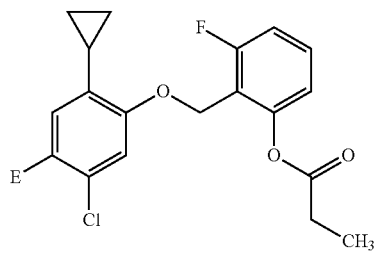
(HB3099)
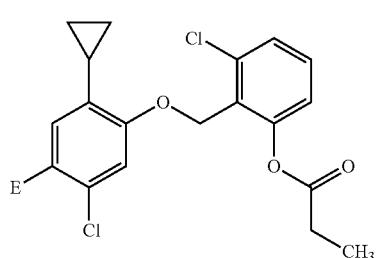
(HB3100)
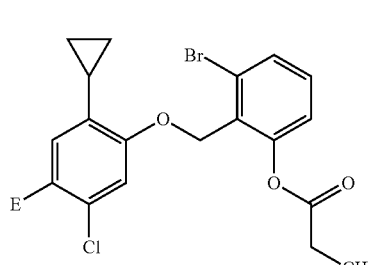
(HB3101)
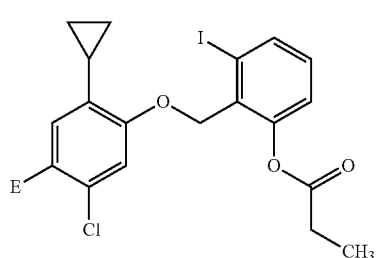
(HB3102)
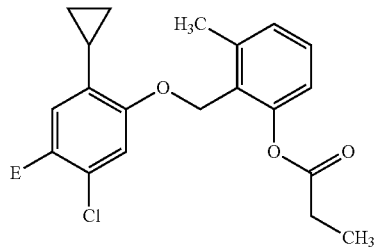
(HB3103)
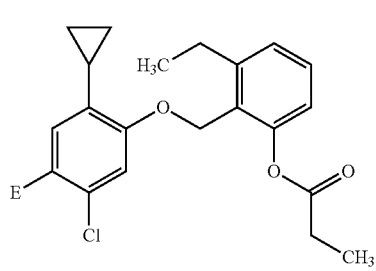

(HB3104)
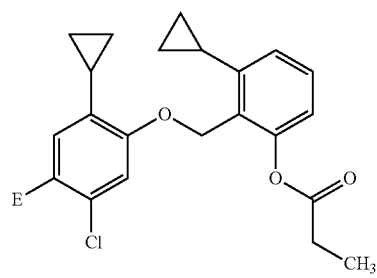
(HB3105)
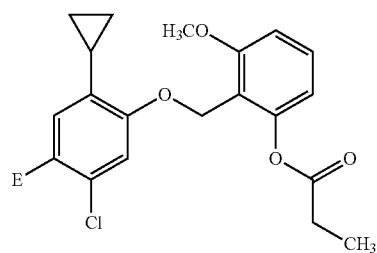
(HB3106)
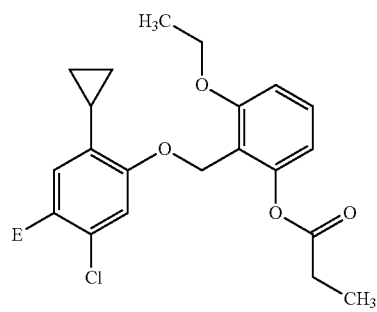
(HB3107)
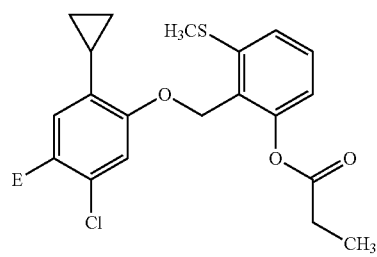
(HB3108)
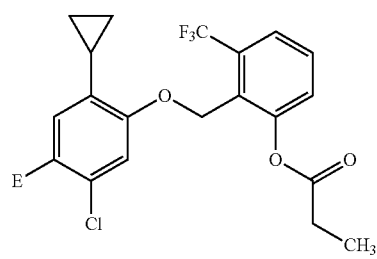
(HB4001)
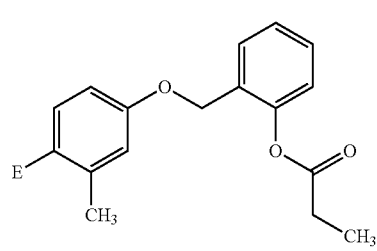
(HB4002)
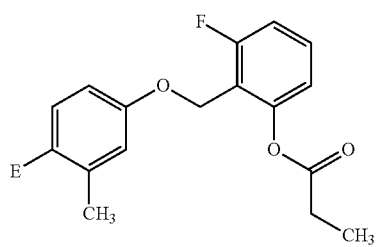
(HB4003)
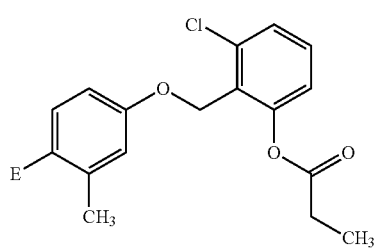
(HB4004)
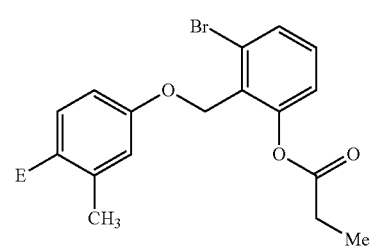
(HB4005)
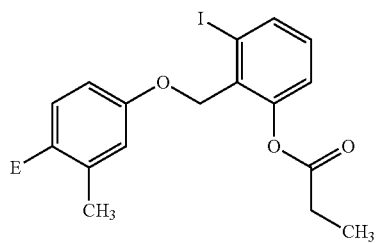
(HB4006)
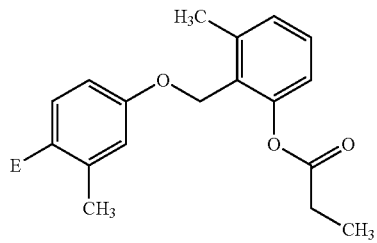
(HB4007)
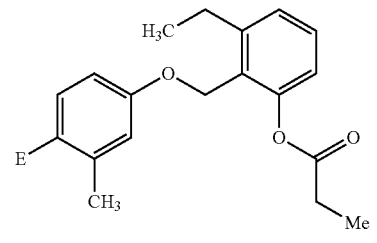

(HB4008)
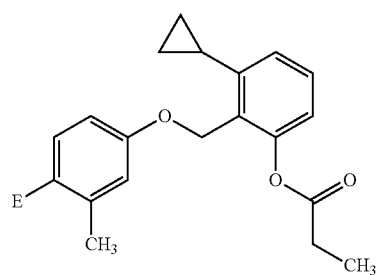
(HB4009)
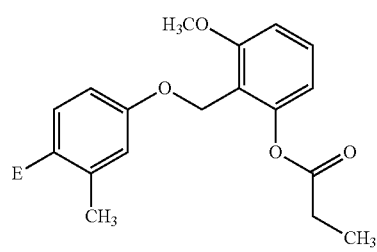
(HB4010)
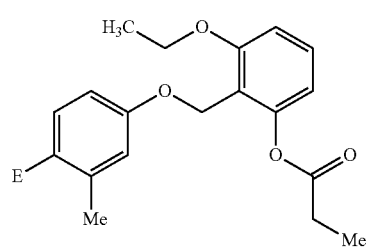
(HB4011)
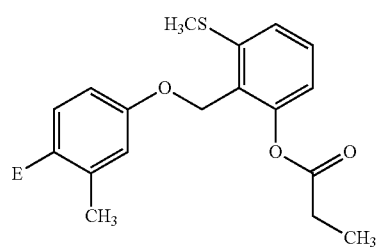
(HB4012)
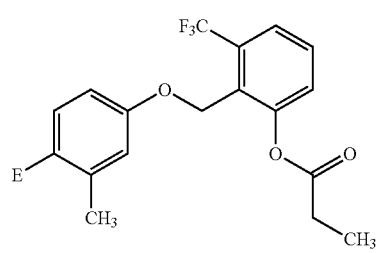
(HB4013)
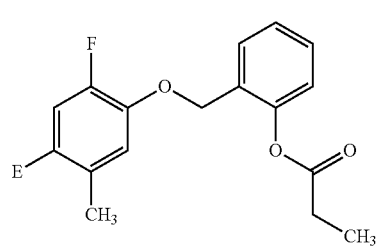
(HB4014)
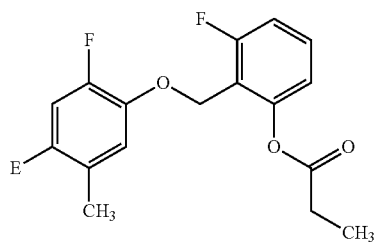
(HB4015)
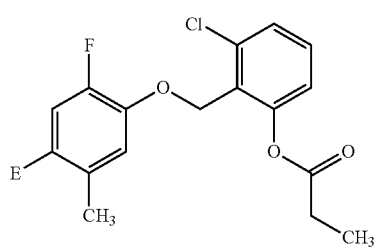
(HB4016)
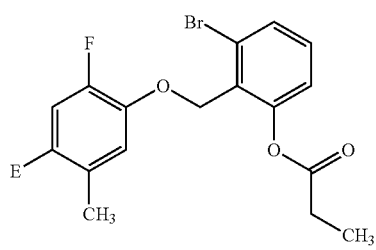
(HB4017)
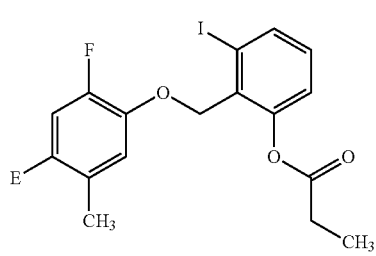
(HB4018)
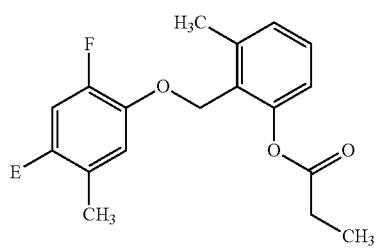
(HB4019)
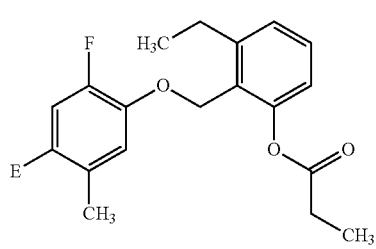

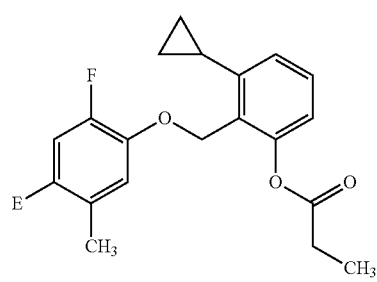
(HB4020)
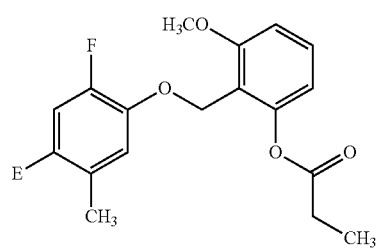
(HB4021)
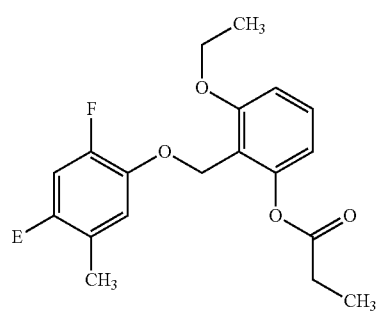
(HB4022)
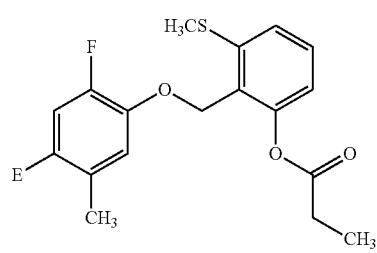
(HB4023)
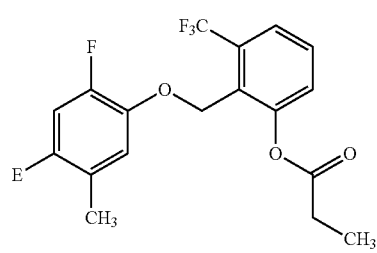
(HB4024)
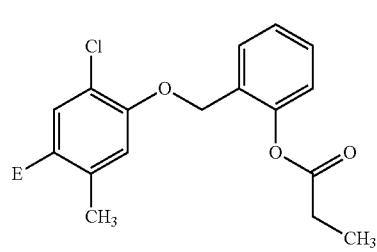
(HB4025)
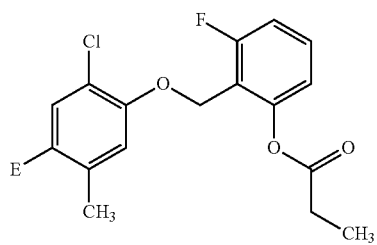
(HB4026)
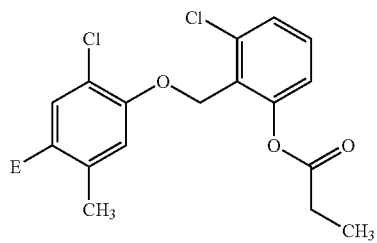
(HB4027)
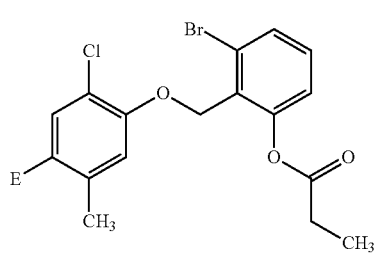
(HB4028)
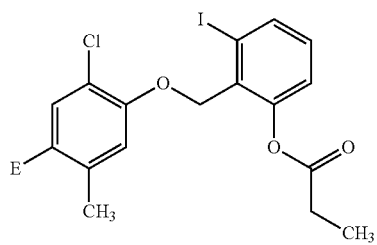
(HB4029)
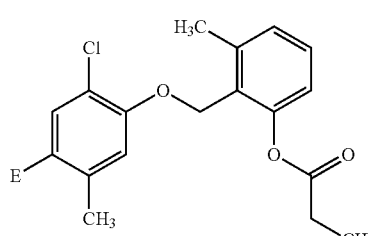
(HB4030)
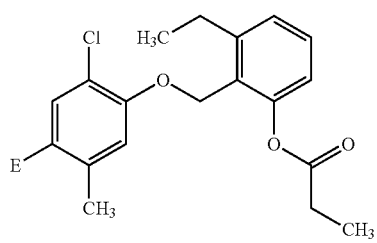
(HB4031)

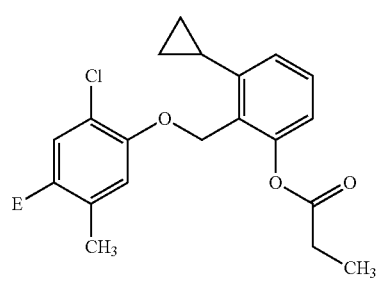
(HB4032)
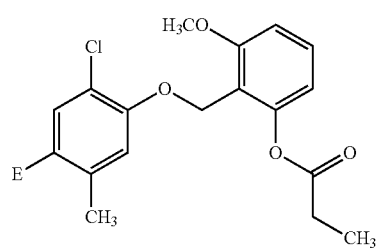
(HB4033)
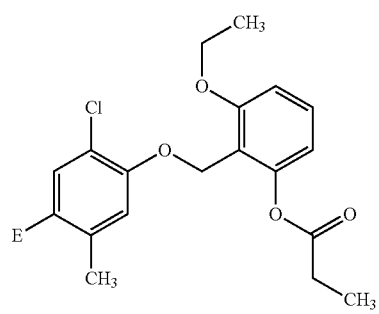
(HB4034)
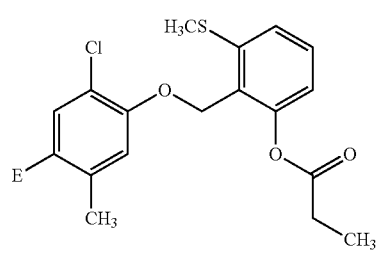
(HB4035)
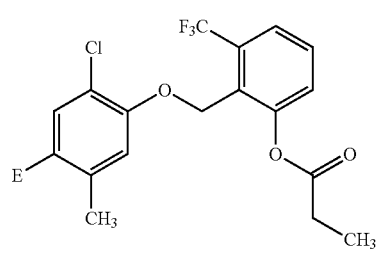
(HB4036)
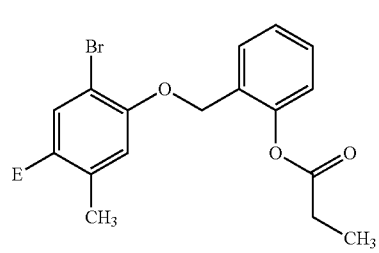
(HB4037)
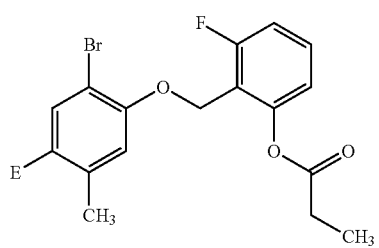
(HB4038)
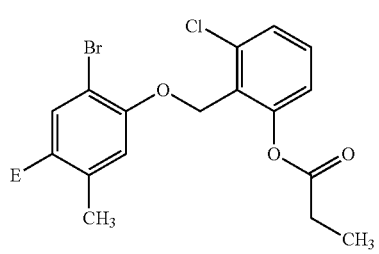
(HB4039)
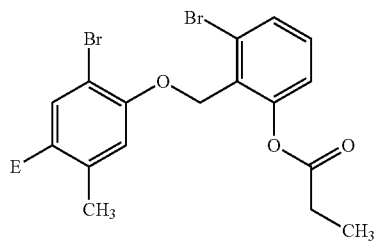
(HB4040)
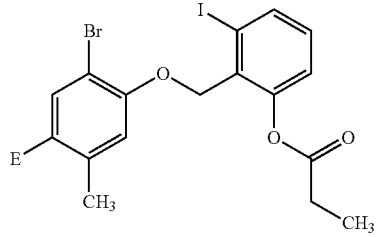
(HB4041)
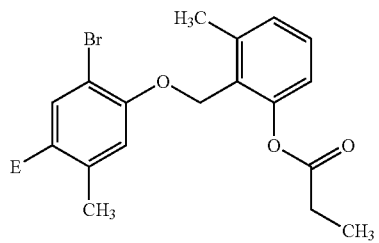
(HB4042)
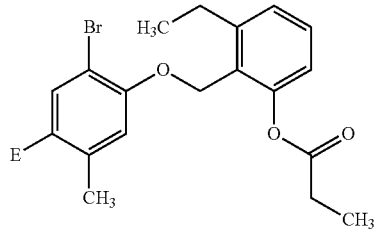
(HB4043)

(HB4044)
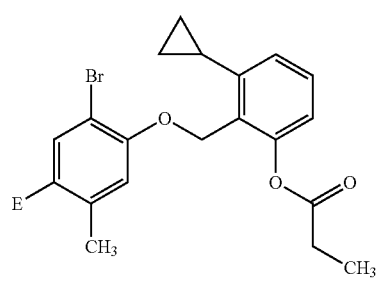
(HB4045)
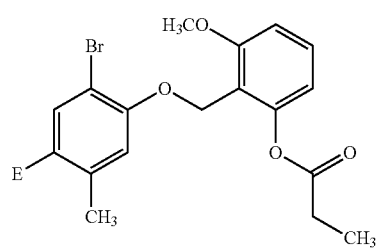
(HB4046)
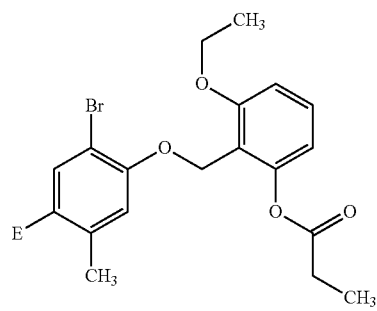
(HB4047)
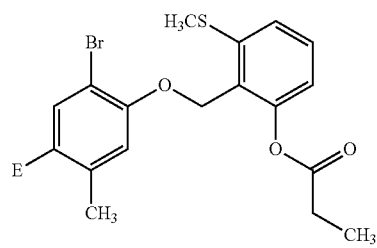
(HB4048)
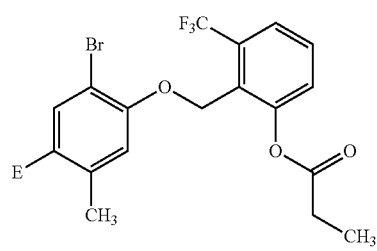
(HB4049)
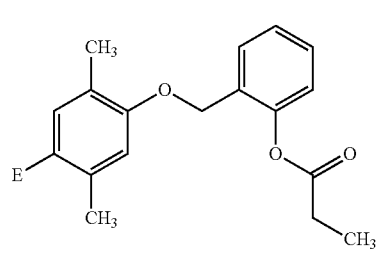
(HB4050)
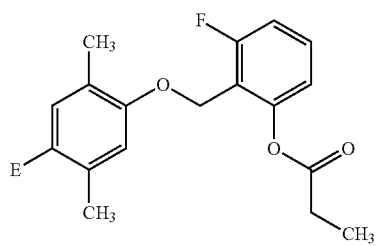
(HB4051)
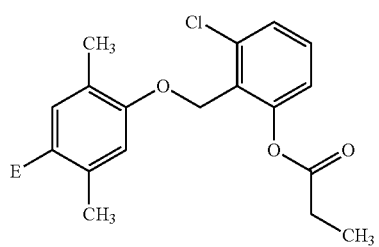
(HB4052)
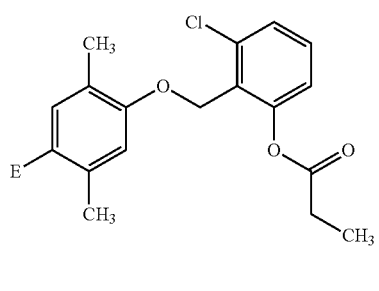
(HB4053)
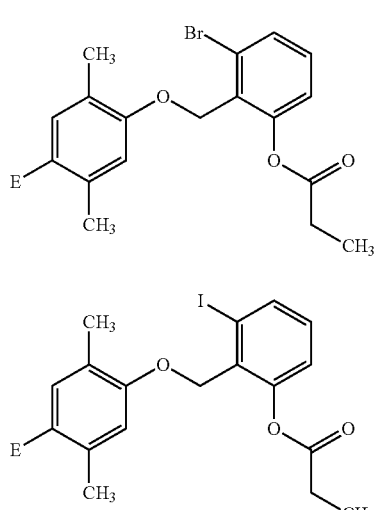
(HB4054)
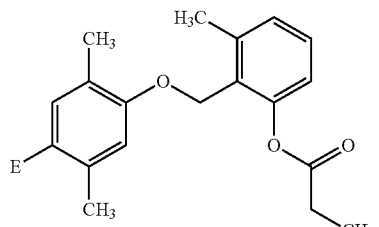
(HB4055)
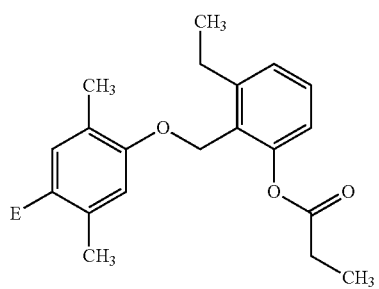

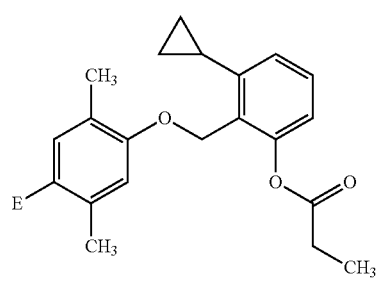
(HB4056)
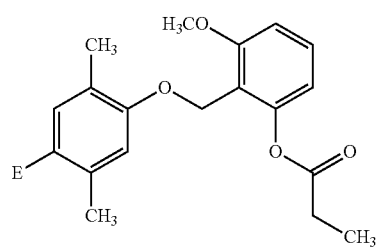
(HB4057)
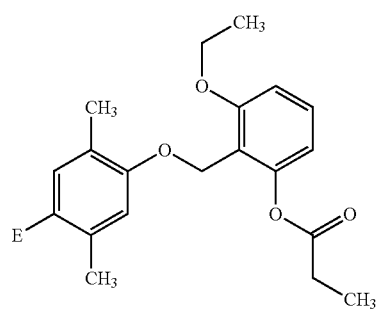
(HB4058)
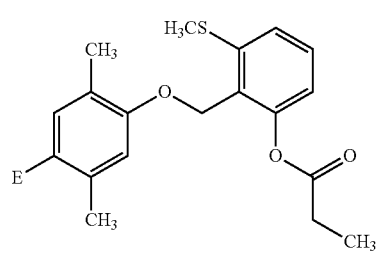
(HB4059)
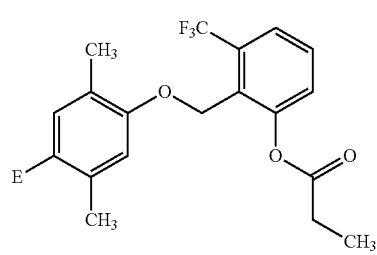
(HB4060)
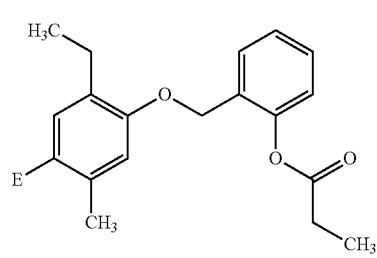
(HB4061)
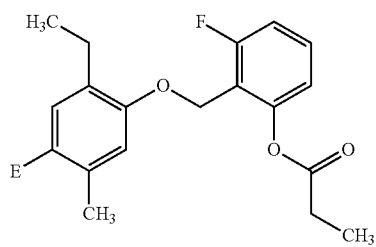
(HB4062)
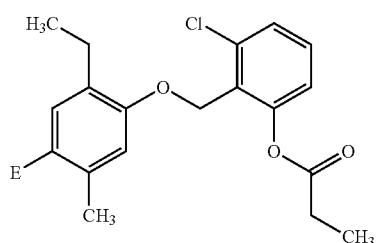
(HB4063)
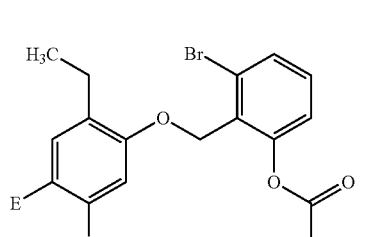
(HB4064)
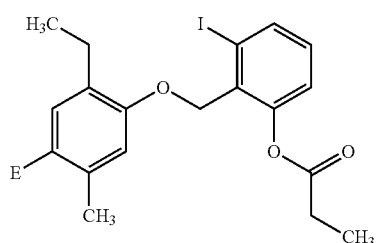
(HB4065)
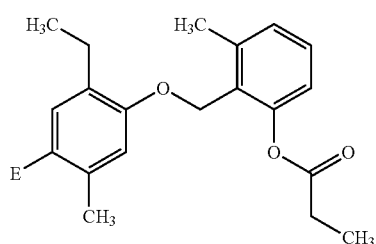
(HB4066)
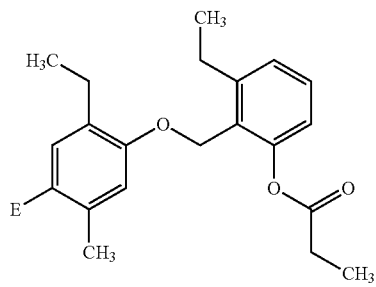
(HB4067)

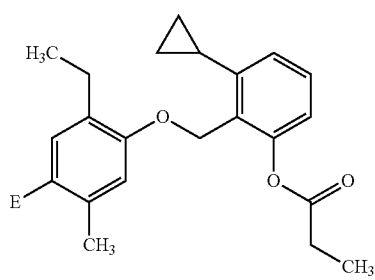
(HB4068)
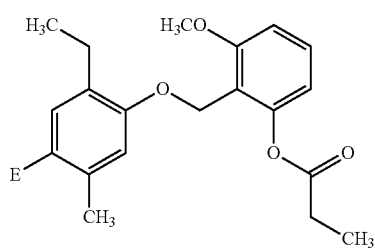
(HB4069)
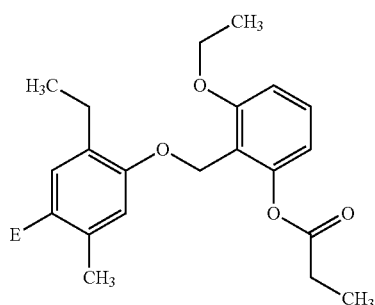
(HB4070)
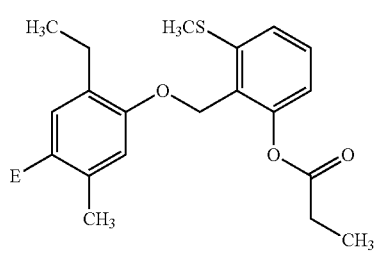
(HB4071)
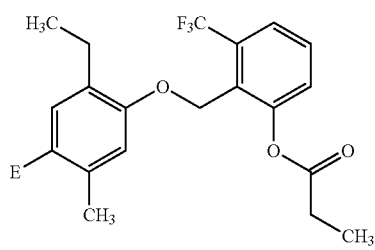
(HB4072)
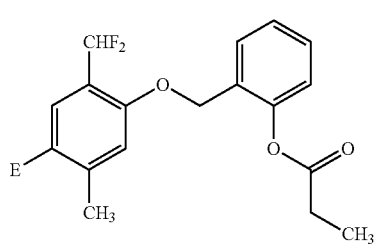
(HB4073)
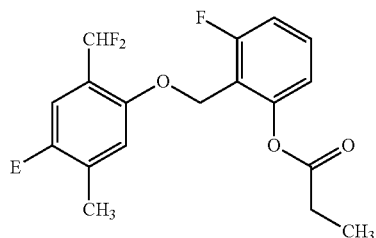
(HB4074)
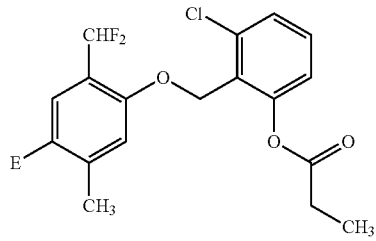
(HB4075)
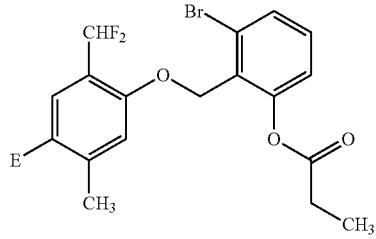
(HB4076)
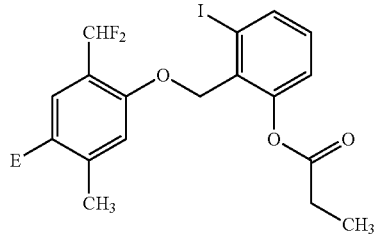
(HB4077)
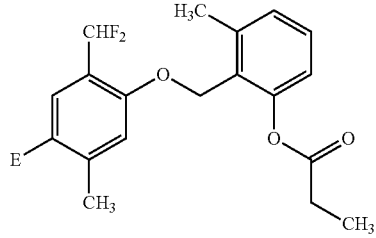
(HB4078)
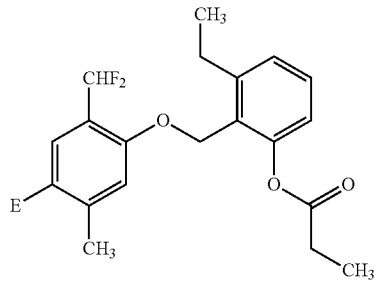
(HB4079)

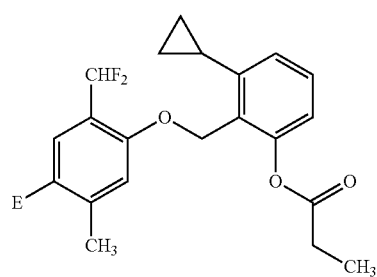
(HB4080)
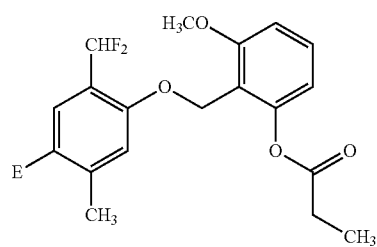
(HB4081)
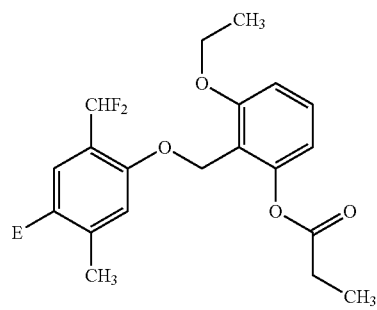
(HB4082)
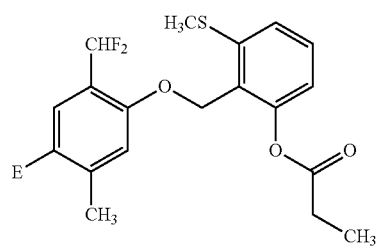
(HB4083)
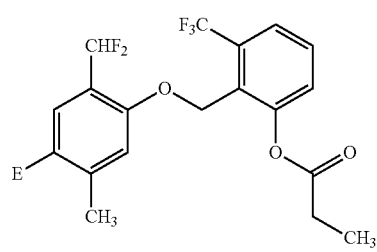
(HB4084)
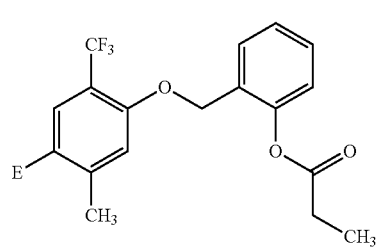
(HB4085)
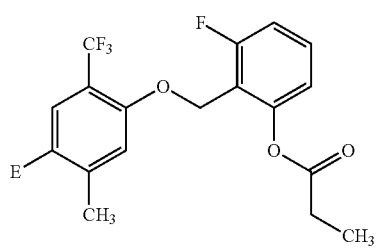
(HB4086)
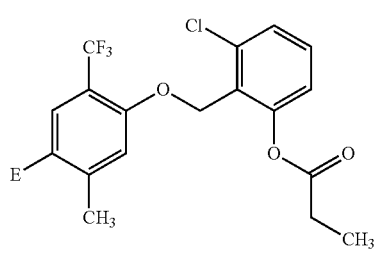
(HB4087)
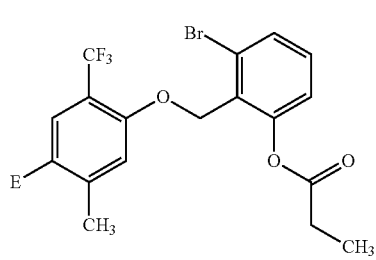
(HB4088)
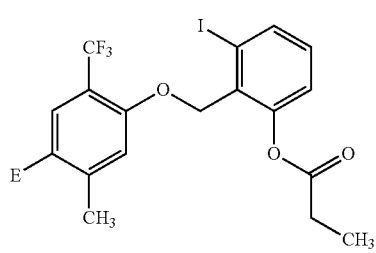
(HB4089)
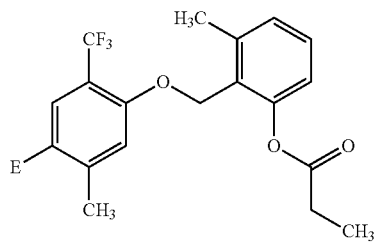
(HB4090)
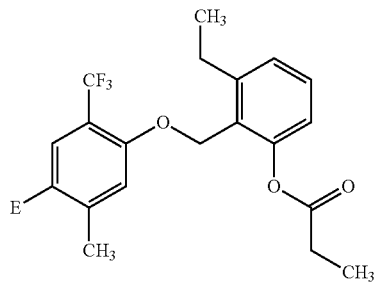
(HB4091)

-continued
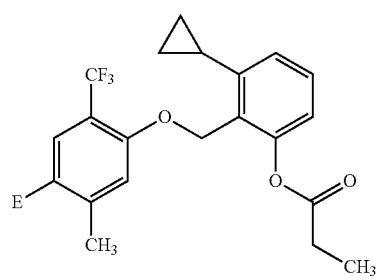 (HB4092)
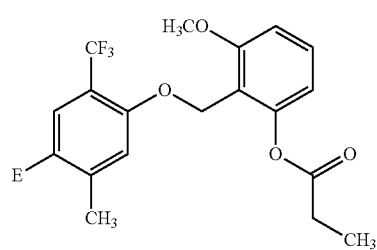 (HB4093)
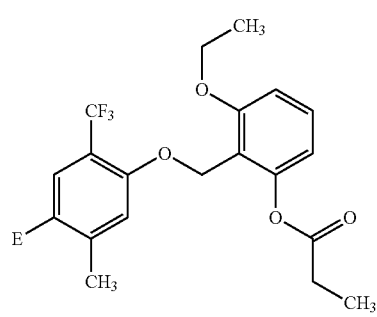 (HB4094)
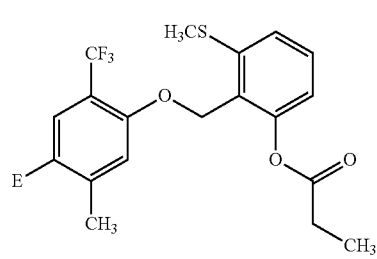 (HB4095)
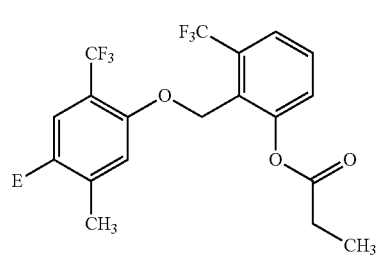 (HB4096)
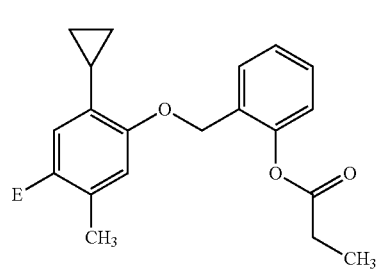 (HB4097)
-continued
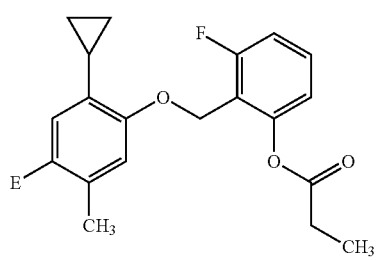 (HB4098)
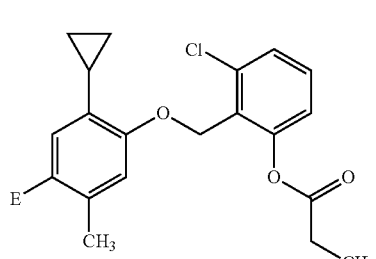 (HB4099)
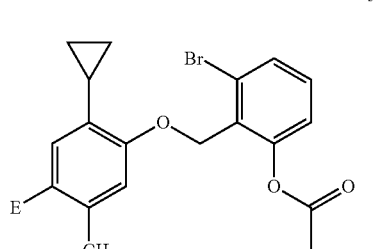 (HB4100)
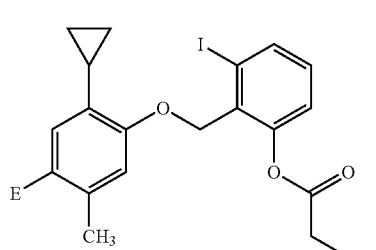 (HB4101)
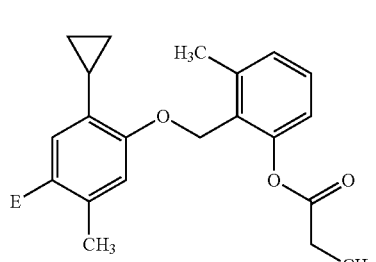 (HB4102)
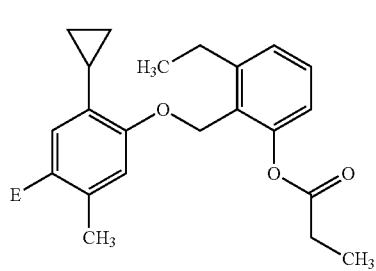 (HB4103)

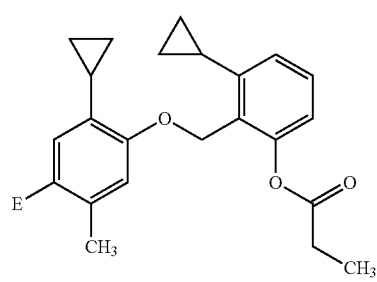
(HB4104)
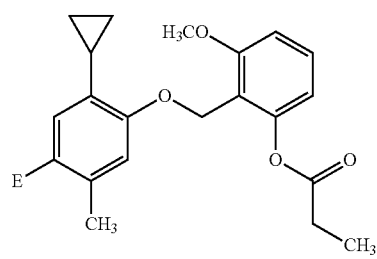
(HB4105)
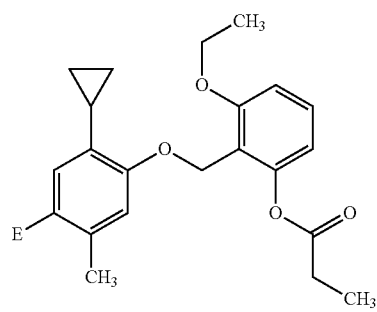
(HB4106)
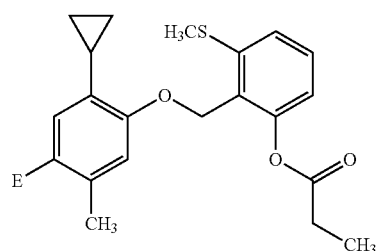
(HB4107)
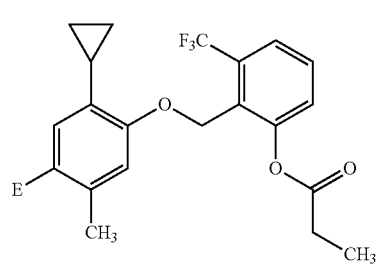
(HB4108)
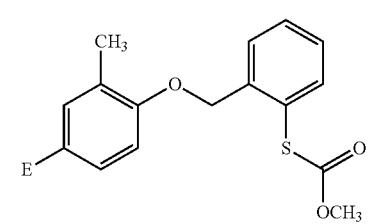
(HC1001)
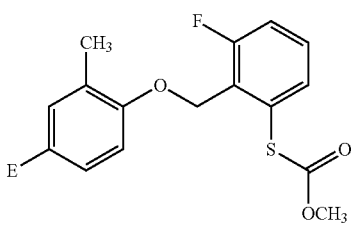
(HC1002)
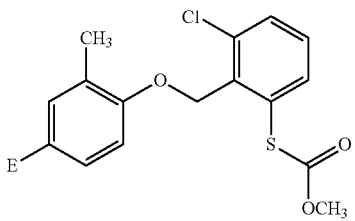
(HC1003)
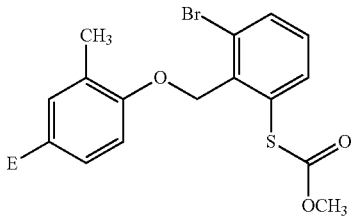
(HC1004)
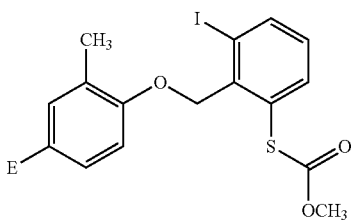
(HC1005)
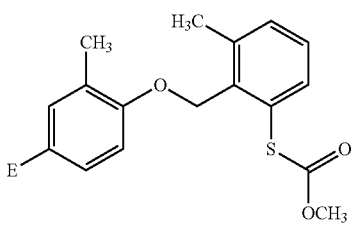
(HC1006)
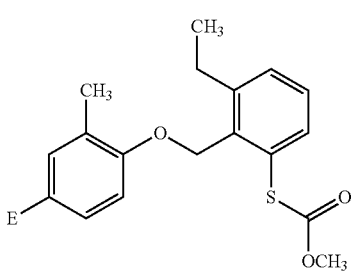
(HC1007)

-continued
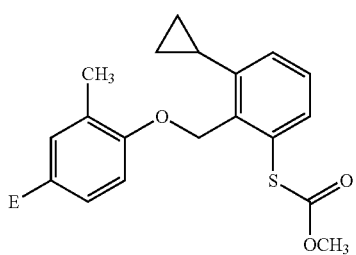 (HC1008)
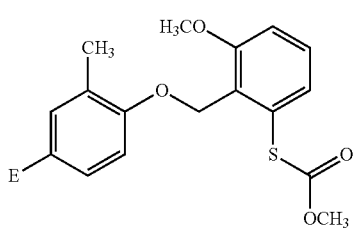 (HC1009)
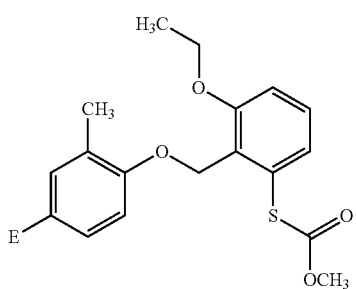 (HC1010)
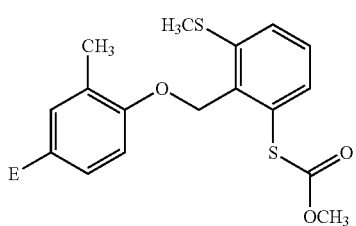 (HC1011)
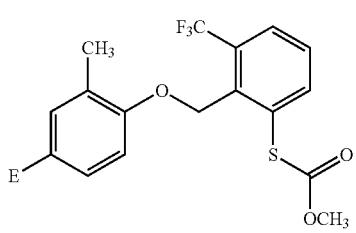 (HC1012)
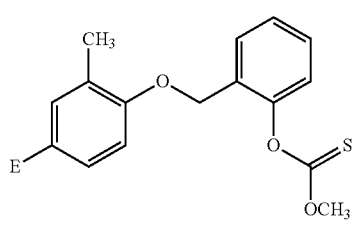 (HC1013)
-continued
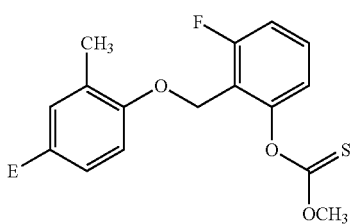 (HC1014)
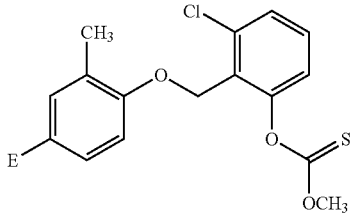 (HC1015)
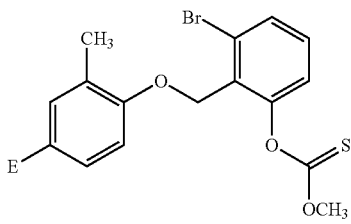 (HC1016)
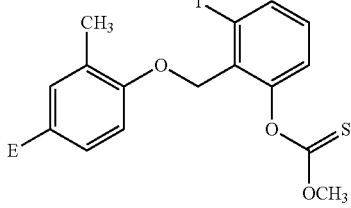 (HC1017)
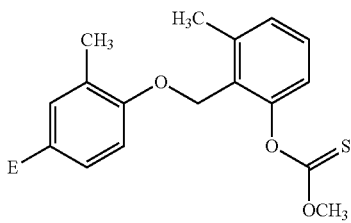 (HC1018)
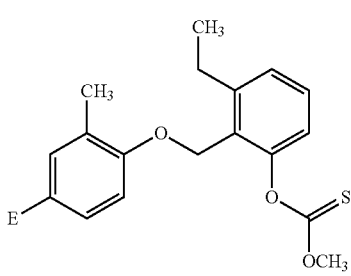 (HC1019)

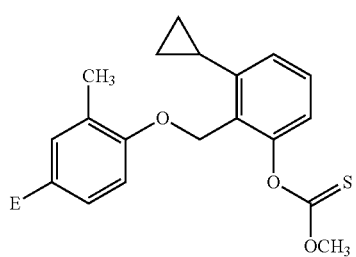
(HC1020)
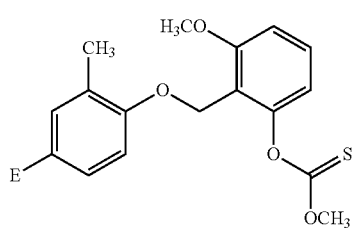
(HC1021)
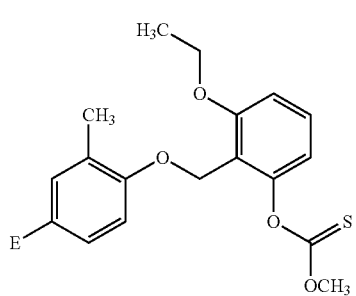
(HC1022)
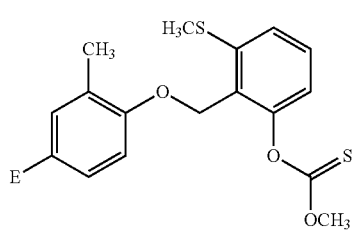
(HC1023)
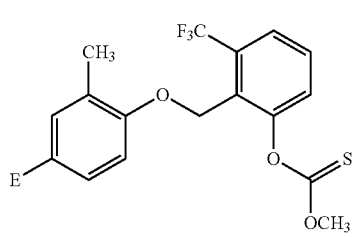
(HC1024)
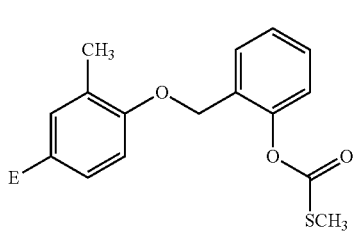
(HC1025)
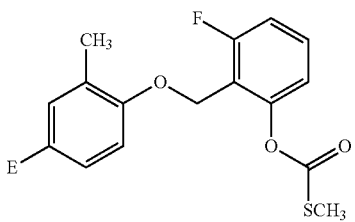
(HC1026)
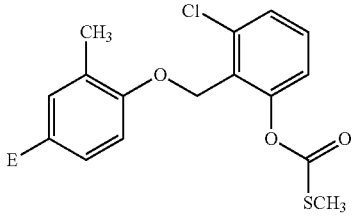
(HC1027)
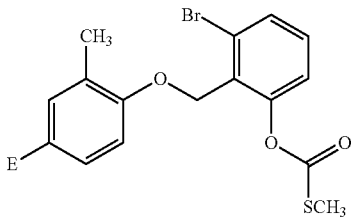
(HC1028)
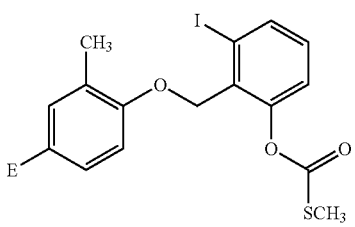
(HC1029)
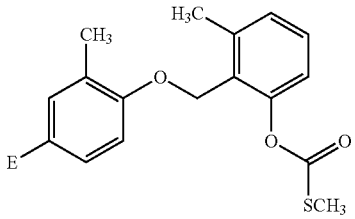
(HC1030)
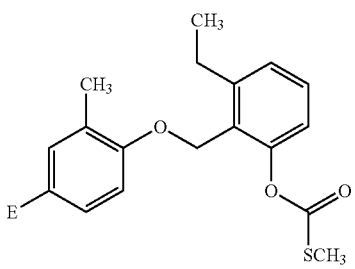
(HC1031)

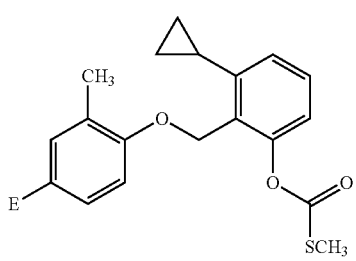 (HC1032)
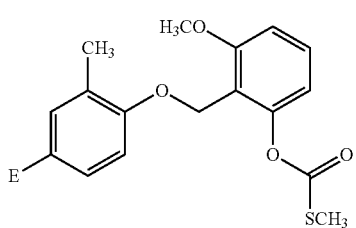 (HC1033)
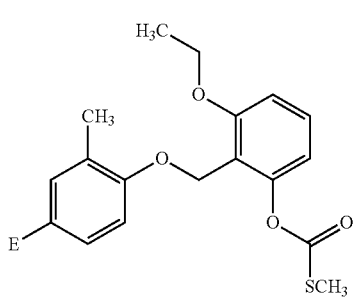 (HC1034)
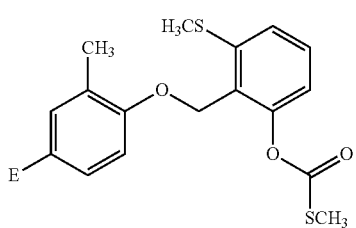 (HC1035)
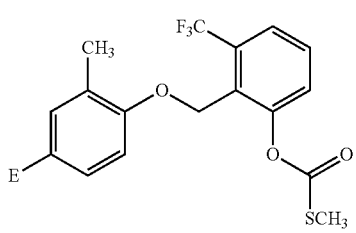 (HC1036)
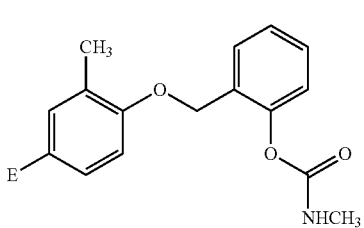 (HC1037)
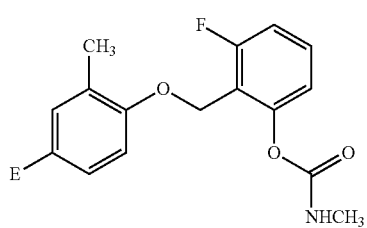 (HC1038)
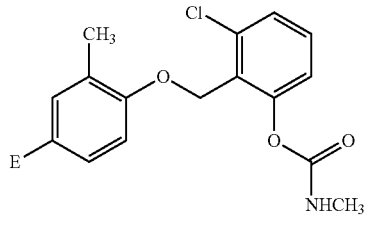 (HC1039)
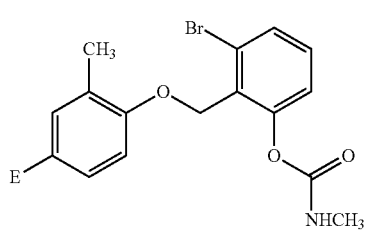 (HC1040)
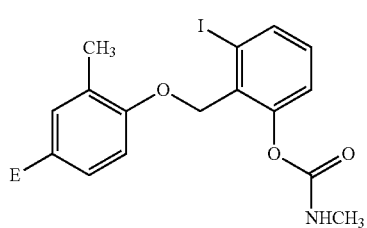 (HC1041)
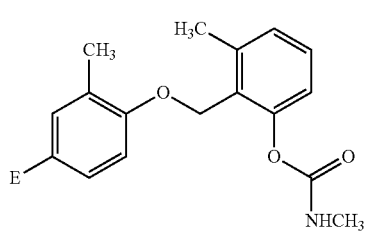 (HC1042)
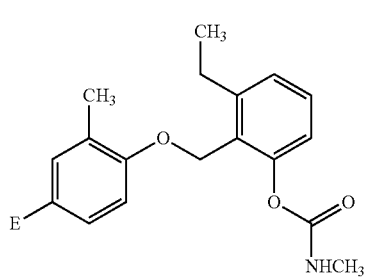 (HC1043)

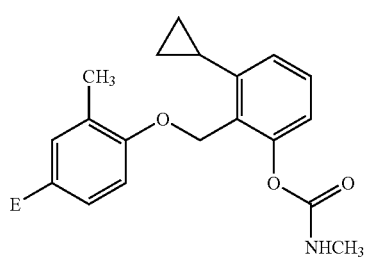
(HC1044)
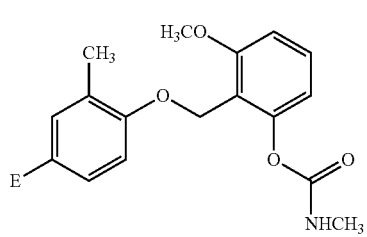
(HC1045)
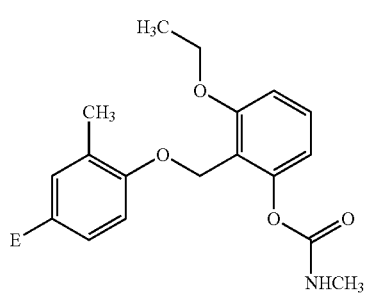
(HC1046)
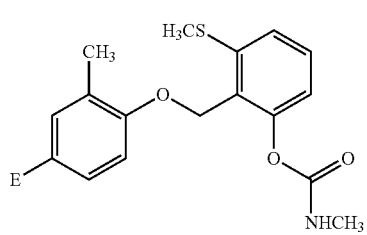
(HC1047)
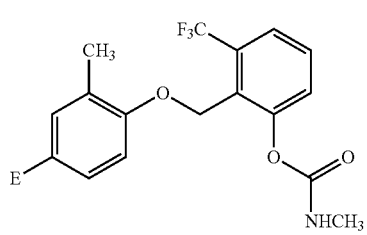
(HC1048)
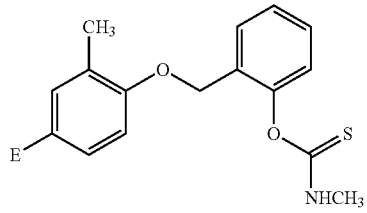
(HC1049)
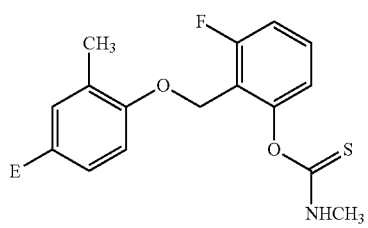
(HC1050)
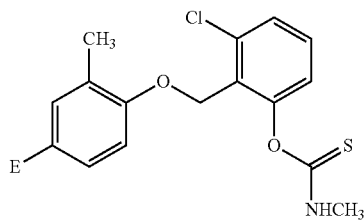
(HC1051)
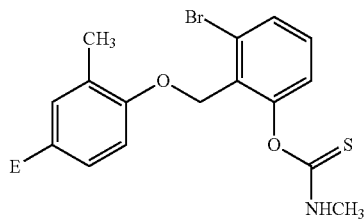
(HC1052)
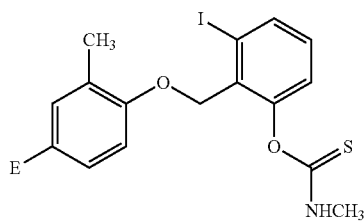
(HC1053)
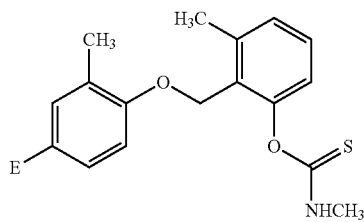
(HC1054)
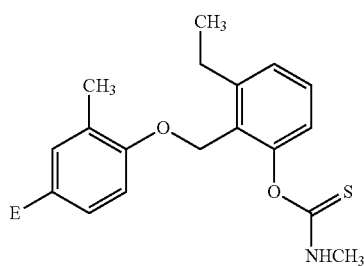
(HC1055)

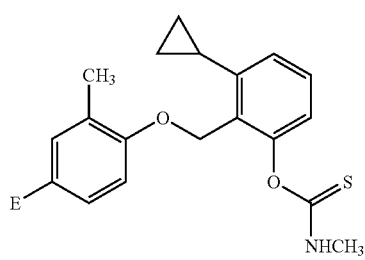
(HC1056)
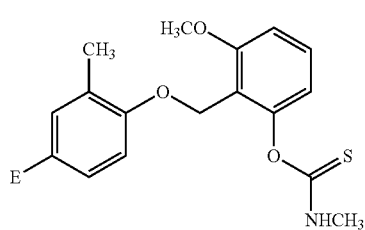
(HC1057)
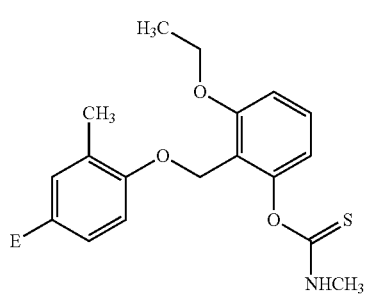
(HC1058)
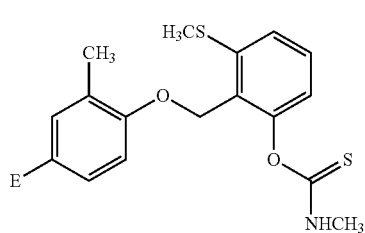
(HC1059)
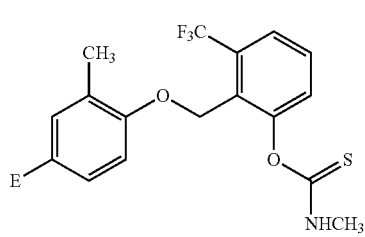
(HC1060)
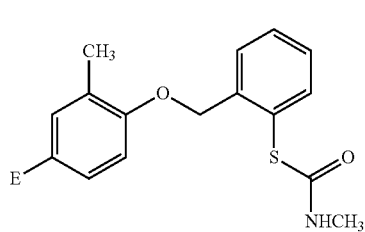
(HC1061)
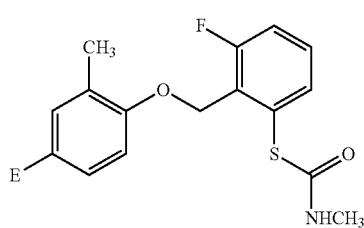
(HC1062)
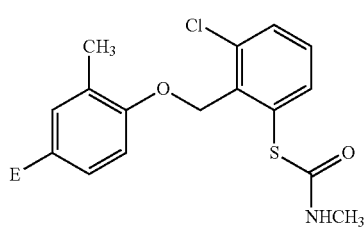
(HC1063)
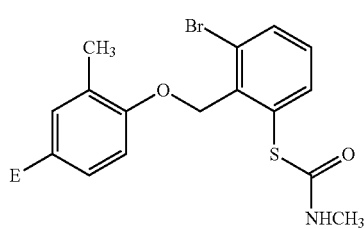
(HC1064)
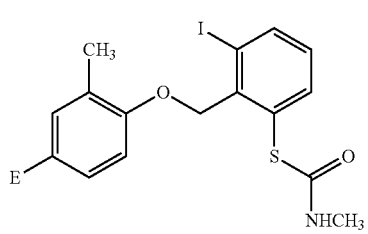
(HC1065)
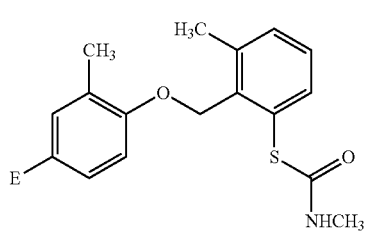
(HC1066)
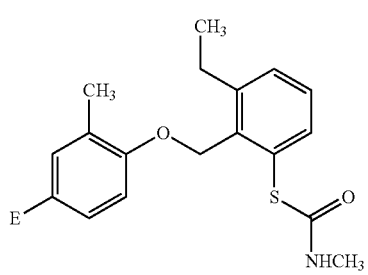
(HC1067)

(HC1068), (HC1069), (HC1070), (HC1071), (HC1072), (HC1073), (HC1074), (HC1075), (HC1076), (HC1077), (HC1078), (HC1079)

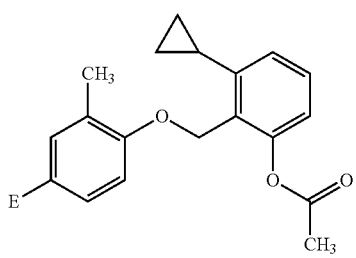 (HC1080)
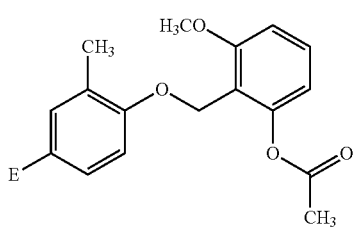 (HC1081)
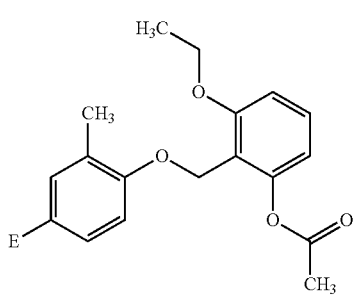 (HC1082)
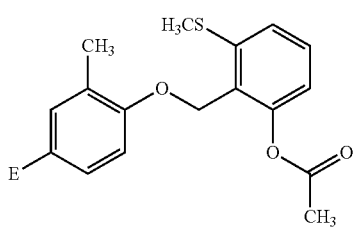 (HC1083)
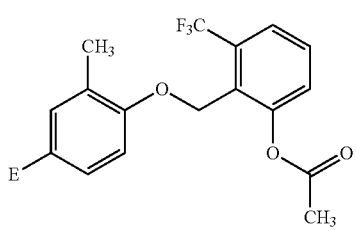 (HC1084)
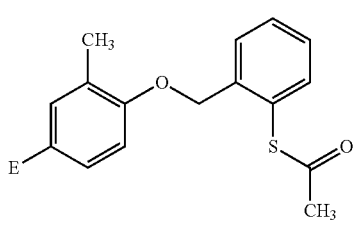 (HC1085)
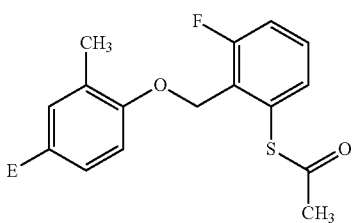 (HC1086)
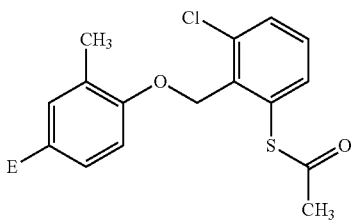 (HC1087)
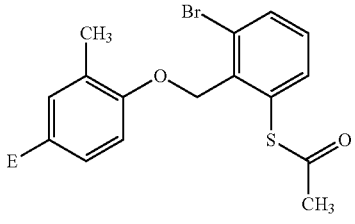 (HC1088)
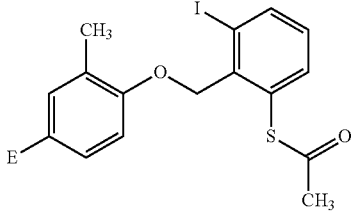 (HC1089)
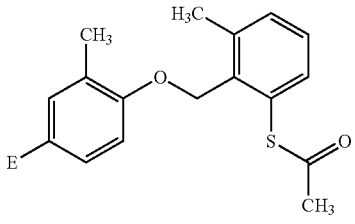 (HC1090)
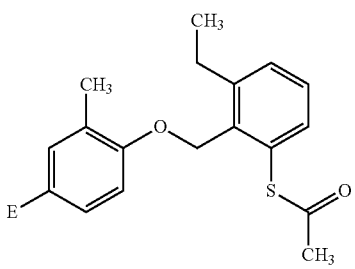 (HC1091)

(HC1092)
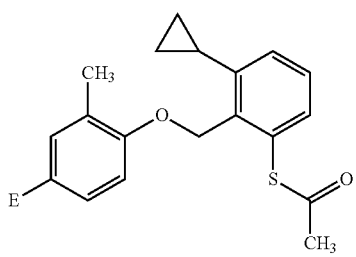
(HC1093)
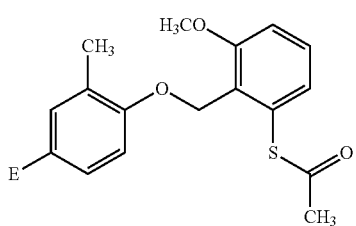
(HC1094)
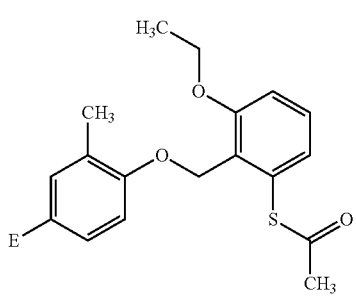
(HC1095)
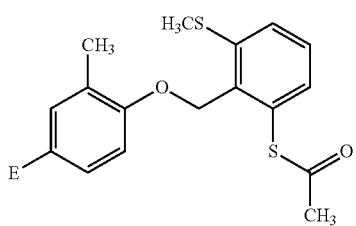
(HC1096)
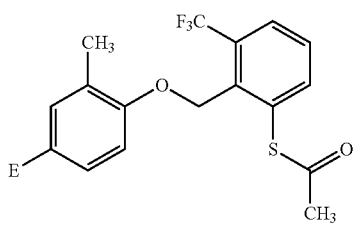
(HC1097)
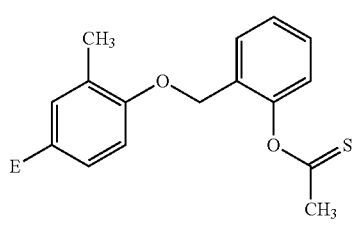
(HC1098)
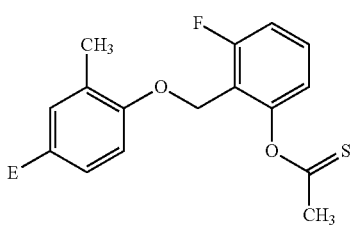
(HC1099)
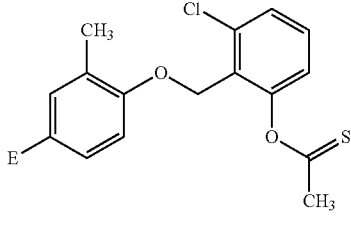
(HC1100)
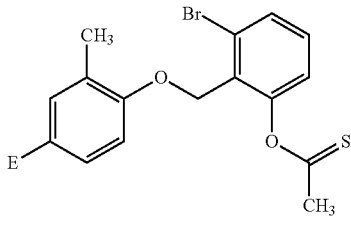
(HC1101)
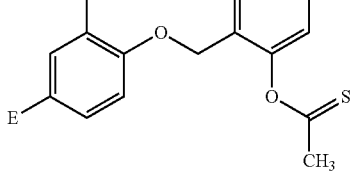
(HC1102)
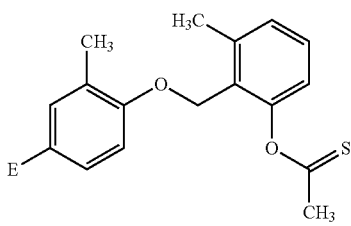
(HC1103)
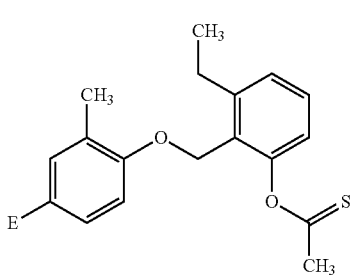

(HC1104)
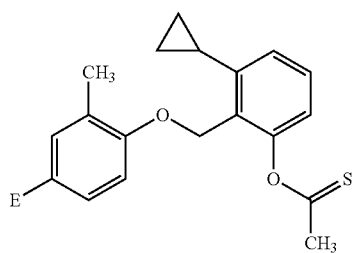
(HC1105)
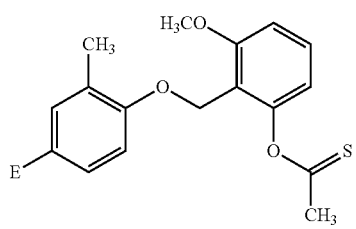
(HC1106)
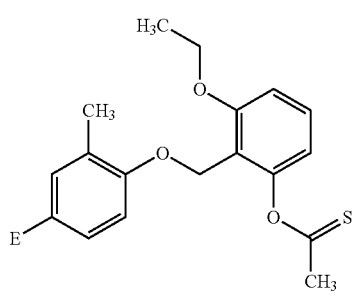
(HC1107)
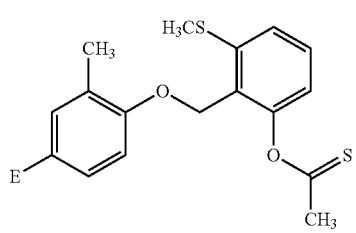
(HC1108)
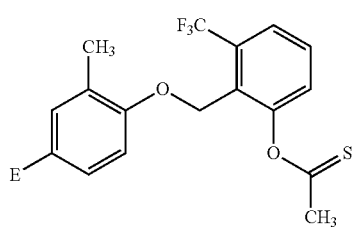
(HC1109)
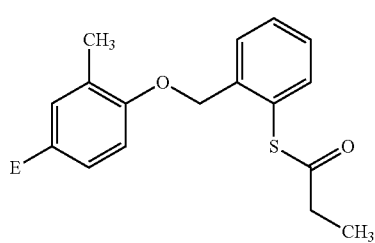
(HC1110)
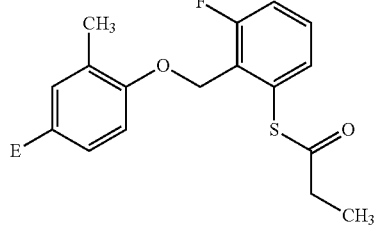
(HC1111)
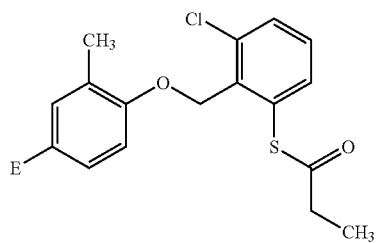
(HC1112)
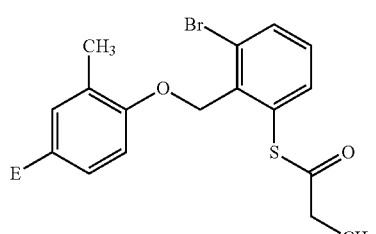
(HC1113)
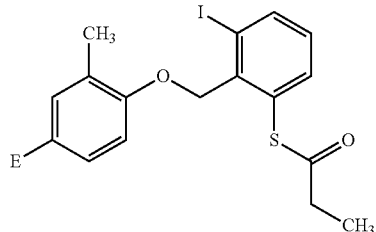
(HC1114)
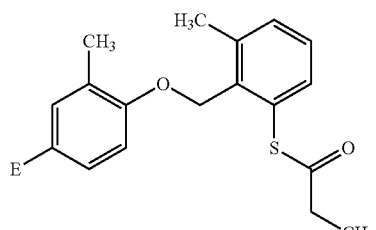
(HC1115)
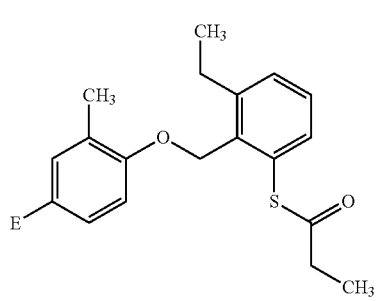

(HC1116)
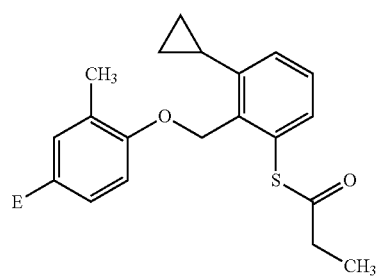
(HC1117)
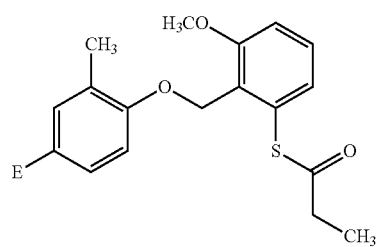
(HC1118)
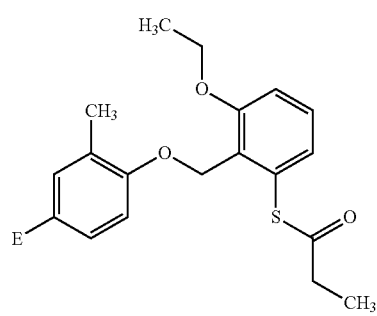
(HC1119)
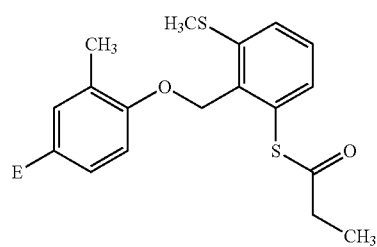
(HC1120)
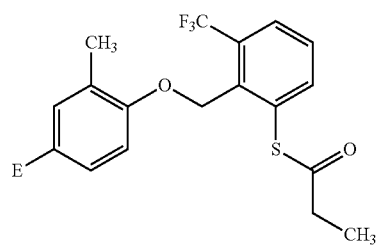
(HC1121)
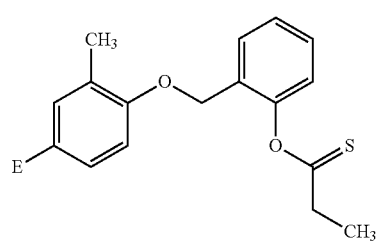
(HC1122)
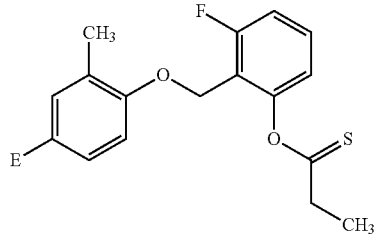
(HC1123)
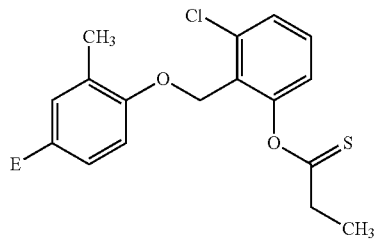
(HC1124)
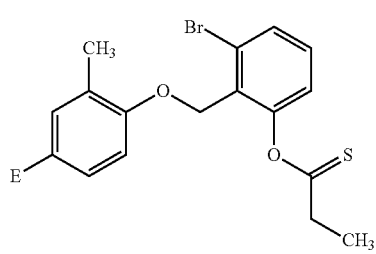
(HC1125)
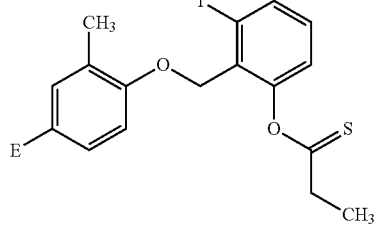
(HC1126)
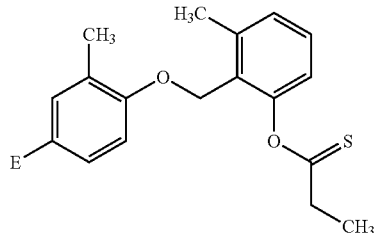
(HC1127)
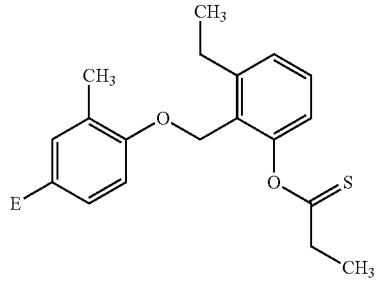

(HC1128)
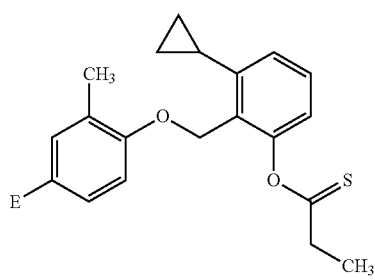
(HC1129)
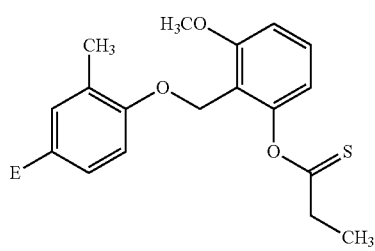
(HC1130)
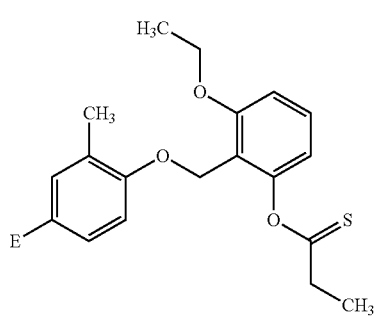
(HC1131)
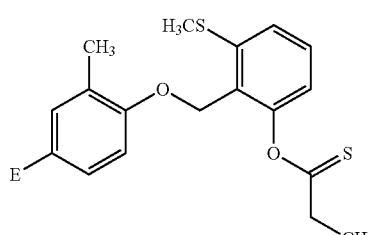
(HC1132)
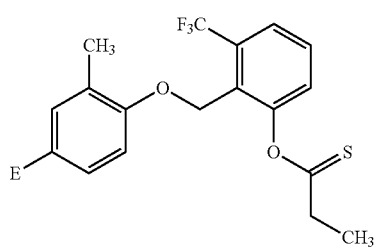
(HC2001)
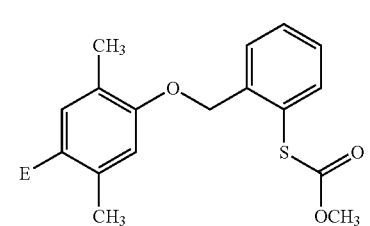
(HC2002)
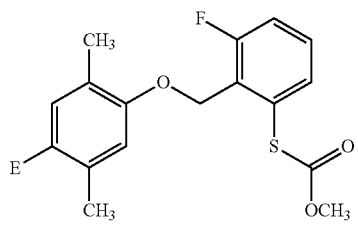
(HC2003)
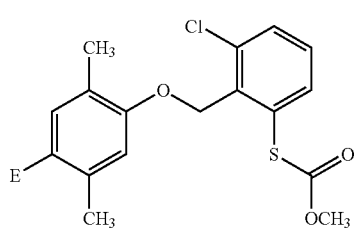
(HC2004)
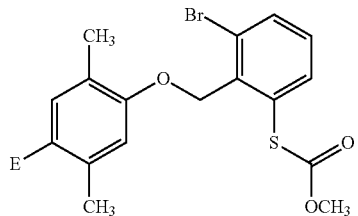
(HC2005)
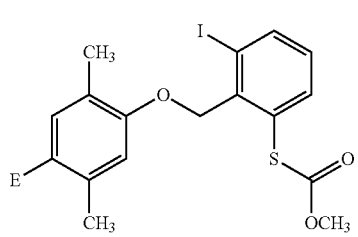
(HC2006)
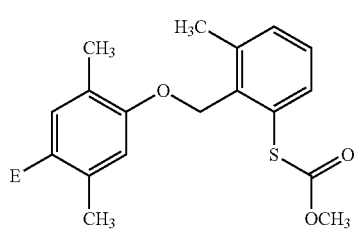
(HC2007)
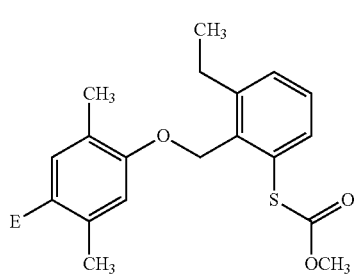

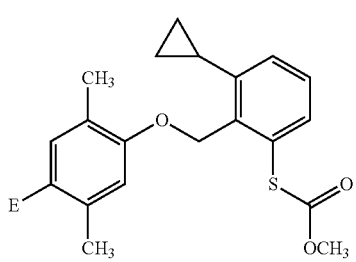
(HC2008)
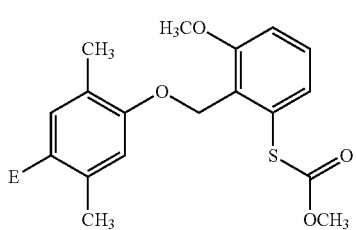
(HC2009)
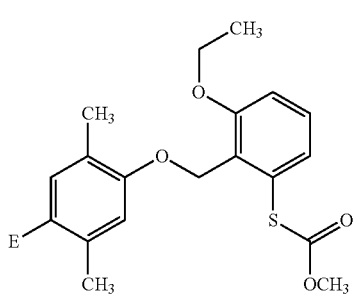
(HC2010)
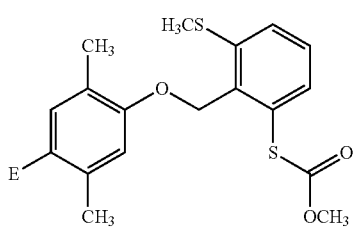
(HC2011)
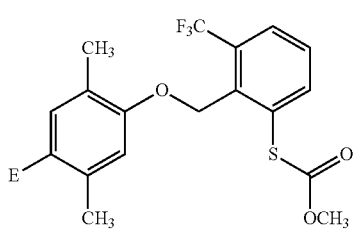
(HC2012)
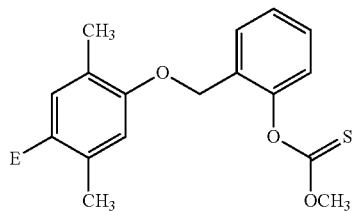
(HC2013)
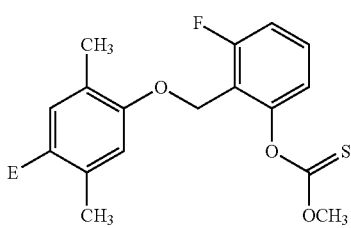
(HC2014)
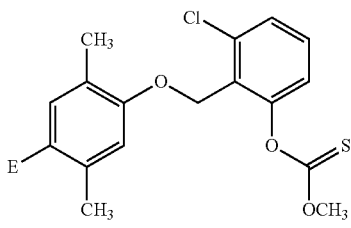
(HC2015)
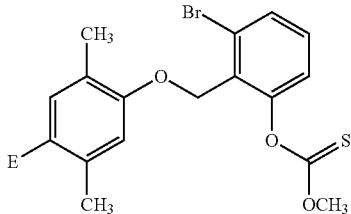
(HC2016)
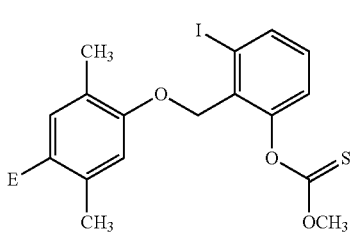
(HC2017)
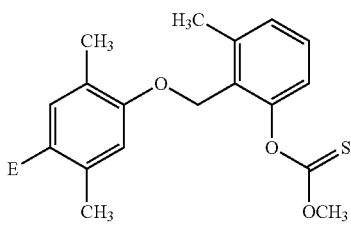
(HC2018)
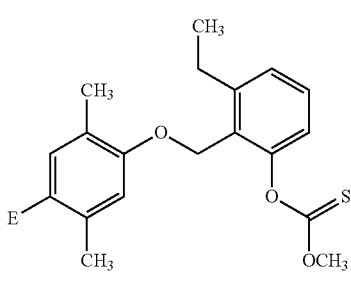
(HC2019)

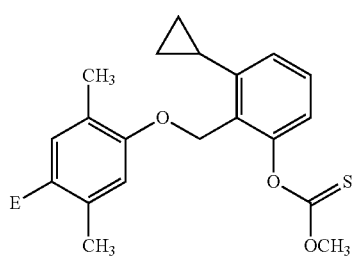
(HC2020)
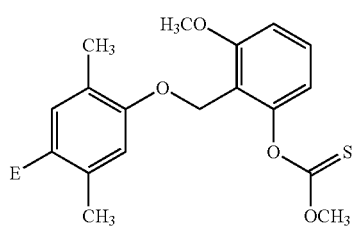
(HC2021)
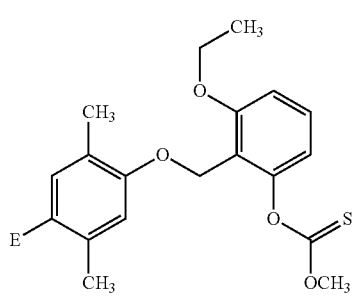
(HC2022)
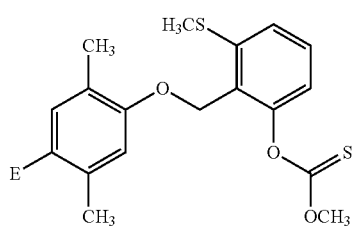
(HC2023)
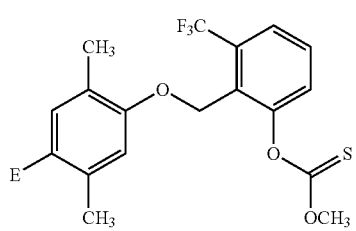
(HC2024)
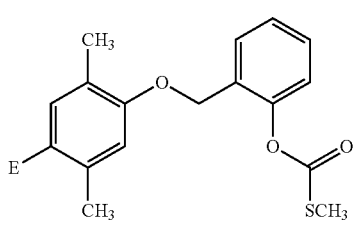
(HC2025)
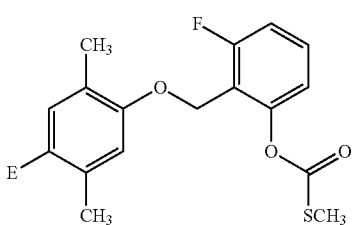
(HC2026)
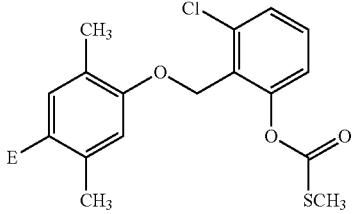
(HC2027)
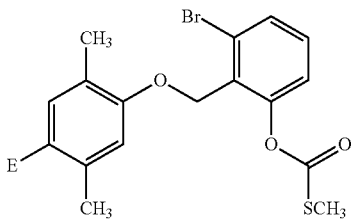
(HC2028)
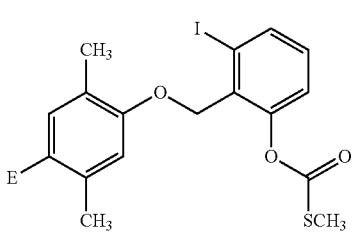
(HC2029)
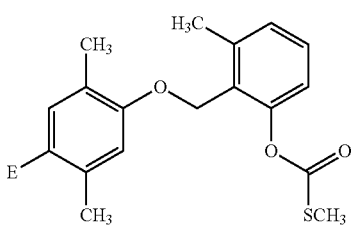
(HC2030)
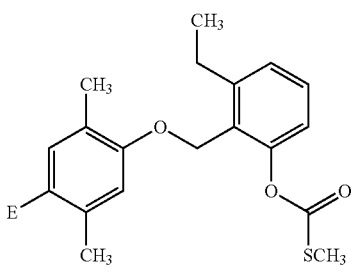
(HC2031)

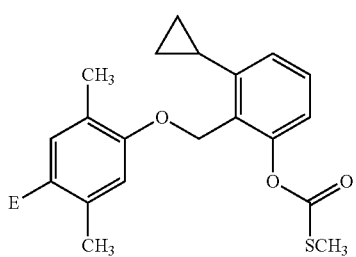
(HC2032)
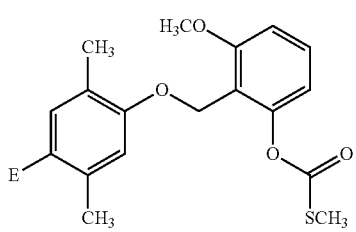
(HC2033)
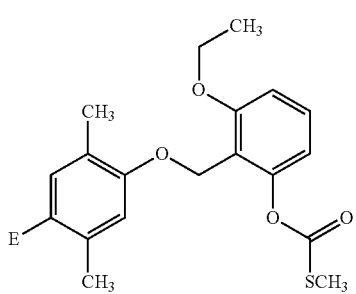
(HC2034)
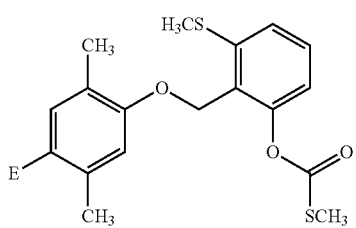
(HC2035)
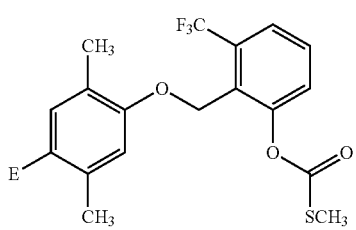
(HC2036)
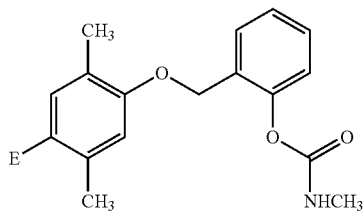
(HC2037)
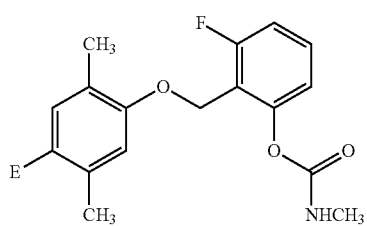
(HC2038)
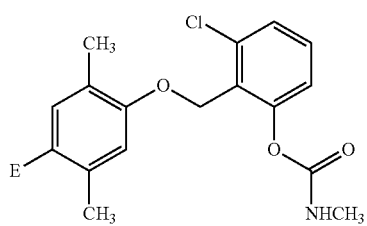
(HC2039)
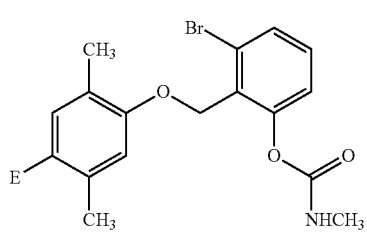
(HC2040)
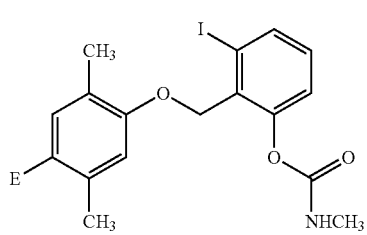
(HC2041)
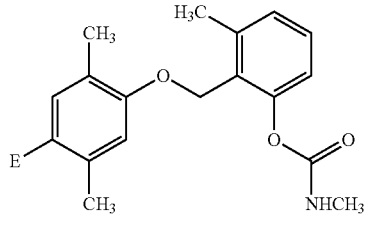
(HC2042)
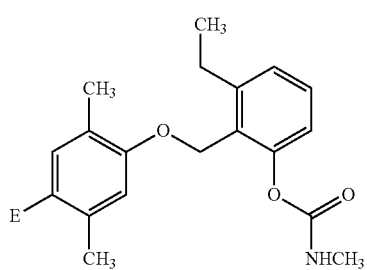
(HC2043)

(HC2044)
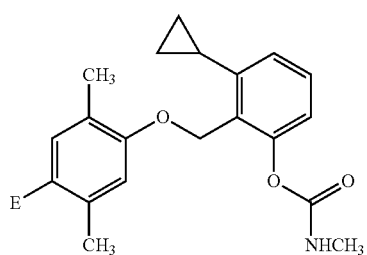
(HC2045)
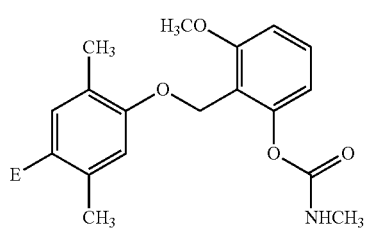
(HC2046)
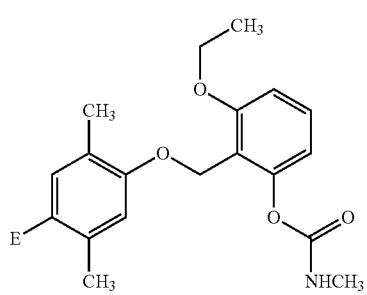
(HC2047)
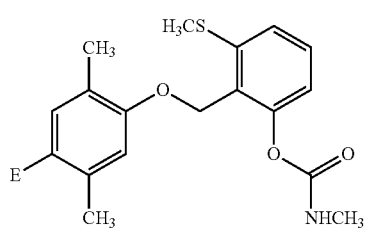
(HC2048)
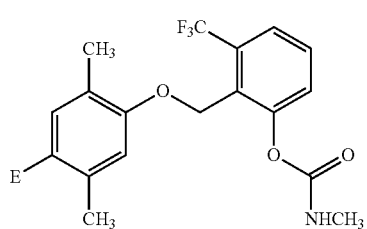
(HC2049)
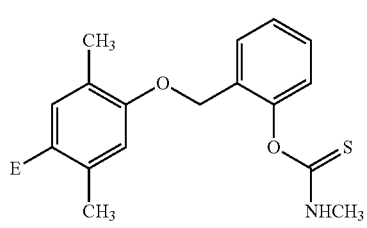
(HC2050)
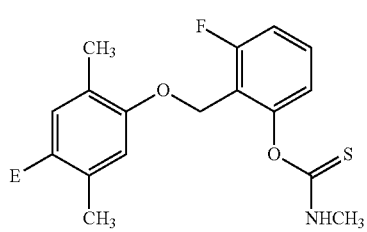
(HC2051)
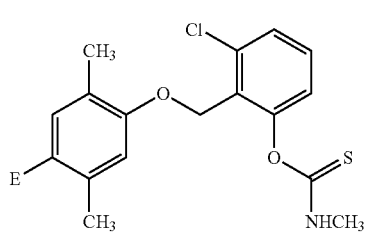
(HC2052)
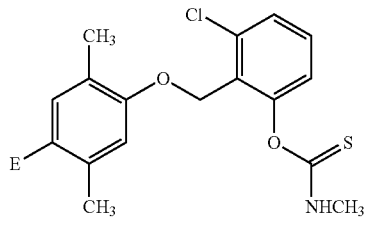
(HC2053)
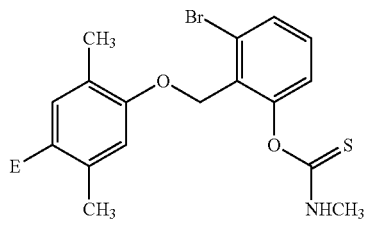
(HC2054)
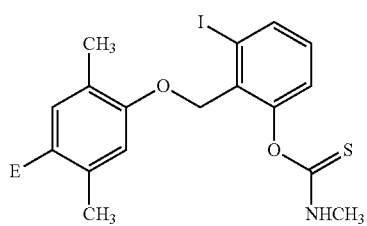
(HC2055)
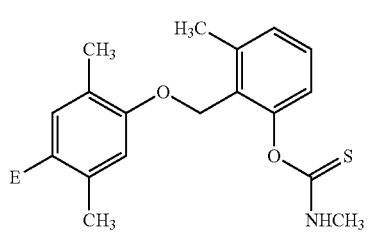

221
-continued
(HC2056)
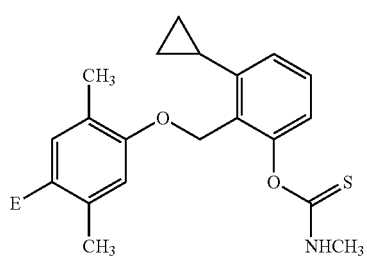
(HC2057)
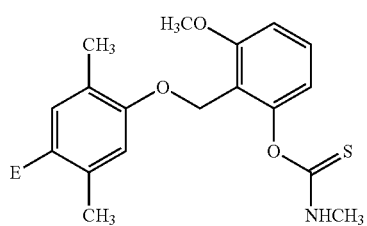
(HC2058)
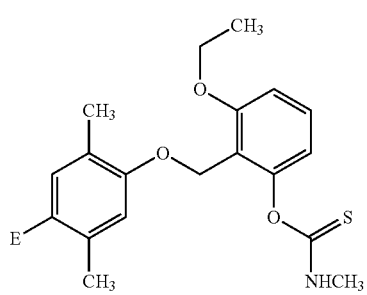
(HC2059)
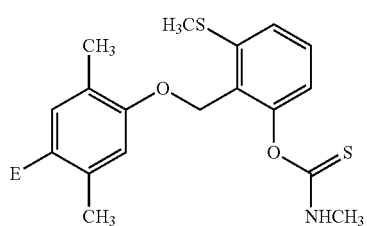
(HC2060)
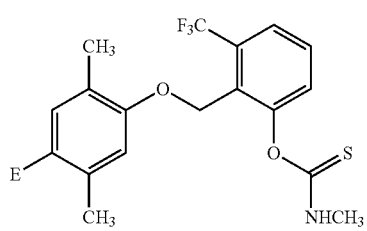
(HC2061)
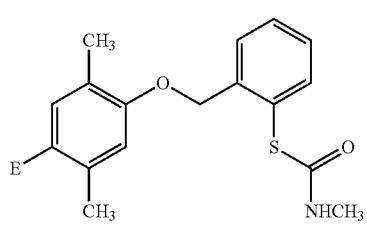
222
-continued
(HC2062)
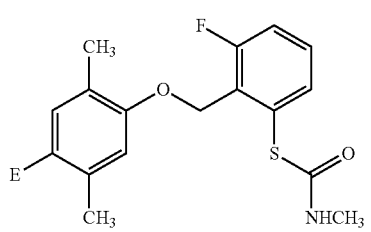
(HC2063)
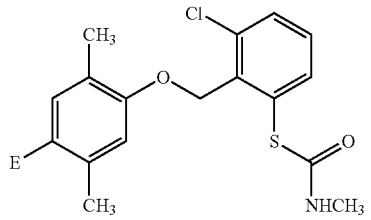
(HC2064)
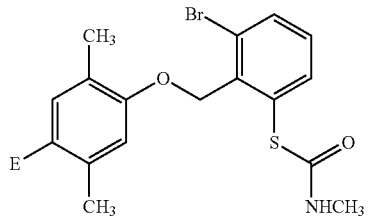
(HC2065)
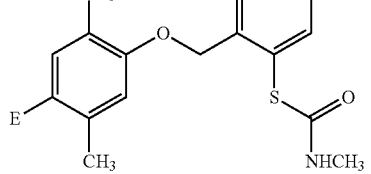
(HC2066)
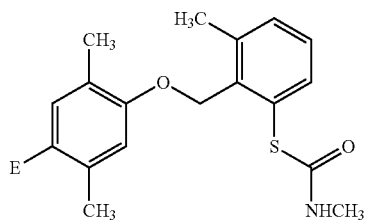
(HC2067)
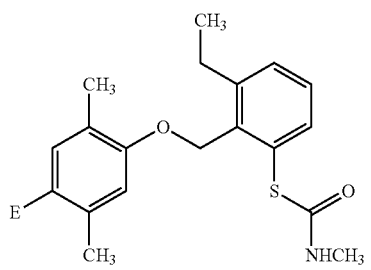

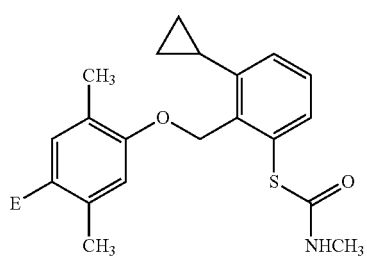
(HC2068)
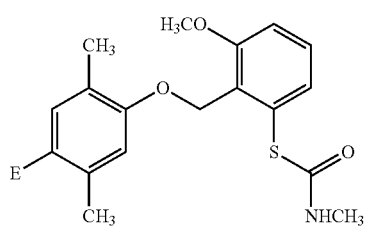
(HC2069)
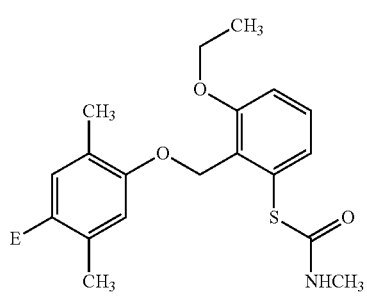
(HC2070)
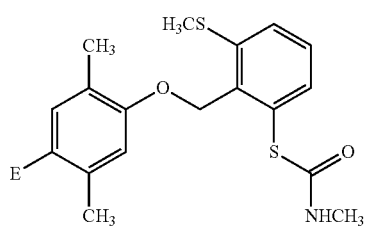
(HC2071)
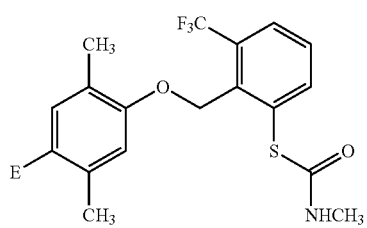
(HC2072)
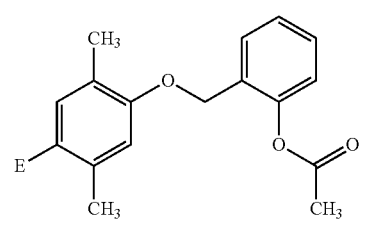
(HC2073)
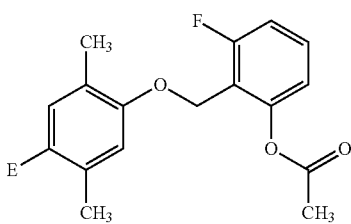
(HC2074)
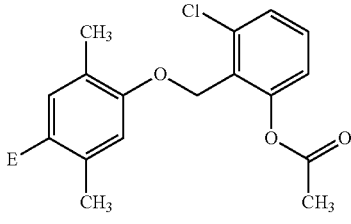
(HC2075)
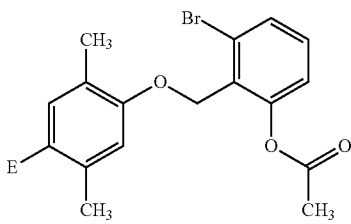
(HC2076)
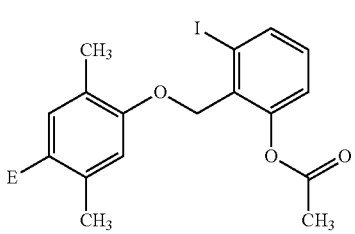
(HC2077)
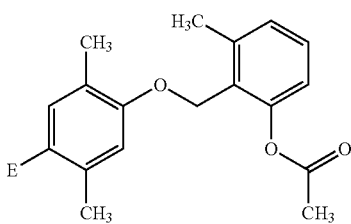
(HC2078)
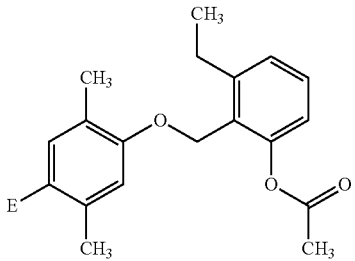
(HC2079)

| 225 -continued | 226 -continued |
|---|---|
| 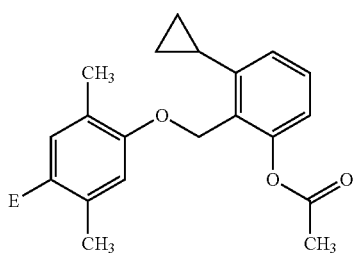 (HC2080) | 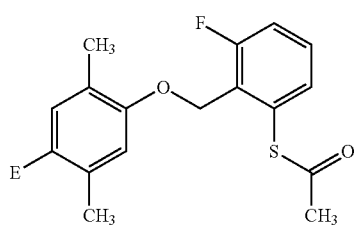 (HC2086) |
| 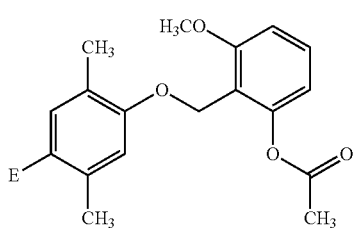 (HC2081) | 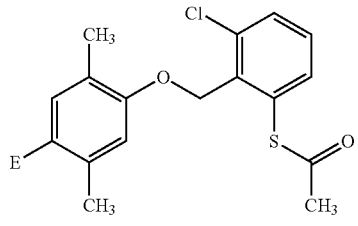 (HC2087) |
| 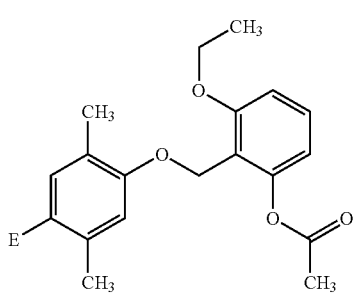 (HC2082) | 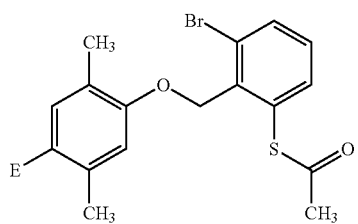 (HC2088) |
| 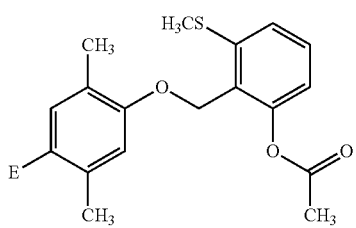 (HC2083) | 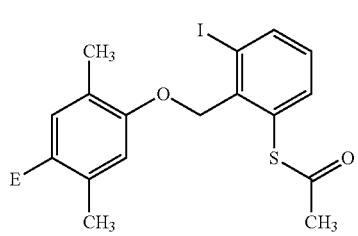 (HC2089) |
| 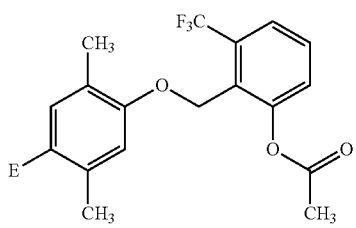 (HC2084) | 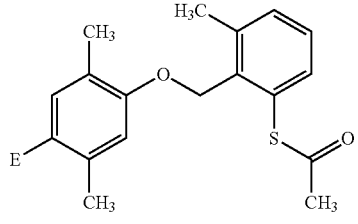 (HC2090) |
| 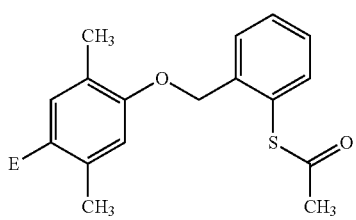 (HC2085) | 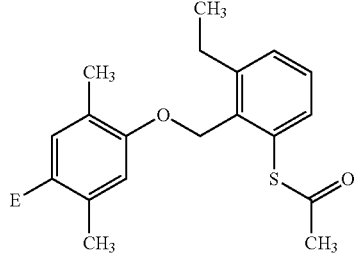 (HC2091) |

(HC2092)
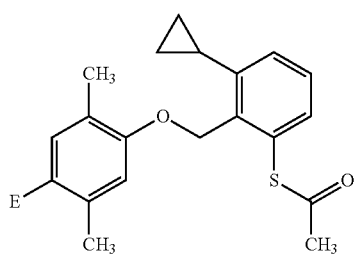
(HC2093)
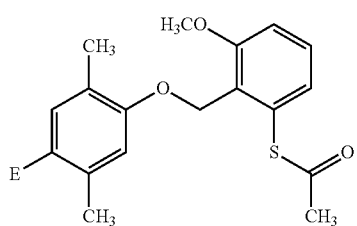
(HC2094)
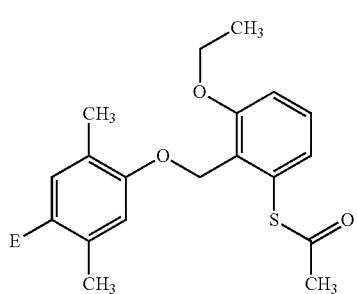
(HC2095)
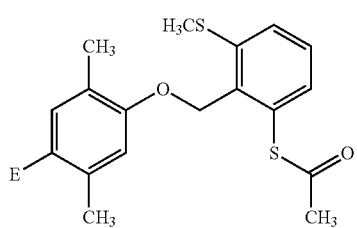
(HC2096)
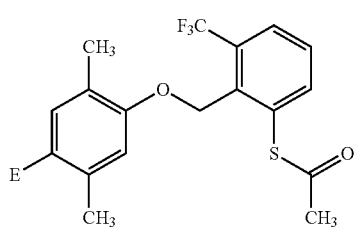
(HC2097)
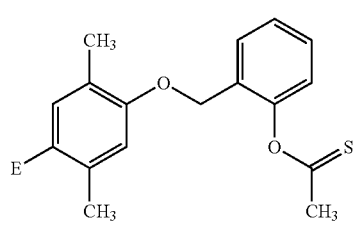
(HC2098)
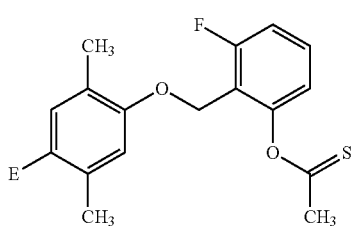
(HC2099)
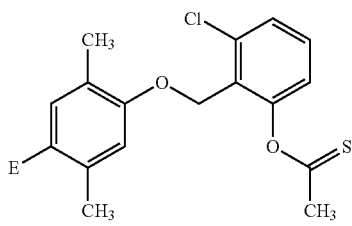
(HC2100)
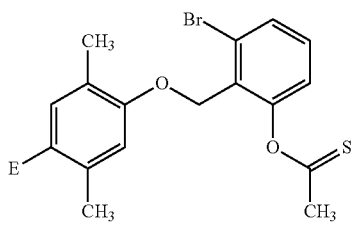
(HC2101)
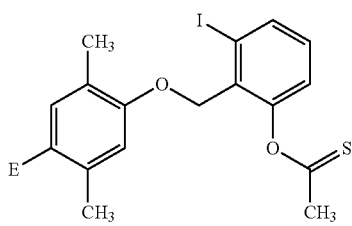
(HC2102)
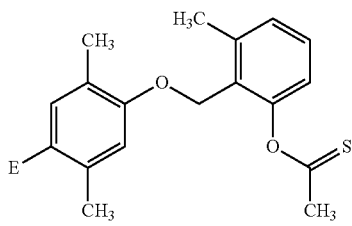
(HC2103)
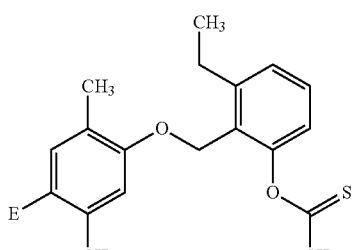

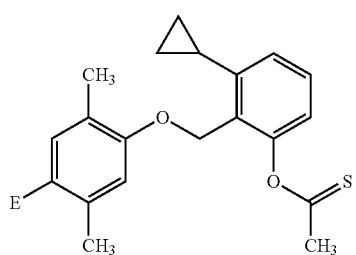 (HC2104)
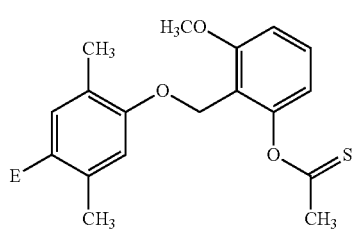 (HC2105)
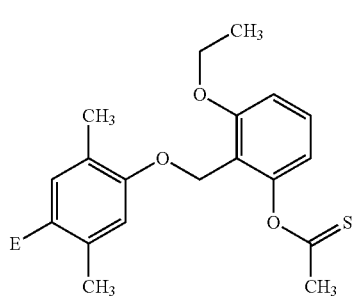 (HC2106)
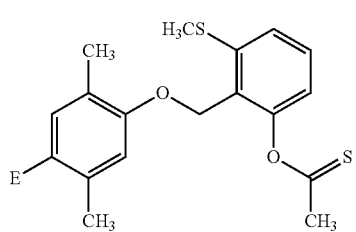 (HC2107)
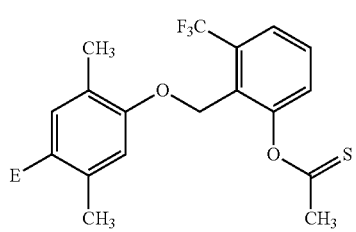 (HC2108)
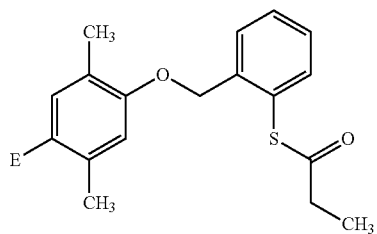 (HC2109)
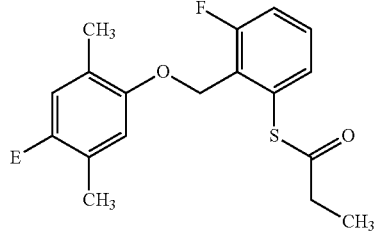 (HC2110)
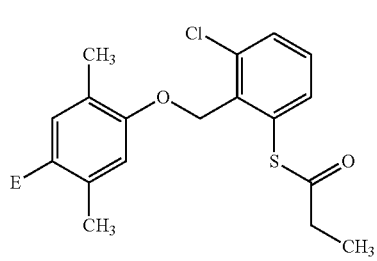 (HC2111)
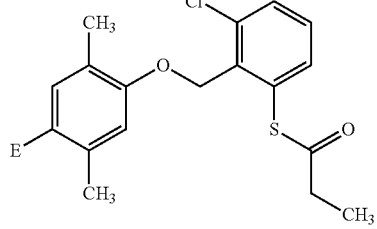 (HC2112)
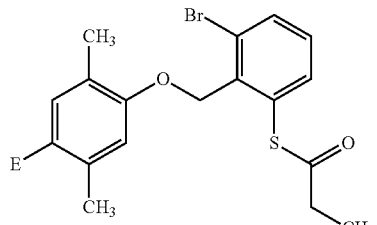 (HC2113)
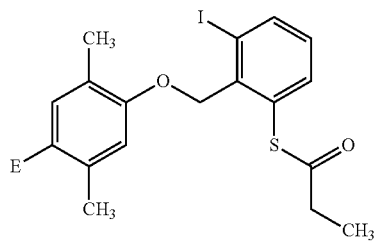 (HC2114)
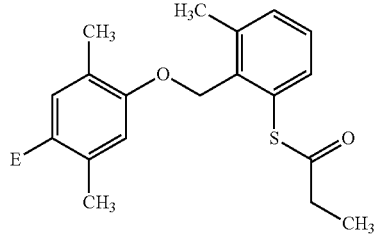 (HC2115)

231
-continued
(HC2116)
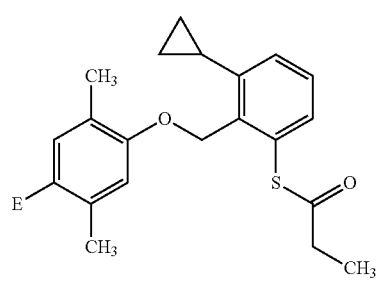
(HC2117)
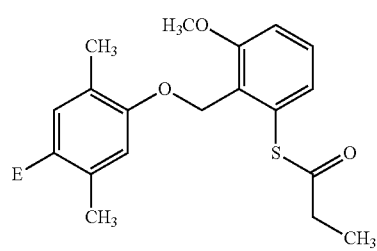
(HC2118)
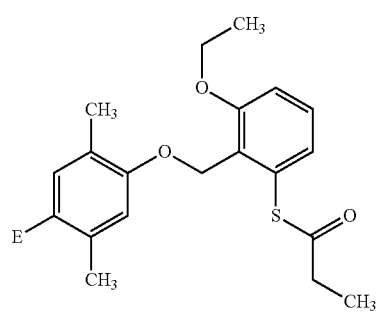
(HC2119)
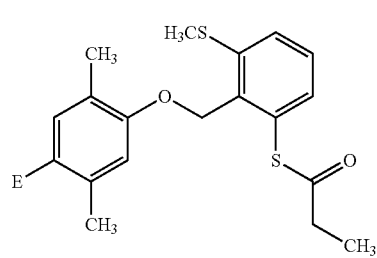
(HC2120)
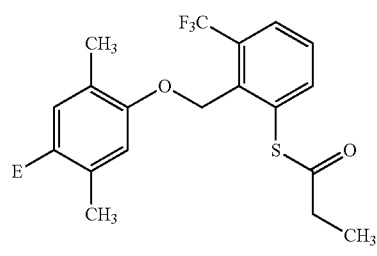
(HC2121)
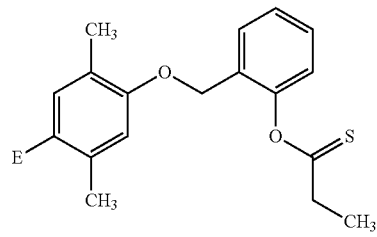
232
-continued
(HC2122)
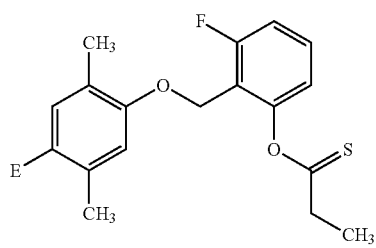
(HC2123)
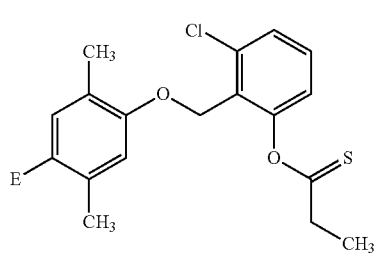
(HC2124)
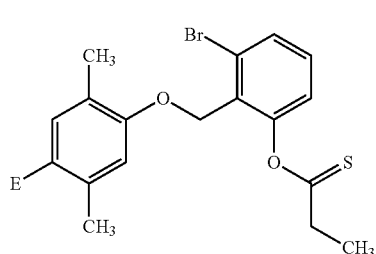
(HC2125)
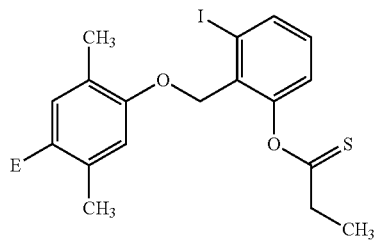
(HC2126)
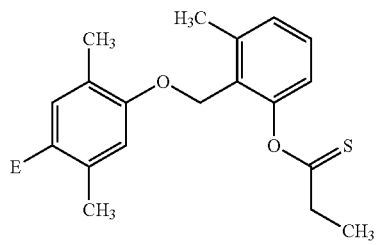
(HC2127)
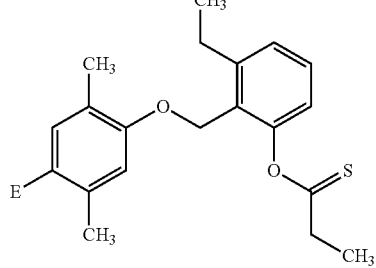

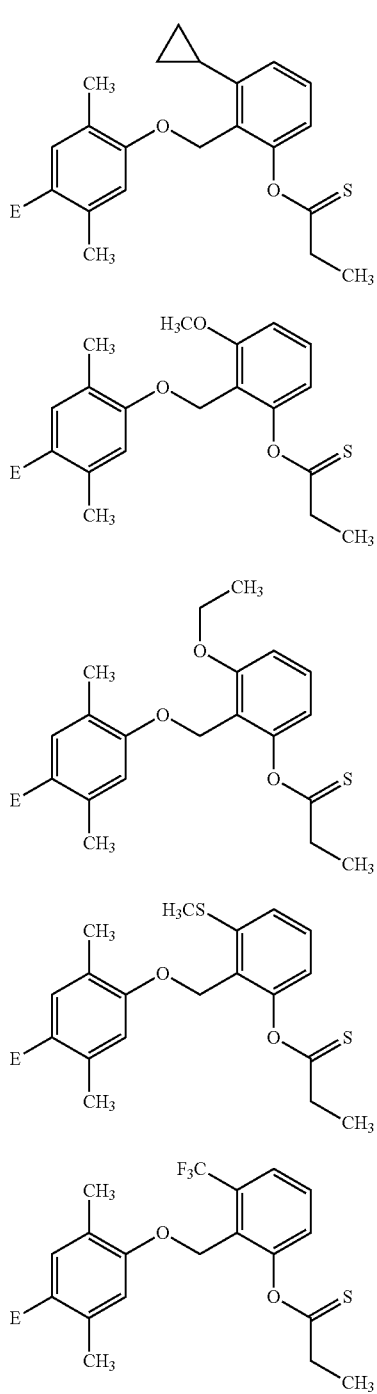

[Substituent Number E]

[1; PYR1], [2; 3-Me-PYR1], [3; 3-Me-4-F-PYR1], [4; 3-Me-4-Cl-PYR1], [5; 3-Me-4-Br-PYR1], [6; 3-Me-4-Me-PYR1], [7; 3-Me-4-Et-PYR1], [8; 3-Me-4-OMe-PYR1], [9; 3-Me-4-OEt-PYR1], [10; 3-Me-4-CN-PYR1], [11; 3-Me-4-c-Pr-PYR1], [12; 3-Me-4-CHF2-PYR1], [13; 3-Me-4-CF3-PYR1], [14; 3-Me-5-F-PYR1], [15; 3-Me-4-F-5-F-PYR1], [16; 3-Me-4-Cl-5-F-PYR1], [17; 3-Me-4-Br-5-F-PYR1], [18; 3-Me-4-Me-5-F-PYR1], [19; 3-Me-4-Et-5-F-PYR1], [20; 3-Me-4-OMe-5-F-PYR1], [21; 3-Me-4-OEt-5-F-PYR1], [22; 3-Me-4-CN-5-F-PYR1], [23; 3-Me-4-c-Pr-5-F-PYR1], [24; 3-Me-4-CHF2-5-F-PYR1], [25; 3-Me-4-CHF3-F-PYR1], [26; 3-Me-5-Cl-PYR1], [27; 3-Me-4-F-5-Cl-PYR1], [28; 3-Me-4-Cl-5-Cl-PYR1], [29; 3-Me-4-Br-5-Cl-PYR1], [30; 3-Me-4-Me-5-Cl-PYR1], [31; 3-Me-4-Et-5-Cl-PYR1], [32; 3-Me-4-OMe-5-Cl-PYR1], [33; 3-Me-4-Cl-5-Cl-PYR1], [34; 3-Me-4-CN-5-Cl-PYR1], [35; 3-Me-4-c-Pr-5-Cl-PYR1], [36; 3-Me-4-CHF2-5-Cl-PYR1], [37; 3-Me-4-CF3-5-Cl-PYR1], [38; 3-Me-5-Br-PYR1], [39; 3-Me-4-F-5-Br-PYR1], [40; 3-Me-4-Cl-5-Br-PYR1], [41; 3-Me-4-Br-5-Br-PYR1], [42; 3-Me-4-Me-5-Br-PYR1], [43; 3-Me-4-Et-5-Br-PYR1], [44; 3-Me-4-OMe-5-Br-PYR1], [45; 3-Me-4-OEt-5-Br-PYR1], [46; 3-Me-4-CN-5-Br-PYR1], [47; 3-Me-4-c-Pr-5-Br-PYR1], [48; 3-Me-4-CHF2-5-Br-PYR1], [49; 3-Me-4-CF3-5-Br-PYR1], [50; 3-Me-5-Me-PYR1], [51; 3-Me-4-F-5-Me-PYR1], [52; 3-Me-4-Cl-5-Me-PYR1], [53; 3-Me-4-Br-5-Me-PYR1], [54; 3-Me-4-Me-5-Me-PYR1], [55; 3-Me-4-Et-5-Me-PYR1], [56; 3-Me-4-OMe-5-Me-PYR1], [57; 3-Me-4-OEt-5-Me-PYR1], [58; 3-Me-4-CN-5-Me-PYR1], [59; 3-Me-4-c-Pr-5-Me-PYR1], [60; 3-Me-4-CHF2-5-Me-PYR1], [61; 3-Me-4-CF3-5-Me-PYR1], [62; 3-Me-5-Et-PYR1][63; 3-Me-4-F-5-Et-PYR1], [64; 3-Me-4-Cl-5-Et-PYR1], [65; 3-Me-4-Br-5-Et-PYR1], [66; 3-Me-4-Me-5-Et-PYR1], [67; 3-Me-4-Et-5-Et-PYR1], [68; 3-Me-4-OMe-5-Et-PYR1], [69; 3-Me-4-OEt-5-Et-PYR1], [70; 3-Me-4-CN-5-Et-PYR1], [71; 3-Me-4-c-Pr-5-Et-PYR1], [72; 3-Me-4-CHF2-5-Et-PYR1], [73; 3-Me-4-CF3-5-Et-PYR1], [74; 3-Me-5-OMe-PYR1], [75; 3-Me-4-F-5-OMe-PYR1], [76; 3-Me-4-Cl-5-Me-PYR1], [77; 3-Me-4-Br-5-OMe-PYR1], [78; 3-Me-4-Me-5-OMe-PYR1], [79; 3-Me-4-Et-5-OMe-PYR1], [80; 3-Me-4-OMe-5-OMe-PYR1], [81; 3-Me-4-OEt-5-OMe-PYR1], [82; 3-Me-4-CN-5-OMe-PYR1], [83; 3-Me-4-c-Pr-5-OMe-PYR1], [84; 3-Me-4-CHF2-5-OMe-PYR1], [85; 3-Me-4-CF3-5-OMe-PYR1], [86; 3-Me-5-OEt-PYR1], [87; 3-Me-4-F-5-OEt-PYR1], [88; 3-Me-4-Cl-5-OEt-PYR1], [89; 3-Me-4-Br-5-OEt-PYR1], [90; 3-Me-4-Me-5-OEt-PYR1], [91; 3-Me-4-Et-5-OEt-PYR1], [92; 3-Me-4-OMe-5-OEt-PYR1], [93; 3-Me-4-OEt-5-OEt-PYR1], [94; 3-Me-4-CN-5-OEt-PYR1], [95; 3-Me-4-c-Pr-5-OEt-PYR1], [96; 3-Me-4-CHF2-5-OEt-PYR1], [97; 3-Me-4-CF3-5-OEt-PYR1], [98; 3-Me-5-CN-PYR1], [99; 3-Me-4-F-5-CN-PYR1], [100; 3-Me-4-Cl-5-CN-PYR1], [101; 3-Me-4-Br-5-CN-PYR1], [102; 3-Me-4-Me-5-CN-PYR1], [103; 3-Me-4-Et-5-CN-PYR1], [104; 3-Me-4-OMe-5-CN-PYR1], [105; 3-Me-4-OEt-5-CN-PYR1], [106; 3-Me-4-CN-5-CN-PYR1], [107; 3-Me-4-c-Pr-5-CN-PYR1], [108; 3-Me-4-CHF2-5-CN-PYR1], [109; 3-Me-4-CF3-5-CN-PYR1], [110; 3-Me-5-c-Pr-PYR1], [111; 3-Me-4-F-5-c-Pr-PYR1], [112; 3-Me-4-Cl-5-c-Pr-PYR1][113; 3-Me-4-Br-5-c-Pr-PYR1], [114; 3-Me-4-Me-5-c-Pr-PYR1], [115; 3-Me-4-Et-5-c-Pr-PYR1], [116; 3-Me-4-OMe-5-c-Pr-PYR1], [117; 3-Me-4-OEt-5-c-Pr-PYR1], [118; 3-Me-4-CN-5-c-Pr-PYR1], [119; 3-Me-4-c-Pr-5-c-Pr-PYR1], [120; 3-Me-4-CHF2-5-c-Pr-PYR1], [121; 3-Me-4-CF3-5-c-Pr-PYR1], [122; 3-Me-5-CHF2-PYR1], [123; 3-Me-4-F-5-CHF2-PYR1], [124; 3-Me-4-Cl-5-CHF2-PYR1], [125; 3-Me-4-Br-5-CHF2-PYR1], [126; 3-Me-4-Me-5-CHF2-PYR1][127; 3-Me-4-Et-5-CHF2-PYR1], [128; 3-Me-4-OMe-5-CHF2-PYR1], [129; 3-Me-4-OEt-5-CHF2-PYR1], [130; 3-Me-4-CN-5-CHF2-PYR1], [131; 3-Me-4-c-Pr-5-CHF2-PYR1], [132; 3-Me-4-CHF2-5-CHF2-PYR1], [133; 3-Me-4-CF3-5-CHF2-PYR1], [134; 3-Me-5-CF3-PYR1], [135; 3-Me-4-F-5-CF3-PYR1], [136; 3-Me-4-Cl-5-CF3-PYR1], [137; 3-Me-4-Br-5-CF3-PYR1], [138; 3-Me-4-Me-5-CF3-PYR1], [139; 3-Me-4-Et-5-CF3-PYR1], [140; 3-Me-4-OMe-5-CF3-PYR1], [141; 3-Me-4-OEt-5-CF3-PYR1], [142; 3-Me-4-CN-5-CF3-PYR1], [143; 3-Me-4-c-Pr-5-CF3-PYR1], [144; 3-Me-4-CHF2-5-CF3-PYR1], [145; 3-Me-4-CF3-5-CF3-

PYR1], [146; 3-Et-PYR1], [147; 3-Et-4-F-PYR1], [148; 3-Et-4-Cl-PYR1], [149; 3-Et-4-Br-PYR1], [150; 3-Et-4-Me-PYR1], [151; 3-Et-4-Et-PYR1], [152; 3-Et-4-OMe-PYR1], [153; 3-Et-4-OEt-PYR1], [154; 3-Et-4-CN-PYR1], [155; 3-Et-4-c-Pr-PYR1], [156; 3-Et-4-CHF2-PYR1], [157; 3-Et-4-CF3-PYR1], [158 3-Et-5-F-PYR1], [159; 3-Et-4-F-5-F-PYR1], [160; 3-Et-4-Cl-5-F-PYR1], [161; 3-Et-4-Br-5-F-PYR1], [162; 3-Et-4-Me-5-F-PYR1], [163; 3-Et-4-Et-5-F-PYR1], [164; 3-Et-4-OMe-5-F-PYR1], [165; 3-Et-4-OEt-5-F-PYR1], [166; 3-Et-4-CN-5-F-PYR1], [167; 3-Et-4-c-Pr-5-F-PYR1][168; 3-Et-4-CHF2-5-F-PYR1], [169; 3-Et-4-CF3-5-F-PYR1], [170; 3-Et-5-Cl-PYR1], [171; 3-Et-4-F-5-Cl-PYR1], [172; 3-Et-Cl-5-Cl-PYR1], [173; 3-Et-4-Br-5-Cl-PYR1], [174; 3-Et-4-Me-5-Cl-PYR1], [175; 3-Et-4-Et-5-Cl-PYR1], [176; 3-Et-4-OMe-5-Cl-PYR1], [177; 3-Et-4-OEt-5-Cl-PYR1], [178; 3-Et-4-CN-5-Cl-PYR1], [179; 3-Et-4-c-Pr-5-Cl-PYR1], [180; 3-Et-4-CHF2-5-Cl-PYR1], [181; 3-Et-4-CF3-5-Cl-PYR1], [182; 3-Et-5-Br-PYR1], [183; 3-Et-4-F-5-Br-PYR1], [184; 3-Et-4-Cl-5-Br-PYR1], [185; 3-Et-4-Br-5-Br-PYR1], [186; 3-Et-4-Me-5-Br-PYR1], [187; 3-Et-4-Et-5-Br-PYR1], [188; 3-Et-4-OMe-5-Br-PYR1], [189; 3-Et-4-OEt-5-Br-PYR1], [190; 3-Et-4-CN-5-Br-PYR1], [191; 3-Et-4-c-Pr-5-Br-PYR1], [192; 3-Et-4-CHF2-5-Br-PYR1], [193; 3-Et-4-CF3-5-Br-PYR1], [194; 3-Et-5-Me-PYR1], [195; 3-Et-4-F-5-Me-PYR1], [196; 3-Et-4-Cl-5-Me-PYR1], [197; 3-Et-4-Br-5-Me-PYR1], [198; 3-Et-4-Me-5-Me-PYR1], [199; 3-Et-4-Et-5-Me-PYR1], [200; 3-Et-4-OMe-5-Me-PYR1],

[201; 3-Et-4-OEt-5-Me-PYR1], [202; 3-Et-4-CN-5-Me-PYR1], [203; 3-Et-4-c-Pr-5-Me-PYR1], [204; 3-Et-4-CHF2-5-Me-PYR1], [205; 3-Et-4-CF3-5-Me-PYR1], [206; 3-Et-5-Et-PYR1], [207; 3-Et-4-F-5-Et-PYR1], [208; 3-Et-4-Cl-5-Et-PYR1], [209; 3-Et-4-Br-5-Et-PYR1], [210; 3-Et-4-Me-5-Et-PYR1], [211; 3-Et-4-Et-5-Et-PYR1], [212; 3-Et-4-OMe-5-Et-PYR1], [213; 3-Et-4-OEt-5-Et-PYR1], [214; 3-Et-4-CN-5-Et-PYR1], [215; 3-Et-4-c-Pr-5-Et-PYR1], [216; 3-Et-4-CHF2-5-Et-PYR1], [217; 3-Et-4-CF3-5-Et-PYR1], [218; 3-Et-5-OMe-PYR1], [219; 3-Et-4-F-5-OMe-PYR1], [220; 3-Et-4-Cl-5-OMe-PYR1], [221; 3-Et-4-Br-5-OMe-PYR1], [222; 3-Et-4-Me-5-OMe-PYR1], [223; 3-Et-4-Et-5-OMe-PYR1], [224; 3-Et-4-OMe-5-OMe-PYR1], [225; 3-Et-4-OEt-5-OMe-PYR1], [226; 3-Et-4-CN-5-OMe-PYR1], [227; 3-Et-4-c-Pr-5-OMe-PYR1], [228; 3-Et-4-CHF2-5-OMe-PYR1], [229; 3-Et-4-CF3-5-OMe-PYR1], [230; 3-Et-5-OEt-PYR1], [231; 3-Et-4-F-5-Et-PYR1], [232; 3-Et-4-Cl-5-OEt-PYR1], [233; 3-Et-4-Br-5-OEt-PYR1], [234; 3-Et-4-Me-5-OEt-PYR1], [235; 3-Et-4-Et-5-OEt-PYR1], [236; 3-Et-4-OMe-5-OEt-PYR1], [237; 3-Et-4-OEt-5-OEt-PYR1], [238; 3-Et-4-CN-5-OEt-PYR1], [239; 3-Et-4-c-Pr-5-OEt-PYR1], [240; 3-Et-4-CHF2-5-OEt-PYR1], [241; 3-Et-4-CF3-5-OEt-PYR1], [242; 3-Et-5-CN-PYR1], [243; 3-Et-4-F-5-CN-PYR1], [244; 3-Et-4-Cl-5-CN-PYR1], [245; 3-Et-4-Br-5-CN-PYR1], [246; 3-Et-4-Me-5-CN-PYR1], [247; 3-Et-4-Et-5-CN-PYR1], [248; 3-Et-4-OMe-5-CN-PYR1], [249; 3-Et-4-OEt-5-CN-PYR1], [250; 3-Et-4-CN-5-CN-PYR1], [251; 3-Et-4-c-Pr-5-CN-PYR1], [252; 3-Et-4-CHF2-5-CN-PYR1], [253; 3-Et-4-CF3-5-CN-PYR1], [254; 3-Et-5-c-Pr-PYR1], [255; 3-Et-4-F-5-c-Pr-PYR1], [256; 3-Et-4-Cl-5-c-Pr-PYR1], [257; 3-Et-4-Br-5-c-Pr-PYR1], [258; 3-Et-4-Me-5-c-Pr-PYR1], [259; 3-Et-4-Et-5-c-Pr-PYR1], [260; 3-Et-4-OMe-5-c-Pr-PYR1], [261; 3-Et-4-OEt-5-c-Pr-PYR1], [262; 3-Et-4-CN-5-c-Pr-PYR1], [263; 3-Et-4-c-Pr-5-c-Pr-PYR1], [264; 3-Et-4-CHF2-5-c-Pr-PYR1], [265; 3-Et-4-CF3-5-c-Pr-PYR1], [266; 3-Et-5-CHF2-PYR1], [267; 3-Et-4-F-5-CHF2-PYR1], [268; 3-Et-4-Cl-5-CHF2-PYR1], [269; 3-Et-4-Br-5-CHF2-PYR1], [270; 3-Et-4-Me-5-CHF2-PYR1], [271; 3-Et-4-Et-5-CHF2-PYR1],

[272; 3-Et-4-OMe-5-CHF2-PYR1], [273; 3-Et-4-OEt-5-CHF2-PYR1], [274; 3-Et-4-CN-5-CHF2-PYR1], [275; 3-Et-4-c-Pr-5-CHF2-PYR1], [276; 3-Et-4-CHF2-5-CHF2-PYR1], [277; 3-Et-4-CF3-5-CHF2-PYR1], [278; 3-Et-5-CF3-PYR1], [279; 3-Et-4-F-5-CF3-PYR1], [286; 3-Et-4-Cl-5-CF3-PYR1], [281; 3-Et-4-Br-5-CF3-PYR1], [282; 3-Et-4-Me-5-CF3-PYR1], [283; 3-Et-4-Et-5-CF3-PYR1][284; 3-Et-4-OMe-5-CF3-PYR1)], [285; 3-Et-4-OEt-5-CF3-PYR1], [286; 3-Et-4-CN-5-CF3-PYR1], [287; 3-Et-4-c-Pr-5-CF3-PYR1], [288; 3-Et-4-CHF2-5-CF3-PYR1], [289; 3-Et-4-CF3-5-CF3-PYR1], [290; 5-Me-PYR1], [291; 3-F-5-Me-PYR1], [292; 3-Cl-5-Me-PYR1], [293; 3-Br-5-Me-PYR1], [294; 3-OMe-5-Me-PYR1], [295; 3-OEt-5-Me-PYR1], [296; 3-CN-5-Me-PYR1], [297; 3-c-Pr-5-Me-PYR1], [298; 3-CHF2-5-Me-PYR1], [299; 3-CF3-5-Me-PYR1], [300; 4-F-5-Me-PYR1],

[301; 3-F-4-F-5-Me-PYR1], [302; 3-C-4-F-5-Me-PYR1], [303; 3-Br-4-F-5-Me-PYR1], [304; 3-OMe-4-F-5-Me-PYR1], [305; 3-OEt-4-F-5-Me-PYR1], [306; 3-CN-4-F-5-Me-PYR1], [307; 3-c-Pr-4-F-5-Me-PYR1], [308; 3-CHF2-4-F-5-Me-PYR1], [309; 3-CF3-4-F-5-Me-PYR1], [310; 4-Cl-5-Me-PYR1], [311; 3-F-4-Cl-5-Me-PYR1], [312; 3-Cl-4-Cl-5-Me-PYR1], [313; 3-Br-4-Cl-5-Me-PYR1], [314; 3-OMe-4-Cl-5-Me-PYR1], [315; 3-OEt-4-Cl-5-Me-PYR1], [316; 3-CN-4-Cl-5-Me-PYR1], [317; 3-c-Pr-4-Cl-5-Me-PYR1], [318; 3-CHF2-4-Cl-5-Me-PYR1], [319; 3-CF3-4-Cl-5-Me-PYR1], [320; 4-Br-5-Me-PYR1], [321; 3-F-4-Br-5-Me-PYR1], [322; 3-Cl-4-Br-5-Me-PYR1], [323; 3-Br-4-Br-5-Me-PYR1], [324; 3-OMe-4-Br-5-Me-PYR1], [325; 3-OEt-4-Br-5-Me-PYR1], [326; 3-CN-4-Br-5-Me-PYR1], [327; 3-c-Pr-4-Br-5-Me-PYR1], [328; 3-CHF2-4-Br-5-Me-PYR1], [329; 3-CF3-4-Br-5-Me-PYR1], [330; 4-Me-5-Me-PYR1], [331; 3-F-4-Me-5-Me-PYR1], [332; 3-Cl-4-Me-5-Me-PYR1], [333; 3-Br-4-Me-5-Me-PYR1], [334; 3-OMe-4-Me-5-Me-PYR1], [335; 3-OEt-4-Me-5-Me-PYR1], [336; 3-CN-4-Me-5-Me-PYR1], [337; 3-c-Pr-4-Me-5-Me-PYR1], [338; 3-CHF2-4-Me-5-Me-PYR1], [339; 3-CF3-4-Me-5-Me-PYR1], [340; 4-Et-5-Me-PYR1], [341; 3-F-4-Et-5-Me-PYR1], [342; 3-Cl-4-Et-5-Me-PYR1], [343; 3-Br-4-Et-5-Me-PYR1], [344; 3-OMe-4-Et-5-Me-PYR1], [345; 3-OEt-4-Et-5-Me-PYR1], [346; 3-CN-4-Et-5-Me-PYR1], [347; 3-c-Pr-4-Et-5-Me-PYR1], [348; 3-CHF2-4-Et-5-Me-PYR1], [349; 3-CF3-4-Et-5-Me-PYR1], [350; 4-Me-5-OMe-5-Me-PYR1], [351; 3-F-4-OMe-5-Me-PYR1], [352; 3-Cl-4-OMe-5-Me-PYR1], [353; 3-Br-4-OMe-5-Me-PYR1], [354; 3-OMe-4-OMe-5-Me-PYR1], [355; 3-OEt-4-OMe-5-Me-PYR1], [356; 3-CN-4-OMe-5-Me-PYR1], [357; 3-c-Pr-4-OMe-5-Me-PYR1], [358; 3-CHF2-4-OMe-5-Me-PYR1], [359; 3-CF3-4-OMe-5-Me-PYR1], [360; 4-OEt-5-Me-PYR1], [361; 3-F-4-OEt-5-Me-PYR1], [362; 3-Cl-4-OEt-5-Me-PYR1], [363; 3-Br-4-OEt-5-Me-PYR1], [364; 3-OMe-4-OEt-5-Me-PYR1], [365; 3-OEt-4-OEt-5-Me-PYR1], [366; 3-CN-4-OEt-5-Me-PYR1], [367; 3-c-Pr-4-OEt-5-Me-PYR1], [368; 3-CHF2-4-OEt-5-Me-PYR1], [369; 3-CF3-4-OEt-5-Me-PYR1], [370; 4-CN-5-Me-PYR1], [371; 3-F-4-CN-5-Me-PYR1], [372; 3-Cl-4-CN-5-Me-PYR1], [373; 3-Br-4-CN-5-Me-PYR1], [374; 3-OMe-4-CN-5-Me-PYR1], [375; 3-OEt-4-CN-5-Me-PYR1], [376; 3-CN-4-CN-5-Me-PYR1], [377; 3-c-Pr-4-CN-5-Me-PYR1], [378; 3-CHF2-4-CN-5-Me-PYR1], [379; 3-CF3-4-CN-5-Me-PYR1], [380; 4-c-Pr-5-Me-PYR1], [381; 3-F-4-c-Pr-5-Me-PYR1], [382; 3-Cl-4-c-Pr-5-Me-PYR1], [383; 3-Br-4-c-Pr-5-Me-PYR1], [384; 3-OMe-4-c-Pr-5-Me-PYR1], [385; 3-OEt-4-c-Pr-5-Me-PYR1], [386; 3-CN-4-c-Pr-5-Me-PYR1], [387; 3-c-Pr-4-c-Pr-5-Me-PYR1], [388; 3-CHF2-4-c-Pr-5-Me-PYR1], [389; 3-CF3-4-c-Pr-5-Me-PYR1], [390; 4-CHF2-5-Me-PYR1], [391; 3-F-4-CHF2-5-

Me-PYR1], [392; 3-Cl-4-CHF2-5-Me-PYR1], [393; 3-Br-4-CHF2-5-Me-PYR1], [394; 3-OMe-4-CHF2-5-Me-PYR1], [395; 3-OEt-4-CHF2-5-Me-PYR1], [396; 3-CN-4-CHF2-5-Me-PYR1], [397; 3-c-Pr-4-CHF2-5-Me-PYR1], [398; 3-CHF2-4-CHF2-5-Me-PYR1], [399; 3-CF3-4-CHF2-5-Me-PYR1], [400; 4-CF3-5-Me-PYR1],

[401; 3-F-4-CF3-5-Me-PYR1], [402; 3-Cl-4-CF3-5-Me-PYR1], [403; 3-Br-4-CF3-5-Me-PYR1], [404; 3-OMe-4-CF3-5-Me-PYR1], [405; 3-OEt-4-CF3-5-Me-PYR1], [406; 3-CN-4-CF3-5-Me-PYR1], [407; 3-c-Pr-4-CF3-5-Me-PYR1], [408; 3-CHF2-4-CF3-5-Me-PYR1], [409; 3-CF3-4-CF3-5-Me-PYR1)][410; 5-Et-PYR1], [411; 3-F-5-Et-PYR1], [412; 3-Cl-5-Et-PYR1], [413; 3-Br-5-Et-PYR1], [414; 3-OMe-5-Et-PYR1], [415; 3-OEt-5-Et-PYR1], [416; 3-CN-5-Et-PYR1], [417; 3-c-Pr-5-Et-PYR1], [418; 3-CHF2-5-Et-PYR1], [419; 3-CF3-5-Et-PYR1], [420; 4-F-5-Et-PYR1], [421; 3-F-4-F-5-Et-PYR1], [422; 3-Cl-4-F-5-Et-PYR1], [423; 3-Br-4-F-5-Et-PYR1], [424; 3-OMe-4-F-5-Et-PYR1], [425; 3-OEt-4-F-5-Et-PYR1], [426; 3-CN-4-F-5-Et-PYR1], [427; 3-c-Pr-4-F-5-Et-PYR1], [428; 3-CHF2-4-F-5-Et-PYR1], [429; 3-CF3-4-F-5-Et-PYR1] [430; 4-Cl-5-Et-PYR1], [431; 3-F-4-Cl-5-Et-PYR1], [432; 3-Cl-4-Cl-5-Et-PYR1], [433; 3-Br-4-Cl-5-Et-PYR1], [434; 3-OMe-4-Cl-5-Et-PYR1], [435; 3-OEt-4-Cl-5-Et-PYR1], [436; 3-CN-4-Cl-5-Et-PYR1], [437; 3-c-Pr-4-Cl-5-Et-PYR1], [438; 3-CHF2-4-Cl-5-Et-PYR1], [439; 3-CF3-4-Cl-Et-PYR1], [440; 4-Br-5-Et-PYR1], [441; 3-F-4-Br-5-Et-PYR1], [442; 3-Cl-4-Br-5-Et-PYR1], [443; 3-Br-4-Br-5-Et-PYR1], [444; 3-OMe-4-Br-5-Et-PYR1], [445; 3-OEt-4-Br-5-Et-PYR1], [446; 3-CN-4-Br-5-Et-PYR1], [447; 3-c-Pr-4-Br-5-Et-PYR1][448; 3-CHF2-4-Br-5-Et-PYR1], [449; 3-CF3-4-Br-5-Et-PYR1], [450; 4-Me-5-Et-PYR1], [451; 3-F-4-Me-5-Et-PYR1], [452; 3-Cl-4-Me-5-Et-PYR1], [453; 3-Br-4-Me-5-Et-PYR1], [454; 3-OMe-4-Me-5-Et-PYR1], [455; 3-OEt-4-Me-5-Et-PYR1], [456; 3-CN-4-Me-5-Et-PYR1], [457; 3-c-Pr-4-Me-5-Et-PYR1], [458; 3-CHF2-4-Me-5-Et-PYR1], [459; 3-CF3-4-Me-5-Et-PYR1], [460; 4-Et-5-Et-PYR1], [461; 3-F-4-Et-5-Et-PYR1], [462; 3-Cl-4-Et-5-Et-PYR1], [463; 3-Br-4-Et-5-Et-PYR1], [464; 3-OMe-4-Et-5-Et-PYR1], [465; 3-OEt-4-Et-5-Et-PYR1], [466; 3-CN-4-Et-5-Et-PYR1], [467; 3-c-Pr-4-Et-5-Et-PYR1], [468; 3-CHF2-4-Et-5-Et-PYR1], [469; 3-CF3-4-Et-5-Et-PYR1], [470; 4-OMe-5-Et-PYR1], [471; 3-F-4-OMe-5-Et-PYR1], [472; 3-Cl-4-OMe-5-Et-PYR1], [473; 3-Br-4-OMe-5-Et-PYR1], [474; 3-OMe-4-OMe-5-Et-PYR1], [475; 3-OEt-4-OMe-5-Et-PYR1], [476; 3-CN-4-OMe-5-Et-PYR1], [477; 3-c-Pr-4-OMe-5-Et-PYR1], [478; 3-CHF2-OMe-5-Et-PYR1], [479; 3-CF3-4-OMe-5-Et-PYR1], [480; 4-OEt-5-Et-PYR1], [481; 3-F-4-OEt-5-Et-PYR1], [482; 3-Cl-4-OEt-5-Et-PYR1], [483; 3-Br-4-OEt-5-Et-PYR1], [484; 3-OMe-4-OEt-5-Et-PYR1], [485; 3-OEt-4-OEt-5-Et-PYR1], [486; 3-CN-4-OEt-5-Et-PYR1], [487; 3-c-Pr-4-Et-5-Et-PYR1], [488; 3-CHF2-4-OEt-5-Et-PYR1], [489; 3-CF3-4-OEt-5-Et-PYR1], [490; 4-CN-5-Et-PYR1], [491; 3-F-4-CN-5-Et-PYR1], [492; 3-Cl-4-CN-5-Et-PYR1], [493; 3-Br-4-CN-5-Et-PYR1], [494; 3-OMe-4-CN-5-Et-PYR1], [495; 3-OEt-4-CN-5-Et-PYR1], [496; 3-CN-4-CN-5-Et-PYR1], [497; 3-c-Pr-4-CN-5-Et-PYR1], [498; 3-CHF2-4-CN-5-Et-PYR1], [499; 3-CF3-4-CN-5-Et-PYR1], [500; 4-c-Pr-5-Et-PYR1],

[501; 3-F-4-c-Pr-5-Et-PYR1], [502; 3-C-4-c-Pr-5-Et-PYR1], [503; 3-Br-4-c-Pr-5-Et-PYR1], [504; 3-OMe-4-c-Pr-5-Et-PYR1], [505; 3-OEt-4-c-Pr-5-Et-PYR1], [506; 3-CN-4-c-Pr-5-Et-PYR1], [507; 3-c-Pr-4-c-Pr-5-Et-PYR1], [508; 3-CHF2-4-c-Pr-5-Et-PYR1], [509; 3-CF3-4-c-Pr-5-Et-PYR1], [510; 4-CHF2-5-Et-PYR1], [511; 3-F-4-CHF2-5-Et-PYR1], [512; 3-Cl-4-CHF2-5-Et-PYR1][513; 3-Br-4-CHF2-5-Et-PYR1], [514; 3-OMe-4-CHF2-5-Et-PYR1], [515; 3-OEt-4-CHF2-5-Et-PYR1], [516; 3-CN-4-CHF2-5-Et-PYR1], [517; 3-c-Pr-4-CHF2-5-Et-PYR1], [518; 3-CHF2-4-CHF2-5-Et-PYR1], [519; 3-CF3-4-CHF2-5-Et-PYR1][520; 4-CF3-5-Et-PYR1], [521; 3-F-4-CF3-5-Et-PYR1], [522; 3-Cl-4-CF3-5-Et-PYR1], [523; 3-Br-4-CF3-5-Et-PYR1], [524; 3-OMe-4-CF3-5-Et-PYR1], [525; 3-OEt-4-CF3-5-Et-PYR1], [526; 3-CN-4-CF3-5-Et-PYR1], [527; 3-c-Pr-4-CF3-5-Et-PYR1], [528; 3-CHF2-4-CF3-5-Et-PYR1], [529; 3-CF3-4-CF3-5-Et-PYR1], [530; 1-Me-PYR3], [531; 1-Me-4-F-PYR3], [532; 1-Me-4-Cl-PYR3], [533; 1-Me-4-Br-PYR3], [534; 1-Me-4-Me-PYR3], [535; 1-Me-4-Et-PYR3], [536; 1-Me-4-OMe-PYR3], [537; 1-Me-4-OEt-PYR3], [538; 1-Me-4-CN-PYR3], [539; 1-Me-4-c-Pr-PYR3], [540; 1-Me-4-CHF2-PYR3], [541; 1-Me-4-CHF2-PYR3], [542; 1-Me-5F-PYR3], [543; 1-Me-4-F-5-F-PYR3], [544; 1-Me-4-Cl-5-PYR3], [545; 1-Me-4-Br-5-F-PYR3], [546; 1-Me-4-Me-5-F-PYR3], [547; 1-Me-4-Et-5-F-PYR3], [548; 1-Me-4-OMe-5-F-PYR3], [549; 1-Me-4-OEt-5-F-PYR3], [550; 1-Me-4-CN-5-F-PYR3], [551; 1-Me-4-c-Pr-5-F-PYR3], [552; 1-Me-4-CHF2-5-F-PYR3], [553; 1-Me-4-CF3-5-F-PYR3], [554; 1-Me-5-Cl-PYR3], [555; 1-Me-4-F-5-Cl-PYR3], [556; 1-Me-4-Cl-5-Cl-PYR3] [557; 1-Me-4-Br-5-Cl-PYR3], [558; 1-Me-4-Me-5-Cl-PYR3], [559; 1-Me-4-Et-5-Cl-PYR3], [560; 1-Me-4-OMe-5-Cl-PYR3], [561; 1-Me-4-OEt-5-Cl-PYR3][562; 1-Me-4-CN-5-Cl-PYR3], [563; 1-Me-4-c-Pr-5-Cl-PYR3], [564; 1-Me-4-CHF2-6-Cl-PYR3], [565; 1-Me-4-CF3-7-Cl-PYR3], [566; 1-Me-5-Br-PYR3][567; 1-Me-4-F-5-Br-PYR3], [568; 1-Me-4-Cl-5-Br-PYR3], [569; 1-Me-4-Br-5-Br-PYR3], [570; 1-Me-4-Me-5-Br-PYR3], [571; 1-Me-4-Et-5-Br-PYR3], [572; 1-Me-4-OMe-5-Br-PYR3], [573; 1-Me-4-OEt-5-Br-PYR3], [574; 1-Me-4-CN-5-Br-PYR3], [575; 1-Me-4-c-Pr-5-Br-PYR3], [576; 1-Me-4-CHF2-5-Br-PYR3], [577; 1-Me-4-CF3-5-Br-PYR3], [578; 1-Me-5-Me-PYR3], [579; 1-Me-4-F-5-Me-PYR3], [580; 1-Me-4-Cl-5-Me-PYR3], [581; 1-Me-Br-5-Me-PYR3], [582; 1-Me-4-Me-5-Me-PYR3], [583; 1-Me-4-Et-5-Me-PYR3], [584; 1-Me-4-OMe-5-Me-PYR3], [585; 1-Me-4-OEt-5-Me-PYR3], [586; 1-Me-4-CN-5-Me-PYR3], [587; 1-Me-4-c-Pr-5-Me-PYR3], [588; 1-Me-4-CHF2-5-Me-PYR3], [589; 1-Me-4-CF3-5-Me-PYR3], [590; 1-Me-5-Et-PYR3], [591; 1-Me-4-F-5-Et-PYR3], [592; 1-Me-4-Cl-5-Et-PYR3], [593; 1-Me-4-Br-5-Et-PYR3], [594; 1-Me-4-Me-5-Et-PYR3], [595; 1-Me-4-Et-5-Et-PYR3], [596; 1-Me-4-OMe-5-Et-PYR3], [597; 1-Me-4-OEt-5-Et-PYR3], [598; 1-Me-4-CN-5-Et-PYR3], [599; 1-Me-4-c-Pr-5-Et-PYR3], [600; 1-Me-4-CHF2-5-Et-PYR3],

[601; 1-Me-4-CF3-5-Et-PYR3], [602; 1-Me-5-OMe-PYR3], [603; 1-Me-4-F-5-OMe-PYR3], [604; 1-Me-4-Cl-5-OMe-PYR3], [605; 1-Me-4-Br-5-OMe-PYR3], [606; 1-Me-4-Me-5-OMe-PYR3], [607; 1-Me-4-Et-5-OMe-PYR3], [608; 1-Me-4-OMe-5-OMe-PYR3], [609; 1-Me-4-OEt-5-OMe-PYR3], [610; 1-Me-4-CN-5-OMe-PYR3], [611; 1-Me-4-c-Pr-5-OMe-PYR3], [612; 1-Me-4-CHF2-5-OMe-PYR3], [613; 1-Me-4-CF3-5-OMe-PYR3], [614; 1-Me-5-OEt-PYR3], [615; 1-Me-4-F-5-OEt-PYR3], [616; 1-Me-4-Cl-5-OEt-PYR3], [617; 1-Me-4-Br-5-OEt-PYR3], [618; 1-Me-4-Me-5-OEt-PYR3], [619; 1-Me-4-Et-5-OEt-PYR3], [620; 1-Me-4-Me-5-OEt-PYR3], [621; 1-Me-4-OEt-5-OEt-PYR3], [622; 1-Me-4-CN-5-OEt-PYR3], [623; 1-Me-4-c-Pr-5-OEt-PYR3], [624; 1-Me-4-CHF2-5-OEt-PYR3], [625; 1-Me-4-CF3-5-OEt-PYR3], [626; 1-Me-5-CN-PYR3], [627; 1-Me-4-F-5-CN-PYR3], [628; 1-Me-Cl-5-CN-PYR3], [629; 1-Me-4-Br-5-CN-PYR3], [630; 1-Me-4-Me-5-CN-PYR3], [631; 1-Me-4-Et-5-CN-PYR3], [632; 1-Me-4-OMe-5-CN-PYR3], [633; 1-Me-4-OEt-5-CN-

PYR3], [634; 1-Me-4-N-5-CN-PYR3], [635; 1-Me-4-c-Pr-5-CN-PYR3], [636; 1-Me-4-CHF2-5-CN-PYR3], [637; 1-Me-4-CF3-5-CN-PYR3], [638; 1-Me-5-c-Pr-PYR3], [639; 1-Me-4-F-5-c-Pr-PYR3], [640; 1-Me-4-Cl-5-c-Pr-PYR3], [641; 1-Me-4-Br-5-c-Pr-PYR3], [642; 1-Me-4-Me-5-c-Pr-PYR3], [643; 1-Me-4-Et-5-c-Pr-PYR3], [644; 1-Me-4-OMe-5-c-Pr-PYR3], [645; 1-Me-4-OEt-5-c-Pr-PYR3], [646; 1-Me-4-CN-5-c-Pr-PYR3], [647; 1-Me-4-c-Pr-5-c-Pr-PYR3], [648; 1-Me-4-CHF2-5-c-Pr-PYR3], [649; 1-Me-4-CF3-5-c-Pr-PYR3], [650; 1-Me-5-CHF2-PYR3], [651; 1-Me-4-F-5-CHF2-PYR3], [652; 1-Me-4-Cl-5-CHF2-PYR3], [653; 1-Me-4-Br-5-CHF2-PYR3], [654; 1-Me-4-Me-5-CHF2-PYR3], [655; 1-Me-4-Et-5-CHF2-PYR3], [656; 1-Me-4-OMe-5-CHF2-PYR3], [657; 1-Me-4-OEt-5-CHF2-PYR3][658; 1-Me-4-CN-5-CHF2-PYR3], [659; 1-Me-4-c-Pr-5-CHF2-PYR3], [660; 1-Me-4-CHF2-5-CHF2-PYR3], [661; 1-Me-4-CF3-5-CHF2-PYR3], [662; 1-Me-5-CF3-PYR3], [663; 1-Me-4-F-5-CF3-PYR3], [664; 1-Me-4-Cl-5-CF3-PYR3], [665; 1-Me-4-Br-5-CF3-PYR3], [666; 1-Me-4-Me-5-CF3-PYR3], [667; 1-Me-4-Et-5-CF3-PYR3], [668; 1-Me-4-OMe-5-CF3-PYR3], [669; 1-Me-4-OEt-5-CF3-PYR3], [670; 1-Me-4-CN-5-CF3-PYR3], [671; 1-Me-4-c-Pr-5-CF3-PYR3], [672; 1-Me-4-CHF2-5-CF3-PYR3], [673; 1-Me-4-CF3-5-CF3-PYR3], [674; 1-Me-5-OPr-PYR3], [675; 1-Me-4-F-5-OPr-PYR3], [676; 1-Me-4-Cl-5-OPr-PYR3], [677; 1-Me-4-Br-5-OPr-PYR3], [678; 1-Me-4-Me-5-OPr-PYR3], [679; 1-M-4-Et-5-Pr-PYR3], [680; 1-Me-4-OMe-5-OPr-PYR3], [681; 1-Me-4-OEt-5-OPr-PYR3], [682; 1-Me-4-CN-5-OPr-PYR3], [683; 1-Me-4-c-Pr-5-OPr-PYR3][684; 1-Me-4-CHF2-5-OPr-PYR3], [685; 1-Me-4-CF3-5-OPr-PYR3], [686; 1-Me-5-OCH2CH=CH2-PYR3], [687; 1-Me-4-F-5-OCH2CH=CH2-PYR3], [688; 1-Me-4-Cl-5-OCH2CH=CH2-PYR3], [689; 1-Me-4-Br-5-OCH2CH=CH2-PYR3], [690; 1-Me-4-Me-5-OCH2CH=CH2-PYR3], [691; 1-Me-4-Et-5-OCH2CH=CH2-PYR3], [692; 1-Me-4-OMe-5-OCH2CH=CH2-PYR3], [693; 1-Me-4-OEt-5-OCH2CH=CH2-PYR3], [694; 1-Me-4-CN-5-OCH2CH=CH2-PYR3], [695; 1-Me-4-c-Pr-5-OCH2CH=CH2-PYR3], [696; 1-Me-4-CHF2-5-OCH2CH=CH2-PYR3], [697; 1-Me-4-CF3-5-OCH2CH=CH2-PYR3], [698; 1-Me-5-OCH2CH=CCl2-PYR3], [699; 1-Me-4-F-5-OCH2CH=CCl2-PYR3], [700; 1-Me-4-Cl-5-OCH2CH=CCl2-
[701; 1-Me-4-Br-5-OCH2CH=CCl2-PYR3], [702; 1-Me-4-Me-5-OCH2CH=CCl2-PYR3], [703; 1-Me-4-Et-5-OCH2CH=CCl2-PYR3], [704; 1-Me-4-OMe-5-OCH2CH=CCl2-PYR3], [705; 1-Me-4-OEt-5-OCH2CH=CCl2-PYR3], [706; 1-Me-4-CN-5-OCH2CH=CCl2-PYR3], [707; 1-Me-4-c-Pr-5-OCH2CH=CCl2-PYR3], [708; 1-Me-4-CHF2-5-OCH2CH=CCl2-PYR3], [709; 1-Me-4-CF3-5-OCH2CH=CCl2-PYR3], [710; 1-Me-5-OCH2C≡CH-PYR3], [711; 1-Me-4-F-5-OCH2C≡CH-PYR3], [712; 1-Me-4-Cl-5-OCH2C≡CH-PYR3], [713; 1-Me-4-Br-5-OCH2C≡CH-PYR3], [714; 1-Me-4-Me-5-OCH2C≡CH-PYR3], [715; 1-Me-4-Et-5-OCH2C≡CH-PYR3], [716; 1-Me-4-OMe-5-OCH2C≡CH-PYR3], [717; 1-Me-4-OEt-5-OCH2C≡CH-PYR3], [718; 1-Me-4-CN-5-OCH2C≡CH-PYR3], [719; 1-Me-4-c-Pr-5-OCH2C≡CH-PYR3], [720; 1-Me-4-CHF2-5-OCH2C≡CH-PYR3], [721; 1-Me-4-CF3-5-OCH2C≡CH-PYR3], [722; 1-Me-5-OCH2CF3-PYR3], [723; 1-Me-4-F-5-OCH2CF3-PYR3], [724; 1-Me-4-Cl-5-OCH2CF3-PYR3], [725; 1-Me-4-Br-5-OCH2CF3-PYR3], [726; 1-Me-4-Me-5-OCH2CF3-PYR3], [727; 1-Me-4-Et-5-OCH2CF3-PYR3], [728; 1-Me-4-OMe-5-OCH2CF3-PYR3], [729; 1-Me-4-OEt-5-OCH2CF3-PYR3], [730; 1-Me-CN-5-OCH12CF3-PYR3], [731; 1-Me-4-c-Pr-5-OCH2CF3-PYR3], [732; 1-Me-4-CHF2-5-OCH2CF3-PYR3], [733; 1-Me-CF3-5-OCH2CF3-PYR3], [734; 1-Me-5-CH2OCH3-PYR3], [735; 1-Me-4-F-5-CH2OCH3-PYR3], [736; 1-Me-4-Cl-5-CH2OCH3-PYR3], [737; 1-Me-4-Br-5-CH2OCH3-PYR3], [738; 1-Me-4-Me-5-CH2OCH3-PYR3], [739; 1-Me-4-Et-5-CH2OCH3-PYR3], [740; 1-Me-4-OMe-5-CH2OCH3-PYR3], [741; 1-Me-4-OEt-5-CH2OCH3-PYR3], [742; 1-Me-4-CN-5-CH2OCH3-PYR3], [743; 1-Me-4-c-Pr-5-CH2OCH3-PYR3], [744; 1-Me-4-CHF2-5-CH2OCH3-PYR3], [745; 1-Me-4-CF3-5-CH2OCH3-PYR3], [746; 1-Et-PYR3], [747; 1-Et-4-F-PYR3], [748; 1-Et-4-Cl-PYR3], [749; 1-Et-4-Br-PYR3] [750; 1-Et-4-Me-PYR3], [751; 1-Et-4-Et-PYR3], [752; 1-Et-4-OMe-PYR3], [753; 1-Et-4-OEt-PYR3], [754; 1-Et-4-CN-PYR3], [755; 1-Et-4-c-Pr-PYR3], [756; 1-Et-4-CHF2-PYR3], [757; 1-Et-4-CF3-PYR3], [758; 1-Et-5-F-PYR3], [759; 1-Et-4-F-5-F-PYR3], [760; 1-Et-4-Cl-5-F-PYR3], [761; 1-Et-4-Br-5-F-PYR3], [762; 1-Et-4-Me-5-F-PYR3], [763; 1-Et-4-Et-5-F-PYR3], [764, 1-Et-4-OMe-5-F-PYR3], [765; 1-Et-4-OEt-5-F-PYR3], [766; 1-Et-4-CN-5-F-PYR3], [767; 1-Et-4-c-Pr-5-F-PYR3], [768; 1-Et-4-CHF2-5-F-PYR3], [769; 1-Et-4-CF3-5-F-PYR3], [770; 1-Et-5-Cl-PYR3], [771; 1-Et-4-F-5-Cl-PYR3], [772; 1-Et-4-Cl-5-Cl-PYR3], [773; 1-Et-4-Br-5-Cl-PYR3], [774; 1-Et-4-Me-5-Cl-PYR3], [775; 1-Et-4-Et-5-Cl-PYR3], [776; 1-Et-4-OMe-5-Cl-PYR3], [777; 1-Et-4-OEt-5-Cl-PYR3], [778; 1-Et-4-CN-5-Cl-PYR3], [779; 1-Et-4-c-Pr-5-Cl-PYR3], [780; 1-Et-4-CHF2-5-Cl-PYR3], [781; 1-Et-4-CF3-5-Cl-PYR3], [782; 1-Et-5-Br-PYR3], [783; 1-Et-4-F-5-Br-PYR3], [784; 1-Et-4-Cl-5-Br-PYR3], [785; 1-Et-4-Br-5-Br-PYR3], [786; 1-Et-4-Me-5-Br-PYR3], [787; 1-Et-4-Et-5-Br-PYR3], [788; 1-Et-4-OMe-5-Br-PYR3], [789; 1-Et-4-OEt-5-Br-PYR3], [790; 1-Et-4-CN-5-Br-PYR3], [791; 1-Et-4-c-Pr-5-Br-PYR3], [792; 1-Et-4-CHF2-5-Br-PYR3], [793; 1-Et-4-CF3-5-Br-PYR3], [794; 1-Et-5-Me-PYR3], [795; 1-Et-4-F-Me-PYR3], [796; 1-Et-4-Cl-5-Me-PYR3], [797; 1-Et-4-Br-5-Me-PYR3], [798; 1-Et-4-Me-5-Me-PYR3], [799; 1-Et-4-Et-5-Me-PYR3], [800; 1-Et-4-OMe-5-Me-PYR3],
[801; 1-Et-4-OEt-5-Me-PYR3], [802; i-Et-4-CN-5-Me-PYR3], [803; 1-Et-4-c-Pr-5-Me-PYR3], [804; 1-Et-4-CHF2-5-Me-PYR3], [805; 1-Et-4-CF3-5-Me-PYR3], [806; 1-Et-5-Et-PYR3], [807; 1-Et-4-F-5-Et-PYR3], [808; 1-Et-4-Cl-5-Et-PYR3], [809; 1-Et-4-Br-5-Et-PYR3], [810; 1-Et-4-Me-5-Et-PYR3], [811; 1-Et-4-Et-5-Et-PYR3], [812; 1-Et-4-OMe-5-Et-PYR3], [813; 1-Et-4-OEt-5-Et-PYR3], [814; 1-Et-4-CN-5-Et-PYR3], [815; 1-Et-4-c-Pr-5-Et-PYR3], [816; 1-Et-CHF2-5-Et-PYR3], [817; 1-Et-4-CF3-5-Et-PYR3], [818; 1-Et-5-OMe-PYR3], [819; 1-Et-4-F-5-OMe-PYR3], [820; 1-Et-4-Cl-5-OMe-PYR3], [821; 1-Et-4-Br-5-OMe-PYR3], [822; 1-Et-4-Me-5-OMe-PYR3], [823; 1-Et-4-Et-5-OMe-PYR3], [824; 1-Et-4-OMe-5-OMe-PYR3], [825; 1-Et-4-OEt-5-OMe-PYR3], [826; 1-Et-4-CN-5-OMe-PYR3], [827; 1-Et-4-c-Pr-5-OMe-PYR3], [828; 1-Et-4-CHF2-5-OMe-PYR3], [829; 1-Et-4-CF3-5-OMe-PYR3], [830; 1-Et-5-OEt-PYR3], [831; 1-Et-4-F-5-OEt-PYR3], [832; 1-Et-4-Cl-5-OEt-PYR3], [833; 1-Et-4-Br-5-OEt-PYR3], [834; 1-Et-4-Me-5-OEt-PYR3], [835; 1-Et-4-Et-5-OEt-PYR3], [836; 1-Et-4-OMe-5-OEt-PYR3], [837; 1-Et-4-OEt-5-OEt-PYR3], [838; 1-Et-4-CN-5-OEt-PYR3], [839; 1-Et-4-c-Pr-5-OEt-PYR3], [840; 1-Et-4-CHF2-5-OEt-PYR3], [841; 1-Et-4-CF3-5-OEt-PYR3], [842; 1-Et-5-CN-PYR3], [843, 1-Et-4-F-5-CN-PYR3], [844; 1-Et-4-Cl-5-CN-PYR3], [845; 1-Et-4-Br-5-CN-PYR3], [846; 1-Et-4-Me-5-CN-PYR3], [847; 1-Et-4-Et-5-CN-PYR3], [848;

1-Et-4-OMe-5-CN-PYR3], [849; 1-Et-4-OEt-5-CN-PYR3], [850; 1-Et-4-CN-5-CN-PYR3], [851; 1-Et-4-c-Pr-5-CN-PYR3], [852; 1-Et-4-CHF2-5-CN-PYR3], [853; 1-Et-4-CF3-5-CN-PYR3], [854; 1-Et-5-c-Pr-PYR3], [855; 1-Et-4-F-5-c-Pr-PYR3], [856; 1-Et-4-Cl-5-c-Pr-PYR3], [857; 1-Et-4-Br-5-c-Pr-PYR3], [858; 1-Et-4-Me-5-c-Pr-PYR3], [859; 1-Et-4-Et-5-c-Pr-PYR3], [860; 1-Et-4-OMe-5-c-Pr-PYR3], [861; 1-Et-4-OEt-5-c-Pr-PYR3][862; 1-Et-4-CN-5-c-Pr-PYR3], [863; 1-Et-4-c-Pr-5-c-Pr-PYR3], [864; 1-Et-4-CHF2-5-c-Pr-PYR3], [865; 1-Et-4-CF3-5-c-Pr-PYR3], [866; 1-Et-5-CHF2-PYR3], [867; 1-Et-4-F-5-CHF2-PYR3], [868; 1-Et-4-Cl-5-CHF2-PYR3], [869; 1-Et-4-Br-5-CHF2-PYR3], [870; 1-Et-4-Me-5-CHF2-PYR3], [871; 1-Et-4-Et-5-CHF2-PYR3], [872; 1-Et-4-OMe-5-CHF2-PYR3], [873; 1-Et-4-OEt-5-CHF2-PYR3], [874; 1-Et-4-CN-5-CHF2-PYR3], [875; 1-Et-4-c-Pr-5-CHF2-PYR3], [876; 1-Et-4-CHF2-5-CH2-PYR3], [877; 1-Et-4-CF3-5-CHF2-PYR3], [878; 1-Et-5-CF3-PYR3], [879; 1-Et-4-F-5-CF3-PYR3], [880; 1-Et-4-Cl-5-CF3-PYR3], [881; 1-Et-4-Br-5-CF3-PYR3], [882; 1-Et-4-Me-5-CF3-PYR3], [883; 1-Et-4-Et-5-CF3-PYR3], [884; 1-Et-OMe-5-CF3-PYR3], [885; 1-Et-4-OEt-5-CF3-PYR3], [886; 1-Et-4-CN-5-CF3-PYR3], [887; 1-Et-4-c-Pr-5-CF3-PYR3], [888; 1-Et-4-CHF2-5-CF3-PYR3], [889; 1-Et-4-CF3-5-CF3-PYR3], [890; 1-Et-5-OPr-PYR3], [891; 1-Et-4-F-5-OPr-PYR3], [892; 1-Et-4-Cl-5-OPr-PYR3], [893; 1-Et-4-Br-5-OPr-PYR3], [894; 1-Et-4-Me-5-OPr-PYR3], [895; t-Et-4-Et-5-OPr-PYR3], [896; 1-Et-4-OMe-5-OPr-PYR3], [897; 1-Et-4-OEt-5-OPr-PYR3], [898; 1-Et-4-CN-5-OPr-PYR3], [899; 1-Et-4-c-Pr-5-OPr-PYR3], [900; 1-Et-4-CHF2-5-OPr-PYR3], [901; 1-Et-4-CF3-5-OPr-PYR3], [902; 1-Et-5-OCH2CH=CH2-PYR3], [903; 1-Et-4-F-5-OCH2CH=CH2-PYR3], [904; 1-Et-4-Cl-5-OCH2CH=CH2-PYR3], [905; 1-Et-4-Br-5-OCH2CH=CH2-PYR3], [906; 1-Et-4-Me-5-OCH2CH=CH2-PYR3], [907; 1-Et-4-Et-5-OCH2CH=CH2-PYR3], [908; 1-Et-4-OMe-5-OCH2CH=CH2-PYR3], [909; 1-Et-4-OEt-5-OCH2CH=CH2-PYR3], [910; 1-Et-4-CN-5-OCH2CH=CH2-PYR3], [911; 1-Et-4-c-Pr-5-OCH12CH=CH2-PYR3], [912; 1-Et-4-CHF2-5-OCH2CH=CH2-PYR3], [913; 1-Et-4-CF3-5-OCH2CH=CH2-PYR3], [914; 1-Et-5-OCH2CH=CCl2-PYR3], [915; 1-Et-4-F-5-OCH2CH=CCl2-PYR3], [916; 1-Et-4-Cl-5-OCH2CH=CCl2-PYR3], [917; 1-Et-4-Br-5-OCH2CH=CCl2-PYR3], [918; 1-Et-Me-5-OCH2CH=CCl2-PYR3], [919; 1-Et-4-Et-5-OCH2CH=CCl2-PYR3], [920; 1-Et-4-OMe-5-OCH2CH=CCl2-PYR3], [921; 1-Et-4-OEt-5-OCH2CH=CCl2-PYR3], [922; 1-Et-4-CN-5-OCH2CH=CCl2-PYR3], [923; 1-Et-4-c-Pr-5-OCH2CH=CCl2-PYR3], [924; 1-Et-4-CHF2-5-OCH2CH=CCl2-PYR3; 925; 1-Et-4-CF3-5-OCH2CH=CCl2-PYR3], [926; 1-Et-5-OCH2C≡CH-PYR3], [927; 1-Et-4-F-5-OCH2C≡CH-PYR3], [928; 1-Et-4-Cl-5-OCH2C≡CH-PYR3], [929; 1-Et-4-Br-5-OCH2C≡CH-PYR3], [930; 1-Et-4-Me-5-OCH2C≡CH-PYR3], [931; 1-Et-4-Et-5-OCH2C≡CH-PYR3], [932; 1-Et-4-OMe-5-OCH2C≡CH-PYR3], [933; 1-Et-4-OEt-5-OCH2C≡CH-PYR3], [934; 1-Et-4-CN-5-OCH2C≡CH-PYR3], [935; 1-Et-4-c-Pr-5-OCH2C≡CH-PYR3], [936; 1-Et-4-CHF2-5-OCH2C≡CH-PYR3], [937; 1-Et-4-CF3-5-OCH2C≡CH-PYR3], [938; 1-Et-5-OCH2CF3-PYR3], [939; 1-Et-4-F-5-OCH2CF3-PYR3], [940; 1-Et-4-Cl-5-OCH2CF3-PYR3], [941; 1-Et-4-Br-5-OCH2CF3-PYR3], [942; 1-Et-4-Me-5-OCH2CF3-PYR3], [943; 1-Et-4-Et-5-OCH2CF3-PYR3], [944; 1-Et-4-OMe-5-OCH2CF3-PYR3], [945; 1-Et-4-OEt-5-OCH2CF3-PYR3], [946; 1-Et-4-CN-5-OCH2CF3-PYR3], [947; 1-Et-4-c-Pr-5-OCH2CF3-PYR3], [948; 1-Et-4-CHF2-5-OCH2CF3-PYR3], [949; 1-Et-4-CF3-5-OCH2CF3-PYR3], [950; 1-Et-5-CH2OCH3-PYR3], [951; 1-Et-4-F-5-CH2OCH3-PYR3], [952; 1-Et-4-Cl-5-CH2OCH3-PYR3], [953; 1-Et-4-Br-5-CH2OCH3-PYR3], [954; 1-Et-4-Me-5-CH2OCH3-PYR3], [955; 1-Et-4-Et-5-CH2OCH3-PYR3], [956; 1-Et-4-OMe-5-CH2OCH3-PYR3], [957; 1-Et-4-OEt-5-CH2OCH3-PYR3], [958; 1-Et-4-CN-5-CH2OCH3-PYR3], [959; 1-Et-4-c-Pr-5-CH2OCH3-PYR3], [960; 1-Et-4-CHF2-5-CH2OCH3-PYR3], [961; 1-Et-4-CF3-5-CH2OCH3-PYR3]

For example, HA1001-0046 is a compound in which a substituent number is 46 in a compound represented by formula (HA1001), and is a compound having the following structure.

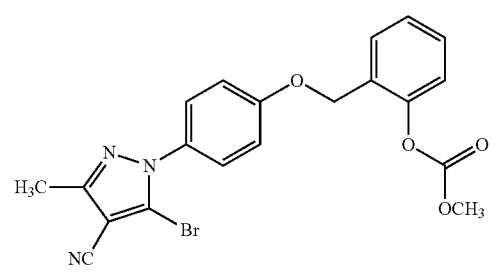

(HA1001-0046)

Formulation Examples will be shown below. Parts are by weight.

Formulation Example 1

Fifty parts (50 parts) of any one of the present compounds A, 3 parts of calcium ligninsulfonate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds A and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds A, 88 parts of kaolin clay, and 10 parts of talc are thoroughly ground and mixed to obtain each formulation.

Formulation Example 4

Five parts (5 parts) of any one of the present compounds A, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds A, 1 part of synthetic hydrated silicon oxide, 2 parts of calcium ligninsulfonate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds A, 35 parts of white carbon containing 50 parts of a polyoxyethylene alkyl ether sulfate ammonium salt, and 55 parts of water were finely ground by a wet grinding method to obtain each formulation.

Next, Test Examples will be shown.

The control effect was evaluated by visually observing the area of lesion on each of test plants at the time of investigation, and comparing the area of lesion on a plant treated with the present compound with that on an untreated plant.

Test Example 1

Each of plastic pots was filled with soil and rice (cultivar: NIHONBARE) was sowed and grown in a greenhouse for 20 days. Then, each water dilution prepared by adjusting so as to contain a predetermined concentration (500 ppm) of any one compound of the present compounds 1, 5, and 6 was sprayed over stems and leaves so that it sufficiently adhered to the surface of the leaves of the rice. After spraying, the plant was air-dried and placed for 6 days at 24° C. in the daytime and 20° C. at night under high humidity condition, while being in contact with the rice seedlings (cultivar: NIHONBARE) infected by the rice blast fungus (*Magnaporthe grisea*), and then the area of lesion was investigated. As a result, the lesion areas on the plant treated with the present compound 1, 5, or 6 were 30% or less with respect to the lesion area on the non-treated plant.

Test Example 2

Each of plastic pots was filled with soil and wheat (cultivar: SHIROGANE) was sowed and grown in a greenhouse for 9 days. Then, each water dilution prepared by adjusting so as to contain a predetermined concentration (500 ppm) of the present compound 6 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was placed at 23° C. for one day under dark and high humidity condition, and cultivated under illumination at 20° C. for 8 days, and then the area of lesion was investigated. As a result, it has been found that the area of lesion on the plant treated with the present compound 6 was 30% or less of that on an untreated plant.

Test Example 3

Each of plastic pots was filled with soil and barley (cultivar: NISHINOHOSHI) was sowed and grown in a greenhouse for 7 days. Then, each water dilution prepared by adjusting so as to contain a predetermined concentration (500 ppm) of any one compound of the present compounds 1, 2, 3, 4, 5, and 6 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with the present compound 1, 2, 3, 4, 5, or 6 was 30% or less of that on an untreated plant.

Test Example 4

Each of plastic pots was filled with soil and kidney bean (cultivar: NAGAUZURA SAITOU) was sowed and grown in a greenhouse for 8 days. Then, each water dilution prepared by adjusting so as to contain a predetermined concentration (500 ppm) of any one compound of the present compounds 1, 3, 4, 5, and 6 was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were placed under high humidity condition only at night. Four days after the inoculation, the area of lesion was investigated. As a result, the area of lesion on the plant treated with the present compound 1, 3, 4, 5, or 6 was 30% or less of that on an untreated plant.

Test Example 5

Each of plastic pots was filled with soil and wheat (cultivar: APOGEE) was sowed and grown in a greenhouse for 10 days. Then, each water dilution prepared by adjusting so as to contain a predetermined concentration (500 ppm) of any one compound of the present compounds 3, 4, and 6 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was placed at 18° C. under high humidity condition for 3 days and placed under illumination for 14 to 18 days, and then the area of lesion was investigated. As a result, the area of lesion on the plant treated with the present compound 3, 4, or 6 was 30% or less of that on an untreated plant.

Test Example 6

Each of plastic pots was filled with soil and cucumber (cultivar: SAGAMI HANJIRO) was sowed and grown in a greenhouse for 12 days. Then, each water dilution prepared by adjusting so as to contain a predetermined concentration (500 ppm) of any one compound of the present compounds 1, 5, and 6 was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24°

C. in the daytime and 20° C. at night for 8 days, and then the area of lesion was investigated. As a result, the area of lesion on the plant treated with the present compound 1, 5, or 6 was 30% or less of that on an untreated plant.

Test Example 7

Each of plastic pots was filled with soil and soybean (cultivar: KUROSENGOKU) was sowed and grown in a greenhouse for 13 days. Then, each water dilution prepared by adjusting so as to contain a predetermined concentration (200 ppm) of any one compound of the present compounds 2, 3, 6, and 7 was sprayed over stems and leaves of the soybean so that it sufficiently adhered to the surface of the leaves of the soybean. After spraying, the plant was air-dried. After 2 days, an aqueous suspension containing spores of soybean rust fungus (*Phakopsora pachyrhizi*) was sprayed to inoculate the spores. After completion of the inoculation, the plant was placed for 3 days in a greenhouse at 23° C. in the daytime and 20° C. at night under high humidity condition and cultivated in a greenhouse for 14 days, and then the area of lesion was investigated. As a result, the area of lesion on the plant treated with the present compound 2, 3, 6, or 7 was 30% or less of that on an untreated plant.

Test Example 8

Each of plastic pots was filled with soil and barley (cultivar: NISHINOHOSHI) was sowed and grown in a greenhouse for 7 days. Then, each water dilution prepared by adjusting so as to contain a predetermined concentration (200 ppm) of any one compound of the present compounds 1, 2, 3, 5, 6 and 7 was sprayed over stems and leaves of the barley so that it sufficiently adhered to the surface of the leaves of the barley. After spraying, the plant was air-dried. After 2 days, an aqueous suspension containing spores of barley scald fungus (*Rhynchosporium secalis*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with of the present compound 1, 2, 3, 5, 6, or 7 was 30% or less of that on an untreated plant.

Test Example 9

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of any one compound of the present compounds 2, 3, 4, 5, 6, and 7 was sprayed over stems and leaves of the cucumber so that it sufficiently adhered to the surface of the leaves of the cucumber. After spraying, the plant was air-dried. After one day, an aqueous suspension containing spores of cucumber anthracnose fungus (*Colletotrichum lagenarium*) was sprayed to inoculate the spores. After the inoculation, the plant was placed at 23° C. for one day under high humidity condition, and then cultivated in a greenhouse at 24° C. in the daytime and 20° C. at night for 6 days, followed by investigation of the area of lesion. As a result, the area of lesion on the plant treated with the present compound 2, 3, 4, 5, 6, or 7 was 30% or less of that on an untreated plant.

Test Example 10

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of the present compound 7 was sprayed over stems and leaves of the cucumber so that it sufficiently adhered to the surface of the leaves of the cucumber. After spraying, the plant was air-dried. After one day, an aqueous suspension containing spores of cucumber target leaf spot fungus (*Corynespora cassiicola*) was sprayed to inoculate the spores. After the inoculation, the plant was cultivated in a greenhouse at 24° C. in the daytime and 20° C. at night for 7 days under high humidity condition, and then the area of lesion was investigated. As a result, the area of lesion on the plant treated with the present compound 7 was 30% or less of that on an untreated plant.

Comparative Test Example

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of 2-[(2,4-dimethylphenoxy)methyl] phenyl=methyl=carbonate was sprayed over stems and leaves of the cucumber so that it sufficiently adhered to the surface of the leaves of the cucumber. After spraying, the plant was air-dried. After one day, an aqueous suspension containing spores of cucumber anthracnose fungus (*Colletotrichum lagenarium*) was sprayed to inoculate the spores. After the inoculation, the plant was placed at 23° C. for one day under high humidity condition, and then cultivated in a greenhouse at 24° C. in the daytime and 20° C. at night for 6 days, followed by investigation of the area of lesion. As a result, the area of lesion on the plant treated with methyl carbonate=2-[(2,4-dimethylphenoxy)methyl]phenyl was 70% or more of that on an untreated plant.

The present compound has control activity against pests and is useful as an active ingredient of a pest control agent.

The invention claimed is:
1. An aromatic compound represented by formula (1):

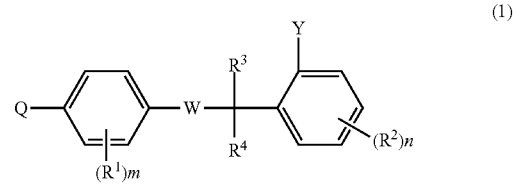

wherein $R^1$ and $R^2$ each independently represents a halogen atom, a C1-C4 alkyl group optionally having one or more halogen atoms, a C3-C4 cycloalkyl group optionally having one or more halogen atoms, a C2-C4 alkenyl group optionally having one or more halogen atoms, a C2-C4 alkynyl group optionally having one or more halogen atoms, a C1-C4 alkoxy group optionally having one or more halogen atoms, a C1-C4 alkylthio group optionally having one or more halogen atoms, a cyano group, or a nitro group (in which when m is an integer of 2 or more, two or more $R^1$(s) may be the same or different to each other and, when n is an integer of 2 or more, two or more R²(s) may be the same or different to each other);

m and n each independently represents an integer of 0 to 4;

R³ and R⁴ each independently represents a hydrogen atom, or a C1-C3 alkyl group optionally having one or more halogen atoms;

Y represents formula: —OC(=X)ZR⁵ or —SC(=X)ZR⁵;

R⁵ represents a C1-C3 alkyl group optionally having one or more halogen atoms;

Z represents an oxygen atom, a sulfur atom, NR⁸, or a direct bond;

R⁸ represents a C1-C3 alkyl group optionally having one or more halogen atoms, or a hydrogen atom;

Q represents pyrazolyl group optionally having one or more atoms or groups selected from Group P¹; and W and X each independently represents an oxygen atom or a sulfur atom:

Group P¹: Group consisting of a halogen atom, a C1-C6 alkyl group optionally having one or more halogen atoms, a C2-C6 alkenyl group optionally having one or more halogen atoms, a C2-C6 alkynyl group optionally having one or more halogen atoms, a C3-C6 cycloalkyl group optionally having one or more halogen atoms, a C1-C6 alkoxy group optionally having one or more halogen atoms, a C1-C6 alkylthio group optionally having one or more halogen atoms, a C3-C6 cycloalkyloxy group optionally having one or more halogen atoms, a C3-C6 cycloalkylthio group optionally having one or more halogen atoms, a C3-C6 alkenyloxy group optionally having one or more halogen atoms, a C3-C6 alkynyloxy group optionally having one or more halogen atoms, a C3-C6 alkenylthio group optionally having one or more halogen atoms, a C3-C6 alkynylthio group optionally having one or more halogen atoms, a C2-C6 alkylcarbonyl group optionally having one or more halogen atoms, a C2-C6 alkylcarbonyloxy group optionally having one or more halogen atoms, a C2-C6 alkylcarbonylthio group optionally having one or more halogen atoms, a carboxy group, a formyl group, a C2-C6 alkoxycarbonyl group optionally having one or more atoms, a nitro group, a cyano group, and an amino group optionally having a C1-C6 alkyl group (in which the alkyl group optionally has one or more halogen atoms).

2. The aromatic compound according to claim 1, wherein the aromatic compound is a compound represented by formula (2):

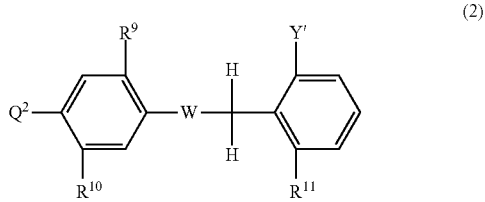

(2)

wherein R⁹ and R¹ each independently represents a hydrogen atom, a C1-C3 alkyl group optionally having one or more halogen atoms, a halogen atom, a C3-C5 cycloalkyl group optionally having one or more halogen atoms, or a C1-C3 alkoxy group optionally having one or more halogen atoms;

R¹¹ represents a hydrogen atom, a C1-C3 alkyl group optionally having one or more halogen atoms, a halogen atom, a C1-C3 alkoxy group optionally having one or more halogen atoms, a C2-C3 alkenyl group optionally having one or more halogen atoms, a C3-C4 cycloalkyl group optionally having one or more halogen atoms, a C2-C3 alkynyl group optionally having one or more halogen atoms, or a C1-C3 alkylthio group optionally having one or more halogen atoms;

Y' represents formula: —OC(=X)Z'R⁵ or —SC(=X)Z'R⁵;

Z' represents a sulfur atom, NR⁸, or a direct bond;

R⁵, R⁸, W, and X are the same as defined above; and

Q² represents a pyrazol-1-yl group optionally having one or more atoms or groups selected from Group P²:

Group P²: Group consisting of a halogen atom, a C1-C6 alkyl group optionally having one or more halogen atoms, a C2-C6 alkenyl group optionally having one or more halogen atoms, a C2-C6 alkynyl group optionally having one or more halogen atoms, a C3-C6 cycloalkyl group optionally having one or more halogen atoms, a C1-C6 alkoxy group optionally having one or more halogen atoms, a C1-C6 alkylthio group optionally having one or more halogen atoms, a C3-C6 alkenyloxy group optionally having one or more halogen atoms, a C3-C6 alkynyloxy group optionally having one or more halogen atoms, and a cyano group.

3. The aromatic compound according to claim 1, wherein the aromatic compound is a compound represented by formula (3):

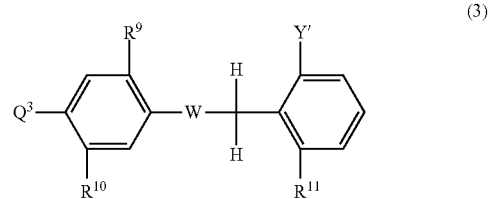

(3)

wherein R⁹, R¹⁰, R¹¹, Y', and W are the same as defined above; and

Q³ represents a pyrazol-3-yl group optionally having one or more atoms or groups selected from Group P².

4. The aromatic compound according to claim 1, wherein the aromatic compound is a compound represented by formula (4):

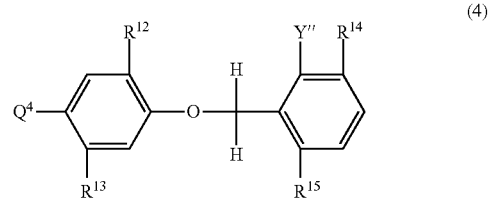

(4)

wherein R¹² represents a C1-C3 alkyl group optionally having one or more halogen atoms, or a halogen atom;

R¹³ and R¹⁴ each independently represents a hydrogen atom or a C1-C3 alkyl group optionally having one or more halogen atoms;

R¹⁵ represents a hydrogen atom, a C1-C3 alkyl group optionally having one or more halogen atoms, a halogen atom, a C1-C3 alkoxy group optionally having one or more halogen atoms, or a C3-C4 cycloalkyl group optionally having one or more halogen atoms;

Y" represents formula: —OC(=X)Z"R$^5$;

Z" represents NR$^8$, or a direct bond;

R$^5$ and R$^8$ are the same as defined above; and

Q$^4$ represents a pyrazol-3-yl group optionally having one or more atoms or groups selected from Group P$^3$, or a pyrazol-1-yl group optionally having one or more atoms or groups selected from Group P$^3$:

Group P$^3$: Group consisting of a hydrogen atom, a halogen atom, a C1-C6 alkyl group optionally having one or more halogen atoms, and a C1-C6 alkoxy group optionally having one or more halogen atoms.

5. A pest control agent comprising the aromatic compound according to claim 1.

6. A method for controlling pests, which comprises applying an effective amount of the aromatic compound according to claim 1 to plants or soil.

* * * * *